United States Patent [19]
Oku et al.

[11] Patent Number: 6,069,156
[45] Date of Patent: May 30, 2000

[54] INDOLE DERIVATIVES AS CGMP-PDE INHIBITORS

[75] Inventors: Teruo Oku; Kozo Sawada; Akio Kuroda; Kazuhiko Ohne, all of Tsukuba; Atsushi Nomoto, Tsuchiura; Naomi Hosogai, Tsukuba; Yoshimitsu Nakajima, Tsukuba; Akira Nagashima, Tsukuba; Keizo Sogabe, Tsuchiura; Kouichi Tamura, Kobe; Masakazu Kobayashi, Takarazuka, all of Japan

[73] Assignee: Fujisawa Pharmaceutical Co., Ltd., Osaka, Japan

[21] Appl. No.: 08/930,597

[22] PCT Filed: Apr. 2, 1996

[86] PCT No.: PCT/JP96/00892

§ 371 Date: Dec. 10, 1997

§ 102(e) Date: Dec. 10, 1997

[87] PCT Pub. No.: WO96/32379

PCT Pub. Date: Oct. 17, 1996

[30] Foreign Application Priority Data

Apr. 10, 1995 [GB] United Kingdom ............... 9507432
Jun. 21, 1995 [GB] United Kingdom ............... 9512560
Aug. 7, 1995 [GB] United Kingdom ............... 9516136
Feb. 27, 1996 [AU] Australia ......................... PN 8294

[51] Int. Cl.[7] ................ A01N 43/40; C07D 401/06; C07D 209/04; C07D 209/08

[52] U.S. Cl. ............... 514/339; 514/365; 514/514; 546/277.4; 548/491; 548/493; 548/159; 548/454; 548/465

[58] Field of Search ................ 548/491, 493, 548/159, 454, 465; 546/277.4; 514/339, 365

[56] References Cited

U.S. PATENT DOCUMENTS 4,898,863  2/1990  Brown et al. .............. 514/235.2
5,234,942  8/1993  Bernstein et al. .............. 514/415
5,767,139  6/1998  Maw et al. .................. 514/38

FOREIGN PATENT DOCUMENTS

WO 96/03377  7/1995  Japan.

*Primary Examiner*—Joseph McKane
*Assistant Examiner*—Dominic Keating
*Attorney, Agent, or Firm*—Oblon, Spivak, McClelland, Maier & Neustadt, P.C.

[57] ABSTRACT

Compounds of the formula (I):

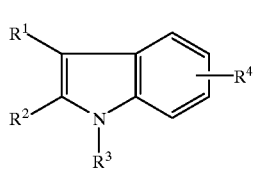

and their pharmaceutically acceptable compositions are useful in inhibiting the activity of cyclic guanosine 3',5'-monophosphate phosphodiesterase.

9 Claims, No Drawings

INDOLE DERIVATIVES AS CGMP-PDE INHIBITORS

This application is a 371 of PCT/JP96/00892, filed Apr. 2, 1996.

BACKGROUND OF THE INVENTION

Field of the Invention

The present invention relates to novel compounds having pharmacological activity, to a process for their production and to a pharmaceutical c position containing the same.

More particularly, it relates to novel indole compounds, which have pharmaceutical activity such as inhibiting activity of cyclic guanosine 3',5'-monophosphate phosphodiesterase (hereinafter described as cGMP-PDE), to a process for their production, to a pharmaceutical composition containing the same and to a use thereof.

SUMMARY OF THE INVENTION

Accordingly, one object of this invention is to provide the novel indole compounds, which have an inhibiting activity of cGMP-PDE.

Another object of this invention is to provide a process for production of the indole compounds.

A further object of this invention is to provide a pharmaceutical composition containing, as active ingredients, the indole compounds.

Still further object of this invention is to provide a use of the indole compounds for treating or preventing various diseases.

Further, this invention also relates to a new use of inhibitors of cyclic nucleotide phosphodiesterases. (hereinafter described as cyclic nucleotide-PDEs)

DETAILED DESCRIPTION OF THE PREFERRED EMBODIMENTS

In more detail, this invention relates to a new use of cyclic nucleotide-PDEs inhibitors for preventing or treating glomerular diseases, tubulo-interstitial diseases or renal failure, or diabetic complications.

Accordingly, this invention provides a new use of cyclic nucleotide-PDE inhibitors for preventing or treating glomerular diseases, tubulo-interstitial diseases or renal failure, or diabetic complications.

Further, this invention provides an agent and a pharmaceutical composition for preventing or treating glomerular diseases, tubulo-interstitial diseases or renal failure, or diabetic complications, which comprises cyclic nucleotide-PDE inhibitors.

Still further, this invention provides a method for preventing or treating glomerular diseases, tubulo-interstitial diseases or renal failure, or diabetic complications, which comprises administering cyclic nucleotide-PDE inhibitors.

The new indole compounds of this invention can be represented by the following general formula:

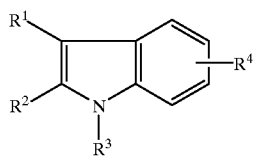

(I)

wherein
  $R^1$ is hydrogen, halogen, nitro, carboxy, protected carboxy, acyl, cyano, hydroxyimino(lower)alkyl, lower alkenyl optionally substituted with oxo, or lower alkyl optionally substituted with protected carboxy, carboxy or hydroxy;
  $R^2$ is hydrogen, halogen, lower alkenyl, acyl, or lower alkyl optionally substituted with protected carboxy, carboxy, lower alkoxy or hydroxy;
  $R^3$ is lower alkenyl or lower alkyl, both of which are optionally substituted with one or more substituent(s) selected from the group consisting of
  (1) oxo,
  (2) aryl optionally substituted with one or more substituent(s) selected from the group consisting of halogen, aryl, lower alkoxy, lower alkylenedioxy, cyano, nitro, carboxy, protected carboxy, acyl, and amino optionally substituted with acyl or protected carboxy, and
  (3) a heterocyclic group optionally substituted with halogen; and
  $R^4$ is carboxy, protected carboxy, acyl, cyano, halogen, a heterocyclic group, amino optionally substituted with acyl or protected carboxy, or lower alkyl optionally substituted with protected carboxy, carboxy or acyl;
in addition to their significances above,
  $R^1$ and $R^2$, together with the carbon atoms to which they are attached, represent a 4- to 7-membered carbocyclic ring optionally substituted with oxo,
or its pharmaceutically acceptable salt.

The compounds of formula (I) may contain one or more asymmetric centers and thus they can exist as enantiomers or diastereoisomers. Furthermore certain compounds of formula (I) which contain alkenyl groups may exist as cis- or trans-isomers. In each instance, the invention includes both mixtures and separate individual isomers.

The compounds of formula (I) may also exist in tautomeric forms and the invention includes both mixtures and separate individual tautomers.

The compound of the formula (I) and its salt can be in the form of a solvate, which is included within the scope of the present invention. The solvate preferably include a hydrate and an ethanolate.

Also included in the scope of invention are radiolabelled derivatives of compounds of formula (I) which are suitable for biological studies.

A preferred group of compounds of formula (I) is that wherein
  $R^1$ is cyano, acyl, or lower alkyl optionally substituted with hydroxy;
  $R^2$ is hydrogen, acyl, lower alkenyl, or lower alkyl optionally substituted with lower alkoxy or hydroxy;
  $R^3$ is methyl substituted with aryl or a heterocyclic group, wherein aryl is optionally substituted with one or more substituent(s) selected from the group consisting of halogen, lower alkylenedioxy, protected carboxy and carboxy; and
  $R^4$ is acyl, cyano, or a heterocyclic group;
in addition to their significances above,
  $R^1$ and $R^2$, together with the carbon atoms to which they are attached, represent a 4- to 7-membered carbocyclic ring optionally substituted with oxo.

A more preferred group of compounds of formula (I) is that wherein
  $R^1$ is lower alkyl, or lower alkanoyl optionally substituted with hydroxy, lower alkoxy or aryl;
  $R^2$ is hydrogen, lower alkenyl, or lower alkyl optionally substituted with lower alkoxy;
  $R^3$ is benzyl optionally substituted with one or more substituent(s) selected from the group consisting of halogen and lower alkylenedioxy; and $R^4$ is acyl, cyano, or a heterocyclic group.

A particularly preferred group of compounds of formula (I) is that wherein $R^1$ is lower alkyl, or lower alkanoyl optionally substituted with hydroxy, lower alkoxy or aryl;

$R^2$ is hydrogen, lower alkenyl, or lower alkyl optionally substituted with lower alkoxy;

$R^3$ is benzyl optionally substituted with one or more substituent(s) selected from the group consisting of halogen and lower alkylenedioxy;

$R^4$ is 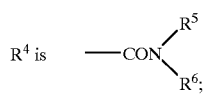

$R^5$ is hydrogen or lower alkyl, and $R^6$ is hydrogen, hydroxy, lower alkoxy, arylsulfonyl, a heterocyclic group, or lower alkyl optionally substituted with lower cycloalkyl or a heterocyclic group;

in addition to their significances above, $R^5$ and $R^6$, together with the nitrogen atom to which they are attached, may represent a heterocyclic group.

An especially preferred group of compounds of formula (I) is that wherein $R^1$ is lower alkanoyl optionally substituted with alkoxy, $R^2$ is lower alkyl, $R^3$ is benzyl optionally substituted with one or more substituent(s) selected from the group consisting of halogen and lower alkylenedioxy, and $R^4$ is carbamoyl.

According to this invention, the object compounds (I) or its salt can be prepared by the following processes.

Process 1

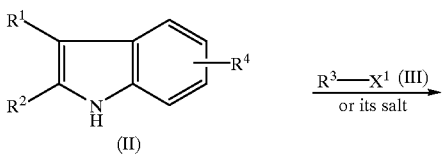

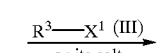

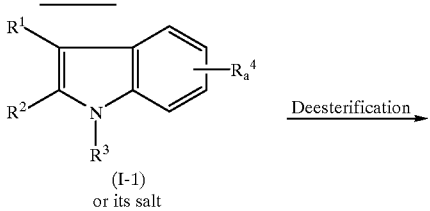

Process 2

Deesterification

Process 3

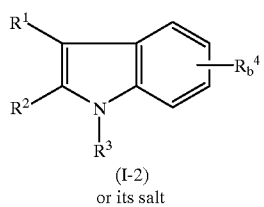

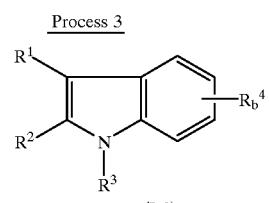

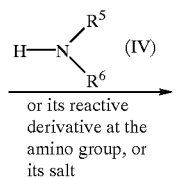

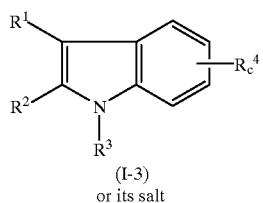

Process 4

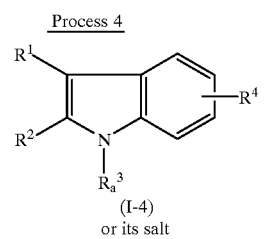

Deesterification

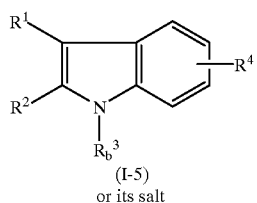

Process 5

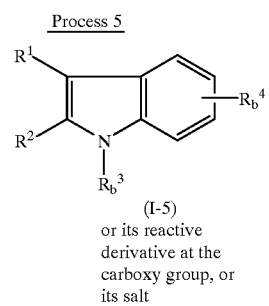

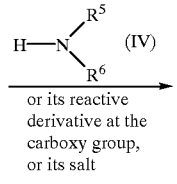

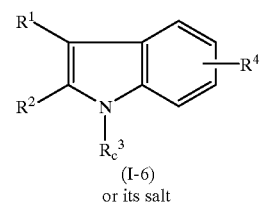

-continued

Process 6

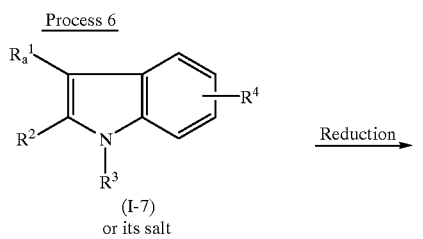
(I-7)
or its salt

↓ Reduction

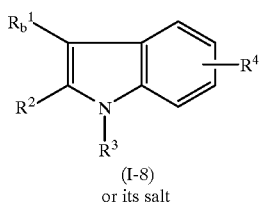
(I-8)
or its salt

Process 7

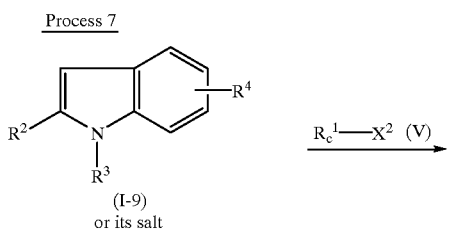
(I-9)
or its salt $R_c^1$—$X^2$ (V) →

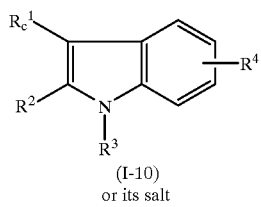
(I-10)
or its salt

Process 8

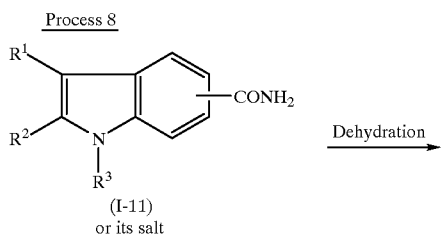
(I-11)
or its salt

Dehydration →

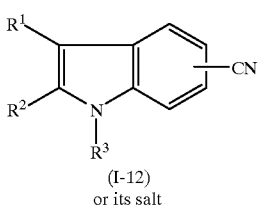
(I-12)
or its salt

Process 9

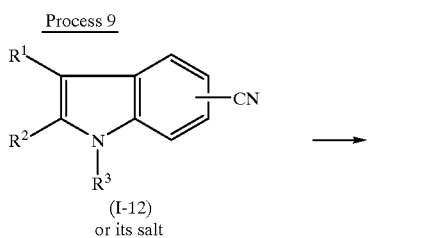
(I-12)
or its salt

→

-continued

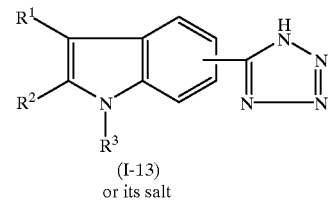
(I-13)
or its salt

Process 10

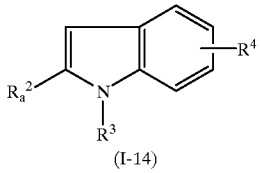
(I-14)
or its salt

Deesterification →

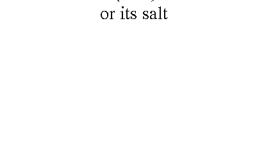
(I-15)
or its salt

Process 11

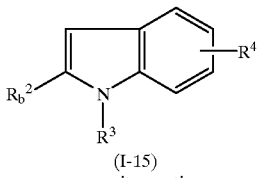
(I-15)
or its reactive
derivative at the
carboxy group,
or its salt

Intramolecular
acylation →

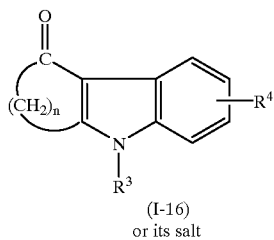
(I-16)
or its salt

Process 12

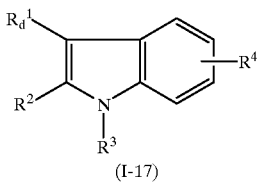
(I-17)
or its salt $H-N\begin{matrix}R^5\\R^6\end{matrix}$ (IV)
———————→
or its salt

(I-18)
or its salt

-continued
Process 13
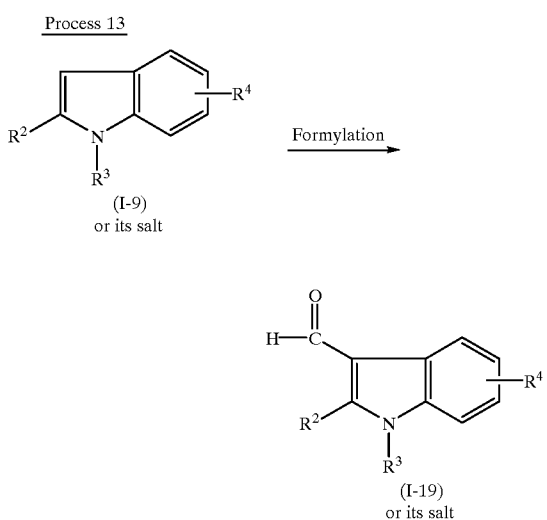
Process 14
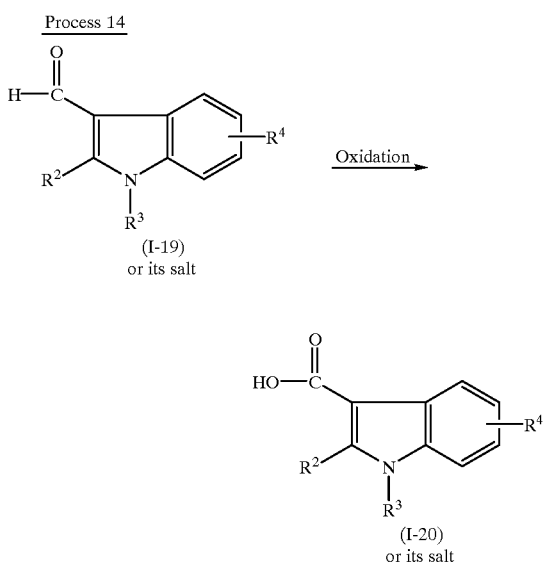
Process 15
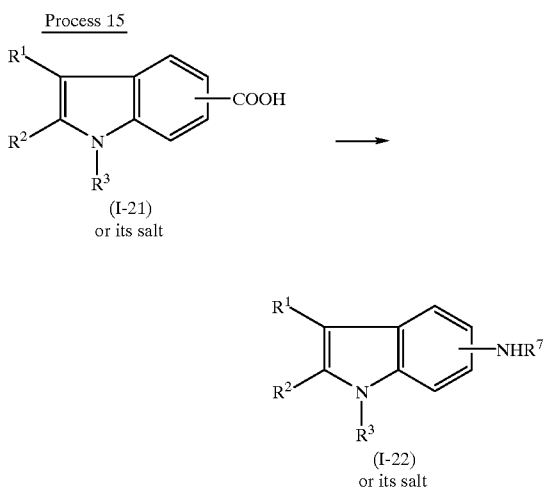
-continued
Process 16
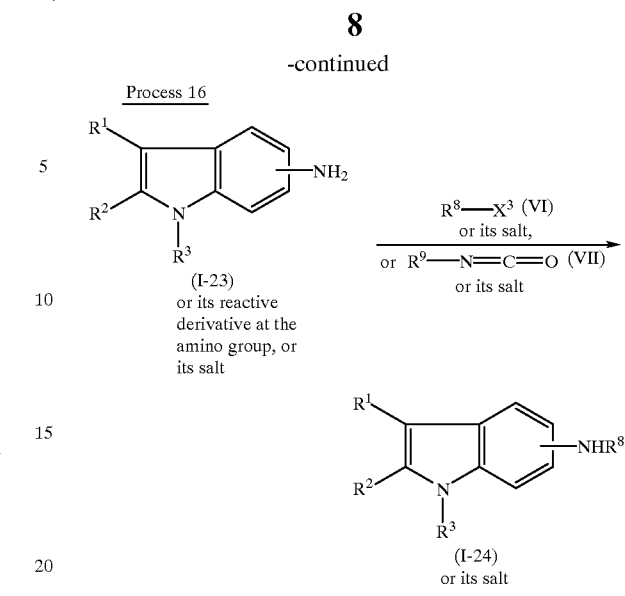
Process 17
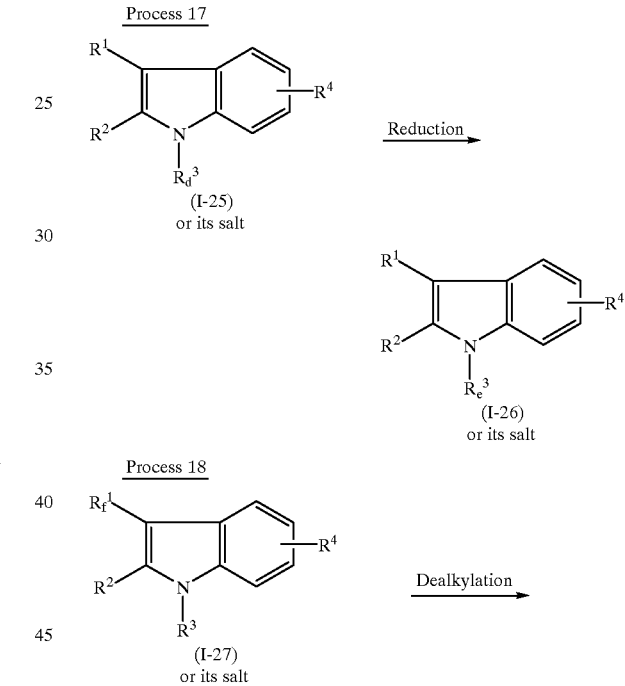
Process 18
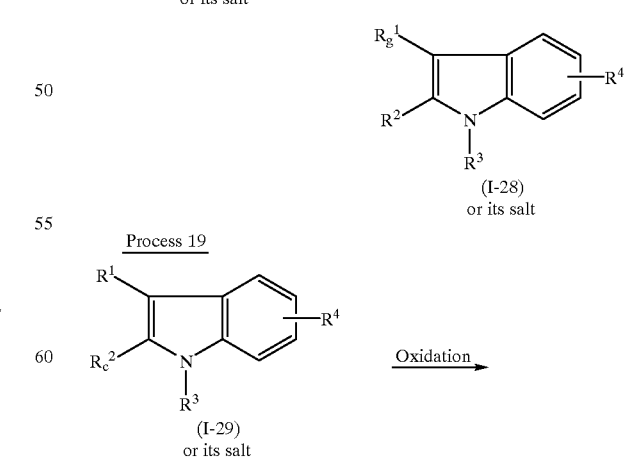
Process 19

-continued

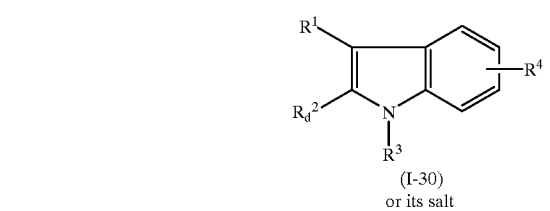
(I-30)
or its salt

Process 20

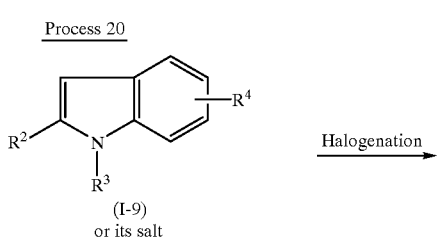
(I-9)
or its salt

Halogenation →

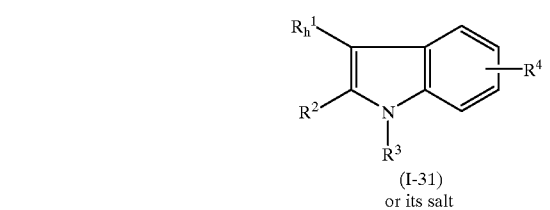
(I-31)
or its salt

Process 21

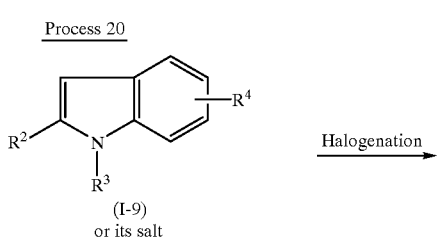
(I-9)
or its salt

Nitration →

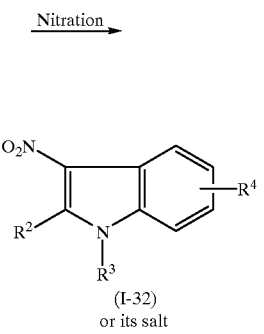
(I-32)
or its salt

Process 22

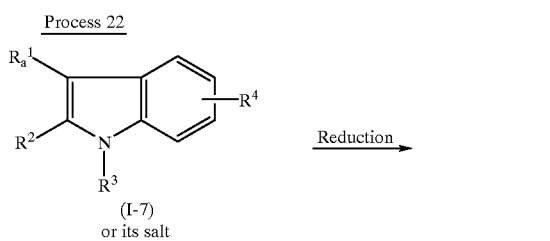
(I-7)
or its salt

Reduction →

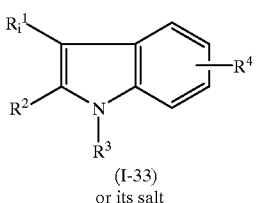
(I-33)
or its salt

-continued

Process 23

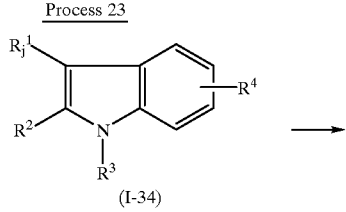
(I-34)
or its salt

→

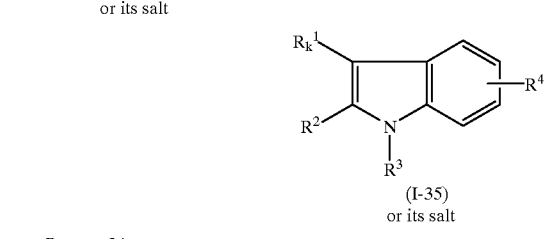
(I-35)
or its salt

Process 24

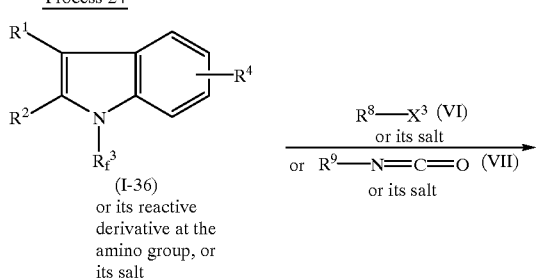
(I-36)
or its reactive
derivative at the
amino group, or
its salt $R^8\!-\!\!X^3$ (VI)
or its salt
or $R^9\!-\!\!N\!=\!\!C\!=\!\!O$ (VII)
or its salt

→

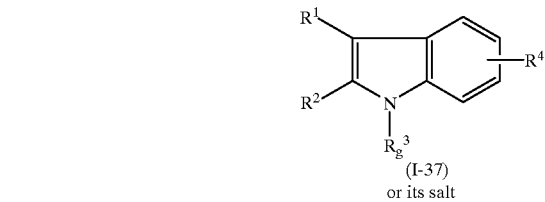
(I-37)
or its salt wherein
$R^1$ to $R^6$ are each as defined above,
$R_a^1$ is lower alkanoyl optionally substituted with protected carboxy or carboxy,
$R_b^1$ is lower alkyl optionally substituted with protected carboxy or carboxy,
$R_c^1$ is lower alkenoyl, aroyl, or lower alkanoyl optionally substituted with protected carboxy, carboxy or aryl,
$R_d^1$ is chloroacetyl,
$R_e^1$ is

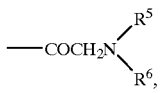

$R_f^1$ is lower alkanoyl substituted with lower alkoxy,
$R_g^1$ is lower alkanoyl substituted with hydroxy,
$R_h^1$ is halogen,
$R_i^1$ is lower alkyl optionally substituted with protected carboxy or carboxy,
$R_j^1$ is lower alkanoyl, $R_k^1$ is hydroxyimino(lower)alkyl, $R_a^2$ is lower alkyl substituted with protected carboxy, $R_b^2$ is lower alkyl substituted with carboxy, $R_c^2$ is 1-hydroxy(lower)alkyl, $R_d^2$ is lower alkanoyl, $R_a^3$ is lower alkenyl or lower alkyl, both of which are optionally substituted with oxo and both of which are substituted with aryl which is substituted with protected carboxy, $R_b^3$ is lower alkenyl or lower alkyl, both of which are optionally substituted with oxo and both of which are substituted with aryl which is substituted with carboxy, $R_c^3$ is lower alkenyl or lower alkyl, both of which are optionally substituted with oxo and both of which are substituted with aryl which is substituted with

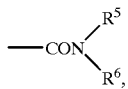

$R_d^3$ is lower alkenyl or lower alkyl, both of which are optionally substituted with oxo and both of which are substituted with aryl which is substituted with nitro, $R_e^3$ is lower alkenyl or lower alkyl, both of which are optionally substituted with oxo and both of which are substituted with aryl which is substituted with amino, $R_f^3$ is lower alkenyl or lower alkyl, both of which are optionally substituted with oxo and both of which are substituted with aryl which is substituted with amino, $R_g^3$ is lower alkenyl or lower alkyl, both of which are optionally substituted with oxo and both of which are substituted with aryl which is substituted with amino substituted with acyl, $R_a^4$ is protected carboxy or lower alkyl substituted with protected carboxy, $R_b^4$ is carboxy or lower alkyl substituted with carboxy, $R_c^4$ is

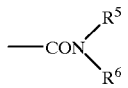

or lower alkyl substituted with

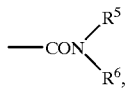

$R^7$ is hydrogen, protected carboxy, or

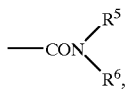

$R^8$ is acyl, $R^9$ is lower alkyl, $X^1$ is leaving group, $X^2$ and $X^3$ are each as the same as $X^1$, and n is 1, 2, 3 or 4.

In the above and subsequent description of the present specification, suitable examples of the various definitions to be included within the scope of the invention are explained in detail in the following.

The term "lower" is intended to mean a group having 1 to 6 carbon atom(s), unless otherwise provided.

Suitable "lower alkyl" and lower alkyl moiety in the terms "lower alkoxy" and "hydroxyimino(lower)alkyl", may be a straight or branched $C_1$–$C_6$ alkyl such as methyl, ethyl, propyl, isopropyl, butyl, isobutyl, tert-butyl, pentyl, hexyl or the like, in which preferable one is $C_1$–$C_4$ lower alkyl such as methyl, ethyl, propyl, butyl, isobutyl or tert-butyl.

Suitable "lower alkenyl" may be a straight or branched $C_2$–$C_6$ alkenyl such as ethenyl, propenyl (i.e. allyl or 1-propenyl), butenyl, isobutenyl, or the like.

Suitable "lower cycloalkyl" may include one having 3 to 6 carbon atoms, for example, cyclopropyl, cyclobutyl, cyclopentyl, or the like.

Suitable "aryl" and aryl moiety in the term of "arylsulfonyl", "aroyl" and "ar(lower)alkanoyl" may include phenyl, naphthyl, tolyl, mesityl, xylyl, or the like.

Suitable "halogen" may be fluoro, chloro, bromo or iodo.

Suitable "lower alkylenedioxy" may include methylenedioxy, ethylenedioxy, or the like.

Suitable "protected carboxy" may be a pharmaceutically acceptable and a common protected carboxy, such as an esterified carboxy, or the like, and concrete examples of the ester moiety in said esterified carboxy may be lower alkyl optionally substituted with aryl (e.g. methyl, ethyl, propyl, tert-butyl, benzyl, and so on).

Suitable "heterocyclic group" may be one containing at least one hetero atom selected from nitrogen, sulfur and oxygen atom, and may include saturated or unsaturated, monocyclic or polycyclic heterocyclic group such as (1) unsaturated 3 to 7-membered, preferably 5 or 6-membered heteromonocyclic group containing 1 to 4 nitrogen atoms, for example, pyrrolyl, pyrrolinyl, imidazolyl, pyrazolyl, pyridyl, pyrimidinyl, pyrazinyl, pyridazinyl, triazolyl [e.g. 4H-1,2,4-triazolyl, 1H-1,2,3-triazolyl, 2H-1,2,3-triazolyl, etc.], tetrazolyl [e.g. 1H-tetrazolyl, 2H-tetrazolyl, etc.], etc.; p0 (2) saturated 3 to 7-membered, preferably 5 or 6-membered heteromonocyclic group containing 1 to 4 nitrogen atoms [e.g. pyrrolidinyl, imidazolidinyl, piperidino, piperazinyl, etc.];

(3) unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g. tetrazolo[1,5-b]pyridazinyl, etc.], etc.;

(4) unsaturated 3 to 7-membered, preferably 5 or 6-membered heteromonocyclic group containing an oxygen atom, for example, pyranyl, furyl, etc.;

(5) unsaturated, 3 to 7-membered, preferably 5 or 6-membered heteromonocyclic group containing 1 to 2 sulfur atoms, for example, thienyl, etc.;

(6) unsaturated 3 to 7-membered, preferably 5 or 6-membered heteromonocyclic group containing 1 to 2 oxygen atoms and 1 to 3 nitrogen atoms, for example, oxazolyl, isoxazolyl, oxadiazolyl [e.g. 1,2,4-oxadiazolyl, 1,3,4-oxadiazolyl, 1,2, 5-oxadiazolyl, etc.], etc.;

(7) saturated 3 to 7-membered, preferably 5 or 6-membered heteromonocyclic group containing 1 to 2 oxygen atoms and 1 to 3 nitrogen atoms [e.g. morpholinyl, etc.];

(8) unsaturated condensed heterocyclic group containing 1 to 2 oxygen atoms and 1 to 3 nitrogen atoms [e.g. benzoxazolyl, benzoxadiazolyl, etc.];

(9) unsaturated 3 to 7-membered, preferably 5 or 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.], etc.

(10) saturated 3 to 7-membered, preferably 5 or 6-membered heteromonocyclic group containing 1 to 2 sulfur atoms and 1 to 3 nitrogen atoms [e.g., thiazolidinyl, etc.];

(11) unsaturated condensed heterocyclic group containing 1 to 2 sulfur atoms and 1 to 3 nitrogen atoms [e.g., benzothiazolyl, benzothiadiazolyl, etc.];

(12) unsaturated condensed heterocyclic group containing 1 to 2 sulfur atoms or 1 to 2 oxygen atoms [e.g., benzothiophen, benzofuran, etc.]; or the like.

"Heterocyclic group" defined above may be substituted with suitable substituent(s) such as lower alkyl, hydroxy, halogen, a heterocyclic group, or the like (e.g., 3-hydroxypyrrolidine, 4-methylpiperadine, 4-hydroxypiperidine, 1-methylimidazole, 4-(pyrimidin-2-yl)piperazin, and so on).

Suitable "acyl" may be aliphatic acyl, aromatic acyl or aliphatic acyl optionally substituted aryl, which are derived from carboxylic acid or carbamic acid.

The aliphatic acyl may include (1) lower alkanoyl optionally substituted with one or more suitable substituent(s) such as hydroxy, lower alkoxy, carboxy, protected carboxy, halogen, lower alkylthio, heterocyclicthio, oxo, cyclo(lower)alkyl or a heterocyclic group (e.g. formyl, acetyl, propionyl, butyryl, isobutyryl, pentanoyl, hexanoyl, 3,3-dimethylbutanoyl, 3-hydroxy-3-methylbutanoyl, 3-oxo-butanoyl, 3-methoxycarbonylpropanoyl, 3-carboxypropanoyl, 4-methoxycarbonylbutanoyl, 4-carboxybutanoyl, methylthioacetyl, (1-methylimidazol-2-yl)thioacetyl, hydroxyacetyl, methoxyacetyl, ethoxyacetyl, 3-methoxybutanoyl, chloroacetyl, morpholinoacetyl, piperidinylacetyl, 4-methylpiperidin-1-ylacetyl, 4-hydroxypiperidinyl, pyrolidinylacetyl, 4-(pyrimidin-2-yl)piperidinylacetyl, 3-hydroxypyrrolidinylacetyl, oxolan-4-ylacetyl, and so on);

(2) cyclo(lower)alkanecarbonyl (e.g. cyclopropylcarbonyl, cyclobutylcarbonyl, cyclopentylcarbonyl, cyclohexylcarbonyl, and so on);

(3) lower alkenoyl (e.g. acryloyl, methacryloyl, crotonoyl, 3-methylbutanoyl, and so on);

(4)

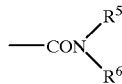

(wherein $R^5$ is hydrogen or lower alkyl, and $R^6$ is hydrogen, hydroxy, lower alkoxy, arylsulfonyl, a heterocyclic group, lower alkyl optionally substituted with lower cycloalkyl or a heterocyclic group, or the like, in addition to their significances above, $R^5$ and $R^6$, together with the nitrogen atom to which they are attached, may represent a heterocyclic group), such as carbamoyl, N-methylcarbamoyl, N,N-dimethylcarbamoyl, N-ethylcarbamoyl, N,N-diethylcarbamoyl, N-propylcarbamoyl, N-phenylsulfonylcarbamoyl, N-methoxycarbamoyl, N-(tetrazol-5-yl)carbamoyl, 1-pyrolidinylcarbonyl, piperidinocarbonyl, 4-methyl-1-piperazinylcarbonyl, 4-cyclohexyl-1-piperazinylcarbonyl, morpholinocarbonyl, 4-thiomorpholinylcarbonyl, or the like.

The aromatic acyl may include aroyl optionally substituted with one or more suitable substituent(s) such as nitro (e.g. benzoyl, naphthoyl, nitrobenzoyl, and so on), or the like.

The aliphatic acyl substituted with aryl may include ar(lower)alkanoyl which may have one or more suitable substituent(s) such as lower alkoxy (e.g. phenylacetyl, 4-methoxyphenylacetyl, and so on) or the like.

Suitable "arylsulfonyl" may include phenylsulfonyl, tosyl, methoxyphenylsulfonyl, or the like.

Suitable "leaving group" may include hydroxy, halogen, acyloxy, in which the halogen and the acyl moiety may be those as exemplified above, or the like.

The starting compound (II) is prepared in similar manners to those of the below-mentioned Preparations.

Suitable salts of the compounds (I), (I-1) to (I-36) and (II) to (VII) may include pharmaceutically acceptable salts such as basic salts, for example, alkali metal salt (e.g. sodium salt, potassium salt, etc.), alkaline earth metal salt (e.g. calcium salt, magnesium salt, etc.), ammonium salt, amine salt (e.g. triethylamine salt, N-benzyl-N-methylamine salt, etc.) and other conventional organic salts, or acid addition salts, for example, hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzenesulfonate, p-toluenesulfonate, or the like.

The processes for preparing the object compound (I) are explained in detail in the following.

PROCESS 1

The compound (I) or its salt can be prepared by reacting the compound (II) or its salt with the compound (III) or its salt.

This reaction is usually carried out in the presence of an inorganic or an organic base.

Suitable inorganic base may include an alkali metal [e.g., sodium, potassium, etc.], an alkali metal hydroxide [e.g., sodium hydroxide, potassium hydroxide, etc.], alkali metal hydrogen carbonate [e.g., sodium hydrogen carbonate, potassium hydrogen carbonate, etc.], alkali metal carbonate [e.g., sodium carbonate, etc.], alkali earth metal carbonate [calcium carbonate, etc.], or the like.

Suitable organic base may include tri(lower)alkylamine [e.g. triethylamine, N,N-diisopropylethylamine, etc.], alkyl lithium [e.g. methyl lithium, butyl lithium, etc.], lithium diisopropylamide, lithium hexamethyldisirazido, alkali metal hydride [e.g., sodium hydride, potassium hydride, etc.] or the like.

The reaction is usually carried out in a conventional solvent such as water, alcohol [e.g., methanol, ethanol, isopropyl alcohol, etc.], tetrahydrofuran, dioxane, toluene, methylene chloride, chloroform, N,N-dimethylformamide or any other organic solvents which do not adversely affect the reaction, or the mixture thereof.

The reaction temperature is not critical and the reaction is usually carried out under cooling to warming.

PROCESS 2

The object compound (I-2) or its salt can be prepared by subjecting a compound (I-1) to deesterification.

The reaction is carried out in accordance with a conventional method such as hydrolysis, reduction or the like.

The hydrolysis is preferably carried out in the presence of a base, an acid, or the combination of Lewis acids and Lewis bases.

Suitable base may include an inorganic base and an organic base.

Suitable inorganic base may be the same as those exemplified in Process 1.

Suitable organic base may include tri(lower)alkylamine [e.g. trimethylamine, triethylamine, etc.], picoline, 1,5-diazabicyclo[4.3.0]non-5-ene, 1,4-diazabicyclo[2.2.2]octane, 1,8-diazabicyclo[5.4.0]undec-7-ene, or the like.

Suitable acid may include an organic acid [e.g. formic acid, acetic acid, propionic acid, trichloroacetic acid, trifluoroacetic acid, etc.], an inorganic acid [e.g. hydrochloric acid, hydrobromic acid, hydroiodic acid, sulfuric acid, etc.].

The hydrolysis is also carried out in the presence of the combination of Lewis acids and Lewis bases.

Suitable Lewis acid may include metal halide [e.g., aluminum chloride, aluminum bromide, titanium(IV) chloride, tin(IV) chloride, etc.], metal alkoxide [e.g., titanium(IV) isopropoxide, etc.] or the like.

Suitable Lewis base may include lower alkyl thiol [e.g., ethanethiol, ethanedithiol, etc.], di(lower)alkyl sulfide [dimethylsulfide, etc.], or the like.

The reaction is usually carried out in a solvent such as water, an alcohol [e.g. methanol, ethanol, etc.], xylene, diethylene glycol monomethyl ether, methylene chloride, tetrahydrofuran, a mixture thereof or any other solvent which does not adversely influence the reaction. A liquid base or acid can be also used as the solvent.

The reaction temperature is not critical and the reaction is usually carried out under cooling to warming.

The reduction can be applied preferably for elimination of the ester moiety such as 4-nitrobenzyl, 2-iodoethyl, 2,2,2-trichloroethyl, or the like. The reduction method applicable for the elimination reaction may include chemical reduction and catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid exemplified above.

Suitable catalysts to be used in catalytic reduction are conventional ones such as platinum catalyst [e.g. platinum on carbon, platinum oxide, etc.], palladium catalyst [e.g. palladium black, palladium oxide, palladium on carbon, etc.] or any other catalyst ordinary employed in the field of organic synthetic chemistry. The catalytic reduction may be carried out in the presence of hydrogen or hydrogen doner such as formic acid, ammonium formate, cyclohexene, or the like.

The reduction is usually carried out in a conventional solvent which does not adversely influence the reaction such as water, an alcohol [e.g. methanol, ethanol, propanol, etc.], N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to warming.

PROCESS 3

The compound (I-3) or its-salt can be prepared by reacting the compound (I-2) or its reactive derivative at the carboxy group, or its salt, with the compound (IV) or its reactive derivative at the amino group, or its salt, according to any well known procedure.

Suitable reactive derivative at the amino group of the compound (IV) may include Schiff's base type imino or its tautomeric enamine type isomer formed by the reaction of the compound (IV) with a carbonyl compound such as aldehyde, ketone or the like; a silyl derivative formed by the reaction of the compound (IV) with a silylating reagent such as trimethylsilyl chloride, N,O-bis(trimethylsilyl)acetamide, N-trimethylsilylacetamide, or the like.

Suitable reactive derivative of the compound (I-2) may include an acid chloride, an acid azide, an acid anhydride, an activated amide, an activated ester, or the like.

The suitable acid anhydride may include a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfuric acid, thiosulfuric acid, alkanesulfonic acid (e.g., methanesulfonic acid, ethanesulfonic acid, etc.), sulfuric acid, alkanoic acid (e.g., pivalic acid, pentanoic acid, isopentanoic acid, etc.), aromatic carboxylic acid (e.g., benzoic acid, chlorobenzoic acid, fluorobenzoic acid, nitrobenzoic acid, etc.), or the like.

Suitable activated amide may be imidazoylamide, 4-substituted imidazoylamide, dimethylpyrazolylamide, triazolylamide tetrazolylamide, or the like.

Suitable activated ester may be dimethyliminomethyl

ester, vinyl ester, propargyl ester, 4-nitrophenyl ester, 2,4-dinitrophenyl ester, trichlorophenyl ester, pentachlorophenyl ester, pentafluorophenyl ester, methanesulfonylphenyl ester, phenyl thioester, p-nitrophenyl thioester, carboxymethyl thioester, pyranyl ester, pyridyl ester, 8-quinolyl thioester, an ester with a N-hydroxy compound (e.g., N,N-dimethylhydroxylamine, 1-hydroxy-2H-pyridone, N-hydroxysuccinimido, N-hydroxybenzotriazole, N-hydroxyphthalimide, etc.), or the like.

These reactive derivatives can optionally be selected from them according to the kind of compound (I-2) to be used.

When the compound (I-2) is used in free acid form or its salt form in the reaction, the reaction is preferably carried out in the presence of condensing agent.

Suitable condensing agent may include a carbodiimide (e.g., N,N-dicyclohexylcarbodiimide, N-cyclohexyl-N'-(4-diethylaminocyclohexyl)carbodiimide, N-ethyl-N'-(3-dimethylaminopropyl)carbodiimide or its hydrochloride, etc.) diphenylphosphinic azido, diphenylphosphinic chloride, diethylphosphoryl cyanide, bis(2-oxo-3-oxazolidinyl)phosphinic chloride, N,N'-carbonyldiimidazole, 2-ethoxy-1-ethoxycarbonyl-1,2-dihydroquinoline, cyanuric chloride, or the like.

The reaction may be also carried out in the presence of organic or inorganic base such as alkali metal carbonate, tri(lower)alkylamine, pyridine, N-(lower)alkylmorphorine, or the like.

The reaction is usually carried out in a conventional solvent such as water, acetone, alcohol [e.g., methanol, ethanol, isopropyl alcohol, etc.], tetrahydrofuran, dioxane, toluene, methylene chloride, chloroform, N,N-dimethylformamide or any other organic solvents which do not adversely affect the reaction, or the mixture thereof.

The reaction temperature is not critical and the reaction is usually carried out under cooling to warming.

PROCESS 4

The compound (I-5) or its salt can be prepared by subjecting the compound (I-4) or its salt to deesterification.

This deesterification can be carried out in a similar manner to that of the Process 2, and therefore the reagents to be used and the reaction conditions (e.g., solvent, reaction temperature, etc.) can be referred to those of the Process 2.

PROCESS 5

The compound (I-6) or its salt can be prepared by reacting the compound (I-5) or its reactive derivative at the carboxy group, or its salt, with the compound (IV) or its reactive derivative at the amino group, or its salt.

This reaction can be carried out in a similar manner to that of the Process 3, and therefore the reagents to be used and the reaction conditions (e.g., solvent, reaction temperature, etc.) can be referred to those of the Process 3.

PROCESS 6

The compound (I-8) or its salt can be prepared by reacting a compound (I-7) or its salt with a reducing agent.

Suitable reducing agent may be diborane, sodium borohydride, lithium aluminum hydride or the like.

The reaction is usually carried out in a conventional solvent such as diethyl ether, tetrahydrofuran or any other organic solvent which dose not adversely influence the reaction.

The reaction temperature is not critical, and the reaction can be carried out under cooling to heating.

PROCESS 7

The compound (I-10) or its salt can be prepared by reacting the compound (I-9) or its salt with an acylating agent (V).

Suitable acylating agent (V) may be a conventional one used in the Friedel-Crafts acylation reaction such as an acid halide [e.g. acid chloride, acid bromide, etc.], an acid anhydride or the like.

This reaction is preferably carried out in the presence of a Lewis acid such as aluminum halide [e.g. aluminum chloride, aluminum bromide, etc.], titanium halide [e.g. titanium tetrachloride, etc.], zinc halide (e.g. zinc chloride), boron trifluoride or the like.

The reaction is usually carried out in a conventional solvent such as carbon disulfide, dichloroethane, tetrachloromethane, benzene or any other organic solvent which does not adversely influence the reaction.

The reaction temperature is not critical, and the reaction is usually carried out under cooling to heating.

PROCESS 8

The compound (I-12) or its salt can be prepared by subjecting the compound (I-11) or its salt to dehydration at the carbamoyl group.

Dehydration is carried out in the conventional manner, which is capable dehydrating a carbamoyl group to cyano group, and suitable dehydrating agent may be phosphorus compound (e.g. phosphorous pentoxide, phosphorus pentachloride, phosphorous oxychloride, pyrocatechyl phosphorus trichloride, and so on); thionyl chloride; or a combination of triaryl phosphine (e.g. triphenyl phosphine, and so on) and chloroform or carbon tetrachloride.

The reaction is usually carried out in a conventional solvent such as water, alcohol [e.g., methanol, ethanol, isopropyl alcohol, etc.], tetrahydrofuran, dioxane, toluene, methylene chloride, chloroform, carbon tetrachloride, N,N-dimethylformamide or any other organic solvents which do not adversely affect the reaction, or the mixture thereof.

The reaction temperature is not critical and the reaction is usually carried out under cooling to warming.

PROCESS 9

The object compound (I-13) or its salt can be prepared by reacting a compound (I-12) or its salt with an azide compound.

Suitable azide compound may be alkali metal azide [e.g. sodium azide, potassium azide, etc.], alkaline earth metal azide [e.g. calcium azide, etc.], aluminum azide, hydrogen azide, trimethyltin azide, or the like.

The reaction is preferably carried out in the presence of ammonium halide [e.g. ammonium chloride, ammonium bromide, etc.], lower alkylammonium halide [e.g. trimethylammonium chloride, triethylammonium chloride, etc.] or the like.

The reaction is usually carried out in a conventional solvent such as tetrahydrofuran, dioxane, N,N-dimethylformamide or any other organic solvent which does not adversely influence the reaction.

The reaction temperature is not critical, and the reaction can be carried out under warming to heating.

PROCESS 10

The compound (I-15) or its salt can be prepared by subjecting the compound (I-14) or its salt to deesterification.

This deesterification can be carried out in a similar manner to that of the Process 2, and therefore the reagents to be used and the reaction conditions (e.g., solvent, reaction temperature, etc.) can be referred to those of the Process 2.

PROCESS 11

The compound (I-16) or its salt can be prepared by subjecting the acid chloride or acid anhydride derived from the compound (I-15) or its salt to intramolecular acylation reaction.

This intramolecular acylation reaction can be carried out in a similar manner to that of the Process 7, and therefore the reagents to be used and the reaction conditions (e.g., solvent, reaction temperature, etc.) can be referred to those of the Process 7.

PROCESS 12

The compound (I-18) or its salt can be prepared by reacting the compound (I-17) or its salt with compound (IV).

This reaction is preferably carried out in the presence of organic or inorganic base exemplified in Process 1, and/or alkali metal iodide (e.g. sodium iodide, potassium iodide, etc.).

The reaction is usually carried out in a solvent such as water, tetrahydrofuran, dioxane, N,N-dimethylformamide or any other solvent which does not adversely influence the reaction.

The reaction temperature is not critical, and the reaction is usually carried out at ambient temperature of under warming to heating.

PROCESS 13

The compound (I-19) or its salt can be prepared by reacting a compound (I-9) or its salt with a formylating agent.

Suitable formylating agent may be N,N-dimethylformamide; $(CH_3)_2N^{+=CHCl.Cl}{}_2PO_2-$ (so-called Vilsmeier reagent prepared by the reaction of N,N-dimethylformamide with phosphorus oxychloride, phosgene, etc.); or the like.

When a formylating agent is N,N-dimethylformamide, the reaction is preferably carried out in the presence of a base such as lower alkyl alkali metal [e.g. n-butyl lithium, ethyl magnesium bromide, etc.], or the like.

The reaction is usually carried out in a solvent such as dioxane, tetrahydrofuran, N,N-dimethylformamide, methylene chloride, chloroform, or any other organic solvent which does not adversely influence the reaction.

The reaction temperature is not critical, and the reaction is usually carried out under cooling to heating.

PROCESS 14

The compound (I-20) or its salt can be prepared by subjecting the compound (I-19) or its salt to oxidation reaction.

Oxidation is carried out in a conventional manner, which is capable of oxidizing formyl group to carboxy group, and suitable oxidizing reagent may be oxygen acid-such as periodate (e.g. sodium periodate, potassium periodate, etc.), peroxy acid such as peroxybenzoic acid (e.g., peroxybenzoic acid, m-chloroperoxybenzoic acid, etc.), potassium permanganate, cromic acid, sodium hypochlorite, or the like.

The reaction is usually carried out in a conventional solvent such as water, alcohol (e.g., methanol, ethanol, isopropyl alcohol, etc.), tetrahydrofuran, dioxane, dichloromethane, ethylene dichloride, chloroform, N,N-dimethylformamide, N,N-dimethylacetamide, or any other organic solvent which does not adversely affect the reaction.

Among these solvents, hydrophilic solvents may be used in a mixture with water.

The reaction temperature is not critical and the reaction is usually carried out under cooling to heating.

PROCESS 15

The compound (I-22) or its salt can be prepared by subjecting the compound (I-21) or its salt to a rearrangement reaction.

The rearrangement reaction, which is capable of converting the carboxy group into amino group optionally substituted with protected carboxy or acyl (e.g. carbamoyl substituted with lower alkyl, etc.), may be the condition such as Curtius Rearrangement, Hoffmann reaction, Schmidt reaction, or the modification thereof.

For example, the Curtius rearrangement consists of the formation of acid azide, the decomposition of acid azide to isocyanate and nitrogen, and the reaction of isocyanate with water, alcohol or amine to afford amine, urethane or urea, respectively.

Acid azide can be prepared by treating corresponding acid hydrazide with nitrous acid, treating corresponding acid chloride with alkali metal azide, treating carboxylic acid with diphenylphosphoryl azide, or the like.

Acid azide can be rearranged in inert solvent (e.g., toluene, dichloromethane, etc.), from which the isocyanate can be isolated, or in the presence of reagents like alcohol or amine which will react with the intermediate isocyanate to form urethan or urea. Amine or its salt can be obtained by hydrolysis of isocyanate, urethan, or urea.

The reaction temperature is not critical and the reaction is usually carried out under cooling to warming.

PROCESS 16

The compound (I-24) or its salt can be prepared by reacting the compound (I-23) or its reactive derivative at the amino group, or its salt, with the compound (VI) or its salt, or the compound (VII) or its salt.

When free acid is used as the compound (VI), the reaction is preferably carried out in the presence of condensing agent exemplified in Process 3.

The reaction is usually carried out in a conventional solvent such as water, alcohol [e.g., methanol, ethanol, isopropyl alcohol, etc.], tetrahydrofuran, dioxane, toluene, methylene chloride, chloroform, N,N-dimethylformamide or any other organic solvents which do not adversely affect the reaction, or the mixture thereof.

The reaction temperature is not critical and the reaction is usually carried out under cooling to warming.

PROCESS 17

The compound (I-26) or its salt can be prepared by subjecting a compound (I-25) or its salt to reduction.

The present reduction is carried out by chemical reduction, catalytic reduction, or the like.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalyst [e.g. platinum, platinum black, platinum oxide, etc.], palladium catalyst [e.g. palladium black, palladium oxide, palladium on carbon, etc.], nickel catalyst [e.g. reduced nickel, nickel oxide, Raney nickel, etc.], cobalt catalyst [e.g. reduced cobalt, Raney cobalt, etc.], iron catalyst [e.g. reduced iron, Raney iron, etc.], copper catalyst [e.g. reduced copper, Raney copper, Ullman copper, etc.] or the like.

The reduction is usually carried out in a conventional solvent which does not adversely influence the reaction such as water, an alcohol [e.g. methanol, ethanol, propanol, etc.], N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent and other conventional solvent such as diethyl ether, methylene chloride, dioxane, tetrahydrofuran, etc., or a mixture thereof.

The reaction temperature of this reduction is not critical and the reaction is usually carried out under cooling to warming.

PROCESS 18

The compound (I-28) or its salt can be prepared by subjecting a compound (I-27) or its salt to cleavage of ether bond.

The cleavage of ether bond is carried out in the presence of an acid including Lewis acid [e.g. hydrochloric acid, hydrobromic acid, hydroiodic acid, boron tribromide, boron trichloride, etc.], tri(lower)alkylsilyliodide [e.g. trimethylsilyliodide, etc.], or any other method ordinary employed in the field of organic synthesis.

The reaction is usually carried out in a solvent such as water, acetic acid, methylene chloride, tetrahydrofuran, a mixture thereof or any other solvent which does not adversely influence the reaction.

The reaction temperature is not critical and the reaction is usually carried out under cooling to heating.

PROCESS 19

The compound (I-30) or its salt can be prepared by subjecting the compound (I-29) or its salt to oxidation.

This oxidation can be performed according to the general procedures ordinarily employed in the field of organic chemistry, which is capable of oxidizing a secondary alcohol to ketone, and suitable oxidizing agent is, for example, derivatives of hexavalent chromium($Cr^{VI}$) (e.g. chromium trioxide, sodium dichromate, chromium trioxide-dipyridine complex, etc.) or heptavalent manganese($Mn^{VII}$) (e.g. potassium permanganate, manganese dioxide, etc.).

The reaction is usually carried out in a conventional solvent such as water, tetrahydrofuran, dioxane, toluene, methylene chloride, chloroform, N,N-dimethylformamide, acetone, or any other organic solvents which do not adversely affect the reaction, or the mixture thereof.

The reaction temperature is not critical and the reaction is usually carried out under cooling to warming.

PROCESS 20

The compound (I-31) or its salt can be prepared by subjecting the compound (I-9) or its salt to halogenation.

This halogenation is usually carried out by using a conventional halogenating agent such as halogen (e.g., chlorine, bromine, etc,), phosphorus trihalide (e.g., phosphorus tribromide, phosphorus tichloride, etc.), phosphorus pentahalide (e.g., phosphorus pentachloride, phosphorus pentabromide, etc.), phosphorus oxychlroide (e.g., phosphoryl trichloride, phosphoryl monochloride, etc.), thionyl halide (e.g., thionyl chloride, thionyl bromide, etc.), oxalyl halide (e.g., oxalyl chloride, oxalyl bromide, etc.), sulfuryl halide (e.g. sulfuryl chloride, etc.), pyridinium hydrobromide perbromide, or the like.

This reaction is usually carried out in a solvent such as water, alcohol (e.g., methanol, ethanol, isopropyl alcohol, etc.), benzene, dioxane, N,N-dimethylformamide, tetrahydrofuran, methylene chloride, ethylene dichloride, chloroform, diethyl ether or any other solvent which dose not adversely affect the reaction.

The reaction temperature is not critical and the reaction is usually carried out under cooling to warming.

PROCESS 21

The compound (I-32) or its salt can be prepared by reacting a compound (I-9) or its salt with a nitrating agent.

Suitable nitrating agent may be nitric acid, fuming nitric acid, potassium nitrate, nitronium tetrafluoroborate or the like.

The reaction is usually carried out in an acid or an acid anhydride such as sulfuric acid, acetic acid, acetic anhydride or the like.

The reaction temperature is not critical, and the reaction is usually carried out under cooling to heating.

PROCESS 22

The compound (I-33) or its salt can be prepared by subjecting the compound (I-7) or its salt to reduction.

This reduction can be performed according to the general procedures ordinarily employed in the field of organic chemistry, which is capable of reducing a ketone to a secondary alcohol, and suitable reducing agent is, for example, metal hydride such as aluminum hydrides (e.g. lithium aluminum hydride, lithium di(lower)alkylaluminum hydride, Red-Al®, etc.), boron hydrides (e.g. sodium borohydride, sodium borocyanohydride, etc.), or the like.

The reaction is usually carried out in a conventional solvent such as water, tetrahydrofuran, dioxane, toluene, methylene chloride, chloroform, N,N-dimethylformamide, acetone, or any other organic solvents which do not adversely affect the reaction, or the mixture thereof.

The reaction temperature is not critical and the reaction is usually carried out under cooling to warming.

PROCESS 23

The compound (I-35) or its salt can be prepared by reacting a compound (I-34) or its salt with hydroxylamine or its salt.

The reaction is usually carried out in a conventional solvent such as water, an alcohol [e.g. methanol, ethanol, etc.], acetone, dioxane, acetonitrile, chloroform, methylene chloride, ethylene chloride, tetrahydrofuran, ethyl acetate, N,N-dimethylformamide, dioxane or any other organic solvent which does not adversely influence the reaction. These conventional solvents may also be used in a mixture with water.

The reaction is preferably carried out in the presence of an inorganic or organic base exemplified in Process 1.

The reaction temperature is not critical, and the reaction is usually carried out under cooling to heating.

PROCESS 24

The compound (I-37) or its salt can be prepared by reacting the compound (I-36) or its reactive derivative at the amino group, or its salt with the compound (VI) or compound (VII).

This reaction can be carried out in a similar manner to that of Process 16 and therefore the regents to be used and the reaction conditions (e.g. reaction temperature, etc.) can be referred to those of the Process 16.

The compounds (I) and pharmaceutically acceptable salts thereof of the present invention possess inhibitory activity of cGMP-PDE (especially PDE-V), relaxant activity of smooth muscle, bronchodilator activity, vasodilative activity, inhibitory activity of smooth muscle cells proliferation, inhibitory activity of allergy, and so on.

The compounds (I) and pharmaceutically acceptable salts thereof, therefore, have utility in the treatment and prevention of various diseases, such as angina, hypertension, pulmonary hypertension, congestive heart failure, glomerular diseases (e.g. diabetic glomerulosclerosis, etc.), renal tubulo-intestinal diseases (e.g. nephropathy induced by FK506, cyclosporins, or the like), renal failure, atherosclerosis, conditions of reduced blood vessel patency (e.g., post-percutaneous transluminal coronary angioplasty), peripheral vascular disease, stroke, chronic reversible obstructive lung diseases (e.g. bronchitis, asthma (chronic asthma, allergic asthma)), allergic rhinitis, urticaria, glaucoma, diseases characterized by disorders of gut motility (e.g., irritable bowel syndrome), impotence (e.g. organic impotence, psychic impotence, etc.), or diabetic complications (e.g. diabetic gangrene, diabetic arthropathy, diabetic glomerulosclerosis, diabetic dermopathy, diabetic neuropathy, diabetic cataract, diabetic retinopathy, etc.).

Besides the compounds of the formula (I), many compounds, disclosed in various prior publications, are known to have a cyclic nucleotide-PDE inhibitory activity.

Particularly, a compound having the following formula:

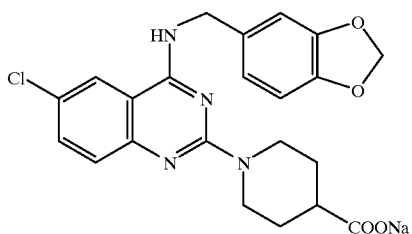

(VIII)

and its analogous compound, and a compound having the following formula:

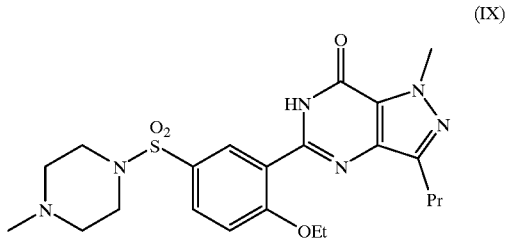

(IX)

and its analogous compounds, which have an inhibiting activity of cyclic nucleotide-PDE (especially cGMP-PDE), were known and disclosed in International Patent Publication No. WO 93/07124 and European Patent Publication No. EP 0 526 004. And, various cyclic nucleotide-PDE inhibitors (e.g. papaverine, dipyridamole, etc.) were known and disclosed in Biochemical Pharmacology, vol 46 No. 5, P 833–839.

And further, until now cGMP-PDE inhibitors as exemplified above have been also known to be useful for treating or preventing of various diseases, for example, according to the International Publication No. W093/07124, angina pectoris, cardiac infarction, ischemic heart disease, for example, chronic and acute cardiac failure, lung hypertension which may be complicated with cor pulmonale, hypertension caused by various factors, peripheral circulatory failure, brain dysfunction, bronchitic asthma and allergic disorder, for example, atopic dermatitis, allergic rhinitis, or the like.

The inventors of this invention have surprisingly found that the cyclic nucleotide-PDE inhibitors are useful for treating or preventing glomerular diseases, renal tubulo-interstitial diseases and chronic renal failure.

According to "International Statistical Classification of Diseases and Related Health Problems (tenth revision)" (W. H. O., 1992), diseases of genitourinary system are divided into several groups, such as glomerular diseases, renal tubulo-interstitial diseases, renal failure and so on.

Glomerular Diseases are divided into several subgroups, such as rapidly progressive nephritis syndrome, recurrent and persistent haematuria, chronic nephritic syndrome, nephritic syndrome, glomerular disorders in other diseases, and so on. The diseases, to which glomerular disorder is ascribed, are for example infectious and parasitic diseases; neoplastic diseases; blood diseases and disorders involving the immune mechanism; diabetes mellitus; other endocrine, nutritional and metabolic diseases; systemic connective tissue disorders (e.g. Goodpasture's syndrome, systemic lupus erythematosus, Wegener's granulomatosis, etc.); and so on.

Renal tubulo-interstitial diseases are also divided into several subgroups, one of which is drug- and heavy-metal-induced tubulo-interstitial and tubular conditions, and another one of which is renal tubulo-interstitial disorders in other diseases. The former subgroup includes analgesic nephropathy; nephropathy induced by drugs (e.g. FK506, cyclosporins, and so on), medicaments and biological substances; nephropathy induced by unspecified drug, medicament and biological substance; nephropathy induced by heavy metals; and toxic nephropathy. In the latter subgroup, the diseases, to which renal tubulo-interstitial disorder is ascribed, are for example infectious and parasitic diseases, neoplastic diseases, blood diseases and disorders involving the immune mechanism, metabolic diseases, systematic connective tissue disorders (e.g. sicca syndrome, systematic lupus erythematosus), transplant rejection, and so on.

Renal failure is divided into three subgroups, one of which is chronic renal failure.

The cyclic nucleotide-PDE inhibitors are useful for treating or preventing glomerular diseases, particularly glomerular disorders in other diseases, more particularly glomerular disorders in diabetes mellitus and glomerular disorders in systemic lupus erythematosus; renal tubulo-interstitial diseases, particularly drug- and heavy-metal-induced tubulo-interstitial and tubular conditions, and renal tubulo-interstitial disorders in other disease, more particularly nephropathy induced by drugs (e.g. FK506, cyclospolins, and so on), medicaments and biological substances, and renal tubulo-interstitial disorders in systemic connective tissue disorder; and chronic renal failure.

The cyclic nucleotide-PDEs include cyclic adenosine 3',5'-monophosphate phosphodiesterase (hereinafter described as cAMP-PDE) and cGMP-PDE. cAMP-PDE and cGMP-PDE play a major role in the regulation of intracellular concentrations of cAMP and cGMP, respectively. The cyclic nucleotide-PDEs are classified into five isozyme families, based largely on primary protein and cDNA sequence information, as follows: $Ca^{++}$-calmodulin(CaM)-dependent family (Type I); cGMP-stimulated family (Type II); cGMP-inhibited by a large number of positive inotropic agents such as milrinone (Type III); cAMP-specific family, selectively inhibited by rolipram (Type IV); cGMP-specific family, selectively inhibited by zaprinast (Type V).

The term "immunophilin" is intended to mean a macromolecular protein or glycoprotein, which is capable of recognizing and selectively binding with immunosuppressive agent such as FK506, cyclosporins, rapamycins and so on, and have a peptidyl-propyl cis-trans isomerase activity; for example, FK506 binding protein (hereinafter indicated as FKBP) and intracellular receptor to the cyclosporins, preferably, FKBP-12 and cyclophilin produced by mammal, for example, cattle or man.

Immunophilin is known and is obtained by substantially the same method of J. Am. Chem. Soc., 113, 1409–1411 (1991), Proc. Natl. Acad. Sci. U.S.A., 88, 6229–6233 (1991), Nature 346, 671–674 (1991) and 337, 473–475, 476–478 (1989), International Patent Application Nos. 91/17493, 92/01052, Japanese Patent Application No. 2-209897 and so on.

The compound designated as FK506 (or FR-900506) and its analogous compounds are well known to have a potent immunosuppressive activity and are produced by fermentation of the genus streptomyces, especially *Streptomyces tukubaensis* No. 9993 (FERM BP-927) or *Streptomyces hygroscopius* subsp. *yakusimaensis* No. 7238 (FERM BP-928) (European Patent No. 0184162-B1).

The cyclosporins, for example, cyclosporin A, B, C, D, E, F and G, and its derivatives, are disclosed in U.S. Pat. Nos. 4,117,118, 4,215,199, 4,288,431, 4,388,307, Helv. Chem.

Acta 60, 1568 (1977) and 65, 1655 (1982), Transplant. Proc., 17, 1362 (1985) and so on, and are well known to have an immunosuppressive activity.

However, FK506 and cyclosporins are also known to induce a renal tubulo-interstitial disease.

The cyclic nucleotide-PDE inhibitors can be administered in a pure or impure form and in a single compound or a mixture thereof, preferably, in a pharmaceutical vehicle or carrier.

The pharmaceutical composition of this invention can be used in the form of a pharmaceutical preparation, for example, in solid, semisolid or liquid form, which contains the cyclic nucleotide PDE inhibitors, as an active ingredient, in admixture with an organic or inorganic carrier or excipient suitable for external, enteral, intravenous, intramuscular, or parenteral applications. The active ingredient may be compounded, for example, with the usual non-toxic, pharmaceutically acceptable, carriers for ointment, cream, plaster, tablets, pellets, capsules, suppositories, solutions (saline, for example), emulsion, suspensions (olive oil, for example), and any other form suitable for use. The carriers which can be used are water, wax, glucose, lactose, gum acacia, gelatin, mannitol, starch paste, magnesium trisilicate, talc, corn starch, keratin, paraffin, colloidal silica, potato starch, urea and other carriers suitable for use in manufacturing preparations, in solid, semisolid, or liquid form, and in addition auxiliary, stabilizing, thickening and coloring agents and perfumes may be used. The active compound is included in the pharmaceutical composition in an effective amount sufficient to produce the desired effect upon the process or condition of the diseases.

Mammals which may be treated by the present invention include livestock mammals such as cows, horses, etc., domestic animals such as dogs, cats, rats, etc. and humans, preferably humans.

For applying this composition to a human, it is preferable to apply-it by external (topical), oral, parenteral, enteral, intravenous, or intramuscular administration.

While the dosage of therapeutically effective amount of the macrolide compounds varies from and also depends upon the age and condition of each individual patient to be treated, in case of the systemic administration, a daily dose of about 0.01–1000 mg, preferably 0.1–500 mg and more preferably 0.5–100 mg of the active ingredient is generally given for treating the diseases, and an average single dose of about 0.2–0.5 mg, 1 mg, 5 mg, 10 mg, 50 mg, 100 mg, 250 mg and 500 mg is generally administered. Daily doses for chronic administration in humans will be in the range of about 0.3 mg/kg/day.

And further, it is considered that the compounds, which have a cyclic nucleotide-PDE inhibitory activity, described in the European Patent Publication Nos. 579,496, 534,443, 526,004, 636,626; U.S. Pat. Nos. 3,819,631, 5,294,612, 5,488,055; International Patent Application Nos. 93/07,124, 94/19,351; Japan Patent Publication No. 07-330,777; and so on, are useful for treating or preventing glomerular diseases, tubulo-interstitial diseases and renal failure.

In order to exhibit the usefulness of the present invention, the activity of compound (I) and the activity of the compound of (VIII) or (IX), papaverine, or dipyridamole, the representative compound of the cyclic nucleotide-PDE inhibitors, is shown in the following.

Test 1
cGMP-phosphodiesterase (PDE) Assay cGMP-PDE was separated from other isozymes in human platelets by a modification of the method of Thompson et. al. (Cyclic Nucleotide Phosphodiesterase (PDE), in Methods of Enzymatic analysis, Vol 4, p127–234, 1984). In enzyme inhibition assays, the test compounds were dissolved in 10% DMSO and then diluted with assay buffer (50 mM Tris-HCl, pH 8.0, 0.1 mM dithiothreitol, 2 mM EGTA and 10 u/ml snake venom), at final concentrations ranging from $10^{-10}$ to $10^{-6}$M. Assays were performed at 0.1 $\mu$M substrate ([$^3$H]-cGMP) concentration, at 30° C. for 10 minutes using enzyme dilutions which gave 10–20% hydrolysis of substrate. Each assay was initiated by addition of substrate and terminated by addition of anion exchange resin (Dowex 1-X8, 25 $\mu$g/mg) followed by centrifugation for 10 minutes (3000 rpm, at 4° C.). Radioactivity of supernatant ($^3$H-GMP) was assayed by liquid scintillation counting.

The compounds prepared in the present Examples 3, 4, 6, 9, 12, 15, 18, 21, 22-(2) to 22-(4), 22-(6), 23, 24-(1), 25-(2), 26, 27-(2), 27-(5), 27-(8), 37-(3), 37-(4), 37-(6), 37-(7), 37-(9), 37-(11), 37-(12), 37-(14), 37-(17), 38-(2), 39, 42, 43, 58, 60, 63, 67-(2), 69, 70, 72, 73-(33), 73-(36), 73-(40), 75-(4), 75-(8), 75-(10), 75-(15), 75-(21), 75-(23) 75-(27), 75-(29), 75-(30), 75-(35), 75-(38) and 75-(39), which were selected as the representative compounds of the present invention, had $IC_{50}$ values below 100 nM.

Test 2
Smooth Muscle Relaxant

The aorta were carefully removed from male Wistar rats, cleaned of fat and extraneous tissue. Spirally cut strips of the aorta were placed in a 25 ml organ bath containing Tyrode solution of the following composition (mM); NaCl, 137; KCl, 2.7; $CaCl_2$, 1.8; $NaH_2PO_4$, 0.4; $NaHCO_3$, 12.0; $MgSO_4$, 1.1; glucose, 5.6. The bath was maintained at 37° C. and bubbled with 95% $O_2$ and 5% $CO_2$. The spirally cut strip was stretched to a resting force of 1.0 g, and the isometric contraction was recorded via a force development transducer on an ink writing recorder. Tissues were equilibrated for 60 minutes before contraction was induced by noradrenaline (NA, 1 $\mu$M). The test compounds were cumulatively added to organ bath in increasing concentrations ranging from $10^{-8}$ to $10^{-5}$ M, after maximum stable constriction to NA had been achieved.

For example, the compounds prepared in the present Examples 6, 12, 27-(8), 37-(4), 37-(7), 37-(9), 37-(12), 43, 72, 73-(33), 73-(36) and 75-(8), which were selected as the representative compounds of the present invention, had $IC_{50}$ values below 100 nM.

Test 3
vSMC Proliferation

Vascular smooth muscle cells (vSMCs) were prepared from explants of the thoracic aorta of 10 week old male Wistar rats by a modification of the method of Ross (J. Cell Biol., 50: 172, 1971). They were cultured in DMEM containing 10% fetal calf serum, 1% penicillin G and 1% streptomycin at 37° C. in a 95% air, 5% $CO_2$ humidified atmosphere. vSMCs were seeded in 24 well plates and cultured in the presence of 10% fetal calf serum for 3 days. Cell growth then was arrested by transfer to serum free DMEA. After 24 hours, each test compound or vehicle was added to medium for 1 hour, and then cells were stimulated by PDGF (10 ng/ml). After 24 hours of additional incubation, [$^3$H]-thymidine (1 $\mu$Ci/ml) was added during the final 4 hours of incubation time, and trichloracetic acid insoluble radioactivity was assayed by liquid scintillation counting.

For example, the compounds prepared in the present Examples 3, 9, 15, 22-(6), 23, 24-(1), 27-(5), 27-(8), 37-(14), 38-(2), 60, 67-(2), 75-(29) and 75-(30), which were selected as representative compounds of the present invention, had $IC_{50}$ below 100 nM.

Test 4
Vasopressin Induced-vasospasm Model

Male Donryu rats, weighing 160–200 g, were anesthetized intraperitoneally with sodium pentobarbital (60 mg/kg) 15 minutes before intravenous administration of vasopressin, and the femoral vein was cannulated with polyethylene tubing (diameter 0.8 mm). Coronary vasospasm was induced with vasopressin (0.2 iu/kg) dissolved in saline through the cannula in the femoral vein. The each test compound (10 mg/kg) was administered orally 30 minutes before the administration of vasopressin. The standard limb lead II of the electrocardiogram was recorded with an electrocardiograph. The depression of ST segment was measured as the difference in the amplitudes of the ST segment after and just before the administration of vasopressin. The amplitudes of ST segment were measured at intervals of 0.5 minutes for 5 minutes after administration of vasopressin.

For example, the compounds prepared in the present Examples 3, 6, 12, 37-(12), 38-(1), 42 and 43 of the present invention, showed more than 50% inhibiting activity, respectively.

Test 5
Cyclosporin Nephritis Model

Spontaneously hypertensive rats weighing 250–300 g were used. Cyclosporin dissolved in olive-oil containing 5% ethanol was given orally to the animals in a daily dose 50 mg/kg for 2 weeks. After the last dosing of cyclosporin, 24-hours urine was collected for urinalysis. Blood was withdrawn from the abdominal aorta under ether anesthesia 24 hours after the last dosing of cyclosporin, and plasma was separated by centrifugation for biochemical analysis. The animal were bled to death and kidneys were removed for histopathological examination.

The each test compound (3.2 mg/kg) was dissolved in PEG 400 and given orally by the volume of 1 ml/kg twice a day for two weeks.

Biochemistry and urinalysis: Urine volume, plasma creatinine, urine creatinine, blood urea nitrogen, plasma sodium, urine sodium, plasma potassium and urine potassium, were measured with an autoanalyzer (TBA-20R Toshiba, OM-6020 Daiichi Kagaku).

Histopathology: The kidneys were fixed in phosphate-buffered 10% formalin and its paraffin specimens were prepared and these sections were stained with hematoxylin.

The compound (VIII), the compound (IX), and the compounds prepared in the present Examples 3 and 6, which were selected as representative compounds of the present invention, showed more than 50% recovery in a measure of blood urea nitrogen, and more than 40% recovery in a measure of creatinine clearance (ml/kg/min), respectively.

Test 6
FK506 Nephritis Model (a) Spontaneously hypertensive rats weighing 250–300 g were used. FK506 dissolved in olive-oil containing 5% ethanol was given orally to the animals in a daily dose 18 mg/kg for 1 week. After the last dosing of FK506, 24-hours urine was collected for urinalysis. Blood was withdrawn from the abdominal aorta under ether anesthesia 24 hours after the last dosing of FK506, and plasma was separated by centrifugation for biochemical analysis.

The each test compound was dissolved in PEG 400 and given orally by the volume of 1 ml/kg twice a day for two weeks.

Biochemistry and urinalysis: Urine volume, plasma creatinine, urine creatinine, blood urea nitrogen, plasma sodium, urine sodium, plasma potassium and urine potassium, were measured with an autoanalyzer (TBA-20R Toshiba, OM-6020 Daiichi Kagaku).

The compound (VIII) and the compound prepared in Example 6, which was selected as representative compounds of this invention, showed more than 50% recovery in urinary sodium excretion, and more than 45%, recovery in a measure of creatinine clearance (ml/kg/min), respectively.

(b) Prevention of Experimental FK506-induced Nephritis by Cyclic Nucleotide Regulating Drugs FK506 was administered orally to male Sprague-Dawley rats (body weights; 292–329 g) fed with low sodium diet (0.05% Sodium) in a daily dose of 10 mg/kg/day for 14 days. FK506 was provided in a solid dispersion formulation and dissolved in distilled water to a final concentration of 2 mg/ml. Papaverine was dissolved in saline to 5 mg/ml. Dipyridamole (i.v. formulation; 5 mg/ml) was purchased from Dainippon Pharmaceutical Co., Ltd. Papaverine (20 mg/kg) or dipyridamole (20 mg/kg) was administered intramuscularly 30 minutes before FK506 dosing. After the final dosing of FK506, 24-hours urine was collected for urinalysis. Blood was withdrawn from the abdominal aorta under ether anesthesia 24 hours after final dosing of FK506, and plasma was separated for biochemical analysis and plasma renin activity measurements. The kidney was removed from each animal and was fixed with in 10% formalin solution for histological analysis.

Papaverine and dipyridamole significantly improved renofunction of FK506 dosed rats. Both compounds showed more than 50% recovery in a measure of blood urea nitrogen, and more than 50% recovery in a serum creatinine.

Test 7
Diabetic Glomerulosclerosis Model 6 weeks old Male SD rats were treated with streptozotocin (60 mg/kg i.v.) to induce diabetes mellitus. One week after streptozotocin treatment, test compound, 3.2, 10 mg/kg was started to be orally administered twice a day for 16 weeks.

The compound prepared in Example 6, which was selected as representative compound of this invention, retarded the onset of diabetic cataract and improved the parameters reflecting the abnormalities of peripheral circulation (improved the decreased blood flow in ears and raised the decreased skin temperature on foot pad).

Said compound, 10 mg/kg, perfectly recovered the reduced valiance of RR intervals in cardioelectrography, reduced on average by 37% the elimination of protein in urine, and perfectly inhibited the increased 4-hydroxyproline contents in renal cortex.

Test 8
Impotence Model (a) Effect of Test Compound on Nitroprusside or Ach-induced Relaxation in Isolated Rat Corpora Cavernosa Male SD rats were anesthetized with sodium pentobarbital 50 mg/kg intraperitoneally, and the corpora cavernosa was excised. The tunica albuginea was dissected according to the methods described by Italiano et al. (Pharmacological Research, 30, No.4, 1994) and used for in vitro pharmacological study. The erectile tissue strip was placed in a 25 ml organ bath containing Krebs-Ringer solution. The bath was maintained at 37° C. and bubbled with 95% $O_2$ and 5% $CO_2$. The strip was stretched with a resting force of 0.25 g, and isometric contraction were recorded via force development transducer on a recorder.

The strip was equilibrated in the Krebs-Ringer solution for about 60 minutes, and preconstructed by 0.1 mM norepinephrine to ascertain the responsibility of each preparation. The strip was washed several times, and then constricted by 0.1 mM norepinephrine. After getting stable constrictile response to norepinephrine, the first dose-response curve for sodium nitroprusside or Ach was obtained. After washing a few times for 60 minutes, the strip was constricted by norepinephrine again, and the second dose-response curve for sodium nitroprusside or Ach was obtained. The test compound was added 30 minutes before adding norepinephrine. The compound prepared in Example 6, which was selected as representative compound of this invention, at 10–7 M potentiated nitroprusside-induced relaxation of corpora cavernosa, and $ED_{50}$ value of dose-response curve to nitroprusside was about 50 μM.

Said compound at 10–7 M also potentiated Ach-induced relaxation of corpora cavernosa. 100 μM Ach-induced relaxant response to the contractile response induced by 10–4 M norepinephrine was only 11.0% in control preparation, but this relaxant response to Ach increased to 18.7% in the presence of 10–7 M said compound.

(b) Effect of Test Compound on the Relaxation Elicited by Electrical Field Stimulation in rat Corpora Cavernosa.

The rat erectile tissue strip prepared according to the method described by Italiano et al. (Pharmacological Research, 30, No4, 1994) was placed 25 ml organ bath containing Krebs-Ringer solution. The bath was maintained at 37° C. and bubbled with 95% $O_2$ and 5% $CO_2$. The solution also contained atropine (1 μM) and guanethidine (50 μM). The erectile tissue strip was stretched with a resting force of 0.25 g, and isometric contraction were recorded via force development transducer on a recorder. The bipolar platinum electrode connected to the electric stimulator was placed around the strip.

The strip was equilibrated in the Krebs-Ringer solution for about 60 minutes and preconstructed by 0.1 mM norepinephrine to ascertain the responsibility of each preparation. The strip was washed several times, and then constricted by 0.1 mM norepinephrine. After getting stable contractile response to norepinephrine, the first electrical field stimulation (1 to 45 Hz, 20V, 0.5 msec duration, 90 sec interval) was delivered. 30 minutes after adding the tested compound, the second electrical field stimulation was delivered.

The compound prepared in Example 6, which was selected as representative compound of this invention, at 10–7 M potentiated relaxation of corpora cavernosa elicited by electrical field stimulation in rat corpora cavernosa.

Relaxant response elicited by 30 Hz was only 14.3% in control preparation, but this relaxant response increased to 17.1% in the presence of 10–7 M said compound.

(c) Male beagle weighing 8.0–12.0 kg were anesthetized with pentobarbital sodium (35 mg/kg, i.v.). After tracheotomy, the animal was artificially ventilated using a volume-cycled ventilator. The femoral artery was cannulated for continuous blood pressure and heart rate monitoring. The femoral vein was cannulated for maintenance of anesthesia and administration of tested compound. Two laser-dopper probes were placed in the corpus spongiosum penis and corpus cavernosum penis for recording blood flow. After a period of stabilization of all parameters, tested compound was injected intravenously at a various concentration. The administration of the compound prepared in Example 6, which was selected as representative compound of this invention, increased in the blood flow of both corpus spongiosum penis and corpus cavernosum penis without hemodynamic change. The increase in blood flow reached a peak value of 55% of baseline and continued for longer than 15 minutes after the administration of said compound 1.0 mg/kg.

(d) Effect of Tested Compound on Genital Grooming and Penile Erection in Male Mice Eight weeks old male ICR mice were housed under standard conditions of temperature, lighting and water supply before the experiment.

The test compound was dissolved in PEG400. After oral administration of the test compound, each mouse was transferred to an individual cage.

The genital grooming and penile erection were observed for one hour.

The compound prepared in Example 27-(8), which were selected as representative compound of this invention markedly increased the frequencies of genital grooming by average of 266% and lengthened the duration of penile erection by average of 171% (n=10).

Test 9

Toxities of Compound (I)

Test on the toxicity by repetitive oral administration of the compounds prepared in Example 6 and 27-(8), which were selected as representative compound of this invention, in SD rat was conducted and the dead at dose of 32 mg/kg once a day for 14 consecutive days could not be observed.

The following preparations and examples are given for the purpose of illustrating the present invention.

PREPARATION 1

(1) To a solution of 2-amino-4-methoxycarbonylphenyl trifluoromethanesulfonate (2.6 g) in a mixture of pyridine (5.6 ml) and dichloromethane (20 ml) was added benzyl chloroformate (2.08 ml) at 0° C., and the mixture was stirred at 20° C. for 4.5 hours. The mixture was diluted with dichloromethane and washed successively with diluted hydrochloric acid, aqueous sodium bicarbonate and brine. The organic layer was dried over sodium sulfate and evaporated in vacuo. The residue was chromatographed on silica gel eluting with dichloromethane to give 2-benzyloxycarbonylamino-4-methoxycarbonylphenyl trifluoromethanesulfonate (2.61 g) as colorless crystals.

NMR ($CDCl_3$, δ): 3.92 (3H, s), 5.23 (2H, s), 6.89 (1H, br s), 7.3–7.45 (6H, m), 7.83 (1H, dd, J=1, 8 Hz), 8.81 (1H, s)

(2) A mixture of 2-benzyloxycarbonylamino-4-methoxycarbonylphenyl trifluoromethanesulfonate (1.01 g), 1-pentynyl(tributyl)stannane (1.02 g), lithium chloride (0.29 g) and tetrakis(triphenylphosphine)palladium (80 mg) in dioxane (24 ml) was heated at 100° C. for 2 hours. The solvent was evaporated in vacuo and the residue was chromatographed on silica gel eluting with a mixture of hexane and ethyl acetate (4:1) to give methyl 3-benzyloxycarbonylamino-4-(1-pentynyl)benzoate (536 mg) as colorless crystals.

NMR ($CDCl_3$, δ): 1.03 (3H, t, J=7 Hz), 1.67 (2H, m), 2.44 (2H, t, J=7 Hz), 3.87 (3H, s), 5.23 (2H, s), 7.25–7.7 (7H, m), 8.78 (1H, s)

(3) To a solution of methyl 3-benzyloxycarbonylamino-4-(1-pentynyl)benzoate (949 mg) in tetrahydrofuran (24 ml) was added gold(III)sodium chloride (24 mg) under argon atmosphere, and the mixture was heated under reflux for 100 minutes. The solvent was evaporated in vacuo and the residue was chromatographed on silica gel eluting with a mixture of hexane, dichloromethane, and ethyl acetate (6:3:2) to give methyl 1-benzyloxycarbonyl-2-propylindole-6-carboxylate (852 mg) as colorless crystals.

NMR ($CDCl_3$, δ): 0.98 (3H, t, J=7 Hz), 1.71 (2H, m), 2.97 (2H, t, J=7 Hz), 3.90 (3H, s), 5.49 (2H, s), 6.39 (1H, s), 7.3–7.6 (6H, m), 7.91 (1H, dd, J=1, 8 Hz), 8.80 (1H, s)

(4) To a solution of methyl 1-benzyloxycarbonyl-2-propylindole-6-carboxylate (200 mg) in a mixture of methanol and ethyl acetate (1:1, 8 ml) was added 10% palladium on carbon (30 mg), and the mixture was stirred under hydrogen atmosphere for 20 minutes. The catalyst was removed by filtration through celite and washed with methanol. The filtrate was evaporated in vacuo to give methyl 2-propylindole-6-carboxylate (112 mg) as colorless crystals.

NMR (CDCl$_3$, δ): 1.02 (3H, t, J=7 Hz), 1.78 (2H, m), 2.76 (2H, t, J=7 Hz), 3.93 (3H, s), 6.29 (1H, s), 7.51 (1H, d, J=8 Hz), 7.77 (1H, d, J=8 Hz), 8.04 (1H, s), 8.15 (1H, br s)

(5) To a stirring suspension of aluminum chloride (294 mg) and acetyl chloride (0.08 ml) in dichloromethane (10 ml) was added methyl 2-propylindole-6-carboxylate (200 mg), and the mixture was stirred at 20° C. for 1 hour. The resulting mixture was poured onto ice and extracted with ethyl acetate. The combined organic phase was washed with aqueous sodium bicarbonate and brine, then dried over sodium sulfate and evaporated in vacuo. The residue was triturated with isopropyl ether to give methyl 3-acetyl-2-propylindole-6-carboxylate (78 mg) as colorless crystals.

NMR (CDCl$_3$, δ): 1.02 (3H, t, J=7 Hz), 1.81 (2H, m), 2.69 (3H, s), 3.18 (2H, t, J=7 Hz), 3.96 (3H, s), 7.93 (1H, dd, J=1, 8 Hz), 8.01 (1H, d, J=8 Hz), 8.12 (1H, d, J=1 Hz), 8.88 (1H, br s)

PREPARATION 2

Methyl 3-isobutyryl-2-propylindole-6-carboxylate (474 mg) was prepared from methyl 2-propylindole-6-carboxylate (700 mg) and isobutyryl chloride (1.01 ml) in a similar manner to that of Preparation 1 (5).

NMR (CDCl$_3$, δ): 1.04 (3H, t, J=8 Hz), 1.28 (6H, d, J=8 Hz), 1.83 (2H, sextet, J=8 Hz), 3.18 (2H, t, J=8 Hz), 3.52 (2H, septet, J=8 Hz), 3.96 (3H, s), 7.92 (2H, s), 8.16 (1H, s), 9.13 (1H, br s)

PREPARATION 3

Methyl 3-propionyl-2-propylindole-6-carboxylate (298 mg) was prepared from methyl 2-propylindole-6-carboxylate (500 mg) and propionyl chloride (0.40 ml) in a similar manner to that of Preparation 1 (5).

NMR (CDCl$_3$, δ): 1.04 (3H, t, J=8 Hz), 1.29 (3H, t, J=8 Hz), 1.83 (2H, sextet, J=8 Hz), 3.06 (2H, q, J=8 Hz), 3.20 (2H, t, J=8 Hz), 3.96 (3H, s), 7.93 (1H, dd, J=1, 8 Hz), 8.00 (1H, d, J=8 Hz), 8.15 (1H, d, J=1 Hz), 9.22 (1H, s),

PREPARATION 4

(1) Methyl 3-benzyloxycarbonylamino-4-(4-methyl-1-pentynyl)benzoate (2.25 g) was prepared from 2-benzyloxycarbonylamino-4-methoxycarbonylphenyl trifluoromethanesulfonate (3.0 g) and (4-methyl-1-pentynyl)(tributyl)stannane (2.7 g) in a similar manner to that of Preparation 1 (2).

NMR (CDCl$_3$, δ): 1.05 (6H, d, J=8 Hz), 1.88–2.02 (1H, m), 2.40 (2H, d, J=8 Hz), 3.90 (3H, s), 5.25 (2H, s), 7.32–7.45 (6H, m), 7.52 (1H, s), 7.66 (1H, d, J=8 Hz), 8.78 (1H, s)

(2) Methyl 1-benzyloxycarbonyl-2-isobutylindole-6-carboxylate (1.67 g) was prepared from methyl 3-benzyloxycarbonylamino-4-(4-methyl-1-pentynyl)benzoate (2.15 g) in a similar manner to that of Preparation 1 (3).

NMR (CDCl$_3$, δ): 0.90 (6H, d, J=8 Hz), 1.90–2.04 (1H, m), 2.86 (2H, d, J=8 Hz), 3.90 (3H, s), 5.48 (2H, s), 6.38 (1H, s), 7.40–7.56 (6H, m), 7.91 (1H, d, J=8 Hz), 8.82 (1H, s)

(3) Methyl 2-isobutylindole-6-carboxylate (752 mg) was prepared from methyl 1-benzyloxycarbonyl-2-isobutylindole-6-carboxylate (1.5 g) in a similar manner to that of Preparation 1 (4).

NMR (CDCl$_3$, δ): 0.98 (6H, d, J=8 Hz), 1.95–2.08 (1H, m), 2.66 (2H, d, J=8 Hz), 3.92 (3H, s), 6.28 (1H, s), 7.53 (1H, d, J=8 Hz), 7.76 (1H, d, J=8 Hz), 8.08 (1H, s), 8.23 (1H, br s)

(4) Methyl 2-isobutyl-3-isobutyrylindole-6-carboxylate (246 mg) was prepared from methyl 2-isobutylindole-6-carboxylate (300 mg) and isobutyryl chloride (0.41 ml) in a similar manner to that of Preparation 1 (5).

NMR (CDCl$_3$, δ): 0.98 (6H, d, J=8 Hz), 1.27 (1H, d, J=8 Hz), 2.10–2.23 (1H, m), 3.06 (2H, d, J=8 Hz), 3.52 (2H, septet, J=8 Hz), 3.96 (3H, s), 7.92 (2H, s), 8.16 (1H, s), 9.02 (1H, s)

PREPARATION 5

(1) Methyl 3-benzyloxycarbonylamino-4-(1-butynyl)benzoate (646 mg) was prepared from 2-benzyloxycarbonylamino-4-methoxycarbonylphenyl trifluoromethanesulfonate (1.82 g) and 1-butynyl(tributyl)stannane (1.51 g) in a similar manner to that of Preparation 1 (2).

NMR (CDCl$_3$, δ): 1.26 (3H, t, J=7 Hz), 2.50 (2H, q, J=7 Hz), 3.91 (3H, s), 5.24 (2H, s), 7.3–7.5 (7H, m), 7.65 (1H, dd, J=1, 8 Hz), 8.79 (1H, br s)

(2) Methyl 1-benzyloxycarbonyl-2-ethylindole-6-carboxylate (551 mg) was prepared from methyl 3-benzyloxycarbonylamino-4-(1-butynyl)benzoate (640 mg) in a similar manner to that of Preparation 1 (3).

NMR (CDCl$_3$, δ): 1.30 (3H, t, J=7 Hz), 3.05 (2H, q, J=7 Hz), 3.88 (3H, s), 4.98 (2H, s), 6.92 (1H, s), 7.35–7.60 (6H, m), 7.89 (1H, dd, J=1, 8 Hz), 8.79 (1H, s)

(3) Methyl 2-ethylindole-6-carboxylate (306 mg) was prepared from methyl 1-benzyloxycarbonyl-2-ethylindole-6-carboxylate (546 mg) in a similar manner to that of Preparation 1 (4).

NMR (CDCl$_3$, δ): 1.38 (3H, t, J=7 Hz), 2.82 (2H, q, J=7 Hz), 3.91 (3H, s), 6.30 (1H, s), 7.50 (1H, d, J=8 Hz), 7.75 (1H, d, J=8 Hz), 8.03 (1H, s), 8.14 (1H, br s)

(4) Methyl 2-ethyl-3-propionylindole-6-carboxylate (435 mg) was prepared from methyl 2-ethylindole-6-carboxylate (660 mg) and propionyl chloride (0.62 ml) in a similar manner to that of Preparation 1 (5).

NMR (CDCl$_3$, δ): 1.29 (3H, t, J=7 Hz), 1.39 (3H, t, J=7 Hz), 3.06 (2H, t, J=7 Hz), 3.26 (2H, t, J=7 Hz), 3.94 (3H, s), 7.24 (1H, s), 7.92 (1H, d, J=8 Hz), 7.98 (1H, d, J=8 Hz), 8.14 (1H, s), 8.92 (1H, br s)

PREPARATION 6

(1) Methyl 3-isobutyrylindole-6-carboxylate (618 mg) was prepared from methyl indole-6-carboxylate (500 mg) and isobutyryl chloride (0.84 ml) in a similar manner to that of Preparation 1 (5).

NMR (CDCl$_3$, δ): 1.28 (6H, d, J=7 Hz), 3.35 (1H, m), 3.96 (3H, s), 7.93–8.06 (2H, m), 8.19 (1H, s), 8.46 (1H, d, J=8 Hz), 8.96 (1H, br s)

(2) To a solution of methyl 3-isobutyrylindole-6-carboxylate (146 mg) in tetrahydrofuran (5 ml) was added 1M solution of brane-tetrahydrofuran complex in tetrahydrofuran (1.8 ml), and the mixture was stirred at 50° C. for 1 hour. The resulting mixture was evaporated in vacuo, and the residue was quenched with aqueous ammonium chloride and extracted with ethyl acetate. The organic phase was washed with brine, and dried over sodium sulfate. After evaporation of solvent, the residue was chromatographed on silica gel eluting with a mixture of hexane and ethyl acetate (2:1) to give methyl 3-isobutylindole-6-carboxylate (105 mg) as colorless crystals.

NMR (CDCl$_3$, δ): 0.94 (6H, d, J=7 Hz), 1.98 (1H, m), 2.62 (2H, d, J=7 Hz), 3.93 (3H, s), 7.12 (1H, s), 7.61 (1H, d, J=8 Hz), 7.78 (1H, d, J=8 Hz), 8.08 (1H, s), 8.16 (1H, br s)

(3) Methyl 2-acetyl-3-isobutylindole-6-carboxylate (43 mg) was prepared from methyl 3-isobutylindole-6-carboxylate (99 mg) and acetyl chloride (0.073 ml) in a similar manner to that of Preparation 1 (5).

NMR (CDCl$_3$, δ): 1.01 (6H, d, J=7 Hz), 2.02 (1H, m), 2.69 (3H, s), 2.98 (2H, d, J=7 Hz), 3.96 (3H, s), 7.73 (1H, d, J=8 Hz), 7.79 (1H, d, J=8 Hz), 8.11 (1H, s), 9.09 (1H, br s)

PREPARATION 7

(1) Methyl 3-acetylindole-6-carboxylate (470 mg) was prepared from methyl indole-6-carboxylate (655 mg) and acetyl chloride (0.27 ml) in a similar manner to that of Preparation 1 (5).

NMR (DMSO-d$_6$, δ): 2.46 (3H, s), 3.88 (3H, s), 7.79 (1H, d, J=8 Hz), 8.10 (1H, s), 8.24 (1H, d, J=8 Hz), 8.52 (1H, s)

(2) Methyl 3-ethylindole-6-carboxylate (327 mg) was prepared from methyl 3-acetylindole-6-carboxylate (470 mg) in a similar manner to that of Preparation 6 (2).

NMR (CDCl$_3$, δ): 1.33 (3H, t, J=7 Hz), 2.78 (2H, q, J=7 Hz), 3.93 (3H, s), 7.15 (1H, s), 7.63 (1H, d, J=8 Hz), 7.79 (1H, d, J=8 Hz), 8.12 (1H, s), 8.14 (1H, br s)

(3) Methyl 3-ethyl-2-propionylindole-6-carboxylate (65.7 mg) was prepared from methyl 3-ethylindole-6-carboxylate (184 mg) and propionyl chloride (0.17 ml) in a similar manner to that of Preparation 1 (5).

NMR (CDCl$_3$, δ): 1.29 (3H, t, J=7 Hz), 1.34 (3H, t, J=7 Hz), 3.03 (2H, q, J=7 Hz), 3.14 (2H, q, J=7 Hz), 3.94 (3H, s), 7.73 (1H, d, J=8 Hz), 7.79 (1H, d, J=8 Hz), 8.13 (1H, s), 9.10 (1H, br s)

PREPARATION 8

(1) 3-Isobutyryl-2-propylindole-6-carboxylic acid (853 mg) was prepared from methyl 3-isobutyryl-2-propylindole-6-carboxylate (935 mg) in a similar manner to that of Example 2.

NMR (DMSO-d$_6$, δ): 0.95 (3H, t, J=8 Hz), 1.14 (6H, d, J=8 Hz), 1.72 (2H, sextet, J=8 Hz), 3.08 (2H, t, J=8 Hz), 3.46 (1H, septet, J=8 Hz), 7.76 (1H, d, J=9 Hz), 7.92 (1H, dd, J=1, 9 Hz), 8.00 (1H, d, J=1 Hz)

(2) 3-Isobutyryl-2-propylindole-6-carboxamide (853 mg) was prepared from 3-isobutyryl-2-propylindole-6-carboxylic acid (935 mg) in a similar manner to that of Example 6.

NMR (DMSO-d$_6$, δ): 0.95 (3H, t, J=8 Hz), 1.15 (6H, d, J=8 Hz), 1.70 (2H, sextet, J=8 Hz), 3.07 (2H, t, J=8 Hz), 3.46 (1H, septet, J=8 Hz), 7.26 (1H, br s), 7.72 (1H, d, J=9 Hz), 7.87 (1H, dd, J=1, 9 Hz), 7.94 (1H, d, J=1 Hz)

PREPARATION 9

Methyl 3-benzoyl-2-propylindole-6-carboxylate (289 mg) was prepared from methyl 2-propylindole-6-carboxylate (500 mg) and benzoyl chloride (970 mg) in a similar manner to that of Preparation 1 (5).

NMR (CDCl$_3$, δ): 0.82 (3H, t, J=8 Hz), 1.66 (2H, sextet, J=8 Hz), 2.78 (2H, t, J=8 Hz), 3.85 (3H, s), 7.29 (1H, d, J=8 Hz), 7.49–7.54 (2H, m), 7.60–7.64 (4H, m), 8.02 (1H, s)

PREPARATION 10

To a stirred solution of methyl 2-propylindole-6-carboxylate (911 mg) in acetonitrile (15 ml) was added chlorosulfonylisocyanate (0.6 g) in acetonitrile (1.5 ml) at 0° C. The mixture was stirred at 0° C. for 30 minutes, then N,N-dimethylformamide (0.35 g) in acetonitrile (15 ml) was added at 0° C. The resultant mixture was stirred at 20° C. for 40 minutes, and then poured into water. The mixture was extracted with methylene chloride three times, and the combined organic phase was dried over sodium sulfate and evaporated in vacuo. The residue was chromatographed on silica gel eluting with a mixture of ethyl acetate and hexane (1:3) to give the crystals which were recrystallized from a mixture of ethyl acetate and hexane to give methyl 3-cyano-2-propylindole-6-carboxylate (535 mg) as colorless crystals.

mp: 148.5–150° C.

IR (KBr): 3251, 2218, 1710, 1284, 1218 cm$^{-1}$

NMR (CDCl$_3$, δ): 1.07 (3H, t, J=7 Hz), 1.89 (2H, sextet, J=7 Hz), 3.00 (2H, t, J=7 Hz), 3.99 (3H, s), 7.70 (1H, d, J=7.5 Hz), 7.95 (1H, d, J=7.5 Hz), 8.19 (1H, s), 9.05 (1H, br s)

MASS (m/z): 243 (M$^+$+1), 76 (bp)

PREPARATION 11

Methyl 3-acetyl-2-ethylindole-6-carboxylate (106 mg) was prepared from methyl 2-ethylindole-6-carboxylate (237 mg) and acetyl chloride (0.19 ml) in a similar manner to that of Preparation 1 (5).

NMR (CDCl$_3$, δ): 1.42 (3H, t, J=7 Hz), 2.69 (3H, s), 3.27 (2H, q, J=7 Hz), 3.96 (3H, s), 7.93 (1H, d, J=8 Hz), 8.01 (1H, d, J=8 Hz), 8.12 (1H, s), 8.93 (1H, br s)

PREPARATION 12

Methyl 2-ethyl-3-isobutyrylindole-6-carboxylate (200 mg) was prepared from methyl 2-ethylindole-6-carboxylate (317 mg) and isobutyryl chloride 0.36 ml) in a similar manner to that of Preparation 1 (5).

NMR (CDCl$_3$, δ) 1.28 (6H, d, J=7 Hz), 1.38 (3H, t, J=7 Hz), 3.25 (2H, q, J=7 Hz), 3.51 (1H, m), 3.94 (3H, s), 7.92 (2H, s), 8.13 (1H, s), 8.92 (1H, br s)

PREPARATION 13

(1) Methyl 3-benzyloxycarbonylamino-4-(1-propynyl) benzoate (1.34 g) was prepared from 2-benzyloxycarbonylamino-4-methoxycarbonylphenyl trifluoromethanesulfonate (2.1 g) and tributyl(1-propynyl)stannane (2.49 g) in a similar manner to that of Preparation 1 (2).

NMR (CDCl$_3$, δ): 2.14 (3H, s), 3.91 (3H, s), 5.24 (2H, s), 7.35–7.50 (6H, m), 7.65 (1H, d, J=8 Hz), 8.82 (1H, s)

(2) Methyl 1-benzyloxycarbonyl-2-methylindole-6-carboxylate (1.2 g) was prepared from methyl 3-benzyloxycarbonylamino-4-(1-propynyl)benzoate (1.32 g) in a similar manner to that of Preparation 1 (3).

NMR (CDCl$_3$, δ): 2.63 (3H, s), 3.89 (3H, s), 5.50 (2H, s), 6.38 (1H, s), 7.35–7.56 (6H, m), 7.91 (1H, d, J=8 Hz), 8.81 (1H, s)

(3) Methyl 2-methylindole-6-carboxylate (562 mg) was prepared from methyl 1-benzyloxycarbonyl-2- methylindole-6-carboxylate (1.18 g) in a similar manner to that of Preparation 1 (4).

NMR (CDCl$_3$, δ) 2.49 (3H, s), 3.92 (3H, s), 6.28 (1H, s), 7.51 (1H, d, J=8 Hz), 7.77 (1H, d, J=8 Hz), 8.03 (1H, s), 8.12 (1H, br s)

(4) Methyl 3-isobutyryl-2-methylindole-6-carboxylate (142 mg) was prepared from methyl 2-methylindole-6-carboxylate (305 mg) and isobutyryl chloride (0.47 ml) in a similar manner to that of Preparation 1 (5).

NMR (CDCl$_3$, δ) 1.26 (6H, d, J=7 Hz), 2.81 (3H, s), 3.47 (1H, m), 3.93 (3H, s), 7.92 (1H, d, J=8 Hz), 8.09 (1H, s), 8.85 (1H, br s)

PREPARATION 14

(1) Methyl 3-benzyloxycarbonylamino-4-(3-methoxy-1-propynyl)benzoate (4.23 g) was prepared from 2-benzyloxycarbonylamino-4-methoxycarbonylphenyl trifluoromethanesulfonate (7.73 g) and (3-methoxy-1-propynyl)tributylstannane (6.67 g) in a similar manner to that of Preparation 1 (2).

NMR (CDCl$_3$, δ): 3.44 (3H, s), 3.91 (3H, s), 4.38 (2H, s), 5.23 (2H, s), 7.3–7.5 (7H, m), 7.69 (1H, d, J=8 Hz), 8.82 (1H, s)

(2) Methyl 1-benzyloxycarbonyl,-2-methoxymethylindole-6-carboxylate (2.14 g) was prepared from methyl 3-benzyloxycarbonylamino-4-(3-methoxy-1-propynyl)benzoate (4.23 g) in a similar manner to that of Preparation 1 (3).

NMR (CDCl$_3$, δ): 3.44 (3H, s), 3.88 (3H, s), 4.80 (2H, s), 5.49 (2H, s), 6.70 (1H, s), 7.38–7.58 (6H, m), 7.92 (1H, d, J=8 Hz), 8.80 (1H, s)

(3) Methyl 2-methoxymethylindole-6-carboxylate (0.42 g) was prepared from methyl 1-benzyloxycarbonyl-2-methoxymethylindole-6-carboxylate (2.12 g) in a similar manner to that of Preparation 1 (4).

NMR (CDCl$_3$, δ): 3.41 (3H, s), 3.94 (3H, s), 4.64 (2H, s), 6.47 (1H, s), 7.59 (1H, d, J=8 Hz), 7.80 (1H, d, J=8 Hz), 8.11 (1H, s), 8.59 (1H, br s)

(4) Methyl 3-isobutyryl-2-methoxymethylindole-6-carboxylate (146 mg) was prepared from methyl 2-methoxymethylindole-6-carboxylate (396 mg) and isobutyryl chloride (0.53 ml) in a similar manner to that of Preparation 1 (5).

NMR (CDCl$_3$, δ): 1.26 (6H, d, J=7 Hz), 3.48 (1H, m), 3.58 (3H, s), 3.94 (3H, s), 5.03 (2H, s), 7.88 (1H, d, J=8 Hz), 7.96 (1H, d, J=8 Hz), 8.18 (1H, s), 9.45 (1H, br s)

PREPARATION 15

(1) To a solution of methyl 2-propylindole-6-carboxylate (300 mg) in dichloromethane (10 ml) was added a 1M solution of tin(IV) chloride in dichloromethane (2.76ml) at 20° C. The mixture was stirred at 20° C. for 30 minutes, then methoxyacetyl chloride (0.25 ml) was added. After stirred at 20° C. for 30 minutes, the mixture was partitioned between ethyl acetate and water. The organic layer was washed with water and brine, dried over magnesium sulfate, and evaporated in vacuo. The residue was chromatographed on silica gel eluting with a mixture of ethyl acetate and hexane (1:10–1:1) to give methyl 3-methoxyacetyl-2-propylindole-6-carboxylate (135 mg) as pale yellow crystals.

mp: 127–129° C.

NMR (CDCl$_3$, δ): 1.05 (3H, t, J=8 Hz), 1.83 (2H, sextet, J=8 Hz), 302 (2H, t, J=8 Hz), 3.57 (3H, s), 3.97 (3H, s), 4.72 (2H, s), 7.83 (1H, d, J=8 Hz), 7.95 (1H, d, J=8 Hz), 8.18 (1H, s), 9.38 (1H, br s)

(2) 3-Methoxyacetyl-2-propylindole-6-carboxylic acid (108 mg) was prepared from methyl 3-methoxyacetyl-2-propylindole-6-carboxylate (120 mg) in a similar manner to that of Example 2.

mp: >250° C.

NMR (DMSO-d$_6$, δ) 0.97 (3H, t, J=8 Hz), 1.74 (2H, sextet, J=8 Hz), 3.09 (2H, t, J=8 Hz), 3.38 (3H, s), 4.61 (2H, s), 7.75 (1H, d, J=8 Hz), 7.91 (1H, d, J=8 Hz), 8.00 (1H, s)

(3) 3Methoxyacetyl-2propylindole-6-carboxamide (89 mg) was prepared from 3-methoxyacetyl-2-propylindole-6-carboxylic acid (95 mg) in a similar manner to that of Example 6.

mp: 165–167° C.

NMR (DMSO-d$_6$, δ): 0.95 (3H, t, J=8 Hz), 1.74 (2H, sextet, J=8 Hz), 3.06 (2H, t, J=8 Hz), 3.38 (3H, s), 4.60 (2H, s), 7.25 (1H, br s), 7.70 (1H, d, J=8 Hz), 7.84 (1H, d, J=8 Hz), 7.94 (1H, s), 7.97 (1H, br s)

PREPARATION 16

To a solution of methyl 2-amino-3-hydroxybenzoate (882 mg) in pyridine (2 ml) was added acetic anhydride (1.2 ml) and the mixture was stirred at 20° C. for 18 hours. The reaction mixture was diluted with diisopropyl ether, and the resulting solid was collected and washed with diisopropyl ether. The solid was triturated with diisopropyl ether to give methyl 2-acetamido-3-acetoxybenzoate (1.25 g) as solid.

NMR (CDCl$_3$, δ): 2.18 (3H, s), 2.26 (3H, s), 3.90 (3H, s), 7.27 (1H, t, J=8 Hz), 7.39 (1H, d, J=8 Hz), 7.83 (1H, d, J=8 Hz), 9.09 (1H, br s)

PREPARATION 17

The following compounds described in (1) to (4) were prepared in a similar manner to that of Preparation 16.

(1) Methyl 3-acetamido-4-acetoxybenzoate

NMR (CDCl$_3$, δ): 2.21 (3H, s), 2.37 (3H, s), 3.93 (3H, s), 7.22 (1H, d, J=8 Hz), 7.83 (1H, d, J=8 Hz), 8.22 (1H, s)

(2) Methyl 4-acetamido-3-acetoxybenzoate

NMR (DMSO-d$_6$, δ): 212 (3H, s), 2.33 (3H, s), 3.84 (3H, s), 7.73 (1H, d, J=2 Hz), 7.82 (1H, dd, J=2, 8 Hz), 8.22 (1H, d, J=8 Hz), 9.64 (1H, s)

(3) Methyl 3-acetamido-2-acetoxybenzoate

NMR (CDCl$_3$, δ) 2.20 (3H, s), 2.43 (3H, s), 3.91 (3H, s), 7.29 (1H, t, J=8 Hz), 7.74 (1H, d, J=8 Hz), 8.51 (1H, d, J=8 Hz)

(4) Methyl 3-acetamido-4trifluoromethanesulfonyloxyphenylacetate mp: 68.5–70° C.

IR (KBr): 3341, 1727, 1699, 1437, 1425 cm$^{-1}$

NMR (CDCl$_3$, δ): 2.24 (3H, s), 3.68 (3H, s), 3.73 (3H, s), 7.11 (1H, dd, J=8, 1 Hz), 7.24–7.30 (2H, m), 8.19 (1H, s)

MASS (m/z): 354 (M$^+$–1), 149 (bp)

PREPARATION 18

To a solution of methyl 2-acetamido-3-acetoxybenzoate (1.72 g) in methanol (9 ml) was added powdered potassium carbonate (1.4 g), and the mixture was stirred for 20 minutes. The resulting solid was removed by filtration and washed with methanol. The filtrate was evaporated in vacuo, and the residue was acidified with 1N hydrochloric acid and extracted with ethyl acetate. The organic phase was washed with brine, dried over sodium sulfate and evaporated in vacuo. The residue was triturated with a mixture of isopropyl ether and hexane to give methyl 2-acetamido-3-hydroxybenzoate (1.21 g) as solid.

NMR (CDCl$_3$, δ): 2.33 (3H, s), 3.93 (3H, s), 7.14 (1H, t, J=8 Hz), 7.23 (1H, d, J=8 Hz), 7.61 (1H, d, J=8 Hz), 9.88 (1H, s)

PREPARATION 19

The following compounds described in (1) to (3) were prepared in a similar manner to that of Preparation 18.

(1) Methyl 3-acetamido-4-hydroxybenzoate

NMR (DMSO-$d_6$, δ): 2.11 (3H, s), 3.80 (3H, s), 6.93 (1H, d, J=8 Hz), 7.56 (1H, d, J=2 Hz), 8.47 (1H, s), 9.20 (1H, s)

(2) Methyl 4-acetamido-3-hydroxybenzoate

NMR (DMSO-$d_6$, δ): 2.14 (3H, s), 3.78 (3H, s), 7.37 (1H, dd, J=2, 8 Hz), 7.45 (1H, d, J=2 Hz), 8.08 (1H, d, J=8 Hz), 9.32 (1H, s)

(3) Methyl 3-acetamido-2-hydroxybenzoate

NMR (CDCl$_3$, δ): 2.33 (3H, s), 4.97 (3H, s), 6.90 (1H, t, J=8 Hz), 7.56 (1H, d, J=8 Hz), 7.81 (1H, br s), 8.57 (1H, d, J=8 Hz)

PREPARATION 20

To a solution or methyl 2-acetamido-3-hydroxybenzoate (1.2 g) in a mixture of pyridine (1.4 ml) and dichloromethane (2 ml) was added slowly trifluoromethanesulfonic anhydride (1.1 ml) at 0° C. When addition was completed, the mixture was stirred at 20° C. for 20 minutes. The resulting mixture was poured into ice and extracted with ethyl acetate. The organic phase was washed with 1N hydrochloric acid, aqueous sodium bicarbonate and brine, dried over sodium sulfate and evaporated in vacuo. The residue was triturated with a mixture of dichloromethane and hexane to give methyl 2-acetamido-3-trifluoromethanesulfonyloxybenzoate (1.78 g) as solid.

NMR (CDCl$_3$, δ) 2.24 (3H, s), 3.93 (3H, s), 7.34 (1H, t, J=8 Hz), 7.49 (1H, d, J=8 Hz), 7.99 (1H, d, J=8 Hz), 8.90 (1H, br s)

PREPARATION 21

The following compounds described in (1) to (4) were prepared in a similar manner to that of Preparation 20.

(1) Methyl 3-acetamido-4-trifluoromethanesulfonyloxybenzoate

NMR (CDCl$_3$, δ): 2.25 (3H, s), 3.93 (3H, s), 7.37 (1H, d, J=8 Hz), 7.92 (1H, m), 8.86 (1H, br s)

(2) Methyl 4-acetamido-3-trifluoromethanesulfonyloxybenzoate

NMR (CDCl$_3$, δ) 2.27 (3H, s), 3.94 (3H, s), 7.51 (1H, br s), 7.94 (1H, d, J=2 Hz), 8.05 (1H, dd, J=2, 8 Hz), 8.47 (1H, d, J=8 Hz)

(3) Methyl 3-acetamido-2-trifluoromethanesulfonyloxybenzoate

NMR (CDCl$_3$, δ): 2.23 (3H, s), 3.93 (3H, s), 7.40 (1H, br s), 7.43 (1H, t, J=8 Hz), 7.76 (1H, d, J=8 Hz), 8.39 (1H, d, J=8 Hz)

(4) Methyl 3-nitro-4-trifluoromethanesulfonyloxyphenylacetate mp: 44–45° C.

IR (KBr): 1736, 1544, 1434, 1340 cm$^{-1}$

NMR (CDCl$_3$, δ) 3.75 (2H, s), 3.76 (3H, s), 7.41 (1H, d, J=8 Hz), 7.68 (1H, dd, J=8, 1 Hz), 8.10 (1H, d, J=1 Hz)

MASS (m/z): 343 (M$^+$), 135 (bp)

PREPARATION 22

The following compounds described in (1) to (3) were prepared from a similar manner to that of Preparation 1 (2).

(1) Methyl 2-acetamido-3-(1-pentynyl)benzoate

NMR (CDCl$_3$, δ): 1.06 (3H, t, J=7 Hz), 1.64 (2H, m), 2.20 (3H, s), 2.43 (2H, t, J=7 Hz), 3.88 (3H, s), 7.16 (1H, t, J=8 Hz), 7.57 (1H, d, J=8 Hz), 7.76 (1H, d, J=8 Hz), 8.42 (1H, br s)

(2) Methyl 4-acetamido-3-(1-pentynyl)benzoate

NMR (CDCl$_3$, δ): 1.11 (3H, t, J=8 Hz), 1.68 (2H, sextet, J=8 Hz), 2.24 (3H, s), 2.52 (2H, t, J=8 Hz), 3.89 (3H, s), 7.94 (1H, dd, J=1, 8 Hz), 8.07 (1H, d, J=1 Hz), 8.12 (1H, br s), 8.48 (1H, d, J=8 Hz)

(3) Methyl 3-acetamido-2-(1-pentynyl)benzoate

NMR (CDCl$_3$, δ): 1.12 (3H, t, J=7 Hz), 1.73 (2H, m), 2.22 (3H, s), 2.59 (2H, t, J=7 Hz), 3.91 (3H, s), 7.32 (1H, t, J=8 Hz), 7.63 (1H, d, J=8 Hz), 8.29 (1H, br s), 8.62 (1H, d, J=8 Hz)

PREPARATION 23

A mixture of methyl 3-acetamido-4-trifluoromethanesulfonyloxybenzoate (1.43 g), methyl 5-hexynoate (582 mg), palladium(II) chloride (14.9 mg), triphenylphosphine (43.8 mg) and copper(I) chloride (32 mg) in diethylamine (18 ml) was stirred at 20° C. for 14 hours. The solvent was evaporated in vacuo an the residue was chromatographed on silica gel eluting with a mixture of hexane and ethyl acetate (1:2) to give methyl 3-acetamido-4-(5-methoxycarbonyl-1-pentynyl)benzoate (1.15 g) as colorless crystals.

NMR (CDCl$_3$, δ): 2.02 (2H, m), 2.27 (3H, s), 2.53 (2H, t, J=7 Hz), 2.63 (2H, t, J=7 Hz), 3.68 (3H, s), 3.90 (3H, s), 7.41 (1H, d, J=8 Hz), 7.70 (1H, d, J=8 Hz), 8.00 (1H, br s), 8.98 (1H, br s)

PREPARATION 24

The following compounds described in (1) to (3) were prepared in a similar manner to that of Preparation 23.

(1) Methyl 3-acetamido-4-(1-pentynyl)benzoate

NMR (CDCl$_3$, δ): 1.12 (3H, t, J=7 Hz), 1.65 (2H, m), 2.23 (3H, s), 2.54 (2H, t, J=7 Hz), 3.90 (3H, s), 7.43 (1H, dd, J=1, 8 Hz), 7.70 (1H, m), 7.95 (1H, br s), 8.98 (1H, br s)

(2) Methyl 3-acetamido-4-(4-methoxycarbonyl-1-butynyl)benzoate

NMR (CDCl$_3$, δ): 2.32 (3H, s), 2.68 (2H, m), 2.80 (2H, m), 3.73 (3H, s), 3.89 (3H, s), 7.38 (1H, d, J=8 Hz), 7.67 (1H, m), 8.28 (1H, br s), 9.04 (1H, br s)

(3) Methyl 3-acetamido-4-(1-pentynyl)phenylacetate mp: 77–78° C.

IR (KBr): 3293, 1739, 1699, 1665, 1428 cm$^{-1}$

NMR (CDCl$_3$, δ): 1.09 (3H, t, J=7 Hz), 1.69 (2H, sextet, J=7 Hz), 2.22 (3H, s), 2.49 (2H, t, J=7 Hz), 3.64 (2H, s), 3.70 (3H, s), 6.94 (1H, d, J=7.5 Hz), 7.31 (1H, d, J=7.5 Hz), 7.93 (1H, br s), 8.33 (1H, s)

MASS (m/z): 274 (M$^+$+1, bp)

PREPARATION 25

The following compounds described in (1) to (7) were prepared in a similar manner to that of Preparation 1 (3).

(1) Methyl 1-acetyl-2-(3-methoxycarbonylpropyl)indole-6-carboxylate

NMR (CDCl$_3$, δ): 2.08 (2H, m), 2.43 (2H, t, J=7 Hz), 2.86 (3H, s), 3.12 (2H, t, J=7 Hz), 3.67 (3H, s), 3.94 (3H, s), 6.49 (1H, s), 7.52 (1H, d, J=8 Hz), 7.93 (1H, d, J=8 Hz), 8.47 (1H, s)

(2) Methyl 1-acetyl-2-propylindole-7-carboxylate

NMR (CDCl$_3$, δ): 1.04 (3H, t, J=7 Hz), 1.78 (2H, m), 2.39 (3H, s), 2.79 (2H, m), 3.91 (3H, s), 6.38 (1H, m), 7.23 (1H, t, J=8 Hz), 7.68 (1H, d, J=8 Hz), 7.79 (1H, d, J=8 Hz)

(3), Methyl 1-acetyl-2-propylindole-6-carboxylate

NMR (CDCl$_3$, δ): 1.06 (3H, t, J=7 Hz), 1.77 (2H, m), 2.82 (3H, s), 3.03 (2H, t, J=8 Hz), 3.94 (3H, s), 6.47 (1H, s), 7.49 (1H, d, J=8 Hz), 7.94 (1H, d, J=8 Hz), 8.53 (1H, s)

(4) Methyl 1-acetyl-2-propylindole-5-carboxylate

NMR (CDCl$_3$, δ): 1.05 (3H, t, J=8 Hz), 1.75 (2H, sextet, J=8 Hz), 2.76 (3H, s), 2.98 (2H, t, J=8 Hz), 3.94 (3H, s), 6.48 (1H, d, J=1 Hz), 7.87 (1H, d, J=8 Hz), 7.95 (1H, d, J=8 Hz), 8.18 (1H, s)

(5) Methyl 1-acetyl-2-propylindole-4-carboxylate

NMR (CDCl$_3$, δ): 1.07 (3H, t, J=7 Hz), 1.80 (2H, m), 2.76 (3H, s), 3.01 (2H, t, J=7 Hz), 3.97 (3H, s), 7.18 (1H, s), 7.28 (1H, t, J=8 Hz), 8.06(1H, d, J=8 Hz), 8.15 (1H, d, J=8 Hz)

(6) Methyl 1-acetyl-2-(2-methoxycarbonylethyl)indole-6-carboxylate

NMR (CDCl$_3$, δ): 2.78 (2H, t, J=7 Hz), 2.87 (3H, s), 3.39 (2H, t, J=7 Hz), 3.68 (3H, s) 3.94 (3H, s), 6.49 (1H, s), 7.52 (1H, d, J=8 Hz), 7.93 (1H, d, J=8 Hz), 8.46 (1H, s)

(7) Methyl 1-acetyl-2-propylindol-6-ylacetate mp: 85–87° C.

IR (KBr): 1736, 1700, 1376, 1320, 1303 cm$^{-1}$

NMR (CDCl$_3$, δ): 1.04 (3H, t, J=7 Hz), 1.74 (2H, sextet, J=7 Hz), 2.75 (3H, s), 2.96 (2H, t, J=7 Hz), 3.70 (2H, s), 3.75 (3H, s), 6.40 (1H, s), 7.14 (1H, d, J=8 Hz), 7.43 (1H, d, J=8 Hz), 7.81 (1H, s)

MASS (m/z): 274 (M$^+$+1), 74 (bp)

PREPARATION 26

To a solution of methyl 1-acetyl-2-(3-methoxycarbonylpropyl)indole-6-carboxylate (2.34 g) in methanol (20 ml) was added powdered potassium carbonate (1.04 g), and the mixture was stirred under reflux for 10 minutes. The resulting mixture was evaporated in vacuo and the residue was acidified with 1N hydrochloric acid and extracted with chloroform. The organic phase was washed with aqueous sodium bicarbonate and brine, dried over sodium sulfate and then evaporated in vacuo. The residue was triturated with ether to give methyl 2-(3-methoxycarbonylpropyl)indole-6-carboxylate (1.23 g) as solid.

NMR (CDCl$_3$, δ): 2.07 (2H, m), 2.42 (2H, t, J=7 Hz), 2.84 (2H, t, J=7 Hz), 3.68 (3H, s), 3.92 (3H, s), 6.31 (1H, s), 7.52 (1H, d, J=8 Hz), 7.78 (1H, d, J=8 Hz), 8.07 (1H, s), 8.39 (1H, br s)

PREPARATION 27

The following compounds described in (1) to (5) were prepared in a similar manner to that of Preparation 26.

(1) Methyl 2-propylindole-7-carboxylate

NMR (CDCl$_3$, δ): 1.02 (3H, t, J=7 Hz), 1.78 (2H, m), 2.78 (2H, t, J=7 Hz), 3.98 (3H, s), 6.28 (1H, m), 7.09 (1H, t, J=8 Hz), 7.72 (1H, d, J=8 Hz), 7.79 (1H, d, J=8 Hz), 9.58 (1H, br s)

(2) Methyl 2-propylindole-6-carboxylate (3) Methyl 2-propylindole-5-carboxylate

NMR (CDCl$_3$, δ): 1.02 (3H, t, J=8 Hz), 1.76 (2H, sextet, J=8 Hz), 2.74 (2H, t, J=8 Hz), 3.92 (3H, s), 6.33 (1H, d, J=1 Hz), 7.28 (1H, d, J=8 Hz), 7.73 (1H, d, J=8 Hz), 8.10 (1H, br s), 8.28 (1H, s)

(4) Methyl 2-propylindole-4-carboxylate

NMR (CDCl$_3$, δ): 1.03 (3H, t, J=7 Hz), 1.80 (2H, m), 2.78 (2H, m), 3.98 (3H, s), 6.89 (1H, s), 7.14 (1H, t, J=8 Hz), 7.48 (1H, d, J=8 Hz), 7.84 (1H, d, J=8 Hz), 8.08 (1H, br s)

(5) Methyl-2-(2-methoxycarbonylethyl)indole-6-carboxylate

NMR (CDCl$_3$, δ): 2.78 (2H, m) 3.10 (2H, m), 3.73 (3H, s), 3.93 (3H, s), 6.30 (1H, s), 7.53 (1H, d, J=8 Hz), 7.76 (1H, d, J=8 Hz), 8.08 (1H, s), 8.88 (1H, br s)

PREPARATION 28

The following compounds described in (1) to (19) were prepared in a similar manner to that of Preparation 1 (5).

(1) Methyl 3-isobutyryl-2-propylindole-7-carboxylate

NMR (CDCl$_3$, δ): 1.04 (3H, t, J=7 Hz), 1.27 (6H, d, J=7 Hz), 1.82 (2H, m), 3.26 (2H, m), 3.47 (1H, m), 3.99 (3H, s), 7.28 (1H, t, J=8 Hz), 7.85 (1H, d, J=8 Hz), 8.18 (1H, s)

(2) Methyl 3-isobutyryl-2-propylindole-5-carboxylate

NMR (CDCl$_3$, δ): 1.04 (3H, t, J=8 Hz), 1.28 (6H, d, J=8 Hz), 1.78 (2H, sextet, J=8 Hz), 3.15 (2H, t, J=8 Hz), 3.56 (1H, septet, J=8 Hz), 3.96 (3H, s), 7.37 (1H, d, J=1 Hz), 7.93 (1H, dd, J=1, 8 Hz), 8.66 (1H, d, J=8 Hz), 8.75 (1H, br s)

(3) Methyl 3-(3-methoxycarbonylpronanoyl)indole-6-carboxylate

NMR (DMSO-d$_6$, δ): 2.65 (2H, t, J=7 Hz), 3.22 (2H, t, J=7 Hz), 3.59 (3H, s), 3.87 (3H, s), 7.80 (1H, d, J=8 Hz), 8.10 (1H, s), 8.23 (1H, d, J=8 Hz), 8.59 (1H, s)

(4) Methyl 3-acetyl-2-methylindole-6-carboxylate

NMR (CDCl$_3$, δ): 2.54 (3H, s), 2.73 (3H, s), 3.86 (3H, s), 7.76 (1H, d, J=8 Hz), 7.97 (1H, s), 8.12 (1H, d, J=8 Hz)

(5) Methyl 2-methyl-3-propionylindole-6-carboxylate

NMR (CDCl$_3$, δ): 1.12 (3H, t, J=7 Hz), 2.72 (3H, s), 2.92 (2H, q, J=7 Hz), 3.86 (3H, s), 7.75 (1H, d, J=8 Hz), 7.96 (1H, s), 8.11 (1H, d, J=8 Hz)

(6) Methyl 3-(3,3-dimethylbutanoyl)indole-6-carboxylate

NMR (CDCl$_3$, δ): 1.11 (9H, m), 2.33 (2H, s), 3.94 (3H, s), 7.92–8.0 (2H, m), 8.19 (1H, s), 8.52 (1H, d, J=8 Hz), 8.90 (1H, br s)

(7) Ethyl 3-isobutyryl-2-propylindol-6-ylacetate

IR (Neat): 3300, 1740, 1625 cm$^{-1}$

NMR (CDCl$_3$, δ): 1.04 (3H, t, J=7 Hz), 1.25 (6H, d, J=7 Hz), 1.26 (3H, t, J=7 Hz), 1.77 (2H, sextet, J=7 Hz), 3.12 (2H, t, J=7 Hz), 3.41–3.55 (1H, m), 3.72 (2H, s), 4.16 (2H, q, J=7 Hz), 7.17 (1H, d, J=7.5 Hz), 7.30 (1H, s), 7.82 (1H, d, J=7.5 Hz), 8.40 (1H, br s)

MASS (m/z): 316 (M$^+$+1), 74 (bp)

(8) Methyl 3-isobutyryl-2-propylindol-6-ylacetate

IR (Neat): 3290, 1730, 1625 cm$^{-1}$

NMR (CDCl$_3$, δ): 1.03 (3H, t, J=7 Hz), 1.26 (6H, d, J=7 Hz), 1.76 (2H, sextet, J=7 Hz), 3.12 (2H, t, J=7 Hz), 3.41–3.54 (1H, m), 3.71 (2H, s), 3.75 (3H, s), 7.16 (1H, d, J=7.5 Hz), 7.30 (1H, s), 7.83 (1H, d, J=7.5 Hz), 8.40 (1H, br s)

MASS (m/z): 302 (M$^+$+1, bp)

(9) Methyl 2-acetyl-3-methylindole-6-carboxylate

NMR (CDCl$_3$, δ): 2.66 (3H, s), 2.67 (3H, s), 3.94 (3H, s), 7.72 (1H, d, J=8 Hz), 7.81 (1H, d, J=8 Hz), 8.11 (1H, s), 9.09 (1H, br s)

(10) Methyl 3-propionylindole-6-carboxylate

NMR (CDCl$_3$, δ): 1.12 (3H, t, J=7 Hz), 2.89 (2H, q, J=7 Hz), 3.87 (3H, s), 7.79 (1H, d, J=8 Hz), 8.11 (1H, s), 8.28 (1H, d, J=8 Hz), 8.53 (1H, s)

(11) Methyl 2-propionyl-3-propylindole-6-carboxylate

NMR (CDCl$_3$, δ): 1.06 (3H, t, J=7 Hz), 1.29 (3H, t, J=7 Hz), 1.74 (2H, m), 2.95–3.13 (4H, m), 3.94 (3H, s), 7.72 (1H, d, J=8 Hz), 7.79 (1H, d, J=8 Hz), 8.12 (1H, s), 9.11 (1H, br s)

(12) Methyl 2-isobutyryl-3-propylindole-6-carboxylate

NMR (CDCl$_3$, δ): 1.04 (3H, t, J=7 Hz), 1.29 (6H, t, J=7 Hz, 1.76 (2H, m), 3.09 (2H, m), 3.44 (1H, m), 3.94 (3H, s), 7.71 (1H, d, J=8 Hz), 7.79 (1H, d, J=8 Hz), 8.12 (1H, s), 9.12 (1H, br s)

(13) Methyl 3-cyclopropanecarbonyl-2-propylindole-6-carboxylate mp: 152.5–154° C.

IR (KBr): 3371, 1687, 1623, 1458 cm$^{-1}$

NMR (CDCl$_3$, δ): 1.00–1.09 (2H, m), 1.02 (3H, t, J=7 Hz), 1.28–1.32 (2H, m), 1.82 (2H, sextet, J=7 Hz), 2.56–2.65 (1H, m), 3.15 (2H, t, J=7 Hz), 3.96 (3H, s), 8.00 (2H, AB, J=8, 8 Hz), 8.15 (1H, s), 8.89 (1H, br s)

MASS (m/z): 286 (M$^+$+1, bp)

(14) Methyl 3-cyclobutanecarbonyl-2-propylindole-6-carboxylate
mp: 159–160° C.
IR (KBr): 1692, 1645, 1623 cm$^{-1}$
NMR (CDCl$_3$, δ): 1.06 (3H, t, J=7 Hz), 1.83 (2H, sextet, J=7 Hz), 1.93–2.13 (2H, m), 2.30–2.51 (4H, m), 3.20 (2H, t, J=7 Hz), 3.95 (3H, s), 3.99 (1H, quintet, J=7 Hz), 7.93 (2H, s), 8.15 (1H, s), 9.08 (1H, br s)
MASS (m/z): 300 (M$^+$+1), 74 (bp)

(15) Methyl 3-cyclopentanecarbonyl-2-propylindole-6-carboxylate
mp: 137–139° C.
IR (KBr): 1692, 1647, 1624 cm$^{-1}$
NMR (CDCl$^3$, δ): 1.02 (3H, t, J=7 Hz), 1.64–1.82 (6H, m), 1.94–2.05 (4H, m), 3.17 (2H, t, J=7 Hz), 3.72 (1H, quintet, J=7 Hz), 3.95 (3H, s), 7.93 (2H, ABX, J=8, 8, 1 Hz), 8.15 (1H, d, J=1 Hz), 9.19 (1H, s)
MASS (m/z): 314 (M$^+$+1, bp)

(16) Methyl 3-cyclohexanecarbonyl-2-propylindole-6-carboxylate
mp: 136–137° C.
IR (KBr): 691, 1651, 1487, 1435 cm$^{-1}$
NMR (CDCl$_3$, δ): 1.03 (3H, t, J=7 Hz), 1.25–2.04 (12H, m), 3.14–3.25 (1H, m), 3.18 (2H, t, J=7 Hz), 3.97 (3H, s), 7.90 (2H, q, J=7.5 Hz), 8.17 (1H, s), 9.16 (1H, br s)
MASS (m/z): 328 (M$^+$+1), 74 (bp)

(17) Methyl 3-(3-methyl-2-butenoyl)-2-propylindole-6-carboxylate
mp: 146–147° C.
IR (KBr): 1715, 1464, 1433, 1220 cm$^{-1}$
NMR (CDCl$_3$, δ): 1.05 (3H, t, J=7 Hz), 1.82 (2H, sextet, J=7 Hz), 2.05 (3H, s), 2.20 (3H, s), 3.18 (2H, t , J=7 Hz), 3.94 (3H, s), 6.63 (1H, s), 7.95 (2H, AB, J=7.5, 7.5 Hz), 8.11 (1H, s), 8.88 (1H, br s)
MASS (m/z): 300 (M$^+$+1), 74 (bp)

(18) Methyl 3-crotonoyl-2-propylindole-6-carboxylate
mp: 153–154° C.
IR (KBr): 1715, 1650, 1583, 1567, 1459, 1432 cm$^{-1}$
NMR (CDCl$_3$, δ): 1.05 (3H, t, J=7 Hz), 1.83 (2H, sextet, J=7 Hz), 2.04 (3H, dd, J=7, 1 Hz), 3.15 (2H, t, J=7 Hz), 3.96 (3H, s), 6.89 (1H, dd, J=15, 1 Hz), 7.04 (1H, dd, J=15, 7 Hz), 7.94 (2H, dq, J=7, 1 Hz), 8.12 (1H, s), 8.99 (1H, br s)
MASS (m/z): 286 (M$^+$+1)

(19) 3-Acetyl-6-chloroindole
NMR (CDCl$_3$, δ): 2.44 (3H, s), 7.19 (1H, d, J=8 Hz), 7.51 (1H, s), 8.14 (1H, d, J=8 Hz), 8.35 (1H, s)

PREPARATION 29

The following compounds described in (1) to (3) were prepared in a similar manner to that of Preparation 6 (2).
(1) Methyl 3-(3-methoxycarbonylpropyl)indole-6-carboxylate
NMR (CDCl$_3$, δ): 2.04 (2H, m), 2.37 (2H, t, J=7 Hz), 2.81 (2H, t, J=7 Hz), 3.64 (3H, s), 3.93 (3H, s), 7.16 (1H, s), 7.61 (1H, d, J=8 Hz), 7.79 (1H, d, J=8 Hz), 8.10 (1H, s), 8.22 (1H, br s)

(2) Methyl 3-methylindole-6-carboxylate
NMR (CDCl$_3$, δ): 2.33 (3H, s), 3.93 (3H, s), 7.12 (1H, s), 7.59 (1H, d, J=8 Hz), 7.80 (1H, d, J=8 Hz), 8.09 (1H, s), 8.10 (1H, br s)

(3) Methyl 3-propylindole-6-carboxylate
NMR (CDCl$_3$, δ): 1.00 (3H, t, J=7 Hz), 1.74 (2H, m), 2.73 (2H, t, J=7 Hz), 3.93 (3H, s), 7.14 (1H, d, J=1Hz), 7.60 (1H, d, J=8 Hz), 7.79 (1H, d, J=8 Hz), 8.10 (1H, s), 8.18 (1H, br s)

PREPARATION 30

To a solution of methyl 3-(3-methoxycarbonylpropyl)indole-6-carboxylate (656 mg) in methanol (24 ml) was added 1N aqueous sodium hydroxide (2.46 ml), and the mixture was stirred at 20° C. for 2 days. The resulting mixture was evaporated in vacuo, and the residue was acidified with 1N hydrochloric acid (2.6 ml) and extracted with ethyl acetate. The organic chase was washed with brine, dried over sodium sulfate and evaporated in vacuo. The residue was triturated with ether to give methyl 3-(3-carboxypropyl)indole-6-carboxylate (486 mg) as solid.

NMR (CDCl$_3$, δ): 2.03 (2H, m), 2.37 (2H, m), 2.80 (2H, m), 3.93 (3H, s), 7.17 (1H, s), 7.59 (1H, d, J=8 Hz), 7.74 (1H, d, J=8 Hz), 8.09 (1H, s)

PREPARATION 31

A. mixture of methyl 3-(3-carboxypropyl)indole-6-carboxylate (173 mg), triphenylphosphine (191 mg) and carbon tetrachloride (1.0 ml) in 1,2-dichloroethane (10 ml) was heated at 80° C. for 2 hours. The resulting mixture was diluted with chloroform and washed with water, aqueous sodium bicarbonate and brine. The organic phase was dried over sodium sulfate and evaporated in vacuo. The residue was purified by silica gel thin layer chromatography with a mixture of hexane and ethyl acetate (4:1) and recrystallized from a mixture of hexane and ethyl acetate to give methyl 8-oxo-5,6,7,8-tetrahydrocarbazole-2-carboxylate (72.2 mg) as colorless crystals.

NMR (CDCl$_3$, δ): 2.29 (2H, m), 2.69 (2H, t, J=7 Hz), 3.03 (2H, t, J=7 Hz), 3.94 (3H, s), 7.69 (1H, d, J=8 Hz), 7.82 (1H, d, J=8 Hz), 8.16 (1H, s), 8.95 (1H, br s)

PREPARATION 32

To a stirred mixture of methyl (E)-4-[2-(dimethylamino)vinyl]-3-nitrobenzoate (500 mg), which was prepared by the method of Brown et al. described in Journal of Medicinal Chemistry, vol. 35, page 2419 (1992), and pyridine (0.16 ml) in tetrahydrofuran (3 ml) was added butyryl chloride (0.21 ml) at 20° C. The reaction mixture was stirred at 40° C. for 24 hours and 50° C. for 4 hours. After cooled to 20° C., the reaction mixture was diluted with water and extracted with ethyl acetate. The organic phase was washed with water and brine, dried over magnesium sulfate and evaporated in vacuo. The residue was chromatographed on silica gel eluting with a mixture of ethyl acetate and hexane (1:1) to give methyl 4-(1-dimethylaminomethylene-2-oxopentyl)-3-nitrobenzoate (426 mg) as colorless amorphous.

NMR (CDCl$_3$, δ): 0.89 (3H, t, J=7 Hz), 1.52–1.65 (2H, m), 2.30 (2H, t, J=7 Hz), 2.78 (6H, s), 3.99 (3H, s), 7.34 (1H, d, J=7.5 Hz), 7.56 (1H, s), 8.18 (1H, dd, J=7.5, 1 Hz), 8.51 (1H, d, J=1Hz)
MASS (m/z): 321 (M$^+$+1)

PREPARATION 33

A solution of methyl 4-(1-dimethylaminomethylene-2-oxopentyl)-3-nitrobenzoate (172 mg) in dioxane (9 ml) was refluxed for 4 days. The resulting mixture was evaporated in vacuo, and the residue was purified by thin layer chromatography with a mixture of hexane and ethyl acetate (2:1) to give methyl 3-nitro-4-(2-oxopentyl)benzoate (127 mg).

NMR (CDCl$_3$, δ): 0.97 (3H, t, J=7 Hz), 1.69 (2H, m), 2.60 (2H, t, J=7 Hz), 3.95 (3H, s), 4.16 (2H, s), 7.36 (1H, d, J=8 Hz), 8.22 (1H, d, J=8 Hz), 8.73 (1H, s)

PREPARATION 34

To a solution of methyl 3-nitro-4-(2-oxopentyl)benzoate (114 mg) in a mixture of tetrahydrofuran (1.5 ml), ethanol (1.5 ml) and water (2.1 ml) was added sodium hydrosulfite (3.0 g), and the mixture was stirred under reflux for 30 minutes. The resulting mixture was evaporated in vacuo, and the residue was diluted with ethyl acetate. The organic phase was washed with water and brine, dried over sodium sulfate and evaporated in vacuo. The residue was purified by thin layer chromatography with a mixture of hexane and ethyl acetate (2:1) to give methyl 2-propylindole-6-carboxylate (54.6 mg).

PREPARATION 35

To a stirred solution of 3-isobutyryl-2-propylindole-6-carboxylic acid (331 mg) in tetrahydrofuran (5 ml) were added benzylalcohol (1.25 ml), dicyclohexylcarbodiimide (303 mg) and 4-dimethylaminopyridine (20 mg) at 20° C. The reaction mixture was stirred at 20° C. for 8 hours. The precipitated urea was filtered off and the filtrate was evaporated in vacuo. The residue was extracted with ethyl acetate and the extract was washed with water two times and brine. The organic phase was dried over sodium sulfate and evaporated in vacuo. The residue was chromatographed on silica gel eluting with a mixture of ethyl acetate and hexane (1:4) to give the crystals which were recrystallized from a mixture of ethyl acetate and hexane to give benzyl 3-isobutyryl-2-propylindole-6-carboxylate (215 mg) as colorless crystals.

mp: 102–104° C.

IR (KBr): 1700, 1655 cm$^{-1}$

NMR (CDCl$_3$, δ): 1.05 (3H, t, J=7 Hz), 1.28 (6H, t, J=7 Hz), 1.73–1.87 (2H, m), 3.17 (2H, t, J=7 Hz), 3.45–3.53 (1H, m), 5.40 (2H, s), 7.32–7.50 (5H, m), 7.95 (2H, AB, J=9, 8 Hz), 8.14 (1H, s), 8.59 (1H, br s)

MASS (m/z): 364 (M$^+$+1), 76 (bp)

PREPARATION 36

The following compound was prepared in a similar manner to that of Example 32.
Methyl 3-formylindole-6-carboxylate
NMR (CDCl$_3$, δ): 3.88 (3H, s), 7.83 (1H, dd, J=1, 8 Hz), 8.12 (1H, s), 8.16 (1H, d, J=8 Hz), 8.49 (1H, s), 12.45 (1H, br s)

PREPARATION 37

To a solution of methyl 3-isobutyryl-2-propylindole-6-carboxylate (201 mg) in carbon tetrachloride (7 ml) was added N-bromosuccinimide (187 mg) and 2,2'-azobis(4-methoxy-2,4-dimethylvaleronitrile) (20 mg) and refluxed for 30 minutes. The resulting mixture was filtered and the filtrate was evaporated in vacuo. The residue was purified by preparative thin layer chromatography on silica gel eluting with a mixture of hexane and ethyl acetate (2:1) to give methyl 2-(1-bromopropyl)-3-isobutyrylindole-6-carboxylate (179 mg).

This compound was used immediately without purification.

PREPARATION 38

To a solution of methyl 2-(1-bromopropyl)-3-isobutyrylindole-6-carboxylate (179 mg) in 1,2-dichloroethane (8 ml) was added N,N-diisopropylethylamine (0.24 ml) and refluxed for 40 minutes. The resulting mixture was evaporated in vacuo, then the residue was diluted with ethyl acetate and washed with diluted hydrochloric acid, water and brine. The organic phase was dried over sodium sulfate and evaporated in vacuo. Trituration with diethyl ether gave methyl 3-isobutyryl-2-(1-propenyl)indole-6-carboxylate (55.2 mg).

NMR (CDCl$_3$, δ): 1.27 (6H, d, J=7 Hz), 2.01 (3H, d, J=7 Hz), 3.47 (1H, m), 3.93 (3H, s), 6.44 (1H, m), 7.32 (1H, d, J=16 Hz), 7.89 (1H, d, J=8 Hz), 7.94 (1H, d, J=8 Hz), 8.11 (1H, s), 8.94 (1H, br s)

PREPARATION 39

To a solution of methyl 2-(1-bromopropyl)-3-isobutyrylindole-6-carboxylate (323 mg) in acetic acid (3 ml) was added potassium acetate (345 mg) and the mixture was stirred at 60° C. for 2 hours. The resulting mixture was evaporated in vacuo, then the residue was diluted with ethyl acetate and washed with water, aqueous sodium bicarbonate and brine. The organic phase was dried over sodium sulfate and evaporated in vacuo. The residue was purified by preparative thin layer chromatography on silica gel eluting with a mixture of hexane and ethyl acetate (2:1) to give methyl 2-(1-acetoxypropyl)-3-isobutyrylindole-6-carboxylate (207 mg).

NMR (CDCl$_3$, δ): 0.99 (3H, t, J=7 Hz), 1.23 (3H, d, J=7 Hz), 1.29 (3H, d, J=7 Hz), 1.94 (1H, m), 2.08 (1H, m), 2.18 (3H, s), 3.52 (1H, m), 3.94 (3H, s), 6.67 (1H, m), 7.88 (1H, d, J=8 Hz), 7.94 (1H, d, J=8 Hz), 8.18 (1H, s), 9.09 (1H, br s)

PREPARATION 40

To a mixture of methyl 2-propylindole-6-carboxylate (10 g), methoxyacetic acid (4.6 ml) and carbontetrachloride (13.4 ml) in 1,2-dichloroethane (45 ml) was added slowly triphenylphosphine (16.7 g) in 1,2-dichloroethane (30 ml) over 1 hour under reflux, and the resulting mixture was heated under reflux for additional 8 hours. After evaporation of solvent, the residue was chromatographed on silica gel eluting with a mixture of hexane and ethyl acetate (1:1) and triturated with diethyl ether to give methyl 3-methoxyacetyl-2-propylindole-6-carboxylate (8.11 g).

PREPARATION 41

The following compound was prepared in a similar manner to that of Preparation 15 (1).
Methyl 3-ethoxyacetyl-2-propylindole-6-carboxylate
NMR (CDCl$_3$, δ): 1.05 (3H, t, J=7 Hz), 1.32 (3H, t, J=7 Hz), 1.84 (2H, sextet, J=8 Hz), 3.22 (2H, t, J=7 Hz), 3.74 (3H, q, J=7 Hz), 3.97 (3H, s), 4.75 (2H, s), 7.83 (1H, d, J=8 Hz), 7.94 (1H, d, J=8 Hz), 8.15 (1H, s), 9.27 (1H, br s)

PREPARATION 42

To a stirred mixture of methyl 4-hydroxyphenylacetate (10.0 g) in acetic acid (55 ml) was added nitric acid (22.1 ml) at 0° C. The reaction mixture was stirred at 0° C. for 2 hours. After warmed to 20° C., the reaction mixture was diluted with water (200 ml) and precipitated crystals were collected. The crystals were dissolved in chloroform, and the solution was washed with water, dried over magnesium sulfate and evaporated in vacuo. The residue was recrystallized from a mixture of chloroform and hexane to give methyl 4-hydroxy-3-nitrophenylacetate (9.3 g) as yellow crystals.

mp: 64–69° C.

IR (KBr): 1734, 1540, 1534, 1263, 1170 cm$^{-1}$

NMR (CDCl$_3$, δ): 3.64 (2H, s), 3.73 (3H, s), 7.14 (1H, d, J=8 Hz), 7.52 (1H, dd, J=8, 1 Hz), 8.02 (1H, d, J=1 Hz)

MASS (m/z): 210 (M$^+$-1)

PREPARATION 43

Iron powder (2.5 g) was added to a stirred mixture of methyl 3-nitro-4-trifluoromethanesulfonyloxyphenylacetate (2.97 g) and conc. hydrochloric acid (7.3 ml) in methanol (22 ml) at 0° C. in some small portion. The reaction mixture was stirred at 20° C. for 2 hours, then poured into a mixture of ethyl acetate and saturated sodium bicarbonate. The organic phase was washed with saturated sodium bicarbonate and brine, dried over sodium sulfate and evaporated in vacuo. The residue was chromatographed on silica gel eluting with a mixture of ethyl acetate and hexane (1:4) to give methyl 3-amino-4-trifluoromethanesulfonyloxyphenylacetate (2.34 g) as colorless crystals.

mp: 66–69° C.

NMR (CDCl$_3$, δ): 3.57 (2H, s), 3.71 (3H, s), 3.94 (2H, s), 6.67 (1H, dd, J=7.5, 1 Hz), 6.79 (1H, d, J=1 Hz), 7.11 (1H, d, J=7.5 Hz)

PREPARATION 44

The following compounds were prepared from methyl 1-acetyl-2-propylindol-6-ylacetate in a similar manner to that of Preparation 26.

Methyl 2-propylindol-6-ylacetate
IR (Neat): 3400, 1740 cm$^{-1}$
NMR (CDCl$_3$, δ): 1.00 (3H, t, J=7 Hz), 1.75 (2H, sextet, J=7 Hz), 2.72 (2H, t, J=7 Hz), 3.70 (3H, s), 3.72 (2H, s), 6.22 (1H, s), 6.99 (1H, d, J=7.5 Hz), 7.22 (1H, s), 7.47 (1H, d, J=7.5 Hz), 7.83 (1H, br s)
MASS (m/z): 232 (M$^+$+1), 74 (bp)

Ethyl 2-propylindol-6-ylacetate
IR (Neat): 3400, 1735 cm$^{-1}$
NMR (CDCl$_3$, δ): 1.00 (3H, t, J=7 Hz), 1.05 (3H, t, J=7 Hz), 1.74 (2H, sextet, J=7 Hz), 2.72 (2H, t, J=7 Hz), 3.69 (3H, s), 4.13 (2H, q, J=7 Hz), 6.20 (1H, s), 6.99 (1H, d, J=7.5 Hz), 7.23 (1H, s), 7.46 (1H, d, J=7.5 Hz), 7.83 (1H, br s)
MASS (m/z): 346 (M$^+$+1), 74 (bp)

2-Propylindol-6-ylacetic acid
mp: 85–87° C.
IR (KBr): 3381, 1701, 1691 cm$^{-1}$
NMR (CDCl$_3$, δ): 1.00 (3H, t, J=7 Hz), 1.73 (2H, sextet, J=7 Hz), 2.72 (2H, t, J=7 Hz), 3.73 (2H, s), 6.21 (1H, s), 6.98 (1H, d, J=7.5 Hz), 7.21 (1H, s), 7.48 (1H, d, J=7.5 Hz), 7.83 (1H, br s)
MASS (m/z): 216 (M$^+$-1, bp)

PREPARATION 45

To a stirred solution of methyl 3-ethylindole-6-carboxylate (138 mg) in dichloromethane (5 ml) was added sulfuryl chloride (0.066 ml), and the mixture was stirred at 20° C. for 1 hour. The resulting mixture was poured into ice and extracted with ethyl acetate. The combined organic phase was washed with aqueous sodium bicarbonate and brine, then dried over sodium sulfate and evaporated in vacuo. The residue was chromatographed on silica gel eluting with a mixture of hexane and ethyl acetate (4:1) to give methyl 2-chloro-3-ethylindole-6-carboxylte (58.2 mg) as a solid.

NMR (CDCl$_3$, δ): 1.26 (3H, t, J=7 Hz), 2.76 (2H, q, J=7 Hz), 3.92 (3H, s), 7.54 (1H, d, J=8 Hz), 7.82 (1H, d, J=8 Hz) 8.02 (1H, s), 8.19 (1H, br s)

PREPARATION 46

To a stirred solution of methyl 3-formylindole-6-carboxylate (368 mg) in 1,4-dioxane (10 ml) was added acetylmethylene triphenylphosphorane (1.15 g), and the mixture was stirred under reflux for 12 hours. The resulting mixture was evaporated in vacuo, redissolved with ethyl acetate and washed with 1N hydrochloric acid and brine. The organic phase was dried over sodium sulfate and evaporated in vacuo. The residue was chromatographed on silica gel eluting with a mixture of chloroform and ethyl acetate (1:2) to give methyl 3-(3-oxo-1-butenyl)indole-6-carboxylate (75 mg) as a solid.

NMR (CDCl$_3$, δ): 2.39 (3H, s), 3.95 (3H, s), 6.79 (1H, d, J=15 Hz), 7.71 (1H, s), 7.80 (1H, d, J=8 Hz), 7.87–7.96 (2H, m), 8.14 (1H, s)

PREPARATION 47

The following compound was prepared from in a similar manner to that of Preparation 46.
Methyl 3-(2-methoxycarbonylethenyl)indole-6-carboxylate
NMR (DMSO-d$_6$, δ): 3.72 (3H, s), 4.87 (3H, s), 6.44 (1H, d, J=15 Hz), 7.76 (1H, d, J=8 Hz), 7.89 (1H, d, J=15 Hz), 7.98 (1H, d, J=8 Hz), 8.10 (1H, s), 8.20 (1H, s)

PREPARATION 48

To a solution of methyl 3-(2-methoxycarbonylethenyl)indole-6-carboxylate (213 mg) in a mixture of 1,4-dioxane (2 ml) and methanol (3 ml) was added 10% palladium on carbon (40 mg) and the mixture was stirred under hydrogen at 20° C. for 6.5 hours. The resulting mixture was filtered through celite and the filtrate was evaporated in vacuo. The residue was triturated with diisopropyl ether to give methyl 3-(2-methoxycarbonylethyl)indole-6-carboxylate (177 mg).

NMR (CDCl$_3$, δ): 2.72 (2H, t, J=7 Hz), 3.12 (2H, t, J=7 Hz), 3.68 (3H, s), 3.94 (3H, s), 7.20 (1H, d, J=2 Hz), 7.62 (1H, d, J=8 Hz), 7.82 (1H, d, J=8 Hz), 8.12 (1H, s), 8.21 (1H, br s)

PREPARATION 49

The following compound was prepared from a similar manner to that of Preparation 30.
3-6-Methoxycarbonylindol-3-yl)propionic acid
NMR (CDCl$_3$, δ): 2.72 (2H, t, J=7 Hz), 3.10 (2H, t, J=7 Hz), 3.94 (3H, s), 7.19 (1H, s), 7.60 (1H, d, J=8 Hz), 7.77 (1H, d, J=8 Hz, 8.10 (1H, s)

PREPARATION 50

The following compound was prepared in a similar manner to that of Preparation 31.
Methyl 3-oxo-1,2,3,4-tetrahydrocyclopent[b] indole-6-carboxylate
NMR (CDCl$_3$, δ): 3.05 (2H, m), 3.1 (2H, m), 3.97 (3H, s), 7.76 (1H, d, J=8 Hz), 7 (1H, d, J=8 Hz), 8.21 (1H, s)

PREPARATION 51

The following compounds described in (1) to (6) were prepare in a similar manner to that of Preparation 8 (1).
(1) 3-Cyclopropanecarbonyl-2-propylindole-6-carboxylic acid
mp: 250.5–251.5° C. (dec.)
IR (KBr): 1685, 1600, 1463, 1424, 1300 cm$^{-1}$
NMR (CDCl$_3$-CD$_3$OD, δ): 1.00–1.09 (2H, m), 1.02 (3H, t, J=7 Hz), 1.25–1.29 (2H, m), 1.81 (2H, sextet, J=7 Hz), 2.59–2.69 (1H, m), 3.12 (2H, t, J=7 Hz), 7.99 (2H, AB, J=7.5, 7.5 Hz), 8.09 (1H, s)
MASS (m/z): 270 (M$^+$-1)

(2) 3-Cyclobutanecarbonyl-2-propylindole-6-carboxylic acid mp: 244–245° C.

IR (KBr): 1688, 1419, 1292 cm$^{-1}$

NMR (CDCl$_3$-CD$_3$OD, δ) 1.05 (3H, t, J=7 Hz, 1.80 (2H, sextet, J=7 Hz), 1.92–2.15 (2H, m), 2.29–2.49 (2H, m), 4.01 (1H, quintet, J=7 Hz), 7.90 (2H, s), 8.08 (1H, s)

MASS (m/z): 286 (M$^+$+1), 74 (bp)

3-Cyclopentanecarbonyl-2-propylindole-6-carboxylic acid mp: 233–235° C.

IR (KBr): 1673, 1611, 1463, 1453 cm$^{-1}$

NMR (CDCl$_3$-CD$_3$OD, δ): 0.99 (3H, t, J=7 Hz), 1.51–1.79 (6H, m), 1.89–1.97 (4H, m), 3.10 (2H, t, J=7 Hz), 3.70 (1H, quintet, J=7 Hz), 7.85–7.94 (2H, m), 8.05 (1H, s)

MASS (m/z): 298 (M$^+$−1, bp)

(4) 3-Cyclohexanecarbonyl-2-propylindole-6-carboxylic acid mp: 217–218° C.

IR (KBr): 1675, 1614, 1457 cm$^{-1}$

NMR (CDCl$_3$-CD$_3$OD, δ): 0.99 (3H, t, J=7 Hz), 1.19–1.56 (6H, m), 1.74 (2H, sextet, J=7 Hz), 1.80–1.95 (4H, m), 3.08 (2H, t, J=7 Hz), 3.09–3.20 (1H, m), 7.80 (1H, d, J=8 Hz), 7.88 (1H, dd, J=8, 1 Hz), 8.03 (1H, d, J=1 Hz)

MASS (m/z): 312 (M$^+$−1, bp, (5) 3-(3-Methyl-2-butenoyl)-2-propylindole-6-carboxylic acid mp: 246–248° C. (dec.)

IR (KBr): 1669, 1465, 1423 cm$^{-1}$

NMR (DMSO-d$_6$, δ): 0.96 (3H, t, J=7 Hz), 1.75 (2H, sextet, J=7 Hz), 2.00 (3H, s), 2.09 (3H, s), 3.08 (2H, t, J=7 Hz), 6.60 (1H, s), 7.73 (1H, d, J=7.5 Hz), 7.95 (1H, d, J=7.5 Hz), 7.99 (1H, s)

MASS (m/z): 284 (M$^+$−1, bp), 82 (bp)

PREPARATION 52

The following compounds described in (1) to (6) were prepared in the similar manner to that of Example 6.

(1) 3-Cyclopropanecarbonyl-2-propylindole-6-carboxamide mp: 120–122° C.

IR (KBr): 1670, 1623, 1598, 1394 cm$^{-1}$

NMR (DMSO-d$_6$, δ): 0.94 (3H, t, J=7 Hz), 0.99–1.04 (4H, m), 1.73 (2H, sextet, J=7 Hz), 2.55–2.62 (1H, m), 3.07 (2H, t, J=7 Hz), 7.22 (1H, br s), 7.69 (1H, dd, J=7.5, 1 Hz), 7.93 (1H, d, J=1 Hz), 7.96 (1H, br s), 8.00 (1H, d, J=7.5 Hz)

MASS (m/z): 269 (M$^+$−1), 98 (bp)

(2) 3-Cyclobutanecarbonyl-2-propylindole-6-carboxamide mp: 253–255° C.

IR (KBr): 1675, 1624, 1605, 1456, 1397 cm$^{-1}$

NMR (DMSO-d$_6$, δ) 0.97 (3H, t, J=7 Hz), 1.66–1.89 (3H, m), 1.97–2.09 (1H, m), 2.23–2.30 (4H, m), 3.09 (2H, t, J=7 Hz), 3.99 (1H, quintet, J=7 Hz), 7.24 (1H, br s), 7.69 (1H, d, J=7.5 Hz), 7.86 (1H, d, J=7.5 Hz), 7.90 (1H, s), 7.97 (1H, br s)

MASS (m/z): 285 (M$^+$+1), 85 (bp)

(3) 3-Cyclopentanecarbonyl-2-propylindole-6-carboxamide mp: 213–215° C.

IR (KBr): 1666, 1628, 1623, 1604 cm$^{-1}$

NMR (CDCl$_3$-CD$_3$OD, δ): 1.01 (3H, t, J=7 Hz), 1.61–1.83 (6H, m), 1.90–1.98 (4H, m), 3.13 (2H, t, J=7 Hz), 3.69 (1H, quintet, J=7 Hz), 7.52 (1H, dd, J=8, 1 Hz), 7.91 (1H, d, J=1 Hz), 7.96 (1H, d, J=8 Hz)

MASS (m/z): 299 (M$^+$+1), 74 (bp)

(4) 3-Cyclohexanecarbonyl-2-propylindole-6-carboxamide mp: 245–247° C.

IR (KBr): 1663, 1627, 1595, 1459, 1402 cm$^{-1}$

NMR (DMSO-d$_6$, δ): 0.95 (3H, t, J=7 Hz), 1.16–1.30 (1H, m), 1.35–1.46 (4H, m), 1.70 (2H, sextet, J=7 Hz), 1.75–1.88 (5H, m), 3.05 (2H, t, J=7 Hz), 3.10–3.17 (1H, m), 7.25 (1H, br s), 7.70 (1H, dd, J=7.5, 1 Hz), 7.81 (1H, d, J=7.5 Hz), 7.93 (1H, d, J=1 Hz), 7.95 (1H, br s)

MASS (m/z): 313 (M$^+$+1), 85 (bp)

(5) 3-(3-Methyl-2-butenoyl)-2-propylindole-6-carboxamide mp: 179–181° C.

IR (KBr): 1669, 1648, 1591, 1458, 1394 cm$^{-1}$

NMR (DMSO-d$_6$, δ): 0.95 (3H, t, J=7 Hz), 1.72 (2H, sextet, J=7 Hz), 1.99 (3H, s), 2.05 (3H, s), 3.05 (2H, t, J=7 Hz), 6.59 (1H, s), 7.22 (1H, br s), 7.67 (1H, d, J=7.5 Hz), 7.88 (1H, d, J=7.5 Hz), 7.90 (1H, s), 7.92 (1H, br s)

MASS (m/z): 285 (M$^+$+1), 85 (bp)

(6) 3-(3-Methoxybutanoyl)-2-propylindole-6-carboxamide mp: 140–144° C.

IR (KBr): 1644, 1623, 1604, 1460, 1394 cm$^{-1}$

NMR (CDCl$_3$, δ): 1.02 (3H, t, J=7 Hz), 1.30 (3H, d, J=7 Hz), 1.80 (2H, sextet, J=7 Hz), 2.98 (1H, dd, J=15, 7 Hz), 3.17 (2H, t, J=7 Hz), 3.39 (1H, dd, J=15, 7 Hz), 3.40 (3H, s), 7.10 (1H, sextet, J=7 Hz), 7.55 (1H, dd, J=8, 1 Hz), 8.02 (1H, d, J=8 Hz), 8.10 (1H, d, J=1 Hz), 9.60 (1H, br s)

MASS (m/z): 303 (M$^+$+1), 74 (bp)

PREPARATION 53

The following compound was prepared from methyl 3-crotonyl-2-propylindole-6-carboxylate in a similar manner to that of Preparation 8 (1).

3-(3-Methoxybutanoyl)-2-propylindole-6-carboxylic acid mp: 286–288° C. (dec.)

IR (KBr): 3288, 1685, 1645, 1620 cm$^{-1}$

NMR (DMSO-d$_6$, δ): 0.96 (3H, t, J=7 Hz), 1.19 (3H, d, J=7 Hz), 1.73 (2H, sextet, J=7 Hz), 2.90 (1H, dd, J=15, 7 Hz), 3.08 (2H, t, J=7 Hz), 3.13 (3H, s), 3.15 (1H, dd, J=15, 7 Hz), 3.91 (1H, sextet, J=7 Hz), 7.26 (1H, d, J=8 Hz), 7.99 (1H, s), 8.00 (1H, d, J=8 Hz)

MASS (m/z): 302 (M$^+$−1), 98 (bp)

EXAMPLE 1

To a solution of methyl 3-acetyl-2-propylindole-6-carboxylate (74 mg) in dimethylformamide (1.4 ml) was added sodium hydride (60%, 15.4 mg). The mixture was stirred at 20° C. for 30 minutes, then 2-chlorobenzyl bromide (0.045 ml) was added. After stirred for 1 hour, the mixture was diluted with ethyl acetate and washed with water and brine. The organic phase was dried over sodium sulfate and evaporated in vacuo to give methyl 3-acetyl-1-(2-chlorobenzyl)-2-propylindole-6-carboxylate (125 mg) as solid.

NMR (CDCl$_3$, δ): 1.01 (3H, t, J=7 Hz), 1.63 (2H, m), 2.74 (3H, s), 3.05 (2H, m), 3.89 (3H, s), 5.49 (2H, s), 6.22 (1H, d, J=8 Hz), 7.03 (1H, t, J=8 Hz), 7.20 (1H, t, J=8 Hz), 7.46 (1H, d, J=8 Hz), 7.93 (1H, s), 7.97 (1H, d, J=8 Hz), 8.04 (1H, d, J=8 Hz)

EXAMPLE 2

To a solution of methyl 3-acetyl-1-(2-chlorobenzyl)-2-propylindole-6-carboxylate (125 mg) in ethanol (6 ml) was added 1N aqueous sodium hydroxide (0.7 ml), and the mixture was stirred under reflux for 1 hour. The resulting mixture was evaporated in vacuo, and the residue was acidified with 1N hydrochloric acid (0.75 ml) and extracted with ethyl acetate. The extract was washed with brine, dried over sodium sulfate and evaporated in vacuo. The residue was triturated with isopropyl ether to give 3-acetyl-1-(2-chlorobenzyl)-2-propylindole-6-carboxylic acid (78 mg) as solid.

NMR (CDCl$_3$, δ): 1.02 (3H, t, J=7 Hz), 1.61 (2H, m), 2.76 (3H, s), 3.08 (2H, m), 5.52 (2H, s), 6.24 (1H, d, J=8 Hz), 7.04 (1H, t, J=8 Hz), 7.22 (1H, t, J=8 Hz), 7.46 (1H, d, J=8 Hz), 7.99 (1H, s), 8.03 (1H, d, J=8 Hz), 8.08 (1H, d, J=8 Hz)

EXAMPLE 3

To a solution of 3-acetyl-1-(2-chlorobenzyl)-2-propylindole-6-carboxylic acid (74 mg) in dimethylformamide (2 ml) were added 1-hydroxybenzotriazole (38 mg), 1-(3-dimethylaminopropyl)-3-ethylcarbodiimide hydrochloride (98 mg) and 3N methanol solution of ammonia (0.5 ml). After stirred at 2° C. for 14 hours, the resulting mixture was diluted with ethyl acetate. The organic phase was washed successively with 1N hydrochloric acid, water, aqueous sodium bicarbonate and brine, dried over sodium sulfate and evaporated in vacuo. The residue was triturated with isopropyl ether to give 3-acetyl-1-(2-chlorobenzyl)-2-propylindole-6-carboxamide (67 mg) as colorless crystals.

mp: 208–211° C.

NMR (CDCl$_3$, δ): 1.01 (3H, t, J=7 Hz), 1.61(2H, m), 2.73 (3H, s), 3.06 (2H, m), 5.49 (2H, s), 6.22 (1H, dd, J=1, 8 Hz), 7.02 (1H, dt, J=1, 8 Hz), 7.21 (1H, dt, J=1, 8 Hz), 7.45 (1H, dd, J=1, 8 Hz), 7.63 (1H, dd, J=1, 8 Hz), 7.84 (1H, d, J=8 Hz), 8.07 (1H, d, J=8 Hz)

EXAMPLE 4

Methyl 1-(2-chlorobenzyl)-3-isobutyryl-2-propylindole-6-carboxylate (533 mg) was prepare from methyl 3-isobutyryl-2-propylindole-6-carboxylate (440 mg) and 2-chlorobenzyl bromide (346 mg) in a similar manner to that of Example 1.

NMR (CDCl$_3$, δ): 1.01 (3H, t, J=8 Hz), 1.30 (6H, d, J=8 Hz), 1.55–1.66 (2H, m) 3.02–3.07 (2H, m), 3.58 (2H, septet, J=8 Hz), 3.90 (3H, s), 5.50 (2H, s), 6.24 (1H, dd, J=1, 8 Hz), 7.05 (1H, dt, J=1, 8 Hz), 7.24 (1H, dt, J=1, 8 Hz), 7.46 (1H, dd, J=1, 8 Hz), 7.95 (1H, s), 7.97 (2H, s)

EXAMPLE 5

1-(2-Chlorobenzyl)-3-isobutyryl-2-propylindole-6-carboxylic acid (450 mg) was prepared from methyl 1-(2-chlorobenzyl)-3-isobutyryl-2-propylindole-6-carboxylate (510 mg) in a similar manner to that of Example 2.

NMR (DMSO-d$_6$, δ): 0.92 (3H, t, J=8 Hz), 1.18 (6H, d, J=8 Hz), 1.38–1.52 (2H, m), 3.02–3.08 (2H, m), 3.55 (2H, septet, J=8 Hz), 5.68 (2H, s), 6.28 (1H, dd, J=1, 8 Hz), 7.18 (1H, dt, J=1, 8 Hz), 7.32 (1H, dt, J=1, 8 Hz), 7.52 (1H, dd, J=1, 8 Hz), 7.84 (1H, dd, J=1, 8 Hz), 7.97 (1H, d, J=1 Hz, 8.00 (1H, d, J=8 Hz)

EXAMPLE 6

To a solution of 1-(2-chlorobenzyl)-3-isobutyryl-2-propylindole-6-carboxylic acid (150 mg) in dimethylformamide (3 ml) were added 1-hydroxybenzotriazole (102 mg), 1-(3-dimethylaminopropyl)-3-ethylcarbodiimide hydrochloride (109 mg). After stirred at 20° C. over night, the resulting mixture was poured into 28% aqueous ammonia (5 ml). The mixture was partitioned between ethyl acetate and water, and the organic phase was washed with 1N hydrochloric acid and brine, dried over sodium sulfate and evaporated in vacuo. The crystalline residue was recrystallized from a mixture of ethyl acetate and hexane to give 1-(2-chlorobenzyl)-3-isobutyryl-2-propylindole-6-carboxamide (123 mg) as colorless crystals.

mp: 185–186° C.

NMR (CDCl$_3$, δ) 1.01 (3H, t, J=8 Hz), 1.30 (6H, d, J=8 Hz), 1.55–1.66 (2H, m), 3.00–3.06 (2H, m), 3.56 (2H, septet, J=8 Hz), 5.49 (2H, s), 6.24 (1H, dd, J=1, 8 Hz), 7.04 (1H, dt, J=1, 8 Hz), 7.23 (1H, dt, J=1, 8 Hz), 7.46 (1H, dd, J=1, 8 Hz), 7.63 (1H, dd, J=1, 8 Hz), 7.85 (1H, d, J=1 Hz), 7.97 (1H, d, J=8 Hz)

EXAMPLE 7

Methyl 1-(2-chlorobenzyl)-3-propionyl-2-propylindole-6-carboxylate (436 mg) was prepared from methyl 3-propionyl-2-propylindole-6-carboxylate (260 mg) and 2-chlorobenzyl bromide (215 mg) in a similar manner to that of Example 1.

NMR (CDCl$_3$, δ) 1.02 (3H, t, J=8 Hz), 1.30 (3H, t, J=8 Hz), 1.55–1.68 (2H, m), 3.00–3.16 (4H, m), 3.90 (3H, s), 5.49 (2H, s), 6.22 (1H, dd, J=1, 8 Hz), 7.05 (1H, dt, J=1, 8 Hz), 7.23 (1H, dt, J=1, 8 Hz), 7.46 (1H, dd, J=1, 8 Hz), 7.93 (1H, d, J=8 Hz), 7.96 (1H, dd, J=1, 8 Hz), 8.03 (1H, d, J=8 Hz)

EXAMPLE 8

1-(2-Chlorobenzyl)-3-propionyl-2-propylindole-6-carboxylic acid (308 mg) was prepared from methyl 1-(2-chlorobenzyl)-3-propionyl-2-propylindole-6-carboxylate (425 mg) in a similar manner to that of Example 2.

NMR (DMSO-d$_6$, δ) 0.94 (3H, t, J=8 Hz), 1.14 (3H, t, J=8 Hz), 1.49 (2H, sextet, J=8 Hz), 3.00–3.10 (4H, m), 5.67 (2H, s), 6.27 (1H, dd, J=1, 8 Hz), 7.18 (1H, dt, J=1, 8 Hz), 7.32 (1H, dt, J=1, 8 Hz), 7.56 (1H, dd, J=1, 8 Hz), 7.83 (1H, dd, J=1, 8 Hz), 7.96 (1H, d, J=1 Hz), 8.09 (1H, d, J=8 Hz)

EXAMPLE 9

1-(2-Chlorobenzyl)-3-propionyl-2-propylindole-6-carboxamide (81 mg) was prepared from 1-(2-chlorobenzyl)-3-propionyl-2-propylindole-6-carboxylic acid (100 mg) in a similar manner to that of Example 6.

mp: 151–152° C.

NMR (CDCl$_3$, δ): 1.02 (3H, t, J=8 Hz), 1.30 (3H, t, J=8 Hz), 1.62 (2H, sextet, J=8 Hz), 3.04–3.14 (4H, m), 5.50 (2H, s), 6.22 (1H, dd, J=1, 8 Hz), 7.03 (1H, d, J=1, 8 Hz), 7.22 (1H, dt, J=1, 8 Hz), 7.4 (1H, dd, J=1, 8 Hz), 7.64 (1H, dd, J=1, 8 Hz), 7.84 (1H, d, J=1 Hz), 8.06 (1H, d, J=8 Hz)

EXAMPLE 10

Methyl 1-(2-chlorobenzyl)-2-isobutyl-3-isobutyrylindole-6-carboxylate (258 mg) was prepared from methyl 2-isobutyl-3-isobutyrylindole-6-carboxylate (210 mg) and 2-chlorobenzyl bromide (157 mg) in a similar manner to that of Example 1.

NMR (CDCl$_3$, δ): 0.97 (6H, d, J=7 Hz), 1.31 (6H, d, J=7 Hz), 1.96–2.10 (1H, m), 3.04 (2H, d, J=7 Hz), 3.60 (1H, septet, J=7 Hz), 3.90 (3H, s), 5.53 (2H, s), 6.18 (1H, d, J=8 Hz), 7.04 (1H, t, J=8 Hz), 7.23 (1H, t, J=8 Hz), 7.46 (1H, t, J=8 Hz), 7.94 (1H, s), 7.96 (2H, s)

EXAMPLE 11

1-(2-Chlorobenzyl)-2-isobutyl-3-isobutyrylindole-6-carboxylic acid (184 mg) was prepared from methyl 1-(2-chlorobenzyl)-2-isobutyl-3-isobutyrylindole-6-carboxylate (213 mg) in a similar manner to that of Example 2.

NMR (DMSO-d$_6$, δ): 0.88 (6H, d, J=8 Hz), 1.17 (6H, d, J=7 Hz), 1.82–1.95 (1H, m), 3.07 (2H, d, J=8 Hz), 3.57 (1H, septet, J=7 Hz), 5.68 (2H, s), 6.25 (1H, d, J=8 Hz), 7.18 (1H, t, J=8 Hz), 7.33 (1H, t, J=8 Hz), 7.57 (1H, d, J=8 Hz), 7.85 (1H, d, J=8 Hz), 7.95 (1H, s), 8.00 (1H, d, J=8 Hz)

EXAMPLE 12

1-(2-Chlorobenzyl)-2-isobutyl-3-isobutyrylindole-6-carboxamide (143 mg) was prepared from 1-(2- chlorobenzyl)-2-isobutyl-3-isobutyrylindole-6-carboxylic acid (160 mg) in a similar manner to that of Example 6.

NMR (DMSO-d$_6$, δ): 0.86 (6H, d, J=8 Hz), 1.17 (6H, d, J=7 Hz), 1.80–1.94 (1H, m), 3.02 (2H, d, J=8 Hz), 3.57 (1H, septet, J=7 Hz), 5.62 (2H, s), 6.16 (1H, d, J=8 Hz), 7.18 (1H, t, J=8 Hz), 7.30–7.35 (2H, m), 7.57 (1H, d, J=8 Hz), 7.82 (1H, d, J=8 Hz), 7.94 (1H, s), 7.96 (1H, d, J=8 Hz), 8.00 (1H, s)

EXAMPLE 13

Methyl 1-(2-chlorobenzyl)-2-ethyl-3-propionylindole-6-carboxylate (278 mg) was prepared from methyl 2-ethyl-3-propionylindole-6-carboxylate (215 mg) and 2-chlorobenzyl bromide (0.24 ml) in a similar manner to that of Example 1.

NMR (CDCl$_3$, δ): 1.22 (3H, t, J=7 Hz), 1.30 (3H, t, J=7 Hz), 3.05–3.20 (4H, m), 3.90 (3H, s), 5.50 (2H, s), 6.22 (1H, d, J=8 Hz), 7.02 (1H, t, J=8 Hz), 7.20 (1H, t, J=8 Hz), 7.46 (1H, d, J=8 Hz), 7.92 (1H, s), 7.95 (1H, d, J=8 Hz), 8.04 (1H, d, J=8 Hz)

EXAMPLE 14

1-(2-Chlorobenzyl)-2-ethyl-3-propionylindole-6-carboxylic acid (417 mg) was prepared from methyl 1-(2-chlorobenzyl)-2-ethyl-3-propionylindole-6-carboxylate (453 mg) in a similar manner to that of Example 2.

NMR (DMSO-d$_6$, δ) 1.09 (3H, t, J=7 Hz), 1.17 (3H, t, J=7 Hz), 3.08 (2H, t, J=7 Hz), 3.11 (2H, t, J=7 Hz), 5.68 (2H, s) 6.24 (1H, d, J=8 Hz), 7.18 (1H, t, J=8 Hz), 7.31 (1H, t, J=8 Hz), 7.57 (1H, d, J=8 Hz), 7.83 (1H, d, J=8 Hz), 7.95 (1H, s), 8.13 (1H, d, J=8 Hz)

EXAMPLE 15

1-(2-Chlorobenzyl)-2-ethyl-3-propionylindole-6-carboxamide (242 mg) was prepared from 1-(2-chlorobenzyl)-2-ethyl-3-propionylindole-6-carboxylic acid (252 mg) in a similar manner to that of Example 3.

NMR (CDCl$_3$, δ): 1.23 (3H, t, J=7 Hz), 1.29 (3H, t, J=7 Hz), 3.08–3.18 (4H, m), 5.49 (2H, s), 6.19 (1H, d, J=8 Hz), 7.02 (1H, t, J=8 Hz), 7.21 (1H, t, J=8 Hz), 7.46 (1H, d, J=8 Hz), 7.62 (1H, d, J=8 Hz), 7.83 (1H, s), 8.09 (1H, d, J=8 Hz)

EXAMPLE 16

Methyl 2-acetyl-1-(2-chlorobenzyl)-3-isobutylindole-6-carboxylate (71.4 mg) was prepared from methyl 2-acetyl-3-isobutylindole-6-carboxylate (58 mg) and 2-chlorobenzyl bromide (0.04 ml) in a similar manner to that of Example 1.

NMR (CDCl$_3$, δ): 1.02 (6H, d, J=7 Hz), 2.02 (1H, m), 2.59 (3H, s), 3.01 (2H, d, J=7 Hz), 3.90 (3H, s), 5.84 (2H, s), 6.19 (1H, d, J=8 Hz), 6.99 (1H, t, J=8 Hz), 7.15 (1H, t, J=8 Hz), 7.40 (1H, d, J=8 Hz), 7.75 (1H, d, J=8 Hz), 7.83 (1H, d, J=8 Hz), 7.98 (1H, s)

EXAMPLE 17

2-Acetyl-1-(2-chlorobenzyl)-3-isobutylindole-6-carboxylic acid (45.3 mg) was prepared from methyl 2-acetyl-1-(2-chlorobenzyl)-3-isobutylindole-6-carboxylate (67 mg) in a similar manner to that of Example 2.

NMR (CDCl$_3$, δ): 1.02 (6H, d, J=7 Hz), 2.03 (1H, m), 2.62 (3H, s), 3.03 (2H, d, J=7 Hz), 5.76 (2H, s), 6.19 (1H, d, J=8 Hz), 7.00 (1H, t, J=8 Hz), 7.14 (H, t, J=8 Hz), 7.41 (1H, d, J=8 Hz), 7.77 (1H, d, J=8 Hz), 7.86 (1H, d, J=8 Hz), 8.02 (1H, s)

EXAMPLE 18

2-Acetyl-1-(2-chlorobenzyl)-3-isobutylindole-6-carboxamide (33.4 mg) was prepared from 2-acetyl-1-(2-chlorobenzyl)-3-isobutylindole-6-carboxylic acid (41.7 mg) in a similar manner to that of Example 3.

NMR (CDCl$_3$, δ): 1.01 (6H, d, J=7 Hz), 2.02 (1H, m), 2.62 (3H, s), 3.03 (2H, d, J=7 Hz), 5.54 (2H, s), 6.22 (1H, d, J=8 Hz), 6.99 (1H, t, J=8 Hz), 7.16 (1H, t, J=8 Hz), 7.41 (1H, d, J=8 Hz), 7.54 (1H, d, J=8 Hz), 7.78 (1H, d, J=8 Hz), 7.79 (1H, s)

EXAMPLE 19

Methyl 1-(2-chlorobenzyl)-3-ethyl-2-propionylindole-6-carboxylate (66 mg) was prepared from methyl 3-ethyl-2-propionylindole-6-carboxylate (88 mg) and 2-chlorobenzyl bromide (0.051 ml) in a similar manner to that of Example 1.

NMR (CDCl$_3$, δ): 1.16 (3H, t, J=7 Hz), 1.38 (3H, t, J=7 Hz), 2.95 (2H, q, J=7 Hz), 3.14 (2H, q, J=7 Hz), 3.90 (3H, s), 5.72 (2H, s), 6.23 (1H, d, J=8 Hz), 6.98 (1H, t, J=8 Hz), 7.14 (1H, t, J=8 Hz), 7.39 (1H, d, J=8 Hz), 7.77 (1H, d, J=8 Hz), 7.85 (1H, d, J=8 Hz), 7.97 (1H, s)

EXAMPLE 20

1-(2-Chlorobenzyl)-3-ethyl-2-propionylindole-6-carboxylic acid (48.7 mg) was prepared from methyl 1-(2-chlorobenzyl)-3-ethyl-2-propionylindole-6-carboxylate (59.4 mg) in a similar manner to that of Example 2.

NMR (CDCl$_3$, δ): 1.16 (3H, t, J=7 Hz), 1.37 (3H, t, J=7 Hz), 2.94 (2H, q, J=7 Hz), 3.15 (2H, q, J=7 Hz), 5.72 (2H, s), 6.25 (1H, d, J=8 Hz), 6.99 (1H, t, J=8 Hz), 7.15 (1H, t, J=8 Hz), 7.40 (1H, d, J=8 Hz), 7.78 (1H, d, J=8 Hz), 7.87 (1H d, J=8 Hz), 8.01 (1H, s)

EXAMPLE 21

1-(2-Chlorobenzyl)-3-ethyl-2-propionylindole-6-carboxamide (40.4 mg) was prepared from 1-(2-chlorobenzyl)-3-ethyl-2-propionylindole-6-carboxylic acid (46 mg) in a similar manner to that of Example 3.

NMR (CDCl$_3$, δ): 1.16 (3H, t, J=7 Hz), 1.38 (3H, t, J=7 Hz), 2.96 (2H, q, J=7 Hz), 3.14 (2H, q, J=7 Hz), 5.72 (2H, s), 6.25 (1H, d, J=8 Hz), 7.00 (1H, t, J=8 Hz), 7.14 (1H, t, J=8 Hz), 7.39 (1H, d, J=8 Hz), 7.56 (1H, d, J=8 Hz), 7.79 (1H, s), 7.80 (1H, d, J=8 Hz)

EXAMPLE 22

The following compounds described in 1) to 6) were prepared by reacting the compound (I-2) obtained in Example 2 or Example 34-19), and a suitable amine (IV) in a similar manner to that of Example 3.

(1) 3-Acetyl-1-(2-chlorobenzyl)-N,N-dimethyl-2-propylindole-6-carboxamide mp: 150–153° C.

NMR (CDCl$_3$, δ): 1.03 (3H, t, J=7 Hz), 1.63 (2H, m), 2.72 (3H, s), 2.98 (6H, br s), 3.09 (2H, m), 5.44 (2H, s), 6.26 (1H, dd, J=1, 8 Hz), 7.03 (1H, dt, J=1, 8 Hz), 7.20 (1H, dt, J=1, 8 Hz), 7.29 (1H, s), 7.35 (1H, d, J=8 Hz), 7.43 (1H, dd, J=1, 8 Hz), 8.03 (1H, d, J=8 Hz)

(2) 3-Acetyl-1-(2-chlorobenzyl)-N-cyclopropylmethyl-2-propylindole-6-carboxamide mp: 158–162° C.

NMR (CDCl$_3$, δ): 0.28 (2H, m), 0.55 (2H, m), 1.03 (3H, t, J=7 Hz), 1.05 (1H, m), 1.60 (2H, m), 2.72 (3H, s), 3.04 (2H, m), 3.31 (2H, m), 5.49 (2H, s), 6.22 (1H, d, J=8 Hz), 6.28 (1H, m), 7.03 (1H, t, J=8 Hz), 7.22 (1H, t, J=8 Hz), 7.45 (1H, d, J=8 Hz), 7.61 (1H, dd, J=1, 8 Hz), 7.82 (1H, d, J=1 Hz), 8.05 (1H, d, J=8 Hz)

(3) 3-Acetyl-1-(2-chlorobenzyl)-N-(2-pyridylmethyl)-2-propylindole-6-carboxamide mp: 172–175° C.

NMR (CDCl$_3$, δ): 1.02 (3H, t, J=7 Hz), 1.63 (2H, m), 2.73 (3H, s), 3.07 (2H, m), 4.75 (2H, d, J=5 Hz), 5.51 (2H, s), 6.22 (1H, d, J=8 Hz), 7.02 (1H, t, J=8 Hz), 7.15–7.27 (2H, m), 7.33 (1H, d, J=8 Hz), 7.44 (1H, d, J=8 Hz), 7.58–7.76 (3H, s), 7.88 (1H, s), 8.07 (1H, d, J=8 Hz), 8.56 (1H, m)

(4) 3-Acetyl-1-(2-chlorobenzyl)-6-(morpholinocarbonyl)-2-propylindole

NMR (CDCl3 δ): 1.03 (3H, t, J=7 Hz), 1.63 (2H, m), 2.73 (3H, s), 3.09 (2H, m), 3.63 (8H, br s), 5.44 (2H, s), 6.23 (1H, d, J=8 Hz), 7.06 (1H, t, J=8 Hz), 7.2–7.4 (3H, m), 7.46 (1H, d, J=8 Hz), 8.06 (1H, d, J=8 Hz)

(5) 3-Acetyl-1-(2-chlorobenzyl)-N-phenylsulfonyl-2-propylindole-6-carboxamide mp: 206–208° C.

NMR (CDCl$_3$, δ): 0.99 (3H, t, J=7 Hz), 1.54 (2H, m), 2.72 (3H, s), 3.02 (2H, m), 5.43 (2H, s), 6.13 (1H, d, J=8 Hz), 7.00 (1H, t, J=8 Hz), 7.21 (1H, t, J=8 Hz), 7.43 (1H, d, J=8 Hz), 7.5–7.7 (4H, m), 7.77 (1H, s), 8.08 (1H, d, J=8 Hz), 8.13–8.18 (2H, m), 8.81 (1H, br s)

(6) 1-(2-Chlorobenzyl)-3-formyl-N-phenylsulfonyl-2-propylindole-6-carboxamide mp: 242–245° C.

NMR (CDCl$_3$, δ): 0.87 (3H, t, J=7 Hz), 1.49 (2H, m), 3.07 (2H, t, J=7 Hz), 5.66 (2H, s), 6.32 (1H, d, J=8 Hz), 7.18 (1H, t, J=8 Hz), 7.33 (1H, t, J=8 Hz), 7.55–7.75 (4H, m), 7.88 (1H, m), 7.96 (1H, s), 7.98 (1H, d, J=8 Hz), 8.09 (1H, s), 8.23 (1H, d, J=8 Hz)

(7) 1-(2-Chlorobenzyl)-3-formyl-2-propyl-N-(1H-tetrazol-5-yl)indole-6-carboxamide mp: 275° C. (dec.)

NMR (DMSO-d$_6$, δ): 0.90 (3H, t, J=7 Hz), 1.54 (2H, m), 3.13 (2H, t, J=7 Hz), 5.69 (2H, s), 6.38 (1H, d, J=8 Hz), 7.19 (1H, t, J=8 Hz), 7.33 (1H, t, J=8 Hz), 7.60 (1H, d, J=8 Hz), 8.03 (1H, d, J=8 Hz), 8.31 (1H, s), 8.32 (1H, d, J=8 Hz), >10 (1H, s)

EXAMPLE 23

1-Hydroxybenzotriazole (68 mg) and 1-(3-dimethylaminopropyl)-3-ethylcarbodiimide hydrochloride (72 mg) were added to a solution of 1-(2-chlorobenzyl)-3-isobutyryl-2-propylindole-6-carboxylic acid (100 mg) in dimethylformamide (3 ml), and the mixture was stirred at 20° C. overnight, then hydroxylamine hydrochloride (35 mg) and diisopropylethylamine (0.088 ml) were added. After stirred at 20° C. for 2 hours, the reaction mixture was partitioned between ethyl acetate and water. The organic phase was washed with 1N hydrochloric acid and brine, dried over sodium sulfate, and evaporated in vacuo. The residue was purified by preparative thin layer chromatography with 10% methanol in chloroform and recrystallization from ethyl acetate to give 1-(2-chlorobenzyl)-3-isobutyryl-2-propylindole-6-carbohydroxamic acid (67 mg) as pale red crystals.

mp: 185–186° C.

NMR (CDCl$_3$, δ): 1.00 (3H, t, J=8 Hz), 1.28 (6H, d, J=8 Hz), 1.60 (2H, sextet, J=8 Hz), 3.02–3.06 (2H, m), 3.53 (2H, septet, J=8 Hz), 5.47 (2H, s), 6.20 (1H, dd, J=1, 8 Hz), 7.03 (1H, t, J=8 Hz), 7.20 (1H, t, J=8 Hz), 7.46 (1H, d, J=8 Hz), 7.57 (1H, d, J=8 Hz), 7.77 (1H, s), 7.97 (1H, d, J=8 Hz)

EXAMPLE 24

The following compounds described in 1) to 2) were prepared by reacting the compound (I-2) obtained in Example 5 and a suitable amine (IV) in a similar manner to that of Example 23.

(1) 1-(2-Chlorobenzyl)-3-isobutyryl-O-methyl-2-propylindole-6-carbohydroxamic acid NMR (CDCl$_3$, δ): 1.00 (3H, t, J=8 Hz), 1.30 (6H, d, J=8 Hz), 1.54–1.66 (2H, m), 3.00–3.06 (2H, m), 3.53 (1H, septet, J=8 Hz), 3.86 (3H, s), 5.49 (2H, s), 6.22 (1H, dd, J=1, 8 Hz), 7.03 (1H, dt, J=1, 8 Hz), 7.23 (1H, dt, J=1, 8 Hz), 7.46 (1H, dd, J=1, 8 Hz), 7.56 (1H, dd, J=1, 8 Hz), 7.75 (1H, d, J=1 Hz), 7.96 (1H, d, J=8 Hz), 8.82 (1H, s)

(2) 1-(2-Chlorobenzyl)-3-isobutyl-2-propyl-N-(2-pyridylmethyl)indole-6-carboxamide NMR (CDCl$_3$, δ): 1.00 (3H, t, J=8 Hz), 1.30 (6H, d, J=8 Hz), 1.62 (2H, sextet, J=8 Hz), 3.03–3.07 (2H, m), 3.57 (1H, septet, J=8 Hz), 4.66 (2H, d, J=6 Hz), 5.50 (2H, s), 6.24 (1H, dd, J=1, 8 Hz), 7.02 (1H, dt, J=1, 8 Hz), 7.18–7.24 (2H, m), 7.33 (1H, d, J=8 Hz), 7.45 (1H, d, J=8 Hz), 7.62–7.68 (2H, m), 7.72 (1H, dd, J=1, 8 Hz), 7.88 (1H, d, J=1 Hz), 7.98 (1H, d, J=8 Hz), 8.56 (1H, d, J=6 Hz)

EXAMPLE 25

The following compounds described in 1) to 2) were prepared by reacting the compound (II) obtained in Preparation 8 (2) and a suitable halide (III) in a similar manner to that of Example 1.

(1) 1-(4-Chloro-2-fluorobenzyl)-3-isobutyryl-2-propylindole-6-carboxamide mp: 200–202° C.

IR (KBr): 3380, 3195, 1650, 1620 cm$^{-1}$

NMR (CDCl$_3$, δ): 1.03 (3H, t, J=7 Hz), 1.30 (6H, d, J=7 Hz), 1.52–1.65 (2H, m), 3.06–3.10 (2H, m), 3.49–3.59 (1H, m), 5.47 (2H, s), 6.34 (1H, ddd, J=8, 8, 1 Hz), 6.94 (1H, dd, J=8, 1 Hz), 7.19 (1H, d, J=8 Hz), 7.60 (1H, d, J=8 Hz), 7.89 (1H, s), 7.97 (1H, d, J=8 Hz)

MASS (m/z): 415 (M$^+$+1), 76 (bp)

(2) 3-Isobutyryl-(2-methoxycarbonylbenzyl)-2-propylindole-6-carboxamide mp: 170–172° C.

IR (KBr): 3420, 1720, 1650 cm$^{-1}$

NMR (CDCl$_3$, δ): 1.00 (3H, t, J=7 Hz), 1.33 (6H, d, J=7 Hz), 1.56–1.69 (2H, m), 3.00–3.06 (2H, m), 3.54–3.63 (1H, m), 4.02 (3H, s), 5.91 (2H, s), 6.69 (1H, d, J=7.5 Hz), 7.24–7.36 (1H, m), 7.63 (1H, dd, J=8, 1 Hz), 7.80 (1H, s), 7.99 (1H, d, J=8 Hz), 8.12–8.16 (1H, m)

MASS (m/z): 421 (M$^+$+1)

EXAMPLE 26

A mixture of 3-isobutyryl-2-propylindole-6-carboxamide (100 mg), 4-chlorobenzyl bromide (113 mg) and potassium carbonate (152 mg) in dimethylformamide (2 ml) was heated at 60° C. for 2 hours, and partitioned between ethyl acetate and water. The organic layer was washed with water and brine, and dried over magnesium sulfate. After evaporation of solvent, the residue was crystallized from a mixture of ethyl acetate and hexane. The crude crystals were recrystallized from a mixture of ethyl acetate and hexane to give 1-(4-chlorobenzyl)-3-isobutyryl-2-propylindole-6-carboxamide (97 mg) as colorless crystals.

mp: 183–184° C.

NMR (CDCl$_3$, δ): 1.01 (3H, t, J=7 Hz), 1.29 (6H, d, J=7 Hz), 1.50–1.64 (2H, m), 3.06–3.12 (2H, m), 3.55 (2H, septet, J=7 Hz), 5.42 (2H, s), 6.87 (2H, d, J=8 Hz), 7.25 (2H, d, J=8 Hz), 7.60 (1H, dd, J=1, 8 Hz), 7.87 (1H, d, J=1Hz), 7.95 (1H, d, J=8 Hz)

EXAMPLE 27

The following compounds described in 1) to 8) were prepared by reacting the compound (II) obtained in Preparation 8 (2) or Preparation 15 (3), and a suitable halide (III) in a similar manner to that of Example 26.

(1) 1-Benzyl-3-isobutyryl-2-propylindole-6-carboxamide
mp: 164–166° C.
NMR (CDCl$_3$, δ): 1.00 (3H, t, J=7 Hz), 1.29 (6H, d, J=7 Hz), 1.60 (2H, sextet, J=7 Hz), 3.09–3.13 (2H, m), 3.55 (2H, septet, J=7 Hz), 5.46 (2H, s), 6.96–6.98 (2H, m), 7.24–7.32 (2H, m), 7.61 (1H, d, J=8 Hz), 7.91 (1H, s), 7.95 (1H, d, J=8 Hz)

(2) 1-(3-Chlorobenzyl)-3-isobutyryl-2-propylindole-6-carboxamide
mp: 164–166° C.
NMR (CDCl$_3$, δ): 1.00 (3H, t, J=7 Hz), 1.30 (6H, d, J=7 Hz), 1.50–1.65 (2H, m), 3.06–3.12 (2H, m), 3.55 (2H, septet, J=7 Hz), 5.42 (2H, s), 6.78 (1H, dd, J=1, 8 Hz), 6.96 (1H, d, J=1 Hz), 7.18–7.27 (2H, m), 7.60 (1H, d, J=8 Hz), 7.88 (1H, s), 7.95 (1H, d, J=8 Hz)

(3) 3-Isobutyryl-2-propyl-1-(2-trifluoromethylbenzyl) indole-6-carboxamide
mp: 86–87° C.
NMR (CDCl$_3$, δ): 0.99 (3H, t, J=7 Hz), 1.30 (6H, d, J=7 Hz), 1.52–1.65 (2H, m), 2.98–3.04 (2H, m), 3.56 (2H, septet, J=7 Hz), 5.62 (2H, s), 6.33 (1H, d, J=8 Hz), 7.30 (1H, t, J=1 Hz), 7.38 (1H, t, J=1 Hz), 7.64 (1H, d, J=8 Hz), 7.75 (1H, d, J=8 Hz), 7.84 (1H, s), 7.98 (1H, d, J=8 Hz)

(4) 3-Isobutyryl-1-(2-phenylbenzyl)-2-propylindole-6-carboxamide
mp: 162–164° C.
NMR (CDCl$_3$, δ): 0.89 (3H, t, J=7 Hz), 1.27 (6H, d, J=7 Hz), 1.36–1.50 (2H, m), 2.90–2.96 (2H, m), 3.53 (2H, septet, J=7 Hz), 5.32 (2H, s), 6.48 (1H, d, J=8 Hz), 7.10–7.16 (1H, m), 7.30–7.34 (2H, m), 7.42– 7.84 (3H, m), 7.52–7.55 (2H, m), 7.60 (1H, d, J=8 Hz), 7.84 (1H, s), 7.93 (1H, d, J=8 Hz)

(5) 1-[(5-Chlorothien-2-yl)methyl]-3-isobutyryl-2-propylindole-6-carboxamide
mp: 178–180° C.
NMR (CDCl$_3$, δ): 1.07 (3H, t, J=7 Hz), 1.27 (6H, d, J=7 Hz), 1.65 (2H, sextet, J=7 Hz), 3.15–3.20 (2H, m), 3.54 (2H, septet, J=7 Hz), 5.46 (2H, s), 6.59 (1H, d, J=2 Hz), 6.72 (2H, d, J=2 Hz), 7.60 (1H, d, J=8 Hz), 7.92 (1H, d, J=8 Hz), 8.04 (1H, s)

(6) 3-Isobutyryl-1-phenethyl-2-propylindole-6-carboxamide
mp: 180–181° C.
NMR (CDCl$_3$, δ): 1.02 (3H, t, J=7 Hz), 1.26 (6H, d, J=7 Hz), 1.61 (2H, septet, J=7 Hz), 2.88–2.92 (2H, m), 3.10 (2H, t, J=7 Hz), 3.52 (2H, septet, J=7 Hz), 4.42 (2H, t, J=7 Hz), 7.05–7.09 (2H, m), 7.22–7.32 (3H, m), 7.52 (1H, d, J=8 Hz), 7.92 (1H, d, J=8 Hz), 7.96 (1H, s)

(7) 1-(2-Chlorobenzyl)-3-methoxyacetyl-2-propylindole-6-carboxamide
mp: 165–167° C.
NMR (DMSO-d$_6$, δ): 0.92 (3H, t, J=8 Hz), 1.46 (2H, sextet, J=8 Hz), 3.01–3.05 (2H, m), 3.42 (3H, s), 4.68 (2H, s), 5.62 (2H, s), 6.22 (1H, d, J=8 Hz), 7.16 (1H, t, J=8 Hz), 7.28 (1H, br s), 7.32 (1H, t, J=8 Hz), 7.56 (1H, d, J=8 Hz), 7.92 (1H, d, J=8 Hz), 7.93 (1H, br s), 8.01 (1H, s)

(8) 1-(6-Chloro-3,4-methylenedioxybenzyl)-3-methoxyacetyl-2-propylindole-6-carboxamide
mp: 204–206° C.
NMR (DMSO-d$_6$, δ): 0.95 (3H, t, J=8 Hz), 1.50 (2H, sextet, J=8 Hz), 3.02–3.06 (2H, m), 3.40 (3H, s), 4.70 (2H, s), 5.51 (1H, s), 5.98 (2H, s), 7.23 (1H, s), 7.32 (1H, br s), 7.80 (1H, d, J=8 Hz), 7.93 (1H, d, J=8 Hz), 7.96 (1H, br s), 8.02 (1H, s)

EXAMPLE 28

The following compounds described in 1) to 16) were prepared by reacting the compound (II) obtained in Preparation 2, Preparation 6 (1), Preparation 9, Preparation 10, Preparation 12, Preparation 13 (4) or Preparation 14 (5) and a suitable halide (III) in a similar manner to that of Example 1.

(1) Methyl 1-(2-fluorobenzyl)-3-isobutyryl-2-propylindole-6-carboxylate
mp: 120–121.5° C.
IR (KBr): 1710, 1700, 1660 cm$^{-1}$
NMR (CDCl$_3$, δ): 1.02 (3H, t, J=7 Hz), 1.29 (6H, d, J=7 Hz), 1.55–1.64 (2H, m), 3.06–3.12 (2H, m), 3.15–3.61 (1H, m), 3.92 (3H, s), 5.50 (2H, s), 6.43 (1H, t, J=7.5 Hz), 6.95 (1H, t, J=7 Hz), 7.10–7.17 (1H, m), 7.22–7.28 (1H, m), 7.95 (2H, s), 8.02 (1H, s)
MASS (m/z): 396 (M$^+$+1), 76 (bp)

(2) Methyl 1-(2-bromobenzyl)-3-isobutyryl-2-propylindole-6-carboxylate
mp: 90–92° C.
IR (KBr): 1705, 1650 cm$^{-1}$
NMR (CDCl$_3$, δ): 1.02 (3H, t, J=7 Hz), 1.30 (6H, d, J=7 Hz), 1.56–1.67 (2H, m), 3.04 (2H, t, J=7 Hz), 3.52–3.61 (1H, m), 3.93 (3H, s), 5.47 (2H, s), 6.20 (1H, t, J=7.5 Hz), 7.06–7.18 (2H, m), 7.65 (1H, t, J=7.5 Hz), 7.95 (1H, s, 7.97 (2H, s)
MASS (m/z) 458 (M$^+$+1+2), 458 (M$^+$+1), 76 (bp)

(3) Methyl 1-(2-iodobenzyl)-3-isobutyryl-2-propylindole-6-carboxylate
IR (KBr): 1710, 1650, 1430 cm$^{-1}$
NMR (CDCl$_3$, δ): 1.03 (3H, t, J=7 Hz), 1.30 (6H, d, J=7 Hz), 1.53–1.67 (2H, m), 2.98–3.05 (2H, m), 3.53–3.62 (1H, m), 3.93 (3H, s), 5.37 (2H, s), 6.16 (1H, t, J=7.5 Hz), 6.99 (1H, t, J=7.5 Hz), 7.12 (1H, t, J=7.5 Hz), 7.90–7.97 (4H, m)
MASS (m/z): 504 (M$^+$+1)

(4) Methyl 3-isobutyryl-1-(2-methylbenzyl)-2-propylindole-6-carboxylate
mp: 99–102° C.
IR (KBr): 1705, 1650, 1285 cm$^{-1}$
NMR (CDCl$_3$, δ): 1.00 (3H, t, J=7 Hz), 1.30 (6H, d, J=7 Hz), 1.54–1.69 (2H, m), 2.50 (3H, s), 3.00–3.06 (2H, m), 3.51–3.65 (1H, m), 3.89 (3H, s), 5.39 (2H, s), 6.17 (1H, t, J=7.5 Hz), 6.98 (1H, t, J=7.5 Hz), 7.18 (1H, t, J=7.5 Hz), 7.25 (1H, d, J=7.5 Hz), 7.92 (1H, s), 7.96 (2H, s)
MASS (m/z): 392 (M$^+$+1)

(5) Methyl 3-isobutyryl-1-(2-methoxybenzyl)-2-propylindole-6-carboxylate
mp: 103–105° C.
IR (KBr): 1710, 1650 cm$^{-1}$
NMR (CDCl$_3$, δ): 1.01 (3H, t, J=7 Hz), 1.30 (6H, d, J=7 Hz), 1.56–1.68 (2H, m), 3.05–3.10 (2H, m), 3.53–3.62 (1H, m), 3.90 (3H, s), 3.98 (3H, s), 5.44 (2H, s), 6.27 (1H, d, J=7.5 Hz), 6.74 (1H, t, J=7.5 Hz), 6.94 (1H, d, J=7.5 Hz), 7.25 (1H, t, J=7.5 Hz), 7.95 (2H, s), 8.00 (1H, d, J=7.5 Hz)
MASS (m/z): 408 (M$^+$+1), 76 (bp)

(6) Methyl 1-(2-cyanobenzyl)-3-isobutyryl-2-propylindole-6-carboxylate
mp: 159–161° C.
IR (KBr): 2220, 1730, 1660 cm$^{-1}$
NMR (CDCl$_3$, δ): 1.04 (3H, t, J=7 Hz), 1.30 (6H, d, J=7 Hz), 1.52–1.65 (2H, m), 3.03–3.08 (2H, m), 3.53–3.60 (1H, m), 3.92 (3H, s), 5.66 (2H, s), 6.44–6.49 (1H, m), 7.38–7.43 (2H, m), 7.76–7.80 (1H, m), 7.95 (1H, s), 7.98 (2H, s)
MASS (m/z): 403 (M$^+$+1), 76 (bp)

(7) Methyl 3-isobutyryl-1-(2-nitrobenzyl)-2-propylindole-6-carboxylate
mp: 165.5–166.5° C.
IR (KBr): 1705, 1650, 1530, 1520 cm$^{-1}$
NMR (CDCl$_3$, δ): 1.00 (3H, t, J=7 Hz), 1.31 (6H, d, J=7 Hz), 1.56–1.65 (2H, m), 3.03 (2H, t, J=7 Hz), 3.54–3.65 (1H, m), 3.90 (3H, s), 5.89 (2H, s), 6.27 (1H, d, J=7.5 Hz), 7.40–7.51 (2H, m), 7.89 (1H, s), 8.00 (2H, s), 8.30 (1H, d, J=7.5 Hz)

MASS (m/z): 423 (M$^+$+1), 76 (bp)

(8) Methyl 1-(2,6-dichlorobenzyl)-3-isobutyryl-2-propylindole-6-carboxylate mp: 129.5–132° C.

IR (KBr): 1710, 1660, 1430-cm$^{-1}$

NMR (CDCl$_3$, δ): 0.96 (3H, t, J=7 Hz), 1.27 (6H, d, J=7 Hz), 1.38–1.50 (2H, m), 3.15–3.20 (2H, m), 3.47–3.60 (1H, m), 3.92 (3H, s), 5.70 (2H, s), 7.17–7.39 (3H, m), 7.88 (2H, s), 8.03 (1H, s)

MASS (m/z): 446 (M$^+$+1)

(9) Methyl-1-(2-chloro-4-fluorobenzyl)-3-isobutyryl-2-propylindole-6-carboxylate IR (KBr): 1705, 1649, 1488, 1279 cm$^{-1}$ NMR (CDCl$_3$, δ): 1.03 (3H, t, J=7 Hz), 1.40 (6H, d, J=7 Hz), 1.52–1.66 (2H, m), 3.01–3.06 (2H, m), 3.52–3.60 (1H, m), 3.93 (3H, s), 5.48 (2H, s), 6.20–6.25 (1H, m), 6.79 (1H, ddd, J=7.5, 7.5, 1 Hz), 7.21–7.25 (1H, m), 7.94 (1H, s), 7.97 (2H, s)

MASS (m/z): 430 (M$^+$+1), 76 (bp)

(10) Methyl 1-(4-bromo-2-fluorobenzyl)-3-isobutyryl-2-propylindole-6-carboxylate mp: 110–111.5° C.

IR (KBr): 1705, 1649, 1488, 1279 cm$^{-1}$

NMR (CDCl$_3$, δ): 1.03 (3H, t, J=7 Hz), 1.29 (6H, d, J=7 Hz), 1.53–1.65 (2H, m), 3.05–3.10 (2H, m), 3.51–3.60 (1H, m), 3.94 (3H, s), 5.44 (2H, s), 6.28 (1H, t, J=7.5 Hz), 7.10 (1H, dd, J=7.5, 1 Hz), 7.35 (1H, d, J=7.5 Hz), 7.96 (1H, s)

MASS (m/z): 476 (M$^+$+1), 474 (M$^+$), 76 (bp)

(11) Methyl 3-benzoyl-1-(2-chlorobenzyl)-2-propylindole-6-carboxylate

NMR (CDCl$_3$, δ): 0.94 (3H, t, J=8 Hz), 1.56–1.70 (2H, m), 2.93–2.98 (2H, m), 3.87 (3H, s), 5.55 (2H, s), 6.33 (1H, ddd, J=1, 8 Hz), 7.08 (1H, dt, J=1, 8 Hz), 7.21 (1H, d, J=8 Hz), 7.22–7.28 (1H, m), 7.46–7.52 (3H, m), 7.57–7.63 (1H, m), 7.72–7.82 (3H, m), 7.93 (1H, d, J=1 Hz)

(12) Methyl 1(2-chlorobenzyl)-3-cyano-2-propylindole-6-carboxylate mp: 132–133° C.

IR (KBr): 2215, 1709, 1284 cm$^{-1}$

NMR (CDCl$_3$, δ): 1.01 (3H, t, J=7 Hz), 1.70 (2H, sextet, J=7 Hz), 2.89 (2H, t, J=7.5 Hz), 3.92 (3H, s, 5.49 (2H, s), 6.24 (1H, d, J=7.5 Hz), 7.08 (1H, t, J=7.5 Hz), 7.22–7.28 (1H, m), 7.47 (1H, d, J=7.5 Hz), 7.77 (1H, d, J=7.5 Hz), 7.95–8.00 (2H, m)

MASS (m/z): 367 (M$^+$+1), 76 (bp)

(13) Methyl 1-(2-chlorobenzyl)-2-ethyl-3-isobutyrylindole-6-carboxylate

NMR (CDCl$_3$, δ): 1.22 (3H, t, J=7 Hz), 1.31 (6H, d, J=7 Hz, 3.08 (2H, q, J=7 Hz), 3.56 (1H, m), 3.91 (3H, s), 5.50 (2H, s), 6.23 (1H, d, J=8 Hz), 7.04 (1H, t, J=8 Hz), 7.22 (1H, t, J=8 Hz), 7.46 (1H, d, J=8 Hz), 7.93–7.98 (3H, m)

(14) Methyl 1-(2-chlorobenzyl)-3-isobutyryl-2-methylindole-6-carboxylate

NMR (CDCl$_3$, δ): 1.32 (6H, d, J=7 Hz), 2.71 (3H, s), 3.56 (1H, m), 3.92 (3H, s), 5.52 (2H, s), 6.24 (1H, d, J=8 Hz), 7.05 (1H, t, J=8 Hz), 7.23 (1H, t, J=8 Hz), 7.46 (1H, d, J=8 Hz), 7.92–8.05 (3H, m)

(15) Methyl 1-(2-chlorobenzyl)-3-isobutyryl-2-methoxymethylindole-6-carboxylate

NMR (CDCl$_3$, δ): 1.29 (6H, d, J=7 Hz), 3.31 (3H, s), 3.55 (1H, m), 3.89 (3H, s), 4.91 (2H, s), 5.63 (2H, s, 6.23 (1H, d, J=8 Hz), 7.02 (1H, t, J=8 Hz), 7.19 (1H, 7, J=8 Hz), 7.44 (1H, d, J=8 Hz), 7.95–8.02 (3H, m)

(16) Methyl 1-(2-chlorobenzyl)-3-isobutyrylindole-6-carboxylate

NMR (CDCl$_3$, δ): 1.26 (6H, d, J=7 Hz), 3.28 (1H, m), 3.93 (3H, s), 5.52 (2H, s), 6.77 (1H, d, J=8 Hz), 7.18 (1H, t, J=8 Hz), 7.29 (1H, t, J=8 Hz), 7.48 (1H, d, J=8 Hz), 7.89 (1H, s, 8.02 (1H, d, J=8 Hz), 8.10 (1H, s), 8.49 (1H, d, J=8 Hz)

EXAMPLE 29

The following compounds described in 1) to 2) were prepared from the compound (II) obtained in Preparation 1 (5) and Preparation 2 in a similar manner to that of Example 26.

(1) Methyl 3-isobutyryl-2-propyl-1-(2-pyridylmethyl) indole-6-carboxylate

NMR (CDCl$_3$, δ): 1.01 (3H, t, J=7 Hz), 1.30 (6H, d, J=7 Hz), 1.60 (2H, sextet, J=7 Hz), 3.12–3.16 (2H, m), 3.56 (2H, septet, J=7 Hz), 3.90 (3H, s), 5.58 (2H, s), 6.58 (1H, d, J=8 Hz), 7.22 (1H, dd, J=5, 8 Hz), 7.55 (1H, dt, J=1, 8 Hz), 7.94 (2H, s), 8.02 (1H, s), 8.63 (1, dd, J=1, 5 Hz)

(2) Methyl 3-acetyl-1-(6-chloro-3,4-methylenedioxybenzyl)-2-propylindole-6-carboxylate mp: 210–212° C.

NMR (CDCl$_3$, δ): 1.04 (3H, t, J=7 Hz), 1.63 (2H, sextet, J=7 Hz), 2.37 (3H, s), 3.04–3.08 (2H, m), 3.92 (3H, s), 5.40 (2H, s), 5.70 (1H, s), 5.90 (2H, s), 6.92 (1H, s), 7.95 (1H, s), 7.97 (1H, d, J=8 Hz), 8.04 (1H, d, J=8 Hz)

EXAMPLE 30

To a solution of methyl 3-acetyl-1-(2-chlorobenzyl)-2-ethylindole-6-carboxylate (110 mg) in tetrahydrofuran (5 ml) was added 1M solution of boran in tetrahydrofuran (0.6 ml) in one portion at 0° C. The mixture was stirred at 20° C. for 1 hour, then quenched with water and extracted with ethyl acetate. The organic phase was washed with brine, dried over magnesium sulfate and evaporated in vacuo. The residue was chromatographed on silica gel eluting with a mixture of hexane and ethyl acetate (2:1) to give methyl 1-(2-chlorobenzyl)-2,3-diethylindole-6-carboxylate (42 mg) as colorless crystals.

mp: 86–88° C.

IR (KBr): 1710, 1240 cm$^{-1}$

NMR (CDCl$_3$, δ): 1.13 (3H, t, J=7 Hz), 1.30 (3H, t, J=7 Hz), 2.69 (2H, t, J=7 Hz), 2.79 (2H, q, J=7 Hz), 3.90 (3H, s), 5.44 (2H, s), 6.17 (1H, d, J=8 Hz), 7.00 (1H, t, J=8 Hz), 7.19 (1H, t, J=8 Hz), 7.42 (1H, d, J=7.5 Hz), 7.60 (1H, d, J=8 Hz), 7.80 (1H, d, J=8 Hz), 7.88 (1H, s)

MASS (m/z): 356 (M$^+$+1)

EXAMPLE 31

Methyl 1-(2-chlorobenzyl)-2-propylindole-6-carboxylate (400 mg) was prepared from methyl 2-propylindole-6-carboxylate (350 mg) and 2-chlorobenzyl bromide (364 mg) in a similar manner to that of Example 1.

NMR (CDCl$_3$, δ): 0.99 (3H, t, J=8 Hz), 1.74 (2H, sextet, J=8 Hz), 2.60 (2H, t, J=8 Hz), 3.87 (3H, s), 5.43 (2H, s), 6.16 (1H, d, J=8 Hz), 6.43 (1H, s), 7.00 (1H, t, J=8 Hz), 7.18 (1H, t, J=8 Hz), 7.43 (1H, d, J=8 Hz), 7.60 (1H, d, J=8 Hz), 7.80 (1H, d, J=8 Hz), 7.90 (1H, s)

EXAMPLE 32

To a stirred solution of dimethylformamide (3 ml) and phosphorus oxychloride (0.056 ml) was added methyl 2-propylindole-6-carboxylate (187 mg), and the mixture was stirred at 0° C. for 20 minutes. The resulting mixture was poured into ammonia water (3 ml) and extracted with ethyl acetate. The combined organic phase was washed with brine, then dried over sodium sulfate and evaporated in vacuo. The residue was chromatographed on silica gel to give methyl 1-(2-chlorobenzyl)-3-formyl-2-propylindole-6-carboxylate (153 mg) as colorless oil.

NMR (CDCl$_3$, δ): 1.00 (3H, t, J=7 Hz), 1.66 (2H, m), 3.01 (2H, t, J=7 Hz), 3.90 (3H, s), 5.48 (2H, s), 6.29 (1H, d, J=8 Hz), 7.06 (1H, t, J8 Hz), 7.24 (1H, t, J=8 Hz), 7.47 (1H, d, J=8 Hz), 7.91 (1H, s), 8.01 (1H, d, J=8 Hz), 8.37 (1H, d, J=8 Hz), >10 (1H, s)

EXAMPLE 33

Methyl 1-(2-chlorobenzyl)-3-phenylacetyl-2-propylindole-6-carboxylate (230 mg) was prepared from methyl 1-(2-chlorobenzyl)-2-propylindole-6-carboxylate (380 mg) and phenylacetyl chloride (189 mg) in a similar manner to that of Preparation 1 (5).

NMR (CDCl$_3$, δ): 0.97 (3H, t, J=8 Hz), 1.55–1.67 (2H, m), 3.02–3.07 (2H, m), 3.91 (3H, s), 4.42 (2H s), 5.52 (2H, s), 6.24 (1H, d, J=8 Hz), 7.05 (1H, t, J=8 Hz), 7.20–7.40 (6H, m), 7.46 (1H, d, J=8 Hz), 7.97 (1H, s), 7.99 (1H, d, J=8 Hz), 8.11 (1H, d, J=8 Hz)

EXAMPLE 34

The following compounds described in 1) to 21) were prepared from the compound (I-1) obtained in Example 28, Example 29, Example 30, Example 32 or Example 33 in a similar manner to that of Example 2.

(1) 1-(2-Fluorobenzyl)-3-isobutyryl-2-propylindole-6-carboxylic acid
mp: 212–213° C.
IR (KBr): 1685, 1650 cm$^{-1}$
NMR (CDCl$_3$, δ): 1.03 (3H, t, J=7 Hz), 1.30 (6H, d, J=7 Hz), 1.55–1.68 (2H, m), 3.09–3.14 (2H, m), 3.52–3.62 (1H, m), 5.50 (2H, s), 6.47 (1H, t, J=7.5 Hz), 6.97 (1H, t, J=7.5 Hz), 7.15 (1H, t, J=7.5 Hz), 7.24–7.30 (1H, m), 7.95–8.04 (2H, m), 8.08 (1H, s)
MASS (m/z): 380 (M$^+$−1)

(2) 1-(2-Bromobenzyl)-3-isobutyryl-2-propylindole-6-carboxylic acid
mp: 193–194° C.
IR (KBr): 1690, 1670 cm$^{-1}$
NMR (CDCl$_3$, δ): 1.03 (3H, t, J=7 Hz), 1.3 (6H, d, J=7 Hz), 1.57–1.65 (2H, m), 3.01–3.07 (2H, m), 3.52–3.61 (1H, m), 5.49 (2H, s), 6.22 (1H, t, J=7.5 Hz), 7.07–7.18 (2H, m), 7.66 (1H, t, J=7.5 Hz), 7.97–8.01 (3H, m)
MASS (m/z): 442 (M$^+$), 440 (M$^+$−2)

(3) 1-(2-Iodobenzyl)-3-isobutyryl-2-propylindole-6-carboxylic acid
mp: 210° C.
IR (KBr): 1710, 1640, 1435, 1200 cm$^{-1}$
NMR (CDCl$_3$, δ): 1.04 (3H, t, J=7 Hz), 1.31 (6H, d, J=7 Hz), 1.55–1.68 (2H, m), 3.00–3.06 (2H, m), 3.53–3.62 (1H, m), 5.38 (2H, s), 6.18 (1H, d, J=7.5 Hz), 6.99 (1H, t, J=7.5 Hz), 7.14 (1H, t, J=7.5 Hz), 7.94 (1H, d, J=7.5 Hz), 7.97–8.03 (3H, m)
MASS (m/z): 488 (M$^+$−1), 61 (bp)

(4) 3-isobutyryl-1-(2-methylbenzyl)-2-propylindole-6-carboxylic acid
mp: 186–188° C.
IR (KBr): 1690 cm$^{-1}$
NMR (CDCl$_3$, δ): 1.01 (3H, t, J=7 Hz), 1.31 (6H, d, J=7 Hz), 1.56–1.69 (2H, m), 2.50 (3H, s), 3.02–3.09 (2H, m), 3.52–3.67 (1H, m), 5.39 (2H, s), 6.17 (1H, d, J=7.5 Hz), 6.98 (1H, t, J=7.5 Hz), 7.17 (1H, t, J=7.5 Hz), 7.25 (1H, t, J=7.5 Hz), 7.97 (1H, s), 8.00 (2H, s)
MASS (m/z): 378 (M$^+$+1), 76 (bp)

(5) Isobutyryl-1-(2-methoxybenzyl)-2-propylindole-6-carboxylic acid
mp: 190–191° C.
IR (KBr): 1685, 1650, 1250 cm$^{-1}$
NMR (CDCl$_3$, δ): 1.03 (3H, t, J=7 Hz), 1.30 (6H, d, J=7 Hz), 1.58–1.68 (2H, m), 3.07–3.13 (2H, m), 3.54–3.63 (1H, m), 3.98 (3H, s), 5.45 (2H, s), 6.30 (1H, d, J=7.5 Hz), 6.75 (1H, t, J=7.5 Hz), 6.94 (1H, d, J=7.5 Hz), 7.24 (1H, t, J=7.5 Hz), 7.94–8.02 (2H, m), 8.05 (1H, s)
MASS (m/z): 394 (M$^+$+1), 76 (bp)

(6) 1-(2-Cyanobenzyl)-3-isobutyryl-2-propylindole-6-carboxylic acid
mp: 213.5–215° C.
IR (KBr): 2220, 1717 cm$^{-1}$
NMR (CDCl$_3$, δ): 1.04 (3H, t, J=7 Hz), 1.31 (6H, d, J=7 Hz), 1.53–1.67 (2H, m), 3.04–3.09 (2H, m), 3.52–3.62 (1H, m), 5.69 (2H, s), 6.47–6.50 (1H, m), 7.39–7.44 (2H, m), 7.77–7.80 (1H, m), 7.99–8.04 (3H, m)
MASS (m/z): 389 (M$^+$−1), 76 (bp)

(7) 3-Isobutyryl-1-(2-nitrobenzyl)-2-propylindole-6-carboxylic acid
mp: 214–215° C.
IR (KBr): 1695, 1655, 1545 cm$^{-1}$
NMR (CDCl$_3$, δ): 1.02 (3H, t, J=7 Hz), 1.32 (6H, d, J=7 Hz), 1.57–1.65 (2H, m), 3.03 (2H, t, J=7 Hz), 3.54–3.63 (1H, m), 5.89 (2H, s), 6.28 (1H, d, J=7.5 Hz), 7.39–7.51 (2H, m), 7.92 (1H, s), 8.02 (2H, s), 8.30 (1H, d, J=7.5 Hz)
MASS (m/z): 409 (M$^+$+1)

(8) 1-(2,6-Dichlorobenzyl)-3-isobutyryl-2-propylindole-6-carboxylic acid
mp: 241.5–243° C. (dec.)
IR (KBr): 1675, 1650 cm$^{-1}$
NMR (CDCl$_3$, δ): 0.99 (3H, t, J=7 Hz), 1.28 (6H, d, J=7 Hz), 1.39–1.52 (2H, m), 3.17–3.22 (2H, m), 3.50–3.59 (1H, m), 5.71 (2H, s), 7.24–7.28 (1H, m), 7.37–7.40 (2H, m), 7.94 (2H, q, J=7.5 Hz), 8.10 (1H, s)
MASS (m/z): 432 (M$^+$+1), 76 (bp)

(9) 1-(2-Chloro-4-fluorobenzyl)-3-isobutyryl-2-propylindole-6-carboxylic acid
mp: 243–244° C.
IR (KBr): 1676, 1648, 1491 cm$^{-1}$
NMR (CDCl$_3$, δ): 1.03 (3H, t, J=7 Hz), 1.30 (6H, d, J=7 Hz), 1.60 (2H, sextet, J=7 Hz), 3.01–3.07 (2H, m), 3.53–3.62 (1H, m), 5.49 (2H, s), 6.20–6.26 (1H, m), 6.79 (1H, ddd, J=7.5, 7.5, 1 Hz), 7.23 (1H, dd, J=7.5, 1 Hz), 7.96 (1H, s), 7.99 (1H, d, J=7.5 Hz)
MASS (m/z): 414 (M$^+$−1)

(10) 1-(4-Bromo-2-fluorobenzyl)-3-isobutyryl-2-propylindole-6-carboxylic acid
mp: 210–211° C.
IR (KBr): 1677, 1646, 1486 cm$^{-1}$
NMR (CDCl$_3$, δ): 1.04 (3H, t, J=7 Hz), 1.30 (6H, d, J=7 Hz), 1.55–1.67 (2H, m), 3.07–3.12 (2H, m), 3.52–3.60 (1H, m), 5.46 (2H, s), 6.32 (1H, t, J=7.5 Hz), 7.11 (1H, d, J=7.5 Hz), 7.35 (1H, d, J=7.5 Hz), 7.96–8.03 (3H, m)
MASS (m/z): 460 (M$^+$), 458 (M$^+$−2)

(11) 3-Benzoyl-1-(2-chlorobenzyl)-2-propylindole-6-carboxylic acid
NMR (DMSO-d$_6$, δ): 0.95 (3H, t, J=8 Hz), 1.66 (2H, sextet, J=8 Hz), 2.98 (2H, t, J=8 Hz), 5.55 (2H, s), 6.35 (1H, dd, J=1, 8 Hz), 7.09 (1H, dt, J=1, 8 Hz), 7.20–7.27 (2H, m), 7.48 (1H, t, J=8hz), 7.57–7.62 (1H, m), 7.72–7.82 (3H, m), 7.98 (1H, s)

(12) 1-(2-Chlorobenzyl)-3-cyano-2-propylindole-6-carboxylic acid
mp: 239.5–241° C.
IR (KBr): 2224, 1671, 1287, 1264 cm$^{-1}$ NMR (CDCl$_3$, δ): 1.00 (3H, t, J=7 Hz), 1.70 (2H, sextet, J=7 Hz), 2.89 (2H, t, J=7 Hz), 5.50 (2H, s), 6.25 (1H, d, J=7.5 Hz), 7.18 (1H, ddt, J=7.5, 7.5, 1 Hz), 7.25 (1H, ddd, J=7.5, 7.5, 1 Hz), 7.47 (1H, d, J=7.5 Hz), 7.78 (1H, dd, J=7.5, 1 Hz), 7.99 (1H, d, J=1 Hz), 8.01 (1H, d, J=7.5 Hz)

MASS (m/z): 351 (M$^+$−1)

(13) 1-(2-Chlorobenzyl)-2-ethyl-3-isobutyrylindole-6-carboxylic acid

NMR (CDCl$_3$, δ): 1.22 (3H, t, J=7 Hz), 1.31 (6H, d, J=7 Hz), 3.12 (2H, q, J=7 Hz), 3.57 (1H, m), 5.51 (2H, s), 6.23 (1H, d, J=8 Hz), 7.04 (1H, t, J=8 Hz), 7.22 (1H, t, J=8 Hz), 7.47 (1H, d, J=8 Hz), 7.95–8.05 (3H, m)

(14) 1-(2-Chlorobenzyl)-3-isobutyryl-2-methylindole-6-carboxylic acid

NMR (CDCl$_3$, δ): 1.31 (6H, d, J=7 Hz), 2.72 (3H, s), 3.56 (1H, m), 5.51 (2H, s), 6.25 (1H, d, J=8 Hz), 7.05 (1H, t, J=8 Hz), 7.23 (1H, t, J=8 Hz), 7.46 (1H, d, J=8 Hz), 8.05 (3H, s)

(15) 1-(2-Chlorobenzyl)-3-isobutyryl-2-methoxymethylindole-6-carboxylic acid

NMR (CDCl$_3$, δ): 1.32 (6H, d, J=7 Hz), 3.35 (3H, s), 3.58 (1H, m), 4.94 (2H, s), 5.68 (2H, s), 6.28 (1H, d, J=8 Hz), 7.03 (1H, t, J=8 Hz), 7.20 (1H, t, J=8 Hz), 7.45 (1H, d, J=8 Hz), 8.0–8.05 (3H, m)

(16) 1-(2-Chlorobenzyl)-3-isobutyrylindole-6-carboxylic acid

NMR (CDCl$_3$, δ): 1.25 (6H, d, J=7 Hz), 3.30 (1H, m), 5.52 (2H, s), 6.79 (1H, d, J=8 Hz), 7.18 (1H, t, J=8 Hz), 7.28 (1H, t, J=8 Hz), 7.47 (1H, d, J=8 Hz), 7.91 (1H, s), 8.03 (1H, d, J=8 Hz), 8.12 (1H, s), 8.48 (1H, d, J=8 Hz)

(17) 3-Isobutyryl-2-propyl-1-(2-pyridylmethyl)indole-6-carboxylic acid

NMR (DMSO-d$_6$, δ): 0.92 (3H, t, J=7 Hz), 1.16 (6H, d, J=7 Hz), 1.46 (2H, sextet, J=7 Hz), 3.12–3.17 (2H, m), 3.52 (2H, septet, J=7 Hz), 5.72 (2H, s), 7.16 (1H, d, J=8 Hz), 7.29 (1H, dd, J=5, 8 Hz), 7.76 (1H, t, J=8 Hz), 7.81 (1H, d, J=8 Hz), 7.96 (1H, t, J=8 Hz), 8.06 (1H, s), 8.48 (1H, d, J=5 Hz)

(18) 1-(2-Chlorobenzyl)-2,3-diethylindole-6-carboxylic acid mp: 258–259° C. (dec.)

IR (KBr): 1675, 1290 cm$^{-1}$

NMR (CDCl$_3$, δ): 1.14 (3H, t, J=7 Hz), 1.30 (3H, t, J=7 Hz), 2.71 (2H, q, J=7 Hz), 2.80 (2H, q, J=7 Hz), 5.45 (2H, s), 6.18 (1H, d, J=7.5 Hz), 7.00 (1H, t, J=7.5 Hz), 7.19 (1H, t, J=7.5 Hz), 7.42 (1H, d, J=7.5 Hz), 7.62 (1H, d, J=7.5 Hz), 7.84 (1H, d, J=7.5 Hz), 7.91 (1H, s)

MASS (m/z): 340 (M$^+$−1)

(19) 1(2-Chlorobenzyl)-3-formyl-2-propylindole-6-carboxylic acid

NMR (CDCl$_3$, δ): 1.01 (3H, t, J=7 Hz), 1.67 (2H, m), 3.03 (2H, t, J=7 Hz), 5.50 (2H, s), 6.40 (1H, d, J=8 Hz), 7.08 (1H, t, J=8 Hz), 7.24 (1H, t, J=8 Hz), 7.48 (1H, d, J=8 Hz), 7.98 (1H, s), 8.07 (1H, d, J=8 Hz), 8.40 (1H, d, J=8 Hz)

(20) (2-Chlorobenzyl)-3-phenylacetyl-2-propylindole-6-carboxylic acid

NMR (DMSO-d$_6$, δ): 0.90 (3H, t, J=8 Hz), 1.45 (2H, sextet, J=8 Hz), 3.04–3.08 (2H, m), 4.43 (2H, s), 5.68 (2H, s), 6.27 (1H, d, J=8 Hz), 7.18 (1H, t, J=8 Hz), 7.23–7.35 (6H, m), 7.58 (1H, d, J=8 Hz), 7.85 (1H, d, J=8 Hz), 7.98 (1H, s), 8.19 (1H, d, J=8 Hz)

(21) 3-Acetyl-1-(6-chloro-3,4-methylenedioxybenzyl)-2-propylindole-6-carboxylic acid mp: 238–239° C.

NMR (CDCl$_3$—CD$_3$OD=1:1, δ): 1.06 (3H, t, J=8 Hz), 1.65 (2H, sextet, J=8 Hz), 2.76 (3H, s), 3.08–3.14 (2H, m), 5.48 (2H, s), 5.74 (1H, s), 5.92 (2H, s), 6.96 (1H, s), 7.99 (1H, d, J=8 Hz), 8.02 (1H, s), 8.08 (1H, d, J=8 Hz)

EXAMPLE 35

Methyl 3-acetyl-1-((2-chlorobenzyl)-2-ethylindole-6-carboxylate (170 mg) was prepared from methyl 3-acetyl-2-ethylindole-6-carboxylate (100 mg) and 2-chlorobenzyl bromide (0.06 ml) in a similar manner to that of Example 1.

This product was used immediately without purification in the below-mentioned Example 36.

EXAMPLE 36

3-Acetyl-1-(2-chlorobenzyl)-2-ethylindole-6-carboxylic acid (137 mg) was prepared from methyl 3-acetyl-1-(2-chlorobenzyl)-2-ethylindole-6-carboxylate (170 mg) in a similar manner to that of Example 2.

NMR (DMSO-d$_6$, δ): 1.11 (3H, t, J=7 Hz), 2.67 (3H, s), 3.11 (2H, q, J=7 Hz), 5.68 (2H, s), 6.26 (1H, d, J=8 Hz), 7.19 (1H, t, J=8 Hz), 7.32 (1H, t, J=8 Hz), 7.58 (1H, d, J=8 Hz), 7.83 (1H, d, J=8 Hz), 7.94 (1H, s), 8.13 (1H, d, J=8 Hz)

EXAMPLE 37

The following compounds described in 1) to 19) were prepared from the compound (I-2) obtained in Example 34 and Example 36 in a similar manner to that of Example 3.

(1) 1-(2-Fluorobenzyl)-3-isobutyryl-2-propylindole-6-carboxyamide mp: 198° C.

IR (KBr): 3200, 1650, 1610 cm$^{-1}$

NMR (CDCl$_3$, δ): 1.03 (3H, t, J=7 Hz), 1.30 (6H, d, J=7 Hz), 1.55–1.64 (2H, m), 3.06–3.12 (2H, m), 3.50–3.60 (1H, m), 5.50 (2H, s), 6.42 (1H, t, J=7.5 Hz), 6.95 (2H, t, J=7.5 Hz), 7.09–7.17 (1H, m), 7.22–7.28 (1H, m), 7.61 (1H, t, J=7.5 Hz), 7.90 (1H, s), 7.96 (1H, t, J=7.5 Hz)

MASS (m/z): 381 (M$^+$+1)

(2) 1-(2-Bromobenzyl)-3-isobutyryl-2-propylindole-6-carboxamide mp: 173–174° C.

IR (KBr): 3400, 1660, 1630 cm$^{-1}$

NMR (CDCl$_3$, δ): 1.03 (3H, t, J=7 Hz), 1.30 (6H, d, J=7 Hz), 1.57–1.68 (2H, m), 3.00–3.06 (2H, m), 3.51–3.61 (1H, m), 5.46 (2H, s), 6.20 (1H, t, J=7.5 Hz), 7.05–7.18 (2H, m), 7.60–7.66 (1H, m), 7.83 (1H, s), 7.99 (1H, t, J=7.5 Hz)

MASS (m/z): 443 (M$^+$+2), 441 (M$^+$), 76 (bp)

(3) 1-(2-Iodobenzyl)-3-isobutyryl-2-propylindole-6-carboxamide mp: 186–187° C.

IR (KBr): 3400, 1665, 1640 cm$^{-1}$

NMR (CDCl$_3$, δ): 1.03 (3H, t, J=7 Hz), 1.30 (6H, d, J=7 Hz), 1.54–1.67 (2H, m), 2.99–3.05 (2H, m), 3.51–3.60 (1H, m), 5.39 (2H, s), 6.15 (1H, d, J=7.5 Hz), 6.99 (1H, t, J=7.5 Hz), 7.11 (1H, t, J=7.5 Hz), 7.64 (1H, d, J=7.5 Hz), 7.82 (1H, s), 7.92 (1H, d, J=7 Hz), 7.99 (1H, d, J=7 Hz)

MASS (m/z): 489 (M$^+$+1), 76 (bp)

(4) 3-Isobutyryl-1-(2-methylbenzyl)-2-propylindole-6-carboxamide mp: 190–191° C.

IR (KBr): 3395, 1650, 1625, 1410 cm$^{-1}$

NMR (CDCl$_3$, δ): 1.00 (3H, t, J=7 Hz), 1.31 (6H, d, J=7 Hz), 1.54–1.68 (2H, m), 2.49 (3H, s), 3.00–3.07 (2H, m), 3.52–3.61 (1H, m), 5.38 (2H, s), 6.14 (1H, d, J=7.5 Hz), 6.98 (1H, t, J=7.5 Hz), 7.17 (1H, t, J=7.5 Hz), 7.24 (1H, d, J=7.5 Hz), 7.60 (1H, d, J=7.5 Hz), 7.82 (1H, s), 7.99 (1H, d, J=7.5 Hz)

MASS (m/z): 377 (M$^+$+1), 76 (bp)

(5) 3-Isobutyryl-1-(2-methoxybenzyl)-2-propylindole-6-carboxamide mp: 174–175° C.

IR (KBr): 3370, 1655, 1650, 1625 cm$^{-1}$

NMR (CDCl$_3$, δ): 1.01 (3H, t, J=7 Hz), 1.30 (6H, d, J=7 Hz), 1.57–1.69 (2H, m), 3.05–3.10 (2H, m), 3.52–3.61 (1H, m), 3.97 (3H, s), 5.43 (2H, s), 6.24 (1H, d, J=7.5 Hz), 6.74 (2H, t, J=7.5 Hz), 6.93 (1H, d, J=7.5 Hz), 7.24 (1H, t, J=7.5 Hz), 7.59 (1H, d, J=7.5 Hz), 7.88 (1H, s), 7.97 (1H, d, J=7.5 Hz)

MASS (m/z): 393 (M$^+$+1), 76 (bp)

(6) 1-(2-Cyanobenzyl)-3-isobutyryl-2-propylindole-6-carboxamide mp: 143–144° C.

IR (KBr): 3377, 3190, 2227, 1645 cm$^{-1}$

NMR (CDCl$_3$, δ): 1.04 (3H, t, J=7 Hz), 1.30 (6H, d, J=7 Hz), 1.52–1.65 (2H, m), 3.02–3.08 (2H, m), 3.50–3.59 (1H, m), 5.68 (2H, s), 6.45–6.49 (1H, m), 7.38–7.43 (2H, m), 7.65 (1H, d, J=7.5 Hz), 7.74–7.78 (1H, m), 7.87 (1H, s), 7.99 (1H, d, J=7.5 Hz)

MASS (m/z): 388 (M$^+$+1), 62 (bp)

(7) 3-Isobutyryl-1-(2-nitrobenzyl)-2-propylindole-6-carboxamide mp: 181–182° C.

IR (KBr): 3190, 1670, 1610, 1535, 1400 cm$^{-1}$

NMR (CDCl$_3$, δ): 1.00 (3H, t, J=7 Hz), 1.32 (6H, d, J=7 Hz), 1.58–1.67 (2H, m), 3.02 (2H, t, J=7 Hz), 3.52–3.61 (1H, m), 5.89 (2H, s), 6.27 (1H, d, J=7.5 Hz), 7.39–7.50 (2H, m), 7.63 (1H, d, J=7.5 Hz), 7.80 (1H, s), 7.99 (1H, d, J=7.5 Hz), 8.28 (1H, d, J=7.5 Hz)

MASS (m/z): 408 (M$^+$+1), 76 (bp)

(8) 1-(2,6-Dichlorobenzyl)-3-isobutyryl-2-propylindole-6-carboxamide mp: 207.5–209° C.

IR (KBr): 3395, 1650, 1615 cm$^{-1}$

NMR (CDCl$_3$, δ): 0.98 (3H, t, J=7 Hz), 1.28 (6H, d, J=7 Hz), 1.39–1.50 (2H, m), 3.16–3.21 (2H, m), 3.49–3.58 (1H, m), 5.70 (2H, s), 7.22–7.25 (1H, m), 7.35–7.39 (2H, m), 7.60 (1H, d, J=7.5 Hz), 7.86–7.90 (2H, m), 7.99 (1H, d, J=7.5 Hz)

MASS (m/z): 431 (M$^+$+1), 76 (bp)

(9) 1-(2-Chloro-4-fluorobenzyl)-3-isobutyryl-2-propylindole-6-carboxamide mp: 192–193° C.

(KBr): 3336, 3180, 1650, 1494, 1411 cm$^{-1}$

NMR (CDCl$_3$, δ): 1.03 (3H, t, J=7 Hz), 1.30 (6H, d, J=7 Hz), 1.53–1.65 (2H, m), 3.01–3.07 (2H, m), 3.50–3.60 (1H, m), 5.47 (2H, s), 6.20 (1H, dd, J=8, 7.5 Hz), 6.78 (1H, ddd, J=7.5, 7.5, 1 Hz), 7.23 (1H, dd, J=8, 1 Hz), 7.63 (1H, d, J=7.5 Hz), 7.85 (1H, s), 7.99 (1H, d, J=8 Hz)

MASS (m/z): 415 (M$^+$+1), 76 (bp)

(10) 1-(4-Bromo-2-fluorobenzyl)-3-isobutyryl-2-propylindole-6-carboxamide mp: 197–198.5° C.

IR (KBr): 3377, 3189, 1652, 1617, 1487, 1408 cm$^{-1}$

NMR (CDCl$_3$, δ): 1.04 (3H, t, J=7 Hz), 1.30 (6H, d, J=7 Hz), 1.53–1.64 (2H, m), 3.05–3.11 (2H, m), 3.48–3.60 (1H, m), 5.44 (2H, s), 6.29 (1H, t, J=7.5 Hz), 7.09 (1H, d, J=7.5 Hz), 7.33 (1H, dd, J=7.5, 1 Hz), 7.62 (1H, d, J=7.5 Hz), 7.90 (1H, d, J=1 Hz), 7.97 (1H, d, J=7.5 Hz)

MASS (m/z): 461 (M$^+$+2), 459 (M$^+$), 76 (bp)

(11) 1-(2-Chlorobenzyl)-3-cyano-2-propylindole-6-carboxamide mp: 222–223.5° C.

IR (KBr): 3443, 3183, 2215, 1679, 1394 cm$^{-1}$

NMR (CDCl$_3$, δ): 1.02 (3H, t, J=7 Hz), 1.70 (2H, sextet, J=7 Hz), 2.89 (2H, t, J=7.5 Hz), 5.50 (2H, s), 6.21 (1H, d, J=7.5 Hz), 7.08 (1H, t, J=7.5 Hz), 7.24 (1H, ddd, J=7.5, 7.5, 1 Hz), 7.47 (1H, d, J=7.5 Hz), 7.61 (1H, d, J=7.5 Hz), 7.77 (7H, d, J=7.5 Hz), 7.89 (1H, d, J=1 Hz)

MASS (m/z): 352 (M$^+$+1), 76 (bp)

(12) 1-(2-Chlorobenzyl)-2-ethyl-3-isobutyrylindole-6-carboxamide mp: 178–180.5° C.

NMR (CDCl$_3$, δ): 1.22 (3H, t, J=7 Hz), 1.30 (6H, d, J=7 Hz), 3.09 (2H, q, J=7 Hz), 3.56 (1H, m), 5.51 (2H, s), 6.22 (1H, d, J=8 Hz), 7.04 (1H, t, J=8 Hz), 7.22 (1H, t, J=8 Hz), 7.44 (1H, d, J=8 Hz), 7.63 (1H, d, J=8 Hz), 7.82 (1H, s), 7.98 (1H, d, J=8 Hz)

(13) 1-(2-Chlorobenzyl)-3-isobutyryl-2-methylindole-6-carboxamide mp: 212–215° C.

NMR (CDCl$_3$, δ): 1.30 (6H, d, J=7 Hz), 2.69 (3H, s), 3.53 (1H, m), 5.48 (2H, s), 6.21 (1H, d, J=8 Hz), 7.04 (1H, t, J=8 Hz), 7.23 (1H, t, J=8 Hz), 7.45 (1H, d, J=8 Hz), 7.62 (1H, d, J=8 Hz), 7.87 (1H, s), 8.03 (1H, d, J=8 Hz)

(14) 1-(2-Chlorobenzyl)-3-isobutyryl-2-methoxymethylindole-6-carboxamide mp: 204–206° C.

NMR (CDCl$_3$, δ): 1.32 (6H, d, J=7 Hz), 3.34 (3H, s), 3.57 (1H, m), 4.92 (2H, s), 5.65 (2H, s), 6.24 (1H, d, J=8 Hz), 7.03 (1H, t, J=8 Hz), 7.21 (1H, t, J=8 Hz), 7.44 (1H, d, J=8 Hz), 7.67 (1H, d, J=8 Hz), 7.83 (1H, s), 8.02 (1H, d, J=8 Hz)

(15) 1-(2-Chlorobenzyl-)-3-isobutyrylindole-6-carboxamide mp: 235–237° C.

NMR (DMSO-d$_6$, δ): 1.16 (6H, d, J=7 Hz), 3.40 (1H, m), 5.67 (2H, s), 6.70 (1H, d, J=8 Hz), 7.2–7.4 (3H, m), 7.56 (1H, d, J=8 Hz), 7.80 (1H, d, J=8 Hz), 7.96 (1H, br s), 8.04 (1H, s), 8.27 (1H, d, J=8 Hz), 8.64 (1H, s)

(16) 3-Isobutyryl-2-propyl-1-(2-pyridylmethyl)indole-6-carboxamide

NMR (DMSO-d$_6$, δ): 0.90 (3H, t, J=7 Hz), 1.17 (6H, d, J=7 Hz), 1.46 (2H, sextet, J=7 Hz), 3.0–3.15 (2H, m), 3.52 (2H, septet, J=7 Hz), 5.66 (2H, s), 7.08 (1H, d, J=8 Hz), 7.28–7.32 (2H, m), 7.78 (1H, d, J=8 Hz), 7.92 (1H, d, J=8 Hz), 8.09 (1H, s), 8.50 (1H, d, J=5 Hz)

(17) 1-(2-Chlorobenzyl)-2,3-diethylindole-6-carboxamide mp: 185–187.5° C.

IR (KBr): 3400, 1650, 1610 cm$^{-1}$

NMR (CDCl$_3$, δ): 1.15 (3H, t, J=7 Hz), 1.29 (3H, t, J=7 Hz), 2.69 (2H, q, J=7 Hz), 2.80 (2H, q, J=7 Hz), 5.44 (2H, s), 6.17 (1H, d, J=7.5 Hz), 7.00 (1H, t, J=7.5 Hz), 7.18 (1H, t, J=7.5 Hz), 7.41 (1H, d, J=7.5 Hz), 7.47 (1H, d, J=7.5 Hz), 7.62 (1H, d, J=7.5 Hz), 7.76 (1H, s)

MASS (m/z): 341 (M$^+$+1), 76 (bp)

(18) 3-Acetyl-1-(2-chlorobenzyl)-2-ethylindole-6-carboxamide mp: 217–220° C.

NMR (CDCl$_3$, δ): 1.22 (3H, t, J=7 Hz), 2.73 (3H, s), 3.12 (2H, q, J=7 Hz), 5.49 (2H, s), 6.20 (1H, d, J=8 Hz), 7.02 (1H, t, J=8 Hz), 7.22 (1H, t, J=8 Hz), 7.43 (1H, d, J=8 Hz), 7.63 (1H, d, J=8 Hz), 7.83 (1H, s), 8.08 (1H, d, J=8 Hz)

(19) 1-(2-Chlorobenzyl)-3-formyl-2-propylindole-6-carboxamide mp: 245° C. (dec.)

NMR (DMSO-D$_6$, δ): 0.92 (3H, t, J=7 Hz), 1.63 (2H, m), 3.11 (2H, t, J=7 Hz), 5.64 (2H, s), 6.32 (1H, d, J=8Hz), 7.21 (1H, t, J=8 Hz), 7.25–7.35 (2H, m), 7.60 (1H, d, J=8 Hz), 7.83 (1H, d, J=8 Hz), 7.95 (1H, d, J=8 Hz), 7.97 (1H, s), 8.21 (1H, d, J=8 Hz), >10 (1H, s)

EXAMPLE 38

The following compounds described in 1) to 3) were prepared from the compound (I-2) obtained in Example 34–11), Example 34–20) or Example 34–21) in a similar manner to that of Example 6.

(1) 3-Benzoyl-1-(2-chlorobenzyl)-2-propylindole-6-carboxamide

NMR (DMSO-d$_6$, δ): 0.78 (3H, t, J=8 Hz), 1.46 (2H, sextet, J=8 Hz), 2.88 (2H, t, J=8 Hz), 5.66 (2H, s), 6.33 (1H, dd, J=1, 8 Hz), 7.08 (1H, dt, J=1, 8 Hz), 7.20–7.38 (3H, m), 7.52–7.72 (7H, m), 7.88 (1H, br s), 7.99 (1H, s)

(2) 1-(2-Chlorobenzyl)-3-phenylacetyl-2-propylindole-6-carboxamide

NMR (DMSO-d$_6$, δ): 0.88 (3H, t, J=8 Hz), 1.47 (2H, sextet, J=8 Hz), 2.98–3.03 (2H, m), 4.42 (2H, s), 5.63 (2H, s), 6.20 (1H, d, J=8 Hz), 7.17 (1H, t, J=8 Hz), 7.24–7.35 (6H, m), 7.57 (1H, d, J=8 Hz), 7.82 (1H, d, J=8 Hz), 7.95 (1H, br s), 8.02 (1H, s), 8.14 (1H, d, J=8 Hz)

(3) 3-Acetyl-1-(6-chloro-3,4-methylenedioxybenzyl)-2-propylindole-6-carboxamide mp: 220–223° C.

NMR (DMSO-d$_6$, δ): 0.94 (3H, t, J=8 Hz), 1.50 (2H, sextet, J=8 Hz), 2.65 (3H, s), 3.02–3.06 (2H, m), 5.52 (2H, s), 5.66 (1H, s), 5.99 (2H, s), 7.23 (1H, s), 7.86 (1H, d, J=8 Hz), 8.01 (1H, s), 8.05 (1H, d, J=8 Hz)

EXAMPLE 39

To a solution of 3-isobutyryl-2-propyl-1-(2-pyridylmethyl)indole-6-carboxamide (80 mg) in chloroform (2 ml) was added 1M solution of hydrogen chloride in methanol (1 ml) at 25° C., and the mixture was stirred for 15 minutes. After evaporation of solvent, the residue was crystallized from a mixture of ethanol and ethyl acetate to give 3-isobutyryl-2-propyl-1-(2-pyridylmethyl)indole-6-carboxamide hydrochloride (80 mg) as colorless crystals.

mp: 230–235° C.

NMR (DMSO-d$_6$, δ): 0.92 (3H, t, J=7 Hz), 1.17 (6H, d, J=7 Hz), 1.45 (2H, sextet, J=7 Hz), 3.08–3.14 (2H, m), 3.52 (2H, septet, J=7 Hz), 5.74 (2H, s), 7.09 (1H, d, J=8 Hz), 7.46 (1H, dd, J=5, 8 Hz), 7.79 (1H, d, J=8 Hz), 7.90 (1H, d, J=8 Hz) 7.92 (1H, t, J=8 Hz), 8.12 (1H, s), 8.62 (1H, d, J=5 Hz)

EXAMPLE 40

1-2-Carboxybenzyl)-3-isobutyryl-2-propylindole-6-carboxamide (242 mg) was prepared from 3-isobutyryl-1-(2-methoxycarbonylbenzyl)-2-propylindole-6-carboxamide (265 mg) in a similar manner to that of Example 2.

mp: 268–269° C. (dec.)

IR (KBr): 1740, 1690, 1625, 1620 cm$^{-1}$

NMR (DMSO-d$_6$, δ): 0.90 (3H, t, J=7 Hz), 1.19 (6H, d, J=7 Hz), 1.42–1.51 (2H, m), 2.94–3.06 (2H, m), 3.50–3.60 (1H, m), 5.96 (2H, s), 6.06–6.10 (1H, m) 7.37–7.40 (2H, m), 7.79–7.82 (1H, m), 7.91–7.95 (1H, m), 7.99 (1H, s), 8.03–8.06 (1H, m)

MASS (m/z): 407 (M$^+$+1), 86 (bp)

EXAMPLE 41

1-(2-Carbamoylbenzyl)-3-isobutyryl-2-propylindole-6-carboxamide (102 mg) was prepared from 1-(2-carboxybenzyl)-3-isobutyryl-2-propylindole-6-carboxamide (164 mg) in a similar manner to that of Example 3.

mp: 273–274° C.

IR (KBr): 1690 cm$^{-1}$

NMR (DMSO-d$_6$, δ): 0.91 (3H, t, J=7 Hz), 1.19 (6H, d, J=7 Hz), 1.41–1.51 (2H, m), 2.94–2.99 (2H, m), 3.48– 3.57 (1H, m), 5.79 (2H, s), 6.17 (1H, d, J=7.5 Hz), 7.22–7.35 (3H, m), 7.61–7.68 (2H, m), 7.80 (1H, d, J=7.5 Hz), 7.92–7.97 (2H, m), 8.04 (1H, s), 8.13 (1H, s)

MASS (m/z): 406 (M$^+$+1), 87 (bp)

EXAMPLE 42

To a solution of phosphorus oxychloride (0.031 ml) in dimethylformamide (1.2 ml) was added 1-(2-chlorobenzyl)-2-ethyl-3-propionylindole-6-carboxamide (112 mg) at 0° C., and the mixture was stirred for 15 minutes. The resulting mixture was poured into ammonia water and ice, and then extracted with ethyl acetate. The organic phase was washed with brine, dried over sodium sulfate and evaporated in vacuo. The residue was triturated with a mixture of hexane and isopropyl ether to give 1-(2-chlorobenzyl)-2-ethyl-3-propionylindole-6-carbonitrile (93 mg) as a solid.

mp: 115–118° C.

NMR (CDCl$_3$, δ): 1.25 (3H, t, J=7 Hz), 1.30 (3H, t, J=7 Hz), 3.09 (2H, q, J=7 Hz), 3.17 (2H, q, J=7 Hz), 5.47 (2H, s), 6.21 (1H, d, J=8 Hz), 7.07 (1H, t, J=8 Hz), 7.25 (1H, t, J=8 Hz), 7.45–7.55 (3H, m), 8.09 (1H, d, J=7 Hz)

EXAMPLE 43

1-(2-Chlorobenzyl)-2-ethyl-3-isobutyrylindole-6-carbonitrile (239 mg) was prepared from 1-(2-chlorobenzyl)-2-ethyl-3-isobutyrylindole-6-carboxamide (280 mg) in a similar manner to that of Example 42.

mp: 132–134° C.

NMR (CDCl$_3$, δ): 1.23 (3H, t, J=7 Hz), 1.31 (6H, d, J=7 Hz), 3.13 (2H, q, J=7 Hz), 3.50 (1H, m), 5.48 (2H, s), 6.22 (1H, d, J=8 Hz), 7.07 (1H, t, J=8 Hz), 7.27 (1H, t, J=8 Hz), 7.27 (1H, d, J=8 Hz), 7.44–7.53 (2H, m), 8.02 (1H, d, J=8 Hz)

EXAMPLE 44

To a solution of 1-(2-chlorobenzyl)-2-ethyl-3-propionylindole-6-carbonitrile (107 mg) in xylene (5 ml) was added trimethyltin azide (190 mg), and the mixture was stirred at 120° C. for 14 hours. The resulting mixture was poured into 1N HCl and extracted with ethyl acetate. The organic phase was washed with brine, dried over sodium sulfate and evaporated in vacuo. The residue was chromatographed on silica gel eluting with 20% methanol in chloroform to give 1-(2-chlorobenzyl)-2-ethyl-3-propionyl-6-(1H-tetrazol-5-yl)indole (77 mg) as a solid.

mp: 178–181° C.

NMR (CDCl$_3$, δ): 1.18 (3H, t, J=7 Hz), 1.34 (3H, t, J=7 Hz), 3.0–3.15 (4H, m), 5.42 (2H, s), 6.21 (1H, d, J=8 Hz), 6.94 (1H, t, J=8 Hz), 7.13 (1H, t, J=8 Hz), 7.33 (1H, d, J=8 Hz), 8.03 (1H, d, J=8 Hz), 8.05 (1H, s), 8.25 (1H, d, J=8 Hz)

EXAMPLE 45

1-(2-Chlorobenzyl)-2-ethyl-3-isobutyryl-6-(1H-tetrazol-5-yl)indole (109 mg) was prepared from 1-(2-chlorobenzyl)-2-ethyl-3-isobutyrylindole-6-carbonitrile (130 mg) in a similar manner to that of Example 44.

mp: 160–163° C.

NMR (CDCl$_3$, δ): 1.18 (3H, t, J=7 Hz), 1.31 (6H, d, J=7 Hz), 3.04 (2H, q, J=7 Hz), 3.52 (1H, m), 5.37 (2H, s), 6.20 (1H, d, J=8 Hz), 6.94 (1H, t, J=8 Hz), 7.11 (1H, t, J=8 Hz), 7.33 (1H, d, J=8 Hz), 8.00 (1H, d, J=8 Hz), 8.00 (1H, s), 8.13 (1H, d, J=8 Hz)

EXAMPLE 46

The following compounds described in (1) to (2) were prepared in a similar manner to that of Preparation 30.

(1) Methyl 2-(3-carboxypropyl)-1-(2-chlorobenzyl)indole-6-carboxylate

NMR (CDCl$_3$, δ): 2.04 (2H, m), 2.45 (2H, t, J=7 Hz), 2.73 (2H, t, J=7 Hz), 3.89 (3H, s), 5.44 (2H, s), 6.14 (1H, d, J=8 Hz), 6.47 (1H, s), 7.01 (1H, t, J=8 Hz), 7.18 (1H, t, J=8 Hz), 7.44 (1H, d, J=8 Hz), 7.62 (1H, d, J=8 Hz), 7.83 (1H, d, J=8 Hz), 7.93 (1H, s)

(2) 2-(2-Carboxyethyl)-1-(2-chlorobenzyl)indole-6-carboxylate

NMR (CDCl$_3$, δ): 2.76 (2H, t, J=7 Hz), 2.96 (2H, t, J=7 Hz), 3.88 (3H, s), 5.46 (2H, s), 6.16 (1H, d, J=8 Hz), 6.46 (1H, s), 7.01 (1H, t, J=8 Hz), 7.20 (1H, t, J=8 Hz), 7.43 (1H, d, J=8 Hz), 7.62 (1H, d, J=8 Hz), 7.82 (1H, d, J=8 Hz), 7.93 (1H, s)

PREPARATION 47

The following compounds described in (1) to (2) were prepared in a similar manner to that of Preparation 31.
(1) Methyl 9-(2-chlorobenzyl)-5-oxo-5,6,7,8-tetrahydrocarbazole-2-carboxylate NMR (CDCl$_3$, δ): 2.24 (2H, m), 2.62 (2H, t, J=7 Hz), 2.86 (2H, t, J=7 Hz), 3.90 (3H, s), 5.47 (2H, s), 6.34 (1H, d, J=8 Hz), 7.09 (1H, t, J=8 Hz), 7.25 (1H, t, J=8 Hz), 7.47 (1H, d, J=8 Hz), 7.97 (1H, s), 7.99 (1H, d, J=8 Hz), 8.33 (1H, d, J=8 Hz)
(2) Methyl 4-(2-chlorobenzyl)-1-oxo-1,2,3,4-tetrahydrocyclopent[b]indole-6-carboxylate NMR (CDCl$_3$, δ): 2.9–3.15 (4H, m), 3.91 (3H, s), 5.46 (2H, s), 6.66 (1H, d, J=8Hz), 7.17 (1H, t, J=8 Hz), 7.29 (1H, t, J=8 Hz), 7.48 (1H, d, J=8 Hz), 7.94–8.06 (3H, m)

EXAMPLE 48

The following compounds described in (1) to (2) were prepared in a similar manner to that of Preparation 1 (5).
(1) Methyl 3-chloroacetyl-1-(2-chlorobenzyl)-2-propylindole-6-carboxylate
mp: 143–145° C.
IR (KBr): 1722, 1666 cm$^{-1}$
NMR (CDCl$_3$, δ): 1.03 (3H, t, J=7 Hz), 1.55–1.66 (2H, m), 3.05–3.10 (2H, m), 3.91 (3H, s), 4.82 (2H, s), 5.53 (2H, s), 6.25 (1H, d, J=7.5 Hz), 7.05 (1H, t, J=7.5 Hz), 7.20–7.25 (1H, m), 7.49 (1H, d, J=7.5 Hz), 7.88 (1H, d, J=8 Hz), 7.98 (1H, s), 8.00 (1H, d, J=8 Hz)
MASS (m/z): 418 (M$^+$–1), 76 (bp)
(1-(2-Chlorobenzyl)-3-crotonoyl-2-propylindole-6-carboxamide
mp: 185.5–186.5° C.
IR (KBr): 1648, 1614, 1443, 1414, 1388 cm$^{-1}$
NMR (CDCl$_3$, δ): 1.00 (3H, t, J=7 Hz), 1.64 (2H, sextet, J=7Hz), 2.04 (3H, d, J=7 Hz), 3.00 (2H, t, J=7 Hz), 5.51 (2H, s), 6.24 (1H, d, J=8 Hz), 6.92 (1H, d, J=15 Hz), 7.00–7.06 (2H, m), 7.23 (1H, t, J=8 Hz), 7.46 (1H, d, J=7.5 Hz), 7.60 (1H, d, J=7.5 Hz), 7.83 (1H, s), 7.99 (1H, d, J=8 Hz)
MASS (m/z): 395 (M$^+$+1), 74 (bp)

EXAMPLE 49

A mixture of methyl 3-chloroacetyl-1-(2-chlorobenzyl)-2-propylindole-6-carboxylate (123 mg) and morpholine (1 ml) was stirred at 50° C. for 2.5 hours. After cooled to 20° C., the reaction mixture was extracted with ethyl acetate. The organic phase was washed with 1N hydrochloric acid and water, dried over magnesium sulfate and evaporated in vacuo. The residue was chromatographed on silica gel eluting with a mixture of ethyl acetate and hexane (1:2) to give methyl 1-(2-chlorobenzyl)-3-morpholinoacetyl-2-propylindole-6-carboxylate (94 mg) as colorless amorphous.
IR (KBr): 1712, 1657 cm$^{-1}$
NMR (CDCl$_3$, δ): 1.01 (3H, t, J=7 Hz), 1.60–1.65 (2H, m), 2.70–2.75 (4H, m), 3.06 (2H, t, J=7 Hz), 3.84 (4H, t, J=7 Hz), 3.90 (2H, s), 3.92 (3H, s), 5.52 (2H, s), 6.24 (1H, d, J=7.5 Hz), 7.06 (1H, t, J=7.5 Hz), 7.24 (1H, t, J=7.5 Hz), 7.48 (1H, d, J=7.5 Hz), 7.94–7.98 (3H, m)
MASS (m/z): 469 (M$^+$+1)

EXAMPLE 50

To a mixture of methyl 1-(2-chlorobenzyl)-3-formyl-2-propylindole-6-carboxylate (263 mg), 2-methyl-2-butene (220 mg) and sodium dihydrogenohosphate (128 mg) in a mixture of tert-butanol (7 ml) and water (1.3 ml) was added sodium chlorite (219 mg) at 20° C. The reaction mixture was stirred at 40° C. for 2 hours. The reaction mixture was acidified with 1N hydrochloric acid at 0° C. and extracted with chloroform three times. The organic phase was dried over sodium sulfate and evaporated in vacuo. The residue was chromatographed on silica gel eluting with a mixture of ethyl acetate and hexane (1:2) to give 1-(2-chlorobenzyl)-6-methoxycarbonyl-2-propylindole-3-carboxylic acid (94 mg) as pale yellow crystals.
mp: 229–231° C. (dec.)
IR (KBr): 1715, 1658, 1441, 1275, 1227 cm$^{-1}$
NMR (CDCl$_3$, δ): 1.05 (3H, t, J=7 Hz), 1.60–1.70 (2H, m), 3.10–3.18 (2H, m), 3.93 (3H, s), 5.54 (2H, s), 6.78 (1H, d, J=7.5 Hz), 7.06 (1H, t, J=7.5 Hz), 7.21–7.25 (1H, m), 7.49 (1H, d, J=7.5 Hz), 7.95 (1H, s), 7.99 (1H, d, J=8 Hz), 8.33 (1H, d, J=8 Hz)
MASS (m/z): 384 (M$^+$–1), 77 (bp)

EXAMPLE 51

To a stirred suspension of 60% sodium hydride (470 mg) in N,N-dimethylformamide (6 ml) was added a solution of methyl 2-ethylindole-6-carboxylate (1.99 g) in N,N-dimethylformamide (12 ml) at 20° C. The mixture was stirred at 20° C. for 30 minutes. To this mixture was added 2-chlorobenzylbromide (2.21 g) at 20° C. and the mixture was stirred at 20° C. for 5.5 hours. N,N-Dimethylformamide was evaporated off, and the residue was extracted with ethyl acetate. The organic phase was washed with water and brine, dried over sodium sulfate and evaporated in vacuo. The residue was chromatographed on silica gel eluting with a mixture of ethyl acetate and hexane (1:8) to give crystals which were washed with hexane to give methyl 1-(2-chlorobenzyl)-2-ethylindole-6-carboxylate (2.71 g) as colorless crystals.
mp: 87–89° C.
IR (KBr): 1709, 1278, 1236 cm$^{-1}$
NMR (CDCl$_3$, δ): 1.35 (3H, t, J=7 Hz), 2.67 (2H, q, J=7 Hz), 3.91 (3H, s), 5.45 (2H, s), 6.17 (1H, d, J=7 Hz), 6.46 (1H, s), 7.02 (1H, dd, J=7, 7 Hz), 7.19 (1H, dd, J=7, 7 Hz), 7.44 (1H, d, J=7 Hz), 7.62 (1H, d, J=7 Hz), 7.72 (1H, d, J=7 Hz), 7.93 (1H, s)
MASS (m/z): 328 (M$^+$+1), 76 (bp)

EXAMPLE 52

The following compound was prepared in a similar manner to that of Example 32.
Methyl 1-(2-chlorobenzyl)-2-ethyl-3-formylindole-6-carboxylate
mp: 168–169° C.
IR (KBr): 1715, 1650 cm$^{-1}$
NMR (CDCl$_3$, δ): 1.27 (3H, t, 7, J=7 Hz), 3.06 (2H, q, J=7 Hz), 3.90 (3H, s), 5.50 (2H, s), 6.18 (1H, d, J=7 Hz), 7.05 (1H, t, J=7 Hz), 7.21–7.24 (1H, m), 7.48 (1H, d, J=7.5 Hz), 7.95 (1H, s), 8.01 (1H, d, J=7 Hz), 8.28 (1H, d, J=7 Hz), 10.25 (1H, s)
MASS (m/z): 356 (M$^+$+1), 76 (bp)

EXAMPLE 53

A mixture of 1-(2-chlorobenzyl)-3-isobutyryl-2-propylindole-6-carboxylic acid (100 mg), diphenylphosphoryl azide (97 mg) and triethylamine (53 mg) in tert-butanol (4 ml) was refluxed for 2 hours, and then partitioned between ethyl acetate and diluted with hydrochloric acid. The organic layer was washed with aqueous sodium bicarbonate and brine, dried over magnesium sulfate and evaporated in vacuo. The residue was purified by silica gel thin layer chromatography with a mixture of hexane and ethyl acetate (2:1) to give 6-tert-butoxycarbonylamino-1-(2-chlorobenzyl)-3-isobutyryl-2-propylindole (125 mg) as a pale yellow oil.

NMR (CDCl$_3$, δ): 0.98 (3H, t, J=7 Hz), 1.28 (6H, d, J=7 Hz), 1.48 (9H, s), 1.52–1.64 (2H, m), 2.96–3.02 (2H, m), 3.54 (1H, septet, J=7 Hz), 5.42 (2H, s), 6.30 (1H, d, J=8 Hz), 6.52 (1H, s), 7.05 (1H, t, J=8 Hz), 7.09 (1H, d, J=8 Hz), 7.20 (1H, t, J=8 Hz), 7.36–7.45 (2H, m), 7.82 (1H, d, J=8 Hz)

EXAMPLE 54

To a solution of 6-tert-butoxycarbonylamino-1-(2-chlorobenzyl)-3-isobutyryl-2-propylindole (110 mg) in ethyl acetate (1 ml) was added 4N hydrogen chloride in ethyl acetate at 20° C., and the mixture was stirred at the same temperature for 4 hours. The precipitates were collected by filtration and washed with ethyl acetate to give 6-amino-1-(2-chlorobenzyl)-3-isobutyryl-2-propylindole hydrochloride (50 mg) as powder.

NMR (DMSO-d$_6$, δ): 0.92 (3H, t, J=7 Hz), 1.18 (6H, d, J=7 Hz), 1.49 (2H, sextet, J=7 Hz), 3.02–3.08 (2H, m), 3.52 (1H, septet, J=7 Hz), 5.58 (2H, s), 6.24 (1H, d, J=8 Hz), 7.17–7.35 (4H, m), 7.57 (1H, d, J=8 Hz), 8.02 (1H, d, J=8 Hz)

EXAMPLE 55

To a stirred solution of 6-tert-butoxycarbonylamino-1-(2-chlorobenzyl)-3-isobutyryl-2-propylindole (581 mg) in ethyl acetate (5 ml) was added 4N hydrogen chloride in ethyl acetate (5 ml) at 20° C. The reaction mixture was stirred at 20° C. for 6.5 hours, then diluted with 1N aqueous sodium hydroxide and extracted. The organic phase was dried over magnesium sulfate and evaporated in vacuo. The residue was chromatographed on silica gel eluting with a mixture of ethyl acetate and hexane (1:6 to 1:4) to give 6-amino-1-(2-chlorobenzyl)-3-isobutyryl-2-propylindole (361 mg) as yellow oil.

NMR (CDCl$_3$, δ): 1.00 (3H, t, J=7 Hz), 1.29 (6H, d, J=7 Hz), 1.51–1.64 (2H, m), 2.98–3.03 (2H, m), 3.49–3.57 (1H, m), 5.34 (2H, s), 6.36 (1H, d, J=7.5 Hz), 6.46 (1H, s), 6.71 (1H, d, J=7.5 Hz), 7.08 (1H, t, J=7.5 Hz), 7.21 (1H, t, J=7.5 Hz), 7.45 (1H, d, J=7.5 Hz), 7.85 (1H, d, J=7.5 Hz)

MASS (m/z): 369 (M$^+$+1)

EXAMPLE 56

To a stirred solution of 6-amino-1-(2-chlorobenzyl)-3-isobutyryl-2-propylindole (79 mg) and triethylamine (0.065 ml) in dichloromethane (2 ml) was added acetyl chloride (0.02 ml) at 0° C. The reaction mixture was stirred at 20° C. for 2 hours, then diluted with dichloromethane. The organic phase was washed with 1N hydrochloric acid, water, aqueous sodium bicarbonate, water and brine, dried over magnesium sulfate and evaporated in vacuo. The residue was chromatographed on silica gel eluting with a mixture of ethyl acetate and hexane (2:3) to give crystals which were recrystallized from a mixture of ethyl acetate and hexane to give 6-acetamide-1-(2-chlorobenzyl)-3-isobutyryl-2-propylindole (48 mg) as colorless crystals.

mp: 147–148° C.

IR (KBr): 1664, 1648, 1507, 1412 cm$^{-1}$

NMR (CDCl$_3$, δ): 1.00 (3H, t, J=7 Hz), 1.29 (6H, d, J=7 Hz), 1.51–1.65 (2H, m), 2.17 (3H, s), 2.99–3.05 (2H, m), 3.49–3.58 (1H, m), 5.43 (2H, s), 6.30 (1H, d, J=7.5 Hz), 7.04 (1H, t, J=7.5 Hz), 7.13–7.23 (3H, m), 7.44 (1H, d, J=7.5 Hz), 7.72 (1H, s), 7.85 (1H, d, J=7.5 Hz)

MASS (m/z): 411 (M$^+$+1)

EXAMPLE 57

To a stirred solution of 6-amino-1-(2-chlorobenzyl)-3-isobutyryl-2-propylindole (100 mg) in chloroform (2 ml) was added methylisocyanate (0.5 ml) at 0° C. The reaction mixture was stirred at 20° C. for 1 hour, then evaporated. The residue was chromatographed on silica gel eluting with a mixture of ethyl acetate and hexane (1:1) to give crystals which were recrystallized from a mixture of ethyl acetate and hexane to give 1-(2-chlorobenzyl)-3-isobutyryl-6-(3-methylureido)-2-propylindole (75 mg) as colorless crystals.

mp: 106–108.5° C.

IR (KBr): 1635, 1550, 1506 cm$^{-1}$

NMR (CDCl$_3$, δ): 1.01 (3H, t, J=7 Hz), 1.30 (6H, d, J=7 Hz), 1.53–1.65 (2H, m), 2.78 (3H, d, J=7 Hz), 3.00–3.06 (2H, m), 3.49–3.57 (1H, m), 4.61 (1H, d, J=7 Hz), 5.42 (2H, s), 6.29–6.32 (2H, m), 7.02–7.07 (2H, m), 7.22 (1H, ddd, J=7.5, 7.5, 1 Hz), 7.46 (1H, d, J=7.5 Hz), 7.88 (1H, d, J=7.5 Hz)

MASS (m/z): 426 (M$^+$+1), 76 (bp)

EXAMPLE 58

To a stirred solution of 6-amino-1-(2-chlorobenzyl)-3-isobutyryl-2-propylindole (147 mg) in dichloromethane (2 ml) was added acetic formic anhydride (0.5 ml) at 0° C. The reaction mixture was stirred at 0° C. for 10 minutes, then diluted with dichloromethane. The organic phase was washed with water and brine, dried over magnesium sulfate and evaporated in vacuo. The residue was chromatographed on silica gel eluting with a mixture of ethyl acetate and hexane (1:2) to give crystals which were recrystallized from a mixture of ethyl acetate and hexane to give 1-(2-chlorobenzyl)-6-formamido-3-isobutyryl-2-propylindole (85 mg) as colorless crystals.

mp: 113–115° C.

IR (KBr): 1666, 1647, 1508 cm$^{-1}$

NMR (CDCl$_3$, δ): 1.00, 1.03 (3H, t and t, J=7 Hz), 1.28, 1.30 (6H, d and d, J=7 Hz), 1.54–1.65 (2H, m), 2.99–3.09 (2H, m), 3.47–3.57 (1H, m), 5.43 (2H, d, J=4 Hz), 6.31 (1H, d, J=7.5 Hz), 6.82–7.10 (2H, m), 7.17–7.25 (2H, m), 7.43–7.77 (2H, m), 7.90 (1H, dd, J=10, 7.5 Hz), 8.37–8.58 (1H, m)

MASS (m/z): 397 (M$^+$+1)

EXAMPLE 59

A solution of 3-isobutyryl-1-(2-nitrobenzyl)-2-propylindole-6-carboxamide (316 mg) in methanol (10 ml) was hydrogenated over 10% palladium on carbon at 20° C. for 6 hours. The catalyst was filtered off and the filtrate was evaporated in vacuo. The residue was chromatographed on silica gel eluting with a mixture of methanol and chloroform (1:30) to give an oil which was dissolved in a mixture of chloroform (10 ml) and methanol (20 ml). To this solution was added 10% hydrogen chloride in methanol (0.9 ml), and the mixture was stirred at 20° C. for 1 hour and evaporated in vacuo. The residue was recrystallized from a mixture of methanol and -isopropenyl ether to give 1-(2-aminobenzyl)-

3-isobutyryl-2-propylindole-6-carboxamide hydrochloride (415 mg) as colorless crystals.

mp: 255–257° C.

IR (KBr): 1650, 1550, 1455 cm$^{-1}$

NMR (DMSO-d$_6$, δ): 0.95 (3H, t, J=7 Hz), 1.20 (3H, t, J=7 Hz), 1.46–1.59 (2H, m), 2.96–3.01 (2H, m), 5.67 (2H, s), 5.89 (1H, d, J=7.5 Hz), 6.87 (1H, br t, J=7 Hz), 7.19–7.34 (3H, m), 7.80 (1H, d, J=7.5 Hz), 7.92–7.98 (2H, m), 8.03 (1H, s)

MASS (m/z): 378 (M$^+$+1), 86 (bp)

EXAMPLE 60

To a solution of 1-(2-chlorobenzyl)-3-methoxyacetyl-2-propylindole-6-carboxamide (168 mg) in a mixture of dichloromethane (10 ml) and methanol (0.5 ml) was added 1M solution or boron tribromide in dichloromethane (2.5 ml) at −53° C. The reaction mixture was warmed gradually to −12° C. during 3 hours. Then 1M solution of boron tribromide in dichloromethane (2.5 ml) was added, and the mixture was stirred for 20 minutes at −12° C. The reaction mixture was diluted with water and extracted with 10% methanol in chloroform. The organic phase was washed with aqueous sodium bicarbonate, water and brine, dried over magnesium sulfate and evaporated in vacuo. The residue was crystallized from ethyl acetate and washed with hexane to give 1-(2-chlorobenzyl)-3-hydroxyacetyl-2-propylindole-6-carboxamide (120 mg) as colorless crystals.

mp: 231–233.5° C.

IR (KBr): 3405, 3159, 1673, 1647, 1616, 1395 cm$^{-1}$

NMR (DMSO-d$_6$, δ): 0.94 (3H, t, J=7 Hz), 1.40–1.52 (2H, m), 3.05 (3H, t, J=7 Hz), 4.75 (2H, t, J=6 Hz), 4.90 (1H, t, J=6 Hz), 5.65 (2H, s), 6.22 (1H, d, J=7.5 Hz), 7.18 (1H, d, J=7.5 Hz), 7.27–7.35 (2H, m), 7.58 (1H, d, J=7.5 Hz), 7.81 (1H, d, J=7.5 Hz), 7.92 (2H, d, J=7.5 Hz), 8.01 (1H, s)

MASS (m/z): 385 (M$^+$+1), 86 (bp)

EXAMPLE 61

To a stirred mixture of benzyl 3-isobutyryl-2-propylindole-6-carboxylate (207 mg) and diisopropylethylamine (295 mg) in dichloromethane (6 ml) were added 2-chlorobenzoyl chloride (299 mg) and 4-dimethylaminopyridine (12 mg) at 0° C. The reaction mixture was refluxed for 15 hours. The reaction mixture was cooled to 20° C. and washed with 1N hydrochloric acid, water, saturated sodium bicarbonate, water and brine. The organic phase was dried over sodium sulfate and evaporated in vacuo. The residue was chromatographed on silica gel eluting with a mixture of ethyl acetate and hexane (1:10) to give benzyl 1-(2-chlorobenzoyl)-3-isobutyryl-2-propylindole-6-carboxylate (330 mg) as yellow crystals.

mp: 67.5–70° C.

IR (KBr): 1780, 1710, 1700, 1300 cm$^{-1}$

NMR (CDCl$_3$, δ): 0.99 (3H, t, J=7 Hz), 1.27 (6H, t, J=7 Hz), 1.74 (2H, sextet, J=7 Hz), 3.12 (2H, t, J=7 Hz), 3.39–3.48 (1H, m), 5.25 (2H, s), 7.33–7.45 (8H, m), 7.53–7.58 (2H, m), 7.80 (1H, d, J=7.5 Hz), 7.98–8.05 (1H, m)

MASS (m/z): 502 (M$^+$+1)

EXAMPLE 62

A solution of benzyl 1-(2-chlorobenzoyl)-3-isobutyryl-2-propylindole-6-carboxylate (304 mg) in methanol (6 ml) was hydrogenated over 10% palladium on carbon at 20° C. for 9 hours. The catalyst was filtered off and the filtrate was evaporated in vacuo. The residue was chromatographed on silica gel eluting with a mixture of methanol and chloroform (1:30) to give crystals which were recrystallized From a mixture of ethyl acetate and hexane to give 1-(2-chlorobenzoyl)-3-isobutyryl-2-propylindole-6-carboxylic acid (189 mg) as colorless crystals.

IR (KBr): 1710, 1695, 1980, 1315 cm$^{-1}$

NMR (CDCl$_3$, δ): 0.95 (3H, t, J=7 Hz), 1.27 (6H, t, J=7 Hz), 1.64–1.75 (2H, m), 3.03–3.09 (1H, m), 3.40–3.49 (1H, m), 7.48–7.52 (2H, m), 7.58–7.67 (3H, m), 7.92 (2H, AB, J=8, 7.5 Hz)

EXAMPLE 63

To a stirred solution of 1-(2-chlorobenzyl)-3-formylindole-6-carboxamide (47 mg) in dimethylformamide (1.6 ml) was added chromic anhydride (125 mg) and sulfuric acid (0.05 ml), and the mixture was stirred at 20° C. for 5 hours. The resulting mixture was evaporated in vacuo and the residue was chromatographed on silica gel eluting with a mixture of chloroform and methanol (9:1) to give 6-carbamoyl-1-(2-chlorobenzyl)indole-3-carboxylic acid (8.3 mg) as a solid.

mp: 240° C. (dec.)

NMR (DMSO-d$_6$, δ): 5.64 (2H, s), 6.71 (1H, d, J=8 Hz), 7.26 (1H, t, J=8 Hz), 7.28 (1H, br s), 7.36 (1H, t, J=8 Hz), 7.56 (1H, d, J=8 Hz), 7.78 (1H, d, J=8 Hz), 7.92 (1H, br s), 8.06 (1H, s), 8.07 (1H, d, J=8 Hz), 8.20 (1H, s)

EXAMPLE 64

To a solution of 1-(2-chlorobenzyl)-2-(1-hydroxypropyl)-3-isobutyrylindole-6-carboxamide (19 mg) in acetone (3 ml) was added Jone's reagent until the red color existed continuously. The reaction was quenched by 2-propanol, then the mixture was diluted with ethyl acetate and washed with aqueous sodium bicarbonate and brine. The organic phase was dried over sodium sulfate and evaporated in vacuo. The residue was triturated with diisopropyl ether to give 1-(2-chlorobenzyl)-3-isobutyryl-2-propionylindole-6-carboxamide (9.3 mg).

mp: 145–147° C.

NMR (CDCl$_3$, δ): 1.15 (3H, t, J=7 Hz), 1.33 (6H, d, J=7 Hz), 2.60 (2H, q, J=7 Hz), 3.47 (1H, m), 5.46 (2H, s), 6.50 (1H, d, J=8 Hz), 7.09 (1H, t, J=8 Hz), 7.21 (1H, t, J=8 Hz), 7.42 (1H, d, J=8 Hz), 7.70 (1H, d, J=8 Hz), 7.88 (1H, s), 7.98 (1H, s)

EXAMPLE 65

The following compound was prepared in a similar manner to that of Preparation 45.

3-Chloro-1-(2-chlorobenzyl)-2-propylindole-6-carboxamide mp: 163–166° C.

NMR (CDCl$_3$, δ): 0.95 (3H, t, J=7 Hz), 1.58 (2H, m), 2.73 (2H, t, J=7 Hz), 5.43 (2H, s), 6.19 (1H, d, J=8 Hz), 7.01 (1H, t, J=8 Hz), 7.18 (1H, t, J=8 Hz), 7.43 (1H, d, J=8 Hz), 7.54 (1H, d, J=8 Hz), 7.67 (1H, d, J=8 Hz), 7.82 (1H, s)

EXAMPLE 66

To a stirred solution of methyl 1-(2-bromobenzyl)-2-propylindole-6-carboxamide (52 mg) in a mixture of dichloromethane (3 ml) and pyridine (1 ml) was added pyridinium bromide perbromide (50 mg), and the mixture was stirred at 0° C. for 1.5 hours. The resulting mixture was diluted with ethyl acetate and washed with diluted hydrochloric acid, aqueous sodium bicarbonate and brine, then dried over sodium sulfate and evaporated in vacuo. The residue was triturated with a mixture of hexane and diisopropyl ether to give 3-bromo-1-(2-bromobenzyl)-2-propylindole-6-carboxamide (33 mg) as a solid.

mp: 122–125° C.

NMR (CDCl$_3$, δ): 0.98 (3H, t, J=7 Hz), 1.57 (2H, m), 2.73 (2H, t, J=7 Hz), 5.42 (2H, s) 6.15 (1H, d, J=8 Hz), 7.0–7.16 (2H, m), 7.5–7.65 (3H, m), 7.79 (1H, s)

EXAMPLE 67

The following compounds described in (1) to (2) were prepared in a similar manner to that of Example 42.
(1) 1-(2-Chlorobenzyl)-3-isobutyryl-2-propylindole-6-carbonitrile mp: 130–131° C.

NMR (CDCl$_3$, δ): 1.03 (3H, t, J=7 Hz), 1.30 (6H, d, J=7 Hz), 1.56–1.68 (2H, m), 3.06–3.12 (2H, m), 3.51 (1H, septet, J=7 Hz), 5.46 (2H, s), 6.23 (1H, d, J=8 Hz), 7.08 (1H, t, J=8 Hz), 7.27 (1H, t, J=8 Hz), 7.46–7.52 (3H, m), 8.01 (1H, d, J=8 Hz)
(2) 9-(2-Chlorobenzyl)-8-oxo-5,6,7,8-tetrahydrocarbazole-2-carbonitrile mp: 173–176° C.

NMR (CDCl$_3$, δ): 2.29 (2H, m), 2.69 (2H, t, J=7 Hz), 3.08 (2H, t, J=7 Hz), 5.94 (2H, s), 6.30 (1H, d, J=8 Hz), 7.02 (1H, t, J=8 Hz), 7.19 (1H, t, J=8 Hz), 7.38 (1H, d, J=8 Hz), 7.42 (1H, d, J=8 Hz), 7.54 (1H, s), 7.78 (1H, d, J=8 Hz)

EXAMPLE 68

To a solution of 1-(2-chlorobenzyl)-3-isobutyryl-2-propylindole-6-carbonitrile (70 mg) in a mixture of methanol (2 ml) and tetrahydrofuran (2 ml) was added sodium borohydride (21 mg) at 25° C. After stirred at 25° C. for 2 hours, the reaction mixture was partitioned between ethyl acetate and 1N hydrochloric acid. The organic layer was washed with water and brine, dried over magnesium sulfate, and evaporated in vacuo. The residue was crystallized from diisopropyl ether to give 1-(2-chlorobenzyl)-3-(1-hydroxy-2-methylpropyl)-2-propylindole-6-carbonitrile (28 mg) as pale yellow crystals.

mp: 126–127° C.

NMR (CDCl$_3$, δ): 0.76 (3H, d, J=7 Hz), 0.98 (3H, t, J=7 Hz), 1.22 (3H, d, J=7 Hz), 1.50–1.64 (2H, m), 1.87 (1H, d, J=2 Hz), 2.32–2.44 (2H, m), 2.63–2.80 (2H, m), 4.58 (1H, dd, J=2, 8 Hz), 5.38 (2H, s), 6.15 (1H, d, J=8 Hz), 7.05 (1H, t, J=8 Hz), 7.22 (1H, t, J=8 Hz), 7.32 (1H, d, J=8 Hz), 7.38 (1H, s), 7.46 (1H, d, J=8 Hz), 7.91 (1H, d, J=8 Hz)

EXAMPLE 69

The following compound was prepared in a similar manner to that of Example 68.
1-(2-Chlorobenzyl)-2-ethyl-3-(1-hydroxy-2-methylpropyl) indole-6-carboxamide mp: 169–172° C.

NMR (CDCl$_3$, δ): 0.78 (3H, d, J=7 Hz), 1.17 (3H, t, J=7 Hz), 1.23 (3H, d, J=7 Hz), 2.41 (1H, m), 2.74 (2H, m), 4.60 (1H, m), 5.43 (2H, s), 6.14 (1H, d, J=8 Hz), 6.98 (1H, t, J=8 Hz), 7.17 (1H, t, J=8 Hz), 7.4–7.5 (2H, m), 7.76 (1H, s), 7.85 (1H, d, J=8 Hz)

EXAMPLE 70

To a suspension of 3-acetyl-1-(2-chlorobenzyl)-2-propylindole-6-carboxamide (36.5 mg) in ethanol (5 ml) was added hydroxylamine hydrochloride (70 mg) and sodium acetate (200 mg), and the mixture was heated in a sealed tube at 100° C. The reaction was evaporated in vacuo, then the residue was diluted with ethyl acetate and washed with water and brine. The organic phase was dried over sodium sulfate and evaporated in vacuo. The residue was triturated with diisopropyl ether to give 1-(2-chlorobenzyl)-3-(1-hydroxyiminoethyl)-2-propylindole-6-carboxamide (32.7 mg).

mp: 212–216° C.

NMR (CDCl$_3$, δ): 0.94 (3H, t, J=7 Hz), 1.56 (2H, m), 2.39 (3H, s), 2.80 (2H, m), 5.45 (2H, s), 6.21 (1H, d, J=8 Hz), 6.99 (1H, t, J=8 Hz), 7.20 (1H, t, J=8 Hz), 7.42 (1H, d, J=8 Hz), 7.50 (1H, m), 7.70–7.78 (2H, m)

EXAMPLE 71

1-(2-Aminobenzyl)-3-isobutyryl-2-propylindole-6-carboxamide hydrochloride (111 mg) was dissolved in chloroform, and the solution was washed with 1N aqueous sodium hydroxide, dried over magnesium sulfate and evaporated in vacuo. The residue was dissolved in chloroform (3 ml), and then methyl isocyanate (1.5 ml) was added at 0° C. After stirred at 20° C. for 2 hours, the mixture was evaporated in vacuo. The residue was dissolved in a mixture of ethyl acetate and tetrahydrofuran, and the solution was washed with water and brine, dried over magnesium sulfate and evaporated in vacuo. The crystalline residue was recrystallized from a mixture of 1,4-dioxane and hexane to give 3-isobutyryl-1-[2-(3-methylureido)benzyl]-2-propylindole-6-carboxamide (74 mg) as colorless crystals.

mp: 222–223° C.

IR (KBr): 1648, 1617, 1557 cm$^{-1}$

NMR (DMSO-d$_6$, δ): 0.91 (3H, t, J=7 Hz), 1.18 (6H, d, J=7 Hz), 1.42–1.50 (2H, m), 2.71 (3H, d, J=5 Hz), 2.92–3.00 (2H, m), 3.50–3.56 (1H, m), 5.48 (2H, s), 5.99 (1H, d, J=8 Hz), 6.34–6.39 (1H, m), 6.86 (1H, t, J=7.5 Hz), 7.18 (1H, t, J=7.5 Hz), 7.28 (1H, s), 7.55 (1H, t, J=7.5 Hz), 7.78 (1H, d, J=7.5 Hz), 7.92–7.97 (3H, m), 8.21 (1H, s)

MASS (m/z): 435 (M$^+$+1), 86 (bp)

EXAMPLE 72

To a solution of methyl 1-(2-chlorobenzyl)-2-propylindole-6-carboxylate (200 mg) in trifluoroacetic acid (2 ml) was added concentrated nitric acid (0.3 ml) at 0° C. After stirred at 0° C. for 30 minutes, the reaction mixture was partitioned between ethyl acetate and water. The organic layer was washed with aqueous sodium bicarbonate, water and brine, dried over magnesium sulfate, and evaporated in vacuo. The residue was purified by preparative thin layer chromatography on silica gel eluting with a mixture of ethyl acetate and hexane (1:3) to give methyl 1-(2-chlorobenzyl)-3-nitro-2-propylindole-6-carboxylate (73 mg) as pale yellow crystals.

NMR (CDCl$_3$, δ): 1.04 (3H, t, J=7 Hz), 1.68 (2H, sextet, J=7 Hz), 3.14–3.18 (2H, m), 3.91 (3H, s), 5.13 (2H, s), 6.32 (1H, d, J=8 Hz), 7.08 (1H, t, J=8 Hz), 7.27 (1H, t, J=8 Hz), 7.48 (1H, d, J=8 Hz), 7.98 (1H, s), 8.08 (1H, d, J=8 Hz), 8.43 (1H, d, J=8 Hz)

EXAMPLE 73

The following compounds described in (1) to (44) were prepared in a similar manner to that of Example 1.
(1) Methyl 1-(2-chlorobenzyl)-2-(3-methoxycarbonylpropyl)indole-6-carboxylate NMR (CDCl$_3$, δ): 2.04 (2H, m), 2.88 (2H, t, J=7 Hz), 2.69 (2H, t, J=7 Hz), 3.62 (3H, s), 3.89 (3H, s), 5.43 (2H, s), 6.14

(1H, d, J=8 Hz), 6.46 (1H, s), 7.01 (1H, t, J=8 Hz), 7.18 (1H, t, J=8 Hz), 7.42 (1H, d, J=8 Hz), 7.59 (1H, d, J=8 Hz), 7.80 (1H, d, J=8 Hz), 7.90 (1H, s)

(2) Methyl 1-(2-chlorobenzyl)-2-(2-methoxycarbonylethyl) indole-6-carboxylate

NMR (CDCl$_3$, δ): 2.77 (2H, m), 2.98 (2H, m), 3.69 (3H, s), 3.88 (3H, s), 5.45 (2H, s), 6.16 (1H, d, J=8 Hz), 6.41 (1H, s), 7.02 (1H, t, J=8 Hz), 7.19 (1H, t, J=8 Hz), 7.42 (1H, d, J=8 Hz), 7.60 (1H, d, J=8 Hz), 7.81 (1H, d, J=8 Hz), 7.91 (1H, s)

(3) Methyl 1-(2-chlorobenzyl)-3-isobutyryl-2-propylindole-7-carboxylate

NMR (CDCl$_3$, δ): 1.02 (3H, t, J=7 Hz), 1.79 (6H, d, J=7 Hz), 1.63 (2H, m), 3.01 (2H, m), 3.52 (1H, m), 3.56 (3H, s), 5.61 (2H, s), 6.08 (1H, d, J=8 Hz), 6.98 (1H, t, J=8 Hz), 7.17 (1H, t, J=8 Hz), 7.2–7.45 (3H, m), 8.12 (1H, d, J=8 Hz)

(4) Methyl 1-(2-chlorobenzyl)-3-isobutyryl-2-propylindole-5-carboxylate

NMR (CDCl$_3$, δ): 1.03 (3H, t, J=8 Hz), 1.34 (6H, d, J=8 Hz), 1.62 (2H, sextet, J=8 Hz), 3.06–3.10 (2H, m), 3.64 (1H, septet, J=8 Hz), 3.96 (3H, s), 5.47 (2H, s), 6.26 (1H, d, J=8 Hz), 7.06 (1H, t, J=8 Hz), 7.20 (1H, t, J=8 Hz), 7.25 (1H, d, J=8 Hz), 7.47 (1H, dd, J=1, 8 Hz), 7.92 (1H, d, J=8 Hz), 8.68 (1H, d, J=1 Hz)

(5) Methyl 1-(6-chloro-3,4-methylenedioxybenzyl)-3-isobutyryl-2-propylindole-5-carboxylate NMR (CDCl$_3$, δ): 1.05 (3H, t, J=8 Hz), 1.32 (6H, d, J=8 Hz), 1.62 (2H, sextet, J=8 Hz), 3.06 (2H, t, J=8 Hz), 3.63 (1H, septet, J=8 Hz), 3.96 (3H, s), 5.36 (2H, s), 5.74 (1H, s), 5.88 (2H, s), 6.92 (1H, s), 7.20 (1H, d, J=10 Hz), 7.82 (1H, d, J=10 Hz), 8.76 (1H, s)

(6) Methyl 1-(2-chlorobenzyl)-2-propylindole-4-carboxylate

NMR (CDCl$_3$, δ): 1.01 (3H, t, J=7 Hz), 1.78 (2H, m), 2.67 (2H, t, J=7 Hz), 3.99 (3H, s), 5.42 (2H, s), 6.18 (1H, d, J=8 Hz), 7.01 (1H, t, J=8 Hz), 7.03 (1H, s), 7.11 (1H, t, J=8 Hz), 7.18 (1H, t, J=8 Hz), 7.30 (1H, d, J=8 Hz), 7.43 (1H, d, J=8 Hz), 7.89 (1H, d, J=8 Hz)

(7) Methyl 9-(2-chlorobenzyl)-8-oxo-5,6,7,8-tetrahydrocarbazole-2-carboxylate

NMR (CDCl$_3$, δ): 2.27 (2H, m), 2.67 (2H, t, J=7 Hz), 3.11 (2H, t, J=7 Hz), 3.90 (3H, s), 5.95 (2H, s), 6.25 (1H, d, J=8 Hz), 6.98 (1H, t, J=8 Hz), 7.15 (1H, t, J=8 Hz), 7.40 (1H, d, J=8 Hz), 7.74 (1H, d, J=8 Hz), 7.84 (1H, d, J=8 Hz), 7.99 (1H, s)

(8) Methyl 9-(6-chloro-3,4-methylenedioxybenzyl)-8-oxo-5,6,7,8-tetrahydrocarbazole-2-carboxylate NMR (CDCl$_3$, δ): 2.18 (2H, m), 2.63 (2H, t, J=7 Hz), 3.07 (2H, t, J=7 Hz), 3.84 (3H, s), 5.68 (1H, s), 5.83 (2H, s), 5.96 (2H, s), 7.18 (1H, s), 7.84 (1H, d, J=8 Hz), 7.92 (1H, d, J=8 Hz), 8.03 (1H, s)

(9) Methyl 1-(4-bromo-2-chlorobenzyl)-3-isobutyryl-2-propylindole-6-carboxylate mp: 65–67° C.

IR (KBr): 1715, 1705, 1656, 1456, 1433 cm$^{-1}$

NMR (CDCl$_3$, δ): 1.03 (3H, t, J=7 Hz), 1.30 (6H, d, J=7 Hz), 1.52–1.64 (2H, m), 2.99–3.05 (2H, m), 3.51–3.60 (1H, m), 3.92 (3H, s), 5.45 (2H, s), 6.09 (1H, d, J=7.5 Hz), 7.18 (1H, d, J=7.5 Hz), 7.66 (1H, s), 7.90 (1H, s), 7.99 (2H, s)

MASS (m/z): 492 (M$^+$+2)

(10) 1-(2-Acetamidobenzyl)-3-isobutyryl-2-propylindole-6-carboxamide mp: 235–236° C.

IR (KBr): 1693, 1656, 1457 cm$^{-1}$

NMR (CDCl$_3$, δ): 0.91 (3H, t, J=7 Hz), 1.18 (6H, d, J=7 Hz), 1.39–1.50 (2H, m), 2.17 (3H, s), 2.92–2.99 (2H, m), 3.50–3.59 (1H, m), 5.49 (2H, s), 6.07 (1H, d, J=7.5 Hz), 7.00 (1H, t, J=7.5 Hz), 7.21–7.29 (2H, m), 7.39 (1H, d, J=7.5 Hz), 7.79 (1H, d, J=7.5 Hz), 7.92–7.96 (3H, m), 9.85 (1H, s)

MASS (m/z): 420 (M$^+$+1), 86 (bp)

(11) Methyl 1-(2-chlorobenzyl)-3-formylindole-6-carboxylate

NMR (CDCl$_3$, δ): 3.93 (3H, s), 5.52 (2H, s), 6.88 (1H, dd, J=1, 8 Hz), 7.21 (1H, dt, J=1, 8 Hz), 7.32 (1H, dt, J=1, 8 Hz), 7.49 (1H, dd, J=1, 8 Hz), 7.82 (1H, s), 8.02 (1H, dd, J=1, 8 Hz), 8.13 (1H, d, J=1 Hz), 8.36 (1H, d, J=8 Hz), 10.0 (1H, s)

(12) Methyl 3-acetyl-1-(2-chlorobenzyl)-2-methylindole-6-carboxylate

This compound was used immediately without purification.

(13) Methyl 1-(2-chlorobenzyl)-2-methyl-3-propionylindole-6-carboxylate

NMR (CDCl$_3$, δ): 1.31 (3H, t, J=7 Hz), 2.70 (3H, s), 3.09 (2H, q, J=7 Hz), 3.90 (3H, s), 5.50 (2H, s), 6.22 (1H, d, J=8 Hz), 7.04 (1H, t, J=8 Hz), 7.24 (1H, t, J=8 Hz), 7.46 (1H, d, J=8 Hz), 7.92–7.98 (2H, m), 8.08 (1H, d, J=8 Hz)

(14) Methyl 1-(2-chlorobenzo[b]thiophen-3-ylmethyl)-3-isobutyryl-2-methylindole-6-carboxylate NMR (DMSO-d$_6$, δ): 1.14 (6H, d, J=7 Hz), 2.72 (3H, s), 3.48 (1H, m), 3.81 (3H, s), 5.91 (2H, s), 7.3–7.5 (3H, m), 7.80 (1H, d, J=8 Hz), 7.98 (1H, d, J=8 Hz), 8.06 (1H, d, J=8 Hz), 8.19 (1H, s)

(15) Methyl 1-(benzothiazol-2-ylmethyl)-2-ethyl-3-isobutyrylindole-6-carboxylate NMR (CDCl$_3$, δ): 1.28 (3H, t, J=7 Hz), 1.30 (6H, d, J=7 Hz), 3.24 (2H, q, J=7 Hz), 3.53 (1H, m), 3.91 (3H, s), 5.82 (2H, s), 7.25–7.53 (2H, m), 7.72 (1H, m), 7.8–8.1 (3H, m), 8.18 (1H, s)

(16) Methyl 1-(benzo[b]thiophen-5-ylmethyl)-3-isobutyryl-2-propylindole-6-carboxylate NMR (CDCl$_3$, δ): 1.02 (3H, t, J=7 Hz), 1.32 (6H, d, J=7 Hz), 1.62 (2H, m), 3.13 (2H, m), 3.57 (1H, m), 3.87 (3H, s), 5.57 (2H, s), 7.03 (1H, d, J=8 Hz), 7.18 (1H, d, J=6 Hz), 7.29 (1H, s), 7.44 (1H, d, J=6 Hz), 7.79 (1H, d, J=8 Hz), 7.94 (2H, s), 8.02 (1H, s)

(17) Methyl 1-allyl-3-isobutyryl-2-propylindole-6-carboxylate

NMR (CDCl$_3$, δ): 1.07 (3H, t, J=7 Hz), 1.28 (6H, d, J=7 Hz), 1.69 (2H, m), 3.12 (2H, m), 3.54 (1H, m), 3.94 (3H, s), 4.84 (2H, m), 4.87 (1H, m), 5.22 (1H, m), 5.98 (1H, m), 7.89 (1H, d, J=8 Hz), 7.94 (1H, d, J=8 Hz), 8.04 (1H, s)

(18) Methyl 1-(2-chlorobenzyl)-3-isobutyryl-2-(1-propenyl)indole-6-carboxylate

NMR (CDCl$_3$, δ): 1.23 (6H, d, J=7 Hz), 1.93 (3H, d, J=7 Hz), 3.51 (1H, m), 3.89 (3H, s), 5.50 (2H, s), 6.41 (1H, m), 6.42 (1H, d, J=8 Hz), 6.73 (1H, d, J=16 Hz), 7.07 (1H, t, J=8 Hz), 7.23 (1H, t, J=8 Hz), 7.47 (1H, d, J=8 Hz), 7.89 (1H, s), 7.95 (1H, d, J=8 Hz), 8.18 (1H, d, J=8 Hz)

(19) Methyl 2-(1-acetoxypropyl)-1-(2-chlorobenzyl)-3-isobutyrylindole-6-carboxylate NMR (CDCl$_3$, δ): 1.04 (3H, t, J=7 Hz), 1.2–1.35 (9H, m), 1.9–2.1 (2H, m), 3.59 (1H, m), 3.89 (3H, s), 5.61 (1H, d, J=17 Hz), 5.79 (1H, d, J=17 Hz), 6.04 (1H, d, J=8 Hz), 6.71 (1H, m), 7.01 (1H, t, J=8 Hz), 7.21 (1H, t, J=8 Hz), 7.47 (1H, d, J=8 Hz), 7.87 (1H, s), 7.92 (1H, d, J=8 Hz), 7.97 (1H, d, J=8 Hz)

(20) Methyl 3-(3,3-dimethylbutanoyl)-1-(2-chlorobenzyl)indole-6-carboxylate

NMR (CDCl$_3$, δ): 1.09 (9H, s), 2.69 (2H, s), 3.93 (3H, s), 5.50 (2H, s), 6.73 (1H, d, J=8 Hz), 7.17 (1H, t, J=8 Hz), 7.28 (1H, t, J=8 Hz), 7.47 (1H, d, J=8 Hz), 7.82 (1H, s), 8.00 (1H, d, J=8 Hz), 8.08 (1H, s), 8.53 (1H, d, J=8 Hz)

(21) Ethyl 1-(2-chlorobenzyl)-3-isobutyryl-2-propylindol-6-ylacetate

IR (Neat): 1730, 1655 cm$^{-1}$

NMR (CDCl$_3$, δ): 1.00 (3H, t, J=7 Hz), 1.20 (3H, t, J=7 Hz), 1.29 (6H, d, J=7 Hz), 1.55–1.65 (2H, m), 3.01–3.08 (2H, m), 3.54–3.60 (1H, m), 3.69 (2H, s), 4.11 (2H, q, J=7 Hz), 5.44 (2H, s), 6.30 (1H, d, J=7.5 Hz), 7.03–7.10 (2H, m), 7.21 (2H, d, J=7.5 Hz), 7.46 (1H, d, J=7.5 Hz), 7.89 (1H, d, J=7.5 Hz)

MASS (m/z): 440 (M$^+$+1), 74 (bp)

(22) Methyl 1-(6-chloro-3,4-methylenedioxybenzyl)-3-isobutyryl-2-propylindol-6-ylacetate mp: 119–120.5° C.

IR (KBr): 1744, 1735, 1732, 1644, 1508 cm$^{-1}$

NMR (CDCl$_3$, δ): 1.03 (3H, t, J=7 Hz), 1.29 (6H, d, J=7 Hz), 1.55–1.65 (2H, m), 3.00–3.07 (2H, m), 3.53–3.61 (1H, m), 3.70 (3H, s), 3.72 (2H, s), 5.33 (2H, s), 5.80 (2H, s), 5.91 (2H, s), 6.93 (1H, s), 7.01 (1H, s), 7.21 (1H, d, J=7.5 Hz), 7.89 (1H, d, J=7.5 Hz)

MASS (m/z): 470 (M$^+$+1), 74 (bp)

(23) Methyl 1-(2-chlorobenzyl)-2-propylindole-6-carboxylate

NMR (CDCl$_3$, δ): 1.02 (3H, t, J=7 Hz), 1.75 (2H, m), 2.62 (2H, t, J=7 Hz), 3.87 (3H, s), 5.42 (2H, s), 6.16 (1H, d, J=8 Hz), 6.42 (1H, s), 7.01 (1H, t, J=8 Hz), 7.19 (1H, t, J=8 Hz), 7.42 (1H, t, J=8 Hz), 7.58 (1H, t, J=8 Hz), 7.79 (1H, d, J=8 Hz), 8.92 (1H, s)

(24) Methyl 1-(2-bromobenzyl)-2-propylindole-6-carboxylate

NMR (CDCl$_3$, δ): 0.99 (3H, t, J=7 Hz), 1.74 (2H, m), 2.59 (2H, t, J=7 Hz), 3.88 (3H, s), 5.37 (2H, s), 6.12 (1H, d, J=8 Hz), 6.42 (1H, s), 7.0–7.15 (2H, m), 7.52–7.65 (2H, m), 7.79 (1H, d, J=8 Hz), 7.89 (1H, s)

(25) Methyl 2-acetyl-1-(2-chlorobenzyl)-3-methylindole-6-carboxylate

NMR (CDCl$_3$, δ): 2.61 (3H, s), 2.71 (3H, s), 3.90 (3H, s), 5.82 (2H, s), 6.19 (1H, d, J=8 Hz), 6.97 (1H, t, J=8 Hz), 7.14 (1H, t, J=8 Hz), 7.41 (1H, d, J=8 Hz), 7.79 (1H, d, J=8 Hz), 7.86 (1H, d, J=8 Hz), 7.99 (1H, s)

(26) Methyl 2-chloro-1-(2-chlorobenzyl)-3-ethylindole-6-carboxylate

NMR (CDCl$_3$, δ): 1.29 (3H, t, J=7 Hz), 2.83 (2H, q, J=7 Hz), 3.90 (3H, s), 5.50 (2H, s), 6.29 (1H, d, J=8 Hz), 7.04 (1H, t, J=8 Hz), 7.19 (1H, t, J=8 Hz), 7.42 (1H, d, J=8 Hz), 7.61 (1H, d, J=8 Hz), 7.83 (1H, d, J=8 Hz), 7.90 (1H, s)

(27) Methyl 1-(2-chlorobenzyl)-2-propionyl-3-propylindole-6-carboxylate

NMR (CDCl$_3$, δ): 1.07 (3H, t, J=7 Hz), 1.17 (3H, t, J=7 Hz), 1.78 (2H, m), 2.94 (2H, q, J=7 Hz), 3.09 (2H, m), 3.89 (3H, s), 5.72 (2H, s), 6.23 (1H, d, J=8 Hz), 6.98 (1H, t, J=8 Hz), 7.15 (1H, t, J=8 Hz), 7.39 (1H, d, J=8 Hz), 7.76 (1H, d, J=8 Hz), 7.83 (1H, d, J=8 Hz), 7.96 (1H, s)

(28) Methyl 1-(2-chlorobenzyl)-2-isobutyryl-3-propylindole-6-carboxylate

NMR (CDCl$_3$, δ): 1.03 (3H, t, J=7 Hz), 1.11 (6H, d, J=7 Hz), 1.75 (2H, m), 3.02 (2H, m), 3.35 (1H, m), 3.89 (3H, s), 5.64 (2H, s), 6.28 (1H, d, J=8 Hz), 6.99 (1H, t, J=8 Hz), 7.16 (1H, t, J=8 Hz), 7.38 (1H, d, J=8 Hz), 7.73 (1H, d, J=8 Hz), 7.84 (1H, d, J=8 Hz), 7.96 (1H, s)

(29) Methyl 1-(2-chlorobenzyl)-3-(3-oxo-1-butenyl)indole-6-carboxylate

NMR (CDCl$_3$, δ): 2.38 (3H, s), 3.93 (3H, s), 5.48 (2H, s), 6.7–6.8 (2H, m), 7.17 (1H, t, J=8 Hz), 7.28 (1H, t, J=8 Hz), 7.47 (1H, d, J=8 Hz), 7.54 (1H, s), 7.74 (1H, d, J=15 Hz), 7.96 (1H, s), 8.11 (1H, s)

(30) Methyl 4-(2-chlorobenzyl)-3-oxo-1,2,3,4-tetrahydrocyclopent[b]indole-6-carboxylate NMR (CDCl$_3$, δ): 3.06 (2H, m), 3.17 (2H, m), 3.92 (3H, s), 5.72 (2H, s), 6.59 (1H, d, J=8 Hz), 7.06 (1H, t, J=8 Hz), 7.19 (1H, t, J=8 Hz), 7.42 (1H, d, J=8 Hz), 7.78 (1H, d, J=8 Hz), 7.87 (1H, d, J=8 Hz), 8.04 (1H, s)

(31) Methyl 4-(6-chloro-3,4-methylenedioxybenzyl)-3-oxo-1,2,3,4-tetrahydrocyclopent[b]indole-6-carboxylate NMR (CDCl$_3$, δ): 3.06 (3H, m), 3.14 (2H, m), 3.94 (3H, s), 5.60 (2H, s), 5.88 (2H, s), 6.11 (1H, s), 6.88 (1H, s), 7.76 (1H, d, J=8 Hz), 7.86 (1H, d, J=8 Hz), 8.09 (1H, s)

(32) 1-(2-Chlorobenzyl)-3-cyclopropanecarbonyl-2-propylindole-6-carboxamide mp: 162–163.5° C.

IR (KBr): 1675, 1612, 1444, 1383 cm$^{-1}$

NMR (DMSO-d$_6$, δ): 0.90 (3H, t, J=7 Hz), 1.08 (4H, d, J=7 Hz), 1.48 (2H, sextet, J=7 Hz), 2.65–2.72 (1H, m), 3.00 (2H, t, J=7 Hz), 5.62 (2H, s), 6.21 (1H, d, J=8 Hz), 7.18 (1H, t, J=8 Hz), 7.32 (1H, t, J=8 Hz), 7.58 (1H, d, J=8 Hz), 7.80 (1H, d, J=8 Hz), 7.93 (1H, s), 8.01 (1H, s), 8.10 (1H, d, J=7 Hz)

MASS (m/z): 395 (M$^+$+1), 74 (bp)

(33) 1-(6-Chloro-3,4-methylenedioxybenzyl)-3-cyclopropanecarbonyl-2-propylindole-6-carboxamide mp: 162–163.5° C.

IR (KBr): 1675, 1612, 1444, 1383 cm$^{-1}$

NMR (DMSO-d$_6$, δ): 0.90 (3H, t, J=7 Hz), 1.08 (4H, d, J=7 Hz), 1.48 (2H, sextet, J=7 Hz), 2.65–2.72 (1H, m), 3.00 (2H, t, J=7 Hz), 5.62 (2H, s), 6.21 (1H, d, J=8 Hz), 7.18 (1H, t, J=8 Hz), 7.32 (1H, t, J=8 Hz), 7.58 (1H, d, J=8 Hz), 7.80 (1H, d, J=8 Hz), 7.93 (1H, s), 8.01 (1H, s), 8.10 (1H, d, J=7 Hz)

MASS (m/z): 395 (M$^+$+1), 74 (bp)

(34) 1-(2-Chlorobenzyl)-3-cyclobutanecarbonyl-2-propylindole-6-carboxamide mp: 162–165° C.

IR (KBr): 1660, 1654, 1445, 1437 cm$^{-1}$

NMR (CDCl$_3$, δ): 1.02 (3H, t, J=7 Hz), 1.62 (2H, sextet, J=7 Hz), 1.95–2.14 (2H, m), 2.35–2.52 (4H, m), 3.05–3.10 (2H, m), 4.05 (1H, quintet, J=7 Hz), 5.50 (2H, s), 6.22 (1H, d, J=7.5 Hz), 7.04 (1H, t, J=7.5 Hz), 7.21 (1H, t, J=7.5 Hz), 7.47 (1H, d, J=7.5 Hz), 7.63 (1H, d, J=7.5 Hz), 7.82 (1H, s), 7.97 (1H, d, J=7.5 Hz)

MASS (m/z): 409 (M$^+$+1), 74 (bp)

(35) 1-(6-Chloro-3,4-methylenedioxybenzyl)-3-cyclobutanecarbonyl-2-propylindole-6-carboxamide mp: 240–241° C.

IR (KBr): 1658, 1636, 1503, 1482, 1451 cm$^{-1}$

NMR (DMSO-d$_6$, δ): 0.94 (3H, t, J=7 Hz), 1.49 (2H, sextet, J=7 Hz), 1.79–1.90 (1H, m), 1.96–2.07 (1H, m), 2.24–2.33 (4H, m), 3.03 (2H, t, J=7 Hz), 4.07 (1H, quintet, J=7 Hz), 5.51 (2H, s), 5.65 (1H, s), 6.00 (2H, s), 7.24 (1H, s), 7.31 (1H, br s), 7.79 (1H, d, J=7.5 Hz), 7.94 (1H, br s), 7.95 (1H, d, J=7.5 Hz), 8.00 (1H, s)

MASS (m/z): 453 (M$^+$+1), 85 (bp)

(36) 1-(2-Chlorobenzyl)-3-cyclopentanecarbonyl-2-propylindole-6-carboxamide mp: 201.5–202.5° C.

IR (KBr): 1654, 1607, 1447, 1437, 1387 cm$^{-1}$

NMR (CDCl$_3$, δ): 1.02 (3H, t, J=7 Hz), 1.59–1.82 (6H, m), 1.99–2.07 (4H, m), 3.02–3.09 (2H, m), 3.79 (1H, quintet, J=7 Hz), 5.52 (2H, s), 6.23 (1H, d, J=7.5 Hz), 7.05 (1H, t, J=7.5 Hz), 7.22 (1H, t, J=7.5 Hz), 7.47 (1H, d, J=7.5 Hz), 7.63 (1H, d, J=7.5 Hz), 7.86 (1H, s), 8.04 (1H, d, J=7.5 Hz)

MASS (m/z): 423 (M$^+$+1), 74 (bp)

(37) 1-(6-Chloro-3,4-methylenedioxybenzyl)-3-cyclopentanecarbonyl-2-propylindole-6-carboxamide
mp: 236–237° C.
IR (KBr): 1662, 1506, 1477 cm$^{-1}$
NMR (DMSO-d$_6$, δ): 0.93 (3H, t, J=7 Hz), 1.40–1.50 (2H, m), 1.61–1.68 (4H, m), 1.81–1.95 (4H, m), 3.00 (2H, t, J=7 Hz), 3.73–3.82 (1H, m), 5.50 (2H, s), 5.64 (1H, s), 6.00 (2H, s), 7.24 (1H, s), 7.30 (1H, br s), 7.80 (1H, d, J=7.5 Hz), 7.95 (1H, br s), 8.00 (1H, d, J=7.5 Hz), 8.01 (1H, s)
MASS (m/z): 467 (M$^+$+1), 85 (bp)

(38) 1-(2-Chlorobenzyl)-3-cyclohexanecarbonyl-2-propylindole-6-carboxamide
mp: 208–210° C.
IR (KBr): 1686, 1625, 1609, 1444, 1410 cm$^{-1}$
NMR (DMSO-d$_6$, δ): 0.90 (3H, t, J=7 Hz), 1.19–1.30 (1H, m), 1.39–1.49 (6H, m), 1.67–1.93 (5H, m), 2.99 (2H, t, J=7 Hz), 3.18–3.27 (1H, m), 5.61 (2H, s), 6.19 (1H, d, J=7.5 Hz), 7.18 (1H, t, J=7.5 Hz), 7.29 (1H, s), 7.32 (1H, t, J=7.5 Hz), 7.58 (1H, d, j=7.5 Hz), 7.80 (1H, d, J=7.5 Hz), 7.90 (2H, d, J=7.5 Hz), 8.00 (1H, s)
MASS (m/z): 437 (M$^+$+1), 85 (bp)

(39) 1-(6-Chloro-3,4-methylenedioxybenzyl)-3-cyclohexanecarbonyl-2-propylindole-6-carboxamide
mp: 209–211° C.
IR (KBr): 1623, 1611, 1506, 1391 cm$^{-1}$
NMR (DMSO-d$_6$, δ): 0.93 (3H, t, J=7 Hz), 1.20–1.28 (1H, m), 1.39–1.51 (6H, m), 1.68–1.92 (5H, m), 2.96–3.01 (2H, m), 3.19–3.27 (1H, m), 5.52 (2H, s), 5.64 (1H, s), 6.00 (2H, s), 7.24 (1H, s), 7.31 (1H, br s), 7.85 (2H, AB, J=7.5, 7.5 Hz), 7.96 (1H, br s), 8.01 (1H, s)
MASS (m/z): 481 (M$^+$+1), 85 (bp)

(40) 1-(2-Chlorobenzyl)-3-(3-methyl-2-butenoyl)-2-propylindole-6-carboxamide
mp: 187–188° C.
IR (KBr): 1680, 1648, 1614, 1598, 1446, 1384 cm$^{-1}$
NMR (DMSO-d$_6$, δ): 0.90 (3H, t, J=7 Hz), 1.49 (2H, sextet, J=7 Hz), 2.01 (3H, s), 2.10 (3H, s), 2.99 (2H, t, J=7 Hz), 5.61 (2H, s), 6.19 (1H, d, J=7.5 Hz), 6.66 (1H, s), 7.19 (1H, t, J=7.5 Hz), 7.29 (1H, br s), 7.32 (1H, t, J=7.5 Hz), 7.58 (1H, d, J=7.5 Hz), 7.78 (1H, d, J=7.5 Hz), 7.90 (1H, br s), 7.97 (2H, d, J=7.5 Hz)
MASS (m/z): 409 (M$^+$+1), 85 (bp)

(41) 1-(6-Chloro-3,4-methylenedioxybenzyl)-3-(3-methyl-2-butenoyl)-2-propylindole-6-carboxamide
mp: 227–229° C.
IR (KBr): 1654, 1606, 1505, 1482, 1449, 1388 cm$^{-1}$
NMR (DMSO-d$_6$, δ): 0.94 (3H, t, J=7 Hz), 1.50 (2H, sextet, J=7 Hz), 2.01 (3H, s), 2.09 (3H, s), 3.00 (2H, t, J=7 Hz), 5.50 (2H, s), 5.67 (1H, s), 6.00 (2H, s), 6.66 (1H, s), 7.25 (1H, s), 7.30 (1H, br s), 7.77 (1H, d, J=7.5 Hz), 7.91–7.99 (3H, m)
MASS (m/z): 453 (M$^+$+1), 85 (bp)

(42) 1-(2-Chlorobenzyl)-3-(3-methoxybutanoyl)-2-propylindole-6-carboxamide
mp: 155–157° C.
IR (KBr): 1656, 1610, 1447, 1437, 1389 cm$^{-1}$
NMR (CDCl$_3$, δ): 1.03 (3H, t, J=7 Hz), 1.34 (3H, d, J=7 Hz), 1.63 (2H, sextet, J=7 Hz), 3.01–3.09 (3H, m), 3.41 (3H, s), 3.47 (1H, dd, J=16, 7 Hz), 4.14 (1H, sextet, J=7 Hz), 5.51 (2H, s), 6.22 (1H, dd, J=7.5, 1 Hz), 7.05 (1H, ddd, J=7.5, 7.5, 1 Hz), 7.23 (1H, ddd, J=7.5, 7.5, 1 Hz), 7.46 (1H, dd, J=7.5, 1 Hz), 7.62 (1H, dd, J=7.5, 1 Hz), 7.76 (1H, d, J=1 Hz), 8.09 (1H, d, J=7.5 Hz)
MASS (m/z): 427 (M$^+$+1), 74 (bp)

(43) 1-(6-Chloro-3,4-methylenedioxybenzyl)-3-(3-methoxybutanoyl)-2-propylindole-6-carboxamide
mp: 190–192.5° C.
IR (KBr): 1654, 1652, 1608, 1505, 1482 cm$^{-1}$
NMR (CDCl$_3$, δ): 1.04 (3H, t, J=7 Hz), 1.33 (3H, d, J=7 Hz), 1.62 (2H, sextet, J=7 Hz), 3.00–3.09 (3H, m), 3.40 (3H, s), 3.45 (1H, dd, J=16, 7 Hz), 4.12 (1H, sextet, J=7 Hz), 5.40 (2H, s), 5.70 (1H, s), 5.90 (2H, s), 6.91 (1H, s), 7.61 (1H, d, J=7.5 Hz), 7.88 (1H, s), 8.08 (1H, d, J=7.5 Hz)
MASS (m/z): 471 (M$^+$+1), 74 (bp)

(44) 3-Acetyl-6-chloro-1-(2-chlorobenzyl)indole
NMR (CDCl$_3$, δ): 2.49 (3H, s), 5.41 (2H, s), 6.75 (1H, d, J=8 Hz), 7.18 (1H, t, J=8 Hz), 7.19 (1H, t, J=8 Hz), 7.2–7.33 (3H, m), 7.48 (1H, d, J=8 Hz), 7.72 (1H, s), 8.33 (1H, d, J=8 Hz)

EXAMPLE 74

The following compounds described in (1) to (43) were prepared in a similar manner to that of Example 2.

(1) 9-(2-Chlorobenzyl)-oxo-5,6,7,8-tetrahydrocarbazole-2-carboxylic acid
NMR (CDCl$_3$, δ): 2.24 (2H, m), 2.63 (2H, t, J=7 Hz), 2.88 (2H, t, J=7 Hz), 5.47 (2H, s), 6.36 (1H, d, J=8 Hz), 7.09 (1H, t, J=8 Hz), 7.26 (1H, t, J=8 Hz), 7.47 (1H, d, J=8 Hz) 8.02 (1H, s), 8.04 (1H, d, J=8 Hz), 8.37 (1H, d, J=8 Hz)

(2) 4-(2-Chlorobenzyl)-1-oxo-1,2,3,4-tetrahydrocyclopent[b]indole-6-carboxylic acid
NMR (DMSO-d$_6$, δ): 2.87 (2H, m), 3.03 (2H, m), 5.64 (2H, s), 6.93 (1H, d, J=8 Hz), 7.29 (1H, t, J=8 Hz), 7.37 (1H, t, J=8 Hz), 7.58 (1H, d, J=8 Hz), 7.78 (1H, d, J=8 Hz), 7.83 (1H, d, J=8 Hz), 8.05 (1H, s)

(3) 1-(2-Chlorobenzyl)-3-isobutyryl-2-propylindole-7-carboxylic acid
NMR (CDCl$_3$, δ):1.03 (3H, t, J=7 Hz), 1.29 (6H, d, J=7 Hz), 1.64 (2H, m), 3.03 (2H, m), 3.56 (1H, m), 5.75 (2H, s), 6.04 (1H, d, J=8 Hz), 6.96 (1H, t, J=8 Hz), 7.12 (1H, t, J=8 Hz), 7.29 (1H, t, J=8 Hz), 7.33 (1H, d, J=8 Hz), 7.67 (1H, d, J=8 Hz) 8.19 (1H, d, J=8 Hz)

(4) 1-(2-Chlorobenzyl)-3-isobutyryl-2-propylindole-5-carboxylic acid
NMR (DMSO-d$_6$, δ): 0.90 (3H, t, J=8 Hz), 1.19 (6H, d, J=8 Hz), 1.62 (2H, sextet, J=8 Hz), 3.02 (2H, t, J=8 Hz), 3.51 (1H, septet, J=8 Hz), 5.64 (2H, s), 6.28 (1H, d, J=8 Hz), 7.18 (1H, t, J=8 Hz), 7.32 (1H, t, J=8 Hz), 7.50 (1H, d, J=8 Hz), 7.56 (1H, d, J=8 Hz), 7.78 (1H, d, J=8 Hz), 8.58 (1H, s)

(5) 1-(6-Chloro-3,4-methylenedioxybenzyl)-3-isobutyryl-2-propylindole-5-carboxylic acid
NMR (CDCl$_3$, δ): 1.04 (3H, t, J=7 Hz), 1.32 (6H, d, J=7 Hz), 1.62 (2H, sextet, J=7 Hz), 3.06–3.12 (2H, m), 3.66 (1H, septet, J=7 Hz), 5.36 (2H, s), 5.74 (1H, s), 5.90 (2H, s), 6.93 (1H, s), 7.23 (1H, d, J=8 Hz), 7.96 (1H, dd, J=1, 8 Hz), 8.76 (1H, d, J=1 Hz)

(6) 1-(2-Chlorobenzyl)-2-propylindole-4-carboxylic acid
NMR (CDCl$_3$, δ): 1.03 (3H, t, J=7 Hz), 1.80 (2H, m), 2.67 (2H, t, J=7 Hz), 5.43 (2H, s), 6.19 (1H, d, J=8 Hz), 7.03 (1H, t, J=8 Hz), 7.1–7.25 (3H, m), 7.34 (1H, d, J=8 Hz), 7.41 (1H, d, J=8HZ), 7.99 (1H, d, J=8 Hz)

(7) 9-(2-Chlorobenzyl)-8-oxo-5,6,7,8-tetrahydrocarbazole-2-carboxylic acid
NMR (CDCl$_3$, δ): 2.28 (2H, m), 2.68 (2H, t, J=7 Hz), 3.13 (2H, t, J=7 Hz), 5.95 (2H, s), 6.27 (1H, d, J=8 Hz), 6.99 (1H, t, J=8 Hz), 7.16 (1H, t, J=8 Hz), 7.42 (1H, d, J=8 Hz), 7.77 (1H, d, J=8 Hz), 7.87 (1H, d, J=8 Hz), 8.03 (1H, s)

(8) 9-(6-Chloro-3,4-methylenedioxybenzyl)-8-oxo-5,6,7,8-tetrahydrocarbazole-2-carboxylic acid
NMR (DMSO-d$_6$, δ): 2.19 (2H, m), 2.63 (2H, t, J=7 Hz), 3.06 (2H, t, J=7 Hz), 5.70 (1H, s), 5.82 (2H, s), 5.96 (2H, s), 7.16 (1H, s), 7.73 (1H, d, J=8 Hz), 7.88 (1H, d, J=8 Hz), 7.98 (1H, s)

(9) 1-(4-Bromo-2-chlorobenzyl)-3-isobutyryl-2-propylindole-6-carboxylic acid
mp: 234–235° C.
IR (KBr): 1677, 1648, 1418 cm$^{-1}$
NMR (CDCl$_3$, δ): 1.04 (3H, t, J=7 Hz), 1.30 (6H, d, J=7 Hz), 1.54–1.64 (2H, m), 3.02–3.08 (2H, m), 3.50–3.61 (1H, m), 5.44 (2H, s), 6.10 (1H, t, J=8 Hz), 7.18 (1H, dd, J=8, 1 Hz), 7.65 (1H, d, J=1 Hz), 7.94–8.05 (3H, m)
MASS (m/z): 476 (M$^+$)

(10) 1-(2-Chlorobenzyl)-3-morpholinoacetyl-2-propylindole-6-carboxylic acid
IR (KBr): 1652, 1441, 1115 cm$^{-1}$
NMR (CDCl$_3$, δ): 1.02 (3H, t, J=7 Hz), 1.60 (2H, sextet, J=7 Hz), 2.74 (4H, t, J=6.5 Hz), 3.03–3.09 (2H, m), 3.86 (4H, t, J=6.5 Hz), 3.93 (2H, s), 5.52 (2H, s), 6.25 (1H, d, J=7.5 Hz), 7.05 (1H, t, J=7.5 Hz), 7.22 (1H, t, J=7.5 Hz), 7.47 (1H, d, J=7.5 Hz), 7.90–8.01 (3H, m)
MASS (m/z): 455 M$^+$−1)

(11) 1-(2-Chlorobenzyl)-3-(N,N-dimethylcarbamoyl)-2-propylindole-6-carboxylic acid
IR (KBr): 1704, 1596, 1219 cm$^{-1}$
NMR (CDCl$_3$, δ): 0.93 (3H, t, J=7 Hz), 1.52–1.63 (2H, m), 2.80–2.90 (2H, m), 3.13 (6H, s), 5.48 (2H, s), 6.30 (1H, d, J=7.5 Hz), 7.04 (1H, t, J=7.5 Hz), 7.20 (1H, t, J=7.5 Hz), 7.44 (1H, d, J=7.5 Hz), 7.50 (1H, d, J=7.5 Hz), 7.91 (1H, d, J=7.5 Hz), 7.96 (1H, s)
MASS (m/z): 399 M$^+$−1)

(12) 1-(2-Chlorobenzyl)-3-morpholinocarbonyl-2-propylindole-6-carboxylic acid
IR (KBr): 3410, 1615, 1540, 1444, 1400 cm$^{-1}$
NMR (DMSO-d$_6$, δ): 0.84 (3H, t, J=7 Hz), 1.39–1.49 (2H, m), 2.76–2.84 (2H, m), 3.56 (6H, br s), 3.68 (2H, br s), 5.52 (2H, s), 6.24 (1H, d, J=7.5 Hz), 7.16 (1H, t, J=7.5 Hz), 7.29 (1H, t, J=7.5 Hz), 7.40 (1H, d, J=7.5 Hz), 7.54 (1H, d, J=7.5 Hz), 7.79 (1H, s), 7.81 (1H, s)
MASS (m/z): 439 (M$^+$−1), 99 (bp)

(13) 1-(2-Chlorobenzyl)-2-propylindole-3,6-dicarboxylic acid
mp: 241–243° C. (dec.)
IR (KBr): 1669, 1525, 1443, 1385 cm$^{-1}$
NMR (DMSO-d$_6$, δ): 0.90 (3H, t, J=7 Hz), 1.44–1.55 (2H, m), 3.12 (2H, t, J=7 Hz), 5.56 (2H, s), 6.22 (1H, d, J=7.5 Hz), 7.17 (1H, t, J=7.5 Hz), 7.30 (1H, t, J=7.5 Hz), 7.57 (1H, d, J=7.5 Hz), 7.79 (1H, s), 8.06 (1H, d, J=7.5 Hz)
MASS (m/z): 370 (M$^+$−1), 99 (bp)

(14) 1-(2-Chlorobenzyl)-2-ethyl-3-formylindole-6-carboxylic acid
mp: 241–242° C. (dec.)
IR (KBr): 1675, 1650, 1295 cm$^{-1}$
NMR (CDCl$_3$, δ): 1.29 (3H, t, J=7 Hz), 3.09 (2H, q, J=7 Hz), 5.52 (2H, s), 6.30 (1H, d, J=7.5 Hz), 7.08 (1H, t, J=7.5 Hz), 7.25 (1H, t, J=7.5 Hz), 7.49 (1H, d, J=7.5 Hz), 7.97 (1H, s), 8.03 (1H, d, J=7.5 Hz), 8.35 (1H, d, J=7.5 Hz), 10.25 (1H, s)
MASS (m/z): 340 (M$^+$−1)

(15) 1-(2-Chlorobenzyl)-3-formylindole-6-carboxylic acid
NMR (DMSO-d$_6$, δ): 5.73 (2H, s), 6.96 (1H, d, J=8 Hz), 7.23–7.4 (2H, m), 7.56 (1H, d, J=8 Hz), 7.89 (1H, d, J=8 Hz), 8.15 (1H, s), 8.21 (1H, s), 8.54 (1H, s), 10.0 (1H, s)

(16) 3-Acetyl-1-(2-chlorobenzyl)-2-methylindole-6-carboxylic acid
NMR (CDCl$_3$, δ): 2.71 (3H, s), 2.76 (3H, s), 5.50 (2H, s), 6.22 (1H, d, J=8 Hz), 7.05 (1H, t, J=8 Hz), 7.22 (1H, t, J=8 Hz), 7.47 (1H, d, J=8 Hz), 7.95–8.15 (3H, m), 8.08 (1H, d, J=8 Hz)

(17) 1-(2-Chlorobenzyl)-2-methyl-3-propionylindole-6-carboxylic acid
NMR (DMSO-d$_6$, δ): 1.14 (3H, t, J=7 Hz), 2.69 (3H, s), 3.04 (2H, q, J=7 Hz), 5.67 (2H, s), 6.24 (1H, d, J=8 Hz), 7.18 (1H, d, J=8 Hz), 7.22 (1H, t, J=8 Hz), 7.58 (1H, d, J=8 Hz), 7.83 (1H, d, J=8 Hz), 7.99 (1H, s), 8.16 (1H, d, J=8 Hz)

(18) 1-(2-Chlorobenzo[b]thiophen-3-ylmethyl)-3-isobutyryl-2-methylindole-6-carboxylic acid
NMR (CDCl$_3$, δ): 1.25 (6H, d, J=7 Hz), 2.71 (3H, s), 3.50 (1H, m), 5.61 (2H, s), 6.99 (1H, d, J=8 Hz), 7.12 (1H, t, J=8 Hz), 7.28 (1H, t, J=8 Hz), 7.68 (1H, d, J=8 Hz), 7.95–8.02 (2H, m), 8.23 (1H, s)

(19) 1-(Benzothiazol-2-ylmethyl)-2-ethyl-3-isobutyrylindole-6-carboxylic acid
NMR (CDCl$_3$, δ): 1.28 (3H, t, J=7 Hz), 1.30 (6H, d, J=7 Hz), 3.24 (2H, q, J=7 Hz), 3.58 (1H, m), 5.86 (2H, s), 7.39 (1H, t, J=8 Hz), 7.52 (1H, t, J=8 Hz), 7.87 (1H, d, J=8 Hz), 7.9–8.06 (3H, m), 8.20 (1H, s)

(20) 1-(Benzo[b]thiophen-5-ylmethyl)-3-isobutyryl-2-propylindole-6-carboxylic acid
NMR (CDCl$_3$, δ): 1.02 (3H, t, J=7 Hz), 1.32 (6H, d, J=7 Hz), 1.63 (2H, m), 3.14 (2H, m), 3.57 (1H, m), 5.58 (2H, s), 7.04 (1H, d, J=8 Hz), 7.19 (1H, d, J=6 Hz), 7.31 (1H, s), 7.43 (1H, d, J=6 Hz), 7.81 (1H, d, J=8 Hz), 7.9–8.02 (2H, m), 8.08 (1H, s)

(21) 1-(2,4-Dichlorobenzyl)-3-isobutyryl-2-propylindole-6-carboxylic acid
NMR (DMSO-d$_6$, δ): 0.92 (3H, t, J=7 Hz), 1.18 (6H, d, J=7 Hz), 1.46 (2H, sextet, J=7 Hz), 3.02–3.07 (2H, m), 3.54 (2H, septet, J=7 Hz), 5.68 (2H, s), 6.27 (1H, d, J=8 Hz), 7.28 (1H, dd, J=2, 8 Hz), 7.76 (1H, d, J=2 Hz), 7.84 (1H, d, J=8 Hz), 7.96 (1H, s), 8.01 (1H, d, J=8 Hz)

(22) 3-Isobutyryl-2-propyl-1-(3-pyridylmethyl)indole-6-carboxylic acid
NMR (CDCl$_3$, δ): 1.04 (3H, t, J=7 Hz), 1.30 (6H, d, J=7 Hz), 1.63 (2H, sextet, J=7 Hz), 3.15 (2H, t, J=7 Hz), 3.57 (2H, septet, J=7 Hz), 5.51 (2H, s), 7.19–7.28 (2H, m), 7.95–8.01 (2H, m), 8.04 (1H, s), 8.52–8.56 (2H, m)

(23) 3-Isobutyryl-2-propyl-1-(1-naphthylmethyl)indole-6-carboxylic acid
NMR (DMSO-d$_6$, δ): 0.86 (3H, t, J=7 Hz), 1.22 (6H, d, J=7 Hz), 1.52 (2H, sextet, J=7 Hz), 3.05–3.10 (2H, m), 3.60 (1H, septet, J=7 Hz), 6.15 (1H, d, J=8 Hz), 6.17 (2H, s), 7.28 (1H, t, J=8 Hz), 7.64 (1H, t, J=8 Hz), 7.72 (1H, t, J=8 Hz), 7.84 (2H, d, J=8 Hz), 7.92 (1H, s), 8.12 (1H, d, J=8 Hz), 8.15 (1H, d, J=8 Hz), 8.36 (1H, d, J=8 Hz)

(24) 3-Isobutyryl-2-propyl-1-(2-naphthylmethyl)indole-6-carboxylic acid
NMR (DMSO-d$_6$, δ): 0.92 (3H, t, J=7 Hz), 1.19 (6H, d, J=7 Hz), 1.48 (2H, sextet, J=7 Hz), 3.14–3.18 (2H, m), 3.57 (1H, septet, J=7 Hz), 5.81 (2H, s), 7.20 (1H, d, J=8 Hz), 7.45–7.52 (3H, m), 7.76–7.90 (4H, m), 8.02 (1H, d, J=8 Hz), 8.08 (1H, s)

(25) 1-Allyl-3-isobutyryl-2-propylindole-6-carboxylic acid
NMR (CDCl$_3$, δ): 1.08 (3H, t, J=7 Hz), 1.28 (6H, d, J=7 Hz), 1.69 (2H, m), 3.13 (2H, m), 3.56 (1H, m), 4.88 (2H, m), 4.90 (1H, m), 5.23 (1H, m), 5.98 (1H, m), 7.94 (1H, d, J=8 Hz), 8.02 (1H, d, J=8 Hz), 8.13 (1H, s)

(26) 1-(2-Chlorobenzyl)-3-isobutyryl-2-(1-propenyl)indole-6-carboxylic acid
NMR (CDCl$_3$, δ): 1.26 (6H, d, J=7 Hz), 1.93 (3H, d, J=7 Hz), 3.51 (1H, m), 5.50 (2H, s), 5.92 (1H, m), 6.44 (1H, d, J=8 Hz), 6.74 (1H, d, J=16 Hz), 7.09 (1H, t, J=8 Hz), 7.23 (1H, t, J=8 Hz), 7.48 (1H, d, J=8 Hz), 7.92 (1H, s), 8.02 (1H, d, J=8 Hz), 8.21 (1H, d, J=8 Hz)

(27) 1-(2-Chlorobenzyl)-2-(1-hydroxypropyl)-3-isobutyrylindole-6-carboxylic acid NMR (CDCl$_3$, δ): 0.92 (3H, t, J=7 Hz), 1.29 (3H, d, J=7 Hz), 1.36 (3H, d, J=7 Hz), 1.52 (1H, m), 1.88 (1H, m), 3.70 (1H, m), 4.73 (1H, m), 5.51 (1H, d, J=17 Hz), 5.69 (1H, d, J=17 Hz), 6.44 (1H, d, J=8 Hz), 7.09 (1H, t, J=8 Hz), 7.23 (1H, t, J=8 Hz), 7.45 (1H, d, J=8 Hz), 7.9–8.1 (3H, m)

(28) 1-(2-Chlorobenzyl)-3-(3,3-dimethylbutanoyl)indole-6-carboxylic acid

NMR (CDCl$_3$, δ): 1.08 (9H, s), 2.70 (2H, s), 5.52 (2H, s), 6.77 (1H, d, J=8 Hz), 7.17 (1H, t, J=8 Hz), 7.28 (1H, t, J=8 Hz), 7.47 (1H, d, J=8 Hz), 7.86 (1H, s), 8.03 (1H, d, J=8 Hz), 8.12 (1H, s), 8.53 (1H, d, J=8 Hz)

(29) 1-(6-Chloro-3,4-methylenedioxybenzyl)-3-methoxyacetyl-2-propylindole-6-carboxylic acid NMR (CDCl$_3$, δ): 0.96 (3H, t, J=7 Hz), 1.45–1.58 (2H, m), 3.10 (2H, t, J=7 Hz), 3.40 (3H, s), 4.69 (2H, s), 5.55 (2H, s), 5.76 (1H, s), 5.98 (2H, s), 7.23 (1H, s), 7.82 (1H, d, J=8 Hz), 7.94 (1H, s), 7.96 (1H, d, J=8 Hz)

(30) 1-(2-Chlorobenzyl)-3-ethoxyacetyl-2-propylindole-6-carboxylic acid

NMR (DMSO-d$_6$, δ): 0.94 (3H, t, J=7 Hz), 1.17 (3H, t, J=7 Hz), 1.48 (2H, sextet, J=7 Hz), 3.08 (3H, t, J=7 Hz), 3.62 (2H, q, J=7 Hz), 4.74 (2H, s), 5.68 (2H, s), 6.28 (1H, d, J=8 Hz), 7.18 (1H, t, J=8 Hz), 7.32 (1H, t, J=8 Hz), 7.56 (1H, d, J=8 Hz), 7.82 (1H, d, J=8 Hz), 7.96 (1H, s), 7.98 (1H, d, J=8 Hz)

(31) 1-(2-Chlorobenzyl)-3-isobutyryl-2-propylindole-6-ylacetic acid

IR (KBr): 1715, 1650 cm$^{-1}$

NMR (CDCl$_3$, δ): 1.00 (3H, t, J=7 Hz), 1.30 (6H, d, J=7 Hz), 1.54–1.66 (2H, m), 3.00–3.08 (2H, m), 3.50–3.62 (1H, m), 3.71 (2H, s), 5.47 (2H, s), 6.30 (1H, d, J=7.5 Hz), 7.01–7.08 (2H, m), 7.19–7.25 (2H, m), 7.45 (1H, d, J=7.5 Hz), 7.89 (1H, d, J=7.5 Hz)

MASS (m/z): 412 (M$^+$+1), 74 (bp)

(32) 1-(6-Chloro-3,4-methylenedioxybenzyl)-3-isobutyryl-2-propylindole-6-ylacetic acid mp: 81–83° C.

IR (KBr): 1715, 1650 cm$^{-1}$

NMR (CDCl$_3$, δ): 1.02 (3H, t, J=7 Hz), 1.29 (6H, d, J=7 Hz), 1.54–1.67 (2H, m), 3.01–3.07 (2H, m), 3.51–3.60 (1H, m), 3.75 (2H, s), 5.33 (2H, s), 5.79 (1H, s), 5.89 (2H, s), 6.91 (1H, s), 7.12 (1H, s), 7.21 (1H, d, J=7.5 Hz), 7.89 (1H, d, J=7.5 Hz)

MASS (m/z): 456 (M$^+$+1), 74 (bp)

(33) 1-(2-Chlorobenzyl)-2-propylindole-6-carboxylic acid

NMR (CDCl$_3$, δ): 1.02 (3H, t, J=7 Hz), 1.74 (2H, m), 2.61 (2H, t, J=7 Hz), 5.42 (2H, s), 6.19 (1H, d, J=8 Hz), 6.46 (1H, s), 7.02 (1H, t, J=8 Hz), 7.18 (1H, t, J=8 Hz), 7.43 (1H, d, J=8 Hz), 7.61 (1H, d, J=8 Hz), 7.85 (1H, d, J=8 Hz), 7.95 (1H, s)

(34) 1-(2-Bromobenzyl)-2-propylindole-6-carboxylic acid

NMR (CDCl$_3$, δ): 1.00 (3H, t, J=7 Hz), 1.73 (2H, m), 2.61 (2H, t, J=7 Hz), 5.37 (2H, s), 6.12 (1H, d, J=8 Hz), 6.46 (1H, s), 7.0–7.18 (2H, m), 7.61 (1H, d, J=8 Hz), 7.85 (1H, d, J=8 Hz), 7.96 (1H, s)

(35) 2-Acetyl-1-(2-chlorobenzyl)-3-methylindole-6-carboxylic acid

NMR (DMSO-d$_6$, δ): 2.62 (3H, s), 2.69 (3H, s), 5.82 (2H, s), 6.10 (1H, d, J=8 Hz), 7.09 (1H, t, J=8 Hz), 7.24 (1H, t, J=8 Hz), 7.51 (1H, d, J=8 Hz), 7.72 (1H, d, J=8 Hz), 7.93 (1H, d, J=8 Hz), 7.96 (1H, s)

(36) 2-Chloro-1-(2-chlorobenzyl)-3-ethylindole-6-carboxylic acid

NMR (CDCl$_3$, δ): 1.30 (3H, t, J=7 Hz), 2.84 (2H, q, J=7 Hz), 5.50 (2H, s), 6.29 (1H, d, J=8 Hz), 7.06 (1H, t, J=8 Hz), 7.19 (1H, t, J=8 Hz), 7.43 (1H, d, J=8 Hz), 7.63 (1H, d, J=8 Hz), 7.88 (1H, d, J=8 Hz), 7.93 (1H, s)

(37) 1-(2-Chlorobenzyl)-2-propionyl-3-propylindole-6-caboxylic acid

NMR (CDCl$_3$, δ): 1.06 (3H, t, J=7 Hz), 1.14 (3H, t, J=7 Hz), 1.76 (2H, m), 2.94 (2H, q, J=7 Hz), 3.09 (2H, m), 5.72 (2H, s), 6.27 (1H, d, J=8 Hz), 6.99 (1H, t, J=8 Hz), 7.14 (1H, t, J=8 Hz), 7.39 (1H, d, J=8 Hz), 7.78 (1H, d, J=8 Hz), 7.87 (1H, d, J=8 Hz), 8.02 (1H, s)

(38) 1-(2-Chlorobenzyl)-2-isobutyryl-3-propylindole-6-carboxylic acid

NMR (CDCl$_3$, δ) 1.03 (3H, t, J=7 Hz), 1.11 (6H, d, J=7 Hz), 1.76 (2H, m), 3.03 (2H, m), 3.34 (1H, m), 5.64 (2H, s), 6.30 (1H, d, J=8 Hz), 7.01 (1H, t, J=8 Hz), 7.14 (1H, t, J=8 Hz), 7.39 (1H, d, J=8 Hz), 7.78 (1H, d, J=8 Hz), 7.88 (1H, d, J=8 Hz), 8.02 (1H, s)

(39) 1-(2-Chlorobenzyl)-3-(3-oxo-1-butenyl)indole-6-carboxylic acid

NMR (DMSO-d$_6$, δ): 2.32 (3H, s), 5.67 (2H, s), 6.76 (1H, d, J=15 Hz), 6.86 (1H, d, J=8 Hz), 7.28 (1H, t, J=8 Hz), 7.37 (1H, t, J=8 Hz), 7.54 (1H, d, J=8 Hz), 7.79 (1H, d, J=8 Hz), 7.83 (1H, d, J=15 Hz), 8.08 (1H, d, J=8 Hz), 8.11 (1H, s), 8.21 (1H, s)

(40) 4-(2-Chlorobenzyl)-3-oxo-1,2,3,4-tetrahydrocyclopent[b]indole-6-carboxylic acid NMR (CDCl$_3$, δ): 3.07 (2H, m), 3.17 (2H, m), 5.72 (2H, s), 6.58 (1H, d, J=8 Hz), 7.06 (1H, t, J=8 Hz), 7.18 (1H, t, J=8 Hz), 7.40 (1H, d, J=8 Hz), 7.78 (1H, d, J=8 Hz), 7.89 (1H, d, J=8 Hz), 8.09 (1H, s)

(41) 4-(6-Chloro-3,4-methylenedioxybenzyl)-3-oxo-1,2,3,4-tetrahydrocyclopent[b]indole-6-carboxylic acid NMR (CDCl$_3$, δ): 3.07 (2H, m), 3.16 (2H, m), 5.61 (2H, s), 5.88 (2H, s), 6.10 (1H, s), 6.88 (1H, s), 7.78 (1H, d, J=8 Hz), 7.88 (1H, d, J=8 Hz), 8.12 (1H, s)

(42) 1-(2-Chlorobenzyl)-3-nitro-2-propylindole-6-carboxylic acid

NMR (DMSO-d$_6$, δ): 0.95 (3H, t, J=7 Hz), 1.55 (2H, sextet, J=7 Hz), 3.18–3.22 (2H, m), 5.78 (2H, s), 6.52 (1H, d, J=8 Hz), 7.22 (1H, t, J=8 Hz), 7.33 (1H, t, J=8 Hz), 7.58 (1H, d, J=8 Hz), 7.97 (1H, d, J=8 Hz), 8.08 (1H, s) 8.27 (1H, d, J=8 Hz)

(43) 1-(2-Chloro-4-carboxybenzyl)-3-isobutyryl-2-propylindole-6-carboxamide

NMR (DMSO-d$_6$, δ): 0.90 (3H, t, J=7 Hz), 1.18 (6H, d, J=7 Hz), 1.46 (2H, sextet, J=7 Hz), 3.00–3.05 (2H, m), 3.55 (1H, septet, J=7 Hz), 5.68 (2H, s), 6.33 (1H, d, J=8 Hz), 7.30 (1H, s), 7.72 (1H, dd, J=2, 8 Hz), 7.92 (1H, s), 7.95–7.99 (2H, m), 8.03 (1H, d, J=8 Hz)

EXAMPLE 75

The following compounds described in (1) to (41) were prepared in a similar manner to that of Example 3.

(1) 9-(2-Chlorobenzyl)-5-oxo-5,6,7,8-tetrahydrocarbazole-2-carboxamide mp: 295° C. (dec.)

NMR (DMSO-d$_6$, δ): 2.13 (2H, m), 2.48 (2H, t, J=7 Hz), 2.92 (2H, t, J=7 Hz), 5.62 (2H, s), 6.41 (1H, d, J=8 Hz), 7.21 (1H, t, J=8 Hz), 7.27 (1H, br s), 7.33 (1H, t, J=8 Hz), 7.57 (1H, d, J=8 Hz), 7.79 (1H, d, J=8 Hz), 7.92 (1H, br s), 8.02 (1H, s), 8.08 (1H, d, J=8 Hz)

(2) 4-(2-Chlorobenzyl)-1-oxo-1,2,3,4-tetrahydrocyclopent[b]indole-6-carboxamide mp: >300° C.

NMR (DMSO-d$_6$, δ): 2.88 (2H, m), 2.97 (2H, m), 5.61 (2H, s), 6.81 (1H, d, J=8 Hz), 7.27 (1H, t, J=8 Hz), 7.36 (1H, br s), 7.38 (1H, t, J=8 Hz), 7.57 (1H, d, J=8 Hz), 7.76 (1H, d, J=8 Hz), 7.79 (1H, d, J=8 Hz), 7.96 (1H, br s), 8.05 (1H, s)

(3) 1-(2-Chlorobenzyl)-3-isobutyryl-2-propylindole-7-carboxamide mp: 181–183° C.

NMR (CDCl$_3$, δ): 1.03 (3H, t, J=7 Hz), 1.27 (6H, d, J=7 Hz), 1.61 (2H, m), 3.02 (2H, m), 3.53 (1H, m), 5.34 (1H, br s), 5.46 (1H, br s), 5.69 (2H, s), 5.99 (1H, d, J=8 Hz), 6.96 (1H, t, J=8 Hz), 7.14 (1H, t, J=8 Hz), 7.15–7.25 (2H, m), 7.37 (1H, d, J=8 Hz), 8.07 (1H, m)

(4) 1-(2-Chlorobenzyl)-3-isobutyryl-2-propylindole-5-carboxamide

NMR (CDCl$_3$, δ): 1.03 (3H, t, J=8 Hz), 1.32 (6H, d, J=8 Hz), 1.64 (2H, sextet, J=8 Hz), 3.06 (2H, t, J=8 Hz), 3.62 (1H, septet, J=8 Hz), 5.46 (2H, s), 6.26 (1H, d, J=8 Hz), 7.05 (1H, t, J=8 Hz), 7.20 (1H, t, J=8 Hz), 7.2 (1H, d, J=8 Hz), 7.47 (1H, d, J=8 Hz), 7.65 (1H, d, J=8 Hz), 8.55 (1H, s)

(5) 1-(6-Chloro-3,4-methylenedioxybenzyl)-3-isobutyryl-2-propylindole-5-carboxamide NMR (CDCl$_3$, δ): 1.05 (3H, t, J=7 Hz), 1.32 (6H, d, J=7 Hz), 1.60–1.72 (2H, m), 3.04–3.10 (2H, m), 3.59 (1H, septet, J=7 Hz), 5.38 (2H, s), 5.74 (1H, s), 5.92 (2H, s), 6.92 (1H, s), 7.22 (1H, d, J=8 Hz), 7.66 (1H, dd, J=1, 8 Hz), 8.50 (1H, d, J=1 Hz)

(6) 1-(2-Chlorobenzyl)-2-propylindole-4-carboxamide mp: 198–200° C.

NMR (CDCl$_3$, δ): 1.02 (3H, t, J=7 Hz), 1.76 (2H, m), 2.66 (2H, t, J=7 Hz), 5.41 (2H, s), 6.18 (1H, d, J=8 Hz), 6.85 (1H, s), 7.1–7.3 (3H, m), 7.43 (1H, d, J=8 Hz), 7.52 (1H, d, J=8 Hz)

(7) 9-(2-Chlorobenzyl)-8-oxo-5,6,7,8-tetrahydrocarbazole-2-carboxamide mp: 255° C. (dec.)

NMR (DMSO-d$_6$, δ): 2.18 (2H, m), 2.56 (2H, t, J=7 Hz), 3.07 (2H, t, J=7 Hz), 5.88 (2H, s), 6.08 (1H, d, J=8 Hz), 7.11 (1H, t, J=8 Hz), 7.25 (1H, t, J=8 Hz), 7.36 (1H, br s), 7.52 (1H, d, J=8 Hz), 7.72 (1H, d, J=8 Hz), 7.85 (1H, d, J=8 Hz), 8.02 (2H, m)

(8) 9-(6-Chloro-3,4-methylenedioxybenzyl)-8-oxo-5,6,7,8-tetrahydrocarbazole-2-carboxamide mp: 270° C. (dec.)

NMR (DMSO-d$_6$, δ): 2.17 (2H, m), 2.58 (2H, t, J=7 Hz), 3.08 (2H, t, J=7 Hz), 5.52 (1H, s), 5.78 (2H, s), 5.96 (2H, s), 7.17 (1H, s), 7.40 (1H, br s), 7.71 (1H, d, J=8 Hz), 7.86 (1H, d, J=8 Hz), 7.96 (1H, s), 8.01 (1H, br s)

(9) 1-(4-Bromo-2-chlorobenzyl)-3-isobutyryl-2-propylindole-6-carboxamide mp: 199–201° C.

IR (KBr): 3382, 1654, 1619, 1488, 1404 cm$^{-1}$

NMR (CDCl$_3$, δ): 1.04 (3H, t, J=7 Hz), 1.30 (6H, d, J=7 Hz), 1.54–1.66 (2H, m), 3.00–3.05 (2H, m), 3.50–3.60 (1H, m), 5.45 (2H, s), 6.09 (1H, t, J=7.5 Hz), 7.17 (1H, dd, J=7.5, 2 Hz), 7.62 (1H, dd, J=7.5, 2 Hz), 7.65 (1H, d, J=2 Hz), 7.83 (1H, s), 7.99 (1H, d, J=7.5 Hz)

MASS (m/z): 477 (M$^+$+2)

(10) 1-(2-Chlorobenzyl)-3-morpholinoacetyl-2-propylindole-6-carboxamide

IR (KBr): 1654, 1616, 1452 cm$^{-1}$

NMR (CDCl$_3$, δ): 1.02 (3H, t, J=7 Hz), 1.58–1.68 (2H, m), 2.73 (4H, t, J=6.5 Hz), 3.05–3.10 (2H, m), 3.84 (4H, t, J=6.5 Hz), 3.89 (2H, s), 5.51 (2H, s), 6.23 (1H, d, J=7.5 Hz), 7.05 (1H, t, J=7.5 Hz), 7.22 (1H, t, J=7.5 Hz), 7.46 (1H, d, J=7.5 Hz), 7.64 (1H, d, J=7.5 Hz), 7.84 (1H, s), 7.98 (1H, d, J=7.5 Hz)

MASS (m/z): 454 (M$^+$+1)

(11) Methyl 1-(2-chlorobenzyl)-3-(N,N-dimethylcarbamoyl)-2-propylindole-6-carboxylate IR (KBr): 1703, 1610 cm$^{-1}$ NMR (CDCl$_3$, δ): 0.94 (3H, t, J=7 Hz), 1.56–1.63 (2H, m), 2.76–2.87 (2H, m), 3.11 (6H, br s), 3.90 (3H, s), 5.49 (2H, s), 6.29 (1H, d, J=7.5 Hz), 7.04 (1H, t, J=7.5 Hz), 7.21 (1H, t, J=7.5 Hz), 7.45 (1H, d, J=7.5 Hz), 7.49 (1H, d, J=7.5 Hz), 7.86 (1H, d, J=7.5 Hz), 7.90 (1H, s)

MASS (m/z): 413 (M$^+$+1)

(12) Methyl 1-(2-chlorobenzyl)-3-(morpholinocarbonyl)-2-propylindole-6-carboxylate IR (KBr): 1715, 1617, 1277, 1227 cm$^{-1}$ NMR (CDCl$_3$, δ): 0.85 (3H, t, J=7 Hz), 1.56–1.63 (2H, m), 2.82–2.90 (2H, m), 3.69 (6H, br s), 3.77 (2H, br s), 3.90 (3H, s), 5.48 (2H, s), 6.29 (1H, d, J=7.5 Hz), 7.04 (1H, t, J=7.5 Hz), 7.21 (1H, ddd, J=7.5, 7.5, 2 Hz), 7.45 (1H, d, J=7.5 Hz), 7.54 (1H, d, J=7.5 Hz), 7.88 (1H, s), 7.91 (1H, d, J=2 Hz)

MASS (m/z): 455 (M$^+$+1), 76 (bp)

(13) 6-Carbamoyl-1-(2-chlorobenzyl)-N,N-dimethyl-2-propylindole-3-carboxamide mp: 213–214° C.

IR (KBr): 1676, 1601 cm$^{-1}$

NMR (CDCl$_3$, δ): 0.93 (3H, t, J=7 Hz), 1.52–1.62 (2H, m), 2.76–2.86 (2H, m), 3.12 (6H, br s), 5.47 (2H, s), 6.27 (1H, d, J=7.5 Hz), 7.03 (1H, t, J=7.5 Hz), 7.20 (1H, t, J=7.5 Hz), 7.44 (1H, d, J=7.5 Hz), 7.49–7.54 (2H, m), 7.78 (1H, s)

MASS (m/z): 398 (M$^+$+1), 76 (bp)

(14) 1-(2-Chlorobenzyl)-3-(morpholinocarbonyl)-2-propylindole-6-carboxamide mp: 229–230° C.

IR (KBr): 3448, 3359, 3326, 1675, 1606 cm$^{-1}$

NMR (CDCl$_3$, δ): 0.95 (3H, t, J=7 Hz), 1.57–1.62 (2H, m), 2.82–2.89 (2H, m), 3.69 (6H, br s), 3.78 (2H, br s), 5.49 (2H, s), 6.28 (1H, d, J=7.5 Hz), 7.04 (1H, t, J=7.5 Hz), 7.21 (1H, t, J=7.5 Hz), 7.45 (1H, t, J=7.5 Hz), 7.55 (2H, s), 7.80 (1H, s)

MASS (m/z): 440 (M$^+$+1), 76 (bp)

(15) 1-(2-Chlorobenzyl)-2-propylindole-3,6-dicarboxamide mp: 296° C. (dec.)

IR (KBr): 3376, 3188, 1644, 1613 cm$^{-1}$

NMR (DMSO-d$_6$, δ): 0.88 (3H, t, J=7 Hz), 1.40–1.51 (2H, m), 2.98 (2H, t, J=7 Hz), 5.57 (2H, s), 6.17 (1H, d, J=7.5 Hz), 7.14–7.35 (6H, m), 7.58 (1H, d, J=8 Hz), 7.73 (1H, d, J=7.5 Hz), 7.83–7.89 (1H, m), 7.95 (1H, s)

MASS (m/z): 370 (M$^+$+1), 86 (bp)

(16) 1-(2-Chlorobenzyl)-2-ethyl-3-formylindole-6-carboxamide mp: 260–261° C.

IR (KBr): 3400, 1685, 1635, 1615, 1390 cm$^{-1}$

NMR (CDCl$_3$, δ): 1.29 (3H, t, J=7 Hz), 3.08 (2H, q, J=7 Hz), 5.52 (2H, s), 6.29 (1H, d, J=7.5 Hz), 7.07 (1H, t, J=7.5 Hz), 7.24 (1H, t, J=7.5 Hz), 7.49 (1H, d, J=7.5 Hz), 7.69 (1H, d, J=7.5 Hz), 7.86 (1H, s), 8.35 (1H, d, J=7.5 Hz), 10.24 (1H, s)

MASS (m/z): 341 (M$^+$+1)

(17) 1-(2-Chlorobenzoyl)-3-isobutyryl-2-propylindole-6-carboxamide mp: 125–126.5° C.

IR (KBr): 1700, 1650 cm$^{-1}$

NMR (CDCl$_3$, δ): 0.90 (3H, t, J=7 Hz), 1.28 (6H, d, J=7 Hz), 1.61–1.74 (2H, m), 2.98–3.05 (2H, m), 3.40–3.49 (1H, m), 7.48–7.53 (3H, m), 7.59–7.65 (2H, m), 7.79 (2H, AB, J=8, 7.5 Hz)

MASS (m/z): 411 (M$^+$+1), 76 (bp)

(18) 1-(2-Chlorobenzyl)-3-formylindole-6-carboxamide mp: 237–240° C.

NMR (DMSO-d$_6$, δ): 5.68 (2H, s), 6.86 (1H, d, J=8 Hz), 6.25–6.4 (3H, m), 7.58 (1H, d, J=8 Hz), 7.84 (1H, d, J=8 Hz), 7.98 (1H, br s), 8.14 (1H, s), 8.17 (1H, d, J=8 Hz), 8.46 (1H, s), 9.98 (1H, s)

(19) 3-Acetyl-1-(2-chlorobenzyl)-2-methylindole-6-carboxamide mp: 272–276° C.

NMR (DMSO-$d_6$, δ) 2.63 (3H, s), 2.65 (3H, s), 5.61 (2H, s), 6.17 (1H, d, J=8 Hz), 7.18 (1H, t, J=8 Hz), 7.27 (1H, br s), 7.32 (1H, t, J=8 Hz), 7.57 (1H, d, J=8 Hz), 7.80 (1H, d, J=8 Hz), 7.94 (1H, br s), 8.03 (1H, s), 8.11 (1H, s)

(20) 1-(2-Chlorobenzyl)-2-methyl-3-propionylindole-6-carboxamide mp: 215–217° C.

NMR (DMSO-$d_6$, δ): 1.14 (3H, t, J=7 Hz), 2.64 (3H, s), 3.04 (2H, q, J=7 Hz), 5.62 (2H, s), 6.18 (1H, d, J=8 Hz), 7.18 (1H, t, J=8 Hz), 7.29 (1H, br s), 7.32 (1H, t, J=8 Hz), 7.57 (1H, d, J=8 Hz), 7.79 (1H, d, J=8 Hz), 8.02 (1H, s), 8.10 (1H, d, J=8 Hz)

(21) 1-(2-Chlorobenzo[b]thiophen-3-ylmethyl)-3-isobutyryl-2-methylindole-6-carboxamide mp: 255° C. (dec.)

NMR (DMSO-$d_6$, δ): 1.13 (6H, d, J=7 Hz), 2.63 (3H, s), 3.47 (1H, m), 5.84 (2H, s), 7.2–7.42 (4H, m), 7.48 (1H, d, J=8 Hz), 7.89 (1H, br s), 7.95–8.0 (2H, m), 8.23 (1H, s)

(22) 1-(Benzothiazol-2-ylmethyl)-2-ethyl-3-isobutyrylindole-6-carboxamide mp: 188–190.5° C. (dec.)

NMR (CDCl$_3$, δ): 1.28 (3H, t, J=7 Hz), 1.29 (6H, d, J=7 Hz), 3.27 (2H, q, J=7 Hz), 3.53 (1H, m), 5.82 (2H, s), 7.36 (1H, t, J=8 Hz), 7.49 (1H, t, J=8 Hz), 7.66 (1H, d, J=8 Hz), 7.74 (1H, d, J=8 Hz), 7.97 (1H, d, J=8 Hz), 8.02 (1H, d, J=8 Hz), 8.07 (1H, s)

(23) 1-(Benzo[b]thiophen-5-ylmethyl)-3-isobutyryl-2-propylindole-6-carboxamide mp: 189–192° C. (dec.)

NMR (CDCl$_3$, δ): 1.02 (3H, t, J=7 Hz), 1.31 (6H, d, J=7 Hz), 1.62 (2H, m), 3.14 (2H, m), 3.57 (1H, m), 5.58 (2H, s), 7.02 (1H, d, J=8 Hz), 7.18 (1H, d, J=6 Hz), 7.29 (1H, s), 7.43 (1H, d, J=6 Hz), 7.60 (1H, d, J=8 Hz), 7.79 (1H, d, J=8 Hz), 7.92 (1H, s), 7.97 (1H, d, J=8 Hz)

(24) 1-(2,4-Dichlorobenzyl)-3-isobutyryl-2-propylindole-6-carboxamide mp: 191–192° C.

NMR (DMSO-$d_6$, δ): 0.92 (3H, t, J=7 Hz), 1.18 (6H, d, J=7 Hz), 1.45 (2H, sextet, J=7 Hz), 3.00–3.05 (2H, m), 3.55 (2H, septet, J=7 Hz), 5.60 (2H, s), 6.18 (1H, d, J=8 Hz), 7.28 (1H, dd, J=2, 8 Hz), 7.31 (1H, s), 7.76 (1H, d, J=2 Hz), 7.82 (1H, d, J=8 Hz), 7.92 (1H, br s), 7.94 (1H, s), 7.98 (1H, d, J=8 Hz)

(25) 3-Isobutyryl-2-propyl-1-(3-pyridylmethyl)indole-6-carboxamide mp: 230–235° C.

NMR (CDCl$_3$, δ): 1.02 (3H, t, J=7 Hz), 1.30 (6H, d, J=7 Hz), 1.60 (2H, sextet, J=7 Hz), 3.08–3.16 (2H, m), 3.56 (2H, septet, J=7 Hz), 5.48 (2H, s), 7.19–7.24 (2H, m), 7.61 (1H, d, J=8 Hz), 7.92 (1H, s), 7.96 (1H, d, J=8 Hz), 8.38 (1H, d, J=2 Hz), 8.52 (1H, dd, J=2, 5 Hz)

(26) 3-Isobutyryl-2-propyl-1-(1-naphthylmethyl)indole-6-carboxamide mp: 202–203° C.

NMR (CDCl$_3$, δ): 0.96 (3H, t, J=7 Hz), 1.34 (6H, d, J=7 Hz), 1.61–1.68 (2H, m), 3.08 (2H, dd, J=7, 8 Hz), 3.61 (1H, septet, J=7 Hz), 5.90 (2H, s), 6.28 (1H, d, J=8 Hz), 7.21 (1H, s), 7.58–7.69 (3H, m), 7.76 (1H, d, J=8 Hz), 7.78 (1H, s), 7.94 (1H, d, J=8 Hz), 8.00 (1H, s), 8.08 (1H, d, J=8 Hz)

(27) 3-Isobutyryl-2-propyl-1-(2-naphthylmethyl)indole-6-carboxamide mp: 189–190° C.

NMR (CDCl$_3$, δ): 0.98 (3H, t, J=7 Hz), 1.30 (6H, d, J=7 Hz), 1.55–1.68 (2H, m), 3.14–3.18 (2H, m), 3.58 (1H, septet, J=7 Hz), 5.58 (2H, s), 7.15 (1H, dd, J=1, 8 Hz), 7.28 (1H, s), 7.42–7.48 (2H, m), 7.60–7.66 (2H, m), 7.78 (2H, d, J=8 Hz), 7.93 (1H, d, J=1 Hz), 7.98 (1H, d, J=8 Hz)

(28) 1-Allyl-3-isobutyryl-2-propylindole-6-carboxamide mp: 155–158° C.

NMR (CDCl$_3$, δ): 1.06 (3H, t, J=7 Hz), 1.27 (6H, d, J=7 Hz), 1.71 (2H, m), 3.11 (2H, m), 3.51 (1H, m), 4.83 (2H, m), 4.86 (1H, m), 5.19 (1H, m), 5.96 (1H, m), 7.58 (1H, d, J=8 Hz), 7.89 (1H, d, J=8 Hz), 7.96 (1H, s)

(29) 1-(2-Chlorobenzyl)-3-isobutyryl-2-(1-propenyl)indole-6-carboxamide mp: 190–193° C.

NMR (CDCl$_3$, δ): 1.23 (6H, d, J=7 Hz), 1.93 (3H, d, J=7 Hz), 3.51 (1H, m), 5.48 (2H, s), 5.91 (1H, dq, J=15, 7 Hz), 6.41 (1H, d, J=8 Hz), 6.71 (1H, d, J=15 Hz), 7.07 (1H, t, J=8 Hz), 7.23 (1H, t, J=8 Hz), 7.46 (1H, d, J=8 Hz), 7.62 (1H, d, J=8 Hz), 7.80 (1H, s), 8.24 (1H, d, J=8 Hz)

(30) 1-(2-Chlorobenzyl)-2-(1-hydroxypropyl)-3-isobutyrylindole-6-carboxamide mp: 220–223° C.

NMR (CDCl$_3$, δ): 0.94 (3H, t, J=7 Hz), 1.32 (3H, d, J=7 Hz), 1.39 (3H, d, J=7 Hz), 1.52 (1H, m), 1.93 (1H, m), 3.69 (1H, m), 4.68 (1H, m), 5.48 (1H, d, J=17 Hz), 5.66 (1H, d, J=17 Hz), 6.33 (1H, d, J=10 Hz), 6.43 (1H, d, J=8 Hz), 7.07 (1H, t, J=8 Hz), 7.21 (1H, t, J=8 Hz), 7.44 (1H, d, J=8 Hz), 7.68 (1H, d, J=8 Hz), 7.92 (1H, s), 7.96 (1H, d, J=8 Hz)

(31) 1-(2-Chlorobenzyl)-3-(3,3-dimethylbutanoyl)indole-6-carboxamide mp: 202–205° C.

NMR (CDCl$_3$, δ): 1.08 (9H, s), 2.69 (2H, s), 5.50 (2H, s), 6.73 (1H, d, J=8 Hz), 7.14 (1H, t, J=8 Hz), 7.28 (1H, t, J=8 Hz), 7.45 (1H, d, J=8 Hz), 7.62 (1H, d, J=8 Hz), 7.80 (1H, s), 7.99 (1H, s), 8.53 (1H, d, J=8 Hz)

(32) 1-(2-Chlorobenzyl)-2-propylindole-6-carboxamide mp: 174–177° C.

NMR (CDCl$_3$, δ): 1.00 (3H, t, J=7 Hz), 1.74 (2H, m), 2.61 (2H, t, J=7 Hz), 5.43 (2H, s), 6.15 (1H, d, J=8 Hz), 6.44 (1H, s), 7.00 (1H, t, J=8 Hz), 7.18 (1H, t, J=8 Hz), 7.4–7.5 (2H, m), 7.61 (1H, d, J=8 Hz), 7.79 (1H, s)

(33) 1-(2-Bromobenzyl)-2-propylindole-6-carboxamide mp: 166–168° C.

NMR (CDCl$_3$, δ): 1.00 (3H, t, J=7 Hz), 1.73 (2H, m), 2.59 (2H, m), 5.36 (2H, s), 6.10 (1H, d, J=8 Hz), 6.42 (1H, s), 7.0–7.15 (2H, m), 7.46 (1H, dd, J=1, 8 Hz), 7.61 (1H, dd, J=1, 8 Hz), 7.76 (1H, s)

(34) 2-Acetyl-1-(2-chlorobenzyl)-3-methylindole-6-carboxamide mp: 234–236° C.

NMR (DMSO-$d_6$, δ): 2.58 (3H, s), 2.71 (3H, s), 5.79 (2H, s), 6.03 (1H, d, J=8 Hz), 7.09 (1H, t, J=8 Hz), 7.24 (1H, t, J=8 Hz), 7.35 (1H, br s), 7.50 (1H, d, J=8 Hz), 7.70 (1H, d, J=8 Hz), 7.92 (1H, d, J=8 Hz), 7.98 (1H, s), 7.99 (1H, br s)

(35) 2-Chloro-1-(2-chlorobenzyl)-3-ethylindole-6-carboxamide mp: 195–198° C.

NMR (CDCl$_3$, δ): 1.27 (3H, t, J=7 Hz), 2.83 (2H, q, J=7 Hz), 5.49 (2H, s), 6.29 (1H, d, J=8 Hz), 7.03 (1H, t, J=8 Hz), 7.18 (1H, t, J=8 Hz), 7.42 (1H, d, J=8 Hz), 7.50 (1H, d, J=8 Hz), 7.63 (1H, d, J=8 Hz), 7.77 (1H, s)

(36) 1-(2-Chlorobenzyl)-2-propionyl-3-propylindole-6-carboxamide mp: 165–167° C.

NMR (CDCl$_3$, δ): 1.05 (3H, t, J=7 Hz), 1.13 (3H, t, J=7 Hz), 1.76 (2H, m), 2.93 (2H, q, J=7 Hz), 3.08 (2H, m), 5.70 (2H, s), 6.23 (1H, d, J=8 Hz), 6.97 (1H, t, J=8 Hz), 7.12 (1H, t, J=8 Hz), 7.47 (1H, d, J=8 Hz), 7.53 (1H, d, J=8 Hz), 7.74 (1H, s), 7.76 (1H, d, J=8 Hz)

(37) 1-(2-Chlorobenzyl)-2-isobutyryl-3-propylindole-6-carboxamide mp: 159–160.5° C.

NMR (CDCl$_3$, δ): 1.03 (3H, t, J=7 Hz), 1.12 (6H, d, J=7 Hz), 1.76 (2H, m), 3.04 (2H, m), 3.36 (1H, m), 5.66 (2H, s), 6.29 (1H, d, J=8 Hz), 6.99 (1H, t, J=8 Hz), 7.14 (1H, t, J=8 Hz), 7.38 (1H, d, J=8 Hz), 7.56 (1H, d, J=8 Hz), 7.76 (1H, d, J=8 Hz), 7.77 (1H, s)

(38) 1-(2-Chlorobenzyl)-3-(3-oxo-1-butenyl)indole-6-carboxamide mp: 248–250° C.

NMR (DMSO-d$_6$, δ): 2.30 (3H, s), 5.61 (2H, s), 6.74 (1H, d, J=8 Hz), 6.75 (1H, d, J=15 Hz), 7.2–7.4 (3H, m), 7.54 (1H, d, J=8 Hz), 7.77 (1H, d, J=8 Hz), 7.80 (1H, d, J=15 Hz), 7.98 (1H, br s), 8.04 (1H, d, J=8 Hz), 8.11 (1H, s), 8.14 (1H, s)

(39) 4-(2-Chlorobenzyl)-3-oxo-1,2,3,4-tetrahydrocyclopent[b]indole-6-carboxamide mp: 289° C. (dec.)

NMR (DMSO-d$_6$, δ): 2.95 (2H, m), 3.10 (2H, m), 5.67 (2H, s), 6.37 (1H, d, J=8 Hz), 7.16 (1H, t, J=8 Hz), 7.28 (1H, t, J=8 Hz), 7.40 (1H, br s), 7.53 (1H, d, J=8 Hz), 7.74 (1H, d, J=8 Hz), 7.88 (1H, d, J=8 Hz), 8.01 (1H, br s), 8.07 (1H, s)

(40) 4-(6-Chloro-3,4-methylenedioxybenzyl)-3-oxo-1,2,3,4-tetrahydrocyclopent[b]indole-6-carboxamide mp: 282° C. (dec.)

NMR (DMSO-d$_6$, δ): 2.98 (2H, m), 3.09 (2H, m), 5.54 (2H, s), 5.97 (2H, s), 5.98 (1H, s), 7.17 (1H, s), 7.43 (1H, br s), 7.71 (1H, d, J=8 Hz), 7.86 (1H, d, J=8 Hz), 8.03 (1H, br s), 8.05 (1H, s)

(41) 1-[2-Chloro-4-(N-phenylsulfonylcarbamoyl)benzyl]-3-isobutyryl-2-propylindole-6-carboxamide mp: 147–150° C.

NMR (DMSO-d$_6$, δ): 0.88 (3H, t, j=7 Hz), 1.18 (6H, d, J=7 Hz), 1.45 (2H, sextet, J=7 Hz), 2.98–3.03 (2H, m), 3.55 (1H, septet, J=7 Hz), 5.68 (2H, s), 6.27 (1H, d, J=8 Hz), 7.28 (1H, s), 7.60–7.64 (3H, m), 7.69 (1H, dd, J=2, 8 Hz), 7.80 (1H, d, J=8 Hz), 7.92–7.96 (4H, m), 8.06 (1H, s)

EXAMPLE 76

The following compound described in (1) to (5) were prepared by a similar manner to that of Example 6.

(1) 1-(6-Chloro-3,4-methylenedioxybenzyl)-3-methoxyacetyl-2-propylindole-6-carboxamide (2) 1-(2-Chlorobenzyl)-3-ethoxyacetyl-2-propylindole-6-carboxamide NMR (DMSO-d$_6$, δ): 0.93 (3H, t, J=7 Hz), 1.18 (3H, t, J=7 Hz), 1.46 (2H, sextet, J=7 Hz), 3.03 (3H, t, J=7 Hz), 3.62 (2H, q, J=7 Hz), 4.74 (2H, s), 5.63 (2H, s), 6.22 (1H, d, J=8 Hz), 7.17 (1H, t, J=8 Hz), 7.30 (1H, s), 7.33 (1H, t, J=8 Hz), 7.58 (1H, d, J=8 Hz), 7.80 (1H, d, J=8 Hz), 7.92 (1H, d, J=8 Hz), 7.94 (1H, s), 8.00 (1H, s)

(3) 1-(2-Chlorobenzyl)-3-isobutyryl-2-propylindole-6-ylacetamide mp: 146–148° C.

IR (KBr): 1715, 1650 cm$^{-1}$

NMR (CDCl$_3$, δ): 1.01 (3H, t, J=7 Hz), 1.30 (6H, d, J=7 Hz), 1.57–1.67 (2H, m), 3.02–3.08 (2H, m), 3.51–3.60 (1H, m), 3.66 (2H, s), 5.45 (2H, s), 6.29 (1H, d, J=7.5 Hz), 7.04–7.09 (2H, m), 7.21 (2H, t, J=7.5 Hz), 7.47 (1H, d, J=7.5 Hz), 7.93 (1H, d, J=7.5 Hz)

MASS (m/z): 411(M$^+$+1), 74 (bp)

(4) 1-(6-Chloro-3,4-methylenedioxybenzyl)-3-isobutyryl-2-propylindole-6-ylacetamide mp: 136–138° C.

IR (KBr): 1655, 1505 cm$^{-1}$

NMR (CDCl$_3$, δ): 1.04 (3H, t, J=7 Hz), 1.29 (6H, d, J=7 Hz), 1.55–1.67 (2H, m), 3.01–3.07 (2H, m), 3.50–3.58 (1H, m), 3.69 (2H, s), 5.33 (2H, s), 5.75 (1H, s), 5.90 (2H, s), 6.92 (1H, s), 7.09 (1H, s), 7.19 (1H, d, J=7.5 Hz), 7.91 (1H, d, J=7.5 Hz)

MASS (m/z): 455 (M$^+$+1), 74 (bp)

(5) 1-(2-Chlorobenzyl)-3-nitro-2-propylindole-6-carboxamide

NMR (DMSO-d$_6$, δ): 0.95 (3H, t, J=7 Hz), 1.54 (2H, sextet, J=7 Hz), 3.13–3.17 (2H, m), 5.72 (2H, s), 6.44 (1H, d, J=8 Hz), 7.20 (1H, t, J=8 Hz), 7.36 (1H, t, J=8 Hz), 7.42 (1H, s), 7.60 (1H, d, J=8 Hz), 7.96 (1H, d, J=8 Hz), 8.03 (1H, s), 8.10 (1H, s), 8.22 (1H, d, J=8 Hz)

EXAMPLE 77

The following compounds described in (1) to (13) were prepared in a similar manner to that of Example 26.

(1) 1-(4-Chloro-2-fluorobenzyl)-3-methoxyacetyl-2-propylindole-6-carboxamide mp: 192–193° C.

NMR (DMSO-d$_6$, δ): 0.94 (3H, t, J=7 Hz), 1.44 (2H, sextet, J=7 Hz), 3.09 (2H, t, J=7 Hz), 3.41 (3H, s), 4.69 (2H, s), 5.64 (2H, s), 6.50 (1H, t, J=8 Hz), 7.18 (1H, dd, J=2, 8 Hz), 7.33 (1H, s), 7.55 (1H, dd, J=2, 8 Hz), 7.79 (1H, d, J=8 Hz), 7.89 (1H, d, J=8 Hz), 7.92 (1H, s), 8.06 (1H, s)

(2) 1-(2,4-Dichlorobenzyl)-3-methoxyacetyl-2-propylindole-6-carboxamide mp: 203–205° C.

NMR (DMSO-d$_6$, δ): 0.94 (3H, t, J=7 Hz), 1.98 (2H, sextet, J=7 Hz), 3.04 (2H, t, J=7 Hz), 3.42 (3H, s), 4.71 (2H, s), 5.60 (2H, s), 6.20 (1H, d, J=8 Hz), 7.27 (1H, dd, J=2, 8 Hz), 7.32 (1H, s), 7.77 (1H, d, J=2 Hz), 7.82 (1H, d, J=8 Hz), 7.92 (1H, d, J=8 Hz), 7.94 (1H, s), 7.98 (1H, s)

(3) 1-(4-Bromo-2-chlorobenzyl)-3-methoxyacetyl-2-propylindole-6-carboxamide mp: 178–180° C.

NMR (DMSO-d$_6$, δ) 0.94 (3H, t, J=7 Hz), 1.48 (2H, sextet, J=7 Hz), 3.04 (2H, t, J=7 Hz), 3.42 (3H, s), 4.68 (2H, s), 5.57 (2H, s), 6.13 (1H, d, j=8 Hz), 7.30 (1H, s), 7.38 (1H, dd, J=2, 8 Hz), 7.80 (1H, d, J=8 Hz), 7.86 (1H, d, J=2 Hz), 7.90 (1H, d, J=8 Hz), 7.93 (1H, s), 7.97 (1H, s)

(4) 1-(4-Bromo-2-fluorobenzyl)-3-methoxyacetyl-2-propylindole-6-carboxamide mp: 197–199° C.

NMR (DMSO-d$_6$, δ): 0.94 (3H, t, J=7 Hz), 1.48 (2H, sextet, J=7 Hz), 3.09 (2H, t, J=7 Hz), 3.40 (3H, s), 4.67 (2H, s), 5.62 (2H, s), 6.43 (1H, d, J=8 Hz), 7.28 (1H, dd, J=2, 8 Hz), 7.65 (1H, dd, J=2, 8 Hz), 7.78 (1H, d, J=8 Hz), 7.90 (1H, d, J=8 Hz), 7.92 (1H, s), 8.05 (1H, s)

(5) 1-(2-Chloro-4-fluorobenzyl)-3-methoxyacetyl-2-propylindole-6-carboxamide mp: 174–176° C.

NMR (DMSO-d$_6$, δ): 0.93 (3H, t, J=7 Hz), 1.48 (2H, sextet, J=7 Hz), 3.04 (2H, t, J=7 Hz), 3.42 (3H, s), 4.70 (2H, s), 5.58 (2H, s), 6.25 (1H, d, J=8 Hz), 7.06 (1H, dt, J=2, 8 Hz), 7.32 (1H, s), 7.50 (1H, dd, J=2, 8 Hz), 7.80 (1H, d, J=8 Hz), 7.92 (1H, d, J=8 Hz), 7.94 (1H, s), 8.00 (1H, s)

(6) 1-(Benzo[b]thiophen-5-ylmethyl)-3-methoxyacetyl-2-propylindole-6-carboxamide mp: 197–199° C. (dec.)

NMR (DMSO-d$_6$, δ): 0.92 (3H, t, J=7 Hz), 1.48 (2H, sextet, J=7 Hz), 3.14 (2H, t, J=7 Hz), 3.42 (3H, s), 4.72 (2H, s), 5.74 (2H, s), 7.10 (1H, d, J=8 Hz), 7.28 (1H, s), 7.38 (1H, d, J=5 Hz), 7.44 (1H, s), 7.75 (1H, d, J=5 Hz), 7.78 (1H, d, J=8 Hz), 7.88 (1H, d, J=8 Hz), 7.92 (1H, d, J=8 Hz), 7.96 (1H, d, J=8 Hz), 8.12 (1H, s)

(7) Methyl 1-(2,4-dichlorobenzyl)-3-isobutyryl-2-propylindole-6-carboxylate
NMR (CDCl$_3$, δ): 1.02 (3H, t, J=7 Hz), 1.31 (6H, d, J=7 Hz), 1.60 (2H, sextet, J=7 Hz), 3.06 (2H, t, J=7 Hz), 3.58 (2H, septet, J=7 Hz), 3.93 (3H, s), 5.46 (2H, s), 6.16 (1H, d, J=8 Hz), 7.04 (1H, d, J=8 Hz), 7.50 (1H, s), 7.90 (1H, s), 7.96 (2H, s)

(8) Methyl 3-isobutyryl-2-propyl-1-(3-pyridylmethyl)indole-6-carboxylate
NMR (CDCl$_3$, δ) 1.02 (3H, t, J=7 Hz), 1.30 (6H, d, J=7 Hz), 1.60 (2H, sextet, J=7 Hz), 3.12 (2H, t, J=7 Hz), 3.56 (2H, septet, J=7 Hz), 3.92 (3H, s), 5.48 (2H, s), 7.14–7.23 (2H, m), 7.92–7.95 (2H, m), 7.98 (1H, s), 8.42 (1H, d, J=2 Hz), 8.54 (1H, d, J=5 Hz)

(9) Methyl 3-isobutyryl-2-propyl-1-(1-naphthylmethyl)indole-6-carboxylate
NMR (CDCl$_3$, δ): 0.97 (3H, t, J=7 Hz), 1.34 (6H, d, J=7 Hz), 1.64 (2H, sextet, J=7 Hz), 3.04–3.10 (2H, m), 3.63 (1H, septet, J=7 Hz), 3.84 (3H, s), 5.92 (2.H, s), 6.28 (1H, d, J=8 Hz), 7.22 (1H, t, J=8 Hz), 7.62 (1H, t, J=8 Hz), 7.69 (1H, t, J=8 Hz), 7.77 (1H, d, J=8 Hz), 7.77 (2H, s), 7.92 (1H, s)

(10) Methyl 3-isobutyryl-2-propyl-1-(2-naphthylmethyl)indole-6-carboxylate
NMR (CDCl$_3$, δ): 1.00 (3H, t, J=7 Hz), 1.32 (6H, d, J=7 Hz), 1.55–1.68 (2H, m), 3.13–3.18 (2H, m), 3.60 (1H, septet, J=7 Hz), 3.88 (3H, s), 5.62 (2H, s), 7.17 (1H, d, J=8 Hz), 7.29 (2H, s), 7.42–7.48 (2H, m), 7.64–7.68 (1H, m), 7.80 (2H, d, J=2 Hz), 7.96 (2H, s), 8.04 (1H, s)

(11) Methyl 1-(6-chloro-3,4-methylenedioxybenzyl)-3-methoxyacetyl-2-propylindole-6-carboxylate
NMR (CDCl$_3$, δ): 1.04 (3H, t, J=7 Hz), 1.56–1.72 (2H, m), 3.06–3.13 (2H, m), 3.58 (3H, s), 3.93 (3H, s), 4.73 (2H, s), 5.40 (2H, s), 5.70 (1H, s), 5.88 (2H, s), 6.92 (1H, s), 7.83 (1H, d, J=8 Hz), 7.96 (1H, s), 7.98 (1H, d, J=8 Hz)

(12) Methyl 1-(2-chlorobenzyl)-3-ethoxyacetyl-2-propylindole-6-carboxylate
NMR (CDCl$_3$, δ): 1.03 (3H, t, J=7 Hz), 1.34 (3H, t, J=7 Hz), 1.56–1.70 (2H, m), 3.10 (3H, t, J=7 Hz), 3.77 (2H, q, J=7 Hz), 3.92 (3H, s), 4.79 (2H, s), 5.52 (2H, s), 6.24 (1H, d, J=8 Hz), 7.03 (1H, t, J=8 Hz), 7.22 (1H, t, J=8 Hz), 7.46 (1H, d, J=8 Hz), 7.85 (1H, d, J=8 Hz), 7.92 (1H, s), 7.98 (1H, d, J=8 Hz)

(13) 1-(2-Chloro-4-methoxycarbonylbenzyl)-3-isobutyryl-2-propylindole-6-carboxamide
NMR (CDCl$_3$, δ): 1.01 (3H, t, J=7 Hz), 1.32 (6H, d, J=7 Hz), 1.60 (2H, sextet, J=7 Hz), 3.02–3.06 (2H, m), 3.56 (1H, septet, J=7 Hz), 3.90 (3H, s), 5.53 (2H, s), 6.28 (1H, d, J=8 Hz), 7.63 (1H, d, J=8 Hz), 7.69 (1H, d, J=8 Hz), 7.82 (1H, s), 7.98 (1H, d, J=8 Hz), 8.14 (1H, s)

What is claimed is:

1. A compound of the formula:

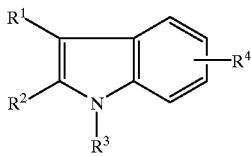

(I)

wherein
R$^1$ is hydrogen, halogen, nitro, acyl, cyano, hydroxyimino(lower)alkyl, lower alkenyl optionally substituted with oxo, or lower alkyl optionally substituted with hydroxy;
R$^2$ is hydrogen, halogen, lower alkenyl, acyl, or lower alkyl optionally substituted with protected carboxy, carboxy, lower alkoxy or hydroxy;
R$^3$ is lower alkenyl, or lower alkyl substituted by
(1) aryl optionally substituted with one or more substituents selected from the group consisting of halogen, aryl, lower alkoxy, lower alkylenedioxy, cyano, nitro, carboxy, protected carboxy, acyl, and amino optionally substituted with acyl or protected carboxy, or
(2) a heterocyclic group selected from the group consisting of pyridyl, thienyl, benzothiazolyl, and benzothiophenyl, each of which is optionally substituted with halogen; and
R$^4$ is acyl, cyano, halogen, a heterocyclic group, amino optionally substituted with acyl or protected carboxy, or lower alkyl optionally substituted with protected carboxy, carboxy or acyl or as defined above; or
R$^1$ and R$^2$ together with the carbon atoms to which they are attached, represent a 4- to 7-membered carbocyclic ring optionally substituted with oxo;
or a pharmaceutically acceptable salt thereof.

2. The compound of claim 1, wherein
R$^1$ is cyano, acyl, or lower alkyl optionally substituted with hydroxy,
R$^2$ is hydrogen, acyl, lower alkenyl, or lower alkyl optionally substituted with lower alkoxy or hydroxy,
R$^3$ is methyl substituted with aryl or heterocyclic group, wherein aryl is optionally substituted with one or more substituents selected from the group consisting of halogen, lower alkylenedioxy, protected carboxy and carboxy; and
R$^4$ is acyl, cyano, or a heterocyclic group; or
R$^1$ and R$^2$, together with the carbon atoms to which they are attached, represent a 4- to 7-membered carbocyclic ring optionally substituted with oxo.

3. The compound of claim 2, wherein
R$^1$ is lower alkyl, or lower alkanoyl optionally substituted with hydroxy, lower alkoxy or aryl;
R$^2$ is hydrogen, lower alkenyl, or lower alkyl optionally substituted with lower alkoxy; and
R$^3$ is benzyl optionally substituted with one or more substituents selected from the group consisting of halogen and lower alkylenedioxy.

4. The compound of claim 3, wherein

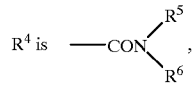

R$^5$ is hydrogen, or lower alkyl; and
R$^6$ is hydrogen, hydroxy, lower alkoxy, arylsulfonyl, a heterocyclic group, or lower alkyl optionally substituted with lower cycloalkyl or a heterocyclic group; or
R$^5$ and R$^6$, together with the nitrogen atom to which they are attached, represent a heterocyclic group.

5. The compound of claim 4, wherein
R$^1$ is lower alkanoyl optionally substituted with alkoxy;
R$^2$ is lower alkyl; and
R$^4$ is carbamoyl.

6. A process for preparing a compound of the formula:

(I)

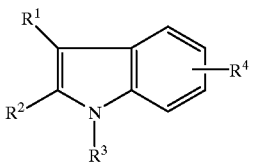

wherein
R¹ is hydrogen, halogen, nitro, acyl, cyano, hydroxyimino (lower)alkyl, lower alkenyl optionally substituted with oxo, or lower alkyl optionally substituted with hydroxy;
R² is hydrogen, halogen, lower alkenyl, acyl, or lower alkyl optionally substituted with protected carboxy, carboxy, lower alkoxy or hydroxy;
R³ is lower alkenyl; or lower alkyl substituted by
  (1) aryl optionally substituted with one or more substituent(s) selected from the group consisting of halogen, aryl, lower alkoxy, lower alkylenedioxy, cyano, nitro, acyl, and amino optionally substituted with acyl or protected carboxy; or
  (2) a heterocyclic group selected from the group consisting of pyridyl, thienyl, benzothiazolyl, and benzothiophenyl, each of which is optionally substituted with halogen; and
R⁴ is acyl, cyano, halogen, a heterocyclic group, amino optionally substituted with acyl or protected carboxy, or lower alkyl optionally substituted with protected carboxy, carboxy or acyl; or
R¹ and R², together with the carbon atoms to which they are attached, represent a 4- to 7-membered carbocyclic ring optionally substituted with oxo;
or a pharmaceutically acceptable salt thereof, which process comprises, a) reacting a compound of the formula:

(II)

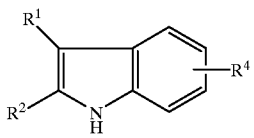

wherein R¹, R² and R⁴ are each as defined above, or a salt thereof, with a compound of the formula:

R³—X¹ (III)

wherein R³ is as defined above, and
X¹ is a leaving group,
to form a compound of the formula:

(I)

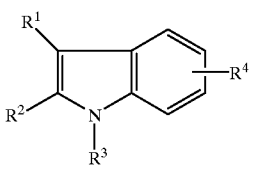

wherein R¹, R², R³ and R⁴ are each as defined above, or a salt thereof; or b) reacting a compound of the formula (I-2)

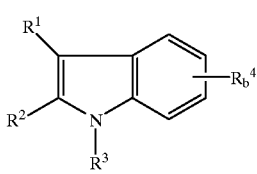

wherein R¹, R² and R³ are each as defined above, and R⁴ is carboxy or lower alkyl substituted with carboxy, or its reactive derivative at the carboxy group, or a salt thereof; with a compound of the formula:

(IV)

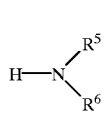

wherein R⁵ is hydrogen or lower alkyl, and

R⁶ is hydrogen, hydroxy, lower alkoxy, arylsulfonyl, a heterocyclic group, or lower alkyl optionally substituted with lower cycloalkyl or a heterocyclic group; or R⁵ and R⁶, together with the nitrogen atom to which they are attached, represent a heterocyclic group, or a reactive derivative at the amino group, or a salt thereof, to give a compound of the formula:

(I-3)

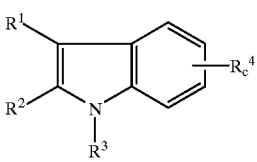

wherein R¹, R², R³, R⁵ and R⁶ are each as defined above, and

R_c⁴ is 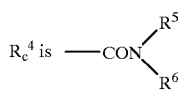

or lower alkyl substituted with

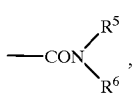, or a salt thereof;

c) reacting a compound of the formula (I–5):

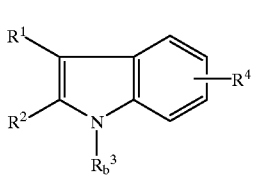
(I-5)

wherein $R^1$, $R^2$ and $R^4$ are each as defined above, and $R_b^3$ is lower alkenyl or alkyl, both of which are optionally substituted with oxo and both of which are substituted with aryl which is substituted with carboxy, or a reactive derivative thereof at the carboxy group, or a salt thereof, with the compound of the formula (IV) as defined above, or a reactive amino compound, or a salt thereof, to form a compound of the formula:

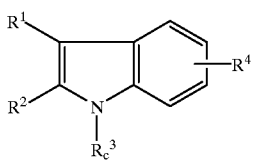
(I-6)

wherein $R^1$, $R^2$, $R^3$, $R^5$ and $R^6$ are each as defined above, and $R_c^3$ is lower alkenyl or lower alkyl, both of which are optionally substituted with oxo and both of which are substituted with aryl which is substituted with

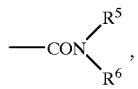

or a salt thereof;

d) reducing a compound of the formula:

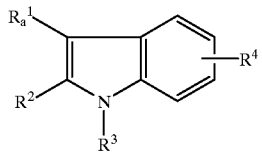
(I-7)

wherein $R^2$, $R^3$ and $R^4$ are each as defined above, and $R_a^1$ is lower alkanoyl optionally substituted with protected carboxy or carboxy, or a salt thereof; to form a compound of the formula:

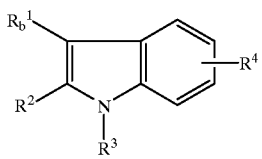
(I-8)

wherein $R^2$, $R^3$ and $R^4$ are each as defined above, and $R_b^1$ is lower alkyl optionally substituted with protected carboxy or carboxy, or a salt thereof;

e) reacting a compound of the formula:

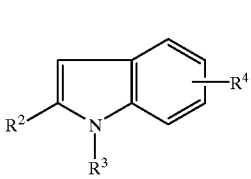
(I-9)

wherein $R^2$, $R^3$ and $R^4$ are each as defined above, or a salt thereof; with a compound of the formula:

$$R_c^1 - X^2 \qquad (V)$$

wherein $R_c^1$ is lower alkenoyl, aryl, or lower alkanoyl optionally substituted with protected carboxy, carboxy, or aryl;

$X^2$ is a leaving group, or a salt thereof; to form a compound of the formula:

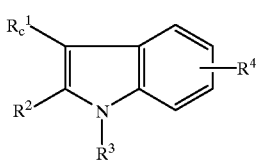
(I-10)

wherein $R_c$, $R^2$, $R^3$ and $R^4$ are each as defined above, or a salt thereof; or f) dehydrating a compound of the formula:

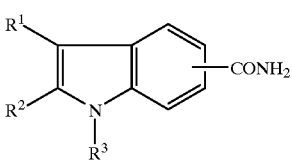
(I-11)

wherein $R^1$, $R^2$ and $R^3$ are each as defined above, or a salt thereof, to form a compound of the formula:

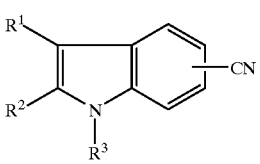
(I-12)

wherein $R^1$, $R^2$ and $R^3$ are each as defined above, or a salt thereof; or g) reacting a compound of the formula (I-12) defined above, or a salt thereof, with an azide compound, to form a compound of the formula:

(I-13)

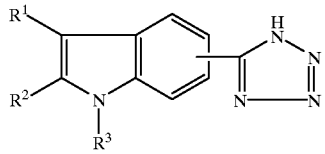

wherein $R^1$, $R^2$ and $R^3$ are each as defined above, or a salt thereof; or h) subjecting a compound of the formula:

(I-14)

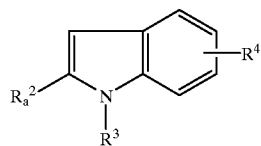

wherein $R^3$ and $R^4$ are each as defined above, and $R_a^2$ is lower alkyl substituted with protected carboxy, or a salt thereof, to deesterification to form a compound of the formula:

(I-15)

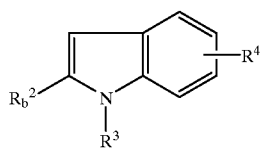

wherein $R^3$ and $R^4$ are each as defined above, and $R_b^2$ is lower alkyl substituted with carboxy, or a salt thereof; or i) subjecting a compound of the formula (I-15) as defined above, or a salt thereof, to intramolecular acrylation to give a compound of the formula:

(I-16)

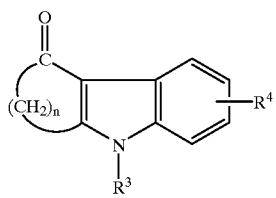

wherein $R^3$ and $R^4$ are each as defined above, and n is 1, 2, 3 or 4, or a salt thereof; or j) reacting a compound of the formula:

(I-17)

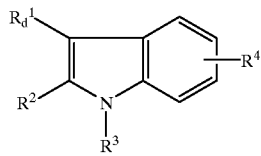

wherein $R^2$, $R^3$ and $R^4$ are each as defined above, and $R_d^1$ is chloroacetyl, or its salt, with a compound of the formula (IV) defined above, or a salt thereof, to form a compound of the formula:

(I-18)

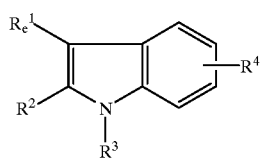

wherein $R^2$, $R^3$ and $R^4$ are each as defined above, and

or a salt thereof; or h) formylating a compound of the formula (I-9) defined above, or a salt thereof, to give a compound of the formula:

(I-19)

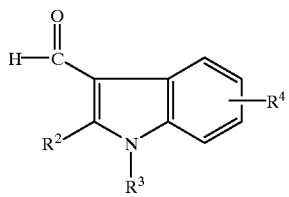

wherein $R^2$, $R^3$ and $R^4$ are each as defined above, or a salt thereof; or l) subjecting a compound of the formula:

(I-21)

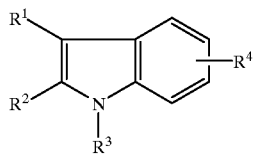

wherein $R^1$, $R^2$ and $R^3$ are each as defined above, or a salt thereof, to a rearrangement reaction to form a compound of the formula:

(I-22)

$$\text{R}^1, \text{R}^2\text{-indole-NHR}^7 \text{ with } \text{R}^3 \text{ on N}$$

wherein $R^1$, $R^2$, $R^3$, $R^5$ and $R^6$ are each as defined above, and $R^7$ is hydrogen, protected carboxy, or $$-\text{CON}\begin{matrix}R^5\\R^6\end{matrix},$$

or a salt thereof; or m) reacting a compound of the formula:

(I-23)

$$\text{R}^1, \text{R}^2\text{-indole-NH}_2 \text{ with } \text{R}^3 \text{ on N}$$

wherein $R^1$, $R^2$ and $R^3$ are each as defined above, or its reactive derivative at the amino group, or a salt thereof, with a compound of the formula:

$$R^8-X^3 \quad (VI)$$

wherein $R^8$ is acyl, and
$X^3$ is leaving group, or a salt thereof, or a compound of the formula:

$$R^9-N=C=O \quad (VII)$$

wherein $R^9$ is lower alkyl, to form a compound of the formula:

(I-24)

$$\text{R}^1, \text{R}^2\text{-indole-NHR}^8 \text{ with } \text{R}^3 \text{ on N}$$

wherein $R^1$, $R^2$, $R^3$ and $R^8$ are same as defined above, or a salt thereof; or n) reducing a compound of the formula:

(I-25)

$$\text{R}^1, \text{R}^2\text{-indole-R}^4 \text{ with } R_d^3 \text{ on N}$$

wherein $R^1$, $R^2$ and $R^4$ are each as defined above, and $R_d^3$ is lower alkyl substituted with aryl which is substituted with nitro, or a salt thereof, to give a compound of the formula:

(I-26)

$$\text{R}^1, \text{R}^2\text{-indole-R}^4 \text{ with } R_e^3 \text{ on N}$$

wherein $R^1$, $R^2$ and $R^4$ are each as defined above, and $R_e^3$ is lower alkyl substituted with aryl which is substituted with amino, or a salt thereof, xviii) subjecting a compound of the formula:

(I-27)

$$R_f^1, \text{R}^2\text{-indole-R}^4 \text{ with } R^3 \text{ on N}$$

wherein $R^2$, $R^3$ and $R^4$ are each as defined above, and $R_f^1$ is lower alkanoyl substituted with lower alkoxy, or a salt thereof, to dealkylation to give a compound of the formula:

(I-28)

$$R_g^1, \text{R}^2\text{-indole-R}^4 \text{ with } R^3 \text{ on N}$$

wherein $R^2$, $R^3$ and $R^4$ are each as defined above, and $R_g^1$ is lower alkanoyl substituted with hydroxy, or a salt thereof; or o) oxidizing a compound of the formula:

(I-29)

$$\text{R}^1, R_c^2\text{-indole-R}^4 \text{ with } R^3 \text{ on N}$$

wherein $R^1$, $R^3$ and $R^4$ are each as defined above, and $R_c^2$ is 1-hydroxy(lower)alkyl, or a salt thereof, to form a compound of the formula:

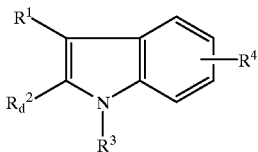

(I-30)

wherein $R^1$, $R^3$ and $R^4$ are each as defined above, and $R_d^2$ is lower alkanoyl, or a salt thereof; or p) halogenating a compound of the formula (I-9) defined above, or a salt thereof, to form a compound of the formula:

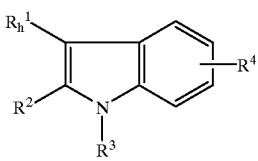

(I-31)

wherein $R^2$, $R^3$ and $R^4$ are each as defined above, and $R_h^1$ is halogen, or a salt thereof; or q) subjecting a compound of the formula (I-9) defined above, or a salt thereof, to nitration to give a compound of the formula:

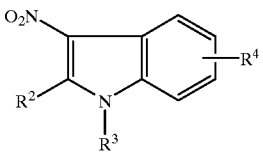

(I-32)

wherein $R^2$, $R^3$ and $R^4$ are each as defined above, or a salt thereof; or r) reducing a compound of the formula (I-7) defined above, or a salt thereof, to give a compound of the formula:

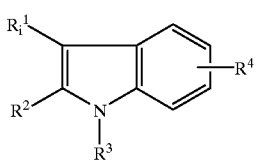

(I-33)

wherein $R^2$, $R^3$ and $R^4$ are each as defined above, and $R_i^1$ is lower alkyl optionally substituted with protected carboxy or carboxy, or a salt thereof; or s) reacting a compound of the formula:

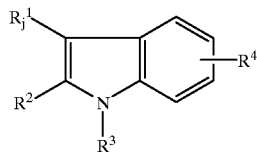

(I-34)

wherein $R^2$, $R^3$ and $R^4$ are each as defined above, and $R_j^1$ is lower alkanoyl, or its salt, with hydroxylamine or a salt thereof, to form a compound of the formula:

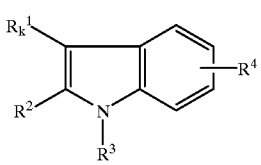

(I-35)

wherein $R^2$, $R^3$ and $R^4$ are each as defined above, and $R_k^1$ is hydroxyimino(lower)alkyl, or a salt thereof, or t) reacting a compound of the formula:

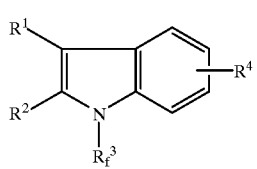

(I-36)

wherein $R^1$, $R^2$ and $R^4$ are each as defined above, $R_f^3$ is lower alkyl substituted with aryl which is substituted with amino, or its reactive derivative at the amino group, or its salt, with a compound of the formula (VI) as defined above or a salt thereof, or a compound of the formula (VII) defined above, to form a compound of the formula:

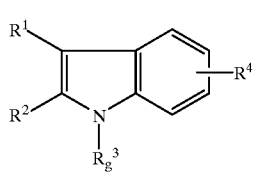

(I-37)

wherein $R^1$, $R^2$ and $R^4$ are each as defined above, and $R_g^3$ is lower alkyl substituted with aryl which is substituted with amino substituted with acyl, or its salt.

7. A pharmaceutical composition comprising one or more compounds of claim 1, as an active ingredient, in association with a pharmaceutically acceptable, substantially non-toxic carrier or excipient.

8. A method for the manufacture of a medicament for inhibiting cGMP-PDE, which comprises incorporating one or more of the compounds of claim 1, into a medicament.

9. A method for treating angina, hypertension, pulmonary hypertension, congestive heart failure, glomerular diseases, renal turbo-intestinal diseases, renal failure, atherosclerosis, conditions of reduced blood vessel patency, peripheral vascular disease, stroke, bronchitis, chronic asthma, allergic asthma, allergic rhinitis, urticaria, impotence, diabetic complication, glaucoma or diseases exhibiting, disorders of gut motility, by administering one or more of the compounds of claim 1 to a patient in need thereof.

* * * * *